(12) United States Patent
Szlávik et al.

(10) Patent No.: US 10,457,687 B2
(45) Date of Patent: Oct. 29, 2019

(54) AMINOACID DERIVATIVES, A PROCESS FOR THEIR PREPARATION AND PHARMACEUTICAL COMPOSITIONS CONTAINING THEM

(71) Applicants: LES LABORATOIRES SERVIER, Suresnes (FR); VERNALIS (R&D) LTD., Winnersh (GB)

(72) Inventors: Zoltán Szlávik, Budapest (HU); Zoltán Szabó, Budapest (HU); Márton Csékei, Dunakeszi (HU); Attila Paczal, Budapest (HU); András Kotschy, Törökbálint (HU); Alain Bruno, Paris (FR); Olivier Geneste, Rueil-Malmaison (FR); I-Jen Chen, Cambridge (GB); James Edward Paul Davidson, Great Shelford (GB); James Brooke Murray, Linton (GB); Levente Ondi, Veresegyház (HU); Gábor Radics, Erd (HU); Szabolcs Sipos, Budapest (HU); Ágnes Proszenyák, Budapest (HU); Françoise Perron-Sierra, Paris (FR); Balázs Bálint, Fót (HU)

(73) Assignees: LES LABORATOIRES SERVIER, Suresnes (FR); VERNALIS (R&D) LTD, Winnersh Berkshire (GB)

( * ) Notice: Subject to any disclaimer, the term of this patent is extended or adjusted under 35 U.S.C. 154(b) by 0 days.

(21) Appl. No.: 15/737,783

(22) PCT Filed: Jun. 22, 2016

(86) PCT No.: PCT/EP2016/064436
§ 371 (c)(1),
(2) Date: Dec. 19, 2017

(87) PCT Pub. No.: WO2016/207226
PCT Pub. Date: Dec. 29, 2016

(65) Prior Publication Data
US 2019/0031675 A1    Jan. 31, 2019

(30) Foreign Application Priority Data
Jun. 23, 2015   (FR) ..................... 15 55747

(51) Int. Cl.
| C07D 495/04 | (2006.01) |
| A61K 31/519 | (2006.01) |
| A61P 37/00 | (2006.01) |
| A61P 35/00 | (2006.01) |

(52) U.S. Cl.
CPC ............ C07D 495/04 (2013.01); A61P 35/00 (2018.01); A61P 37/00 (2018.01)

(58) Field of Classification Search
CPC ........................ C07D 495/04; A61K 31/519
See application file for complete search history.

(56) References Cited

U.S. PATENT DOCUMENTS

2015/0051189 A1    2/2015  Le Diguarher et al.

FOREIGN PATENT DOCUMENTS

| CN | 102464667 | 5/2012 |
| WO | WO2013/072694 | 5/2013 |
| WO | WO2013110890 | 8/2013 |
| WO | WO2014/078957 | 5/2014 |

OTHER PUBLICATIONS

English translation of CN102464667, 2012.
International Search Report for PCT/EP2016/064436 dated Sep. 13, 2016.

*Primary Examiner* — Rebecca L Anderson
(74) *Attorney, Agent, or Firm* — Hueschen and Sage

(57) ABSTRACT

Compounds of formula (I):

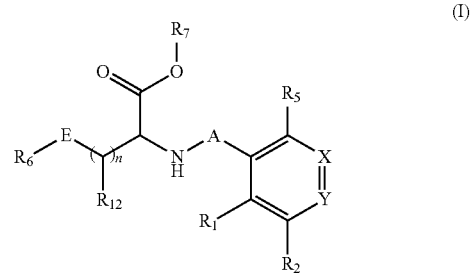

wherein $R_1$, $R_2$, $R_5$, $R_6$, $R_7$, $R_{12}$, X, Y, A, E and n are as defined in the description.
Medicinal products containing the same which are useful in treating a condition requiring a pro-apoptotic agent.

33 Claims, No Drawings

AMINOACID DERIVATIVES, A PROCESS FOR THEIR PREPARATION AND PHARMACEUTICAL COMPOSITIONS CONTAINING THEM

The present invention relates to new aminoacid derivatives, to a process for their preparation and to pharmaceutical compositions containing them.

The compounds of the present invention are new and have very valuable pharmacological characteristics in the field of apoptosis and cancerology.

Apoptosis, or programmed cell death, is a physiological process that is crucial for embryonic development and maintenance of tissue homeostasis.

Apoptotic-type cell death involves morphological changes such as condensation of the nucleus, DNA fragmentation and also biochemical phenomena such as the activation of caspases which cause damage to key structural components of the cell, so inducing its disassembly and death. Regulation of the process of apoptosis is complex and involves the activation or repression of several intracellular signalling pathways (Cory S. et al., Nature Review Cancer 2002, 2, 647-656).

Deregulation of apoptosis is involved in certain pathologies. Increased apoptosis is associated with neurodegenerative diseases such as Parkinson's disease, Alzheimer's disease and ischaemia. Conversely, deficits in the implementation of apoptosis play a significant role in the development of cancers and their chemoresistance, in auto-immune diseases, inflammatory diseases and viral infections. Accordingly, absence of apoptosis is one of the phenotypic signatures of cancer (Hanahan D. et al., Cell 2000, 100, 57-70).

The anti-apoptotic proteins of the Bcl-2 family are associated with numerous pathologies. The involvement of proteins of the Bcl-2 family is described in numerous types of cancer, such as colon cancer, breast cancer, small-cell lung cancer, non-small-cell lung cancer, bladder cancer, ovarian cancer, prostate cancer, chronic lymphoid leukaemia, lymphoma, myeloma, acute myeloid leukemia, pancreatic cancer, etc. Overexpression of the anti-apoptotic proteins of the Bcl-2 family is involved in tumorigenesis, in resistance to chemotherapy and in the clinical prognosis of patients affected by cancer. Notably, Mcl-1, an anti-apoptotic Bcl-2 family member, is overexpressed in various types of cancer (Beroukhim R. et al., Nature 2010, 899-905). There is, therefore, a therapeutic need for compounds that inhibit the anti-apoptotic activity of the proteins of the Bcl-2 family.

In addition to being new, the compounds of the present invention have pro-apoptotic properties making it possible to use them in pathologies involving a defect in apoptosis, such as, for example, in the treatment of cancer and of immune and auto-immune diseases.

The present invention relates more especially to compounds of formula (I):

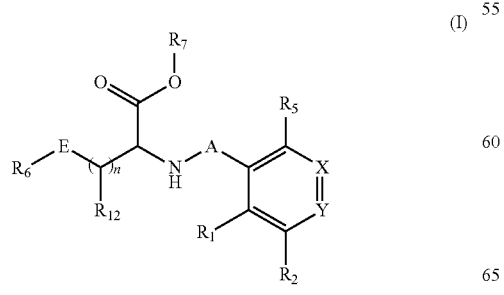

wherein:

A represents the group

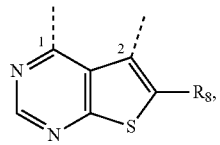

in which 1 is linked to the —NH— group and 2 is linked to the aromatic ring,

E represents a cycloalkyl group, a heterocycloalkyl group, an aryl group or a heteroaryl group, X represents a nitrogen atom or a C—$R_4$ group, Y represents a nitrogen atom or a C—$R_3$ group, $R_1$ represents a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl group, a hydroxy group, a hydroxy($C_1$-$C_6$)alkyl group, a linear or branched ($C_1$-$C_6$)alkoxy group, —S—($C_1$-$C_6$)alkyl, a cyano group, a nitro group, -alkyl($C_0$-$C_6$)—$NR_9R_9'$, —O-alkyl($C_1$-$C_6$)—$NR_9R_9'$, —O-alkyl($C_1$-$C_6$)—$R_{10}$, —C(O)—$OR_9$, —O—C(O)—$R_9$, —C(O)—$NR_9R_9'$, —$NR_9$—C(O)—$R_9'$, —$NR_9$—C(O)—$OR_9'$, -alkyl($C_1$-$C_6$)—$NR_9$—C(O)—$R_9'$, —$SO_2$—$NR_9R_9'$, —$SO_2$-alkyl($C_1$-$C_6$), $R_2$, $R_3$, $R_4$ and $R_5$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl group, a hydroxy group, a hydroxy($C_1$-$C_6$)alkyl group, a linear or branched ($C_1$-$C_6$)alkoxy group, —S—($C_1$-$C_6$)alkyl, a cyano group, a nitro group, -alkyl($C_0$-$C_6$)—$NR_9R_9'$, —O-alkyl($C_1$-$C_6$)—$NR_9R_9'$, —O-alkyl($C_1$-$C_6$)—$R_{10}$, —C(O)—$OR_9$, —O—C(O)—$R_9$, —C(O)—$NR_9R_9'$, —$NR_9$—C(O)—$R_9'$, —$NR_9$—C(O)—$OR_9'$, -alkyl($C_1$-$C_6$)—$NR_9$—C(O)—$R_9'$, —$SO_2$—$NR_9R_9'$, or —$SO_2$-alkyl($C_1$-$C_6$), or the substituents of the pair ($R_1$, $R_2$) form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by from 1 to 2 groups selected from halogen, linear or branched ($C_1$-$C_6$)alkyl, -alkyl($C_0$-$C_6$)—$NR_9R_9'$, —$NR_{11}R_{11}'$, -alkyl ($C_0$-$C_6$)-$Cy_1$, or oxo, $R_6$ represents a hydrogen atom, a halogen atom, a linear or branched ($C_1$-$C_6$)alkyl group, a linear or branched ($C_2$-$C_6$)alkenyl group, a linear or branched ($C_2$-$C_6$) alkynyl group, a linear or branched ($C_1$-$C_6$)polyhaloalkyl group, a hydroxy group, a linear or branched ($C_1$-$C_6$)alkoxy group, —S—($C_1$-$C_6$)alkyl, a cyano group, a nitro group, -alkyl($C_0$-$C_6$)—$NR_9R_9'$, —O-$Cy_1$, -alkyl($C_0$-$C_6$)-$Cy_1$, -alkenyl($C_2$-$C_6$)-$Cy_1$, -alkynyl ($C_2$-$C_6$)-$Cy_1$, —O-alkyl($C_1$-$C_6$)—$R_{10}$, —C(O)—$OR_9$, —O—C(O)—$R_9$, —C(O)—$NR_9R_9'$, —$NR_9$—C(O)—$R_9'$, —$NR_9$—C(O)—$OR_9'$, -alkyl($C_1$-$C_6$)—$NR_9$—C (O)—$R_9'$, —$SO_2$—$NR_9R_9'$, or —$SO_2$-alkyl($C_1$-$C_6$), $R_7$ represents a hydrogen atom, a linear or branched ($C_1$-$C_8$)alkyl group, a —$CHR_aR_b$ group, an aryl group, a heteroaryl group, an arylalkyl($C_1$-$C_6$) group, or a heteroarylalkyl($C_1$-$C_6$) group, R₈ represents a linear or branched (C₁-C₆)alkyl group, a linear or branched (C₂-C₆)alkenyl group, a linear or branched (C₂-C₆)alkynyl group, -Cy₂, a halogen atom, a cyano group, —C(O)—R₁₁, or —C(O)—NR₁₁R₁₁', R₉ and R₉' independently of one another represent a hydrogen atom, a linear or branched (C₁-C₆)alkyl group, or the substituents of the pair (R₉, R₉') form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the nitrogen in question may be substituted by a group representing a hydrogen atom, or a linear or branched (C₁-C₆)alkyl group, R₁₀ represents -Cy₃, -Cy₃-alkyl(C₀-C₆)-Cy₄, —C(O)—NR₉R₉', —NR₉R₉', —OR₉, —NR₉—C(O)—R₉', —O-alkyl(C₁-C₆)—OR₉, —SO₂—R₉, —C(O)—OR₉, or —NH—C(O)—NH—R₉, R₁₁ and R₁₁' independently of one another represent a hydrogen atom or an optionally substituted linear or branched (C₁-C₆)alkyl group, R₁₂ represents a hydrogen atom, a hydroxy group, or a hydroxy(C₁-C₆)alkyl group, R_a represents a hydrogen atom or a linear or branched (C₁-C₆)alkyl group, R_b represents a —O—C(O)—O—R_c group, a —O—C(O)—NR_cR_c' group, or a —O—P(O)(OR_c)₂ group, R_c and R_c' independently of one another represent a hydrogen atom, a linear or branched (C₁-C₈)alkyl group, a cycloalkyl group, a (C₁-C₆)alkoxy(C₁-C₆)alkyl group, a (C₁-C₆)alkoxycarbonyl(C₁-C₆)alkyl group, or the substituents of the pair (R_c, R_c') form together with the nitrogen atom carrying them a non-aromatic ring composed of from 5 to 7 ring members, which may contain in addition to the nitrogen atom from 1 to 3 heteroatoms selected from oxygen and nitrogen, it being understood that the nitrogen in question may be substituted by a group representing a linear or branched (C₁-C₆)alkyl group, Cy₁, Cy₂, Cy₃ and Cy₄ independently of one another, represent a cycloalkyl group, a heterocycloalkyl group, an aryl group or a heteroaryl group, n is an integer equal to 0, 1 or 2, it being understood that:

"aryl" means a phenyl, naphthyl, biphenyl group,

"heteroaryl" means any mono- or bi-cyclic group composed of from 5 to 10 ring members, having at least one aromatic moiety and containing from 1 to 3 heteroatoms selected from oxygen, sulphur and nitrogen, "cycloalkyl" means any mono- or bi-cyclic non-aromatic carbocyclic group containing from 3 to 10 ring members, "heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, it being possible for the aryl, heteroaryl, cycloalkyl and heterocycloalkyl groups so defined and the alkyl, alkenyl, alkynyl, alkoxy groups, to be substituted by from 1 to 4 groups selected from optionally substituted linear or branched (C₁-C₆)alkyl, optionally substituted linear or branched (C₂-C₆)alkenyl, optionally substituted linear or branched (C₂-C₆)alkynyl, optionally substituted linear or branched (C₁-C₆)alkoxy, optionally substituted (C₁-C₆)alkyl-S—, hydroxy, hydroxy(C₁-C₆)alkyl, oxo (or N-oxide where appropriate), nitro, cyano, —C(O)—OR', —O—C(O)—R', —C(O)—NR'R", —O—C(O)—NR'R", —NR'R", —(C=NR')—OR", —O—P(O)(OR')₂, —O—P(O)(O⁻M⁺)₂, linear or branched (C₁-C₆)polyhaloalkyl, trifluoromethoxy, halogen, or an aldohexose of formula:

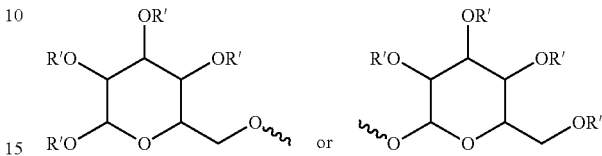

in which each R' is independent;

it being understood that R' and R" independently of one another represent a hydrogen atom or an optionally substituted linear or branched (C₁-C₆)alkyl group and M⁺ represents a pharmaceutically acceptable monovalent cation, their enantiomers, diastereoisomers and atropisomers, and addition salts thereof with a pharmaceutically acceptable acid or base.

Advantageously, the present invention relates to compounds of formula (I) wherein:

R₁ and R₂ independently of one another represent a halogen atom, a linear or branched (C₁-C₆)alkyl group, a hydroxy group, a hydroxy(C₁-C₆)alkyl group, a linear or branched (C₁-C₆)alkoxy group, or the substituents of the pair (R₁, R₂) form together with the carbon atoms carrying them an aromatic ring composed of from 5 to 7 ring members, which may contain from 1 to 3 nitrogen atoms, it being understood that resulting ring may be substituted by from 1 to 2 groups selected from halogen, linear or branched (C₁-C₆)alkyl, or -alkyl(C₀-C₆)—NR₉R₉', R₃ represents a hydrogen atom, a halogen atom, a linear or branched (C₁-C₆)alkyl group, a hydroxy group, a linear or branched (C₁-C₆)alkoxy group, or —O-alkyl(C₁-C₆)—NR₉R₉', R₄ and R₅ independently of one another represent a hydrogen atom, a halogen atom, a linear or branched (C₁-C₆)alkyl group, a hydroxy group, a linear or branched (C₁-C₆)alkoxy group, R₆ represents a hydrogen atom, a halogen atom, a linear or branched (C₁-C₆)alkyl group, a linear or branched (C₁-C₆)polyhaloalkyl group, a hydroxy group, a linear or branched (C₁-C₆)alkoxy group, a cyano group, a nitro group, -alkyl(C₀-C₆)—NR₉R₉', -alkyl(C₀-C₆)-Cy₁, —O-alkyl(C₁-C₆)—R₁₀ or —C(O)—NR₉R₉', R₇ represents a hydrogen atom, a linear or branched (C₁-C₈)alkyl group, a —CHR_aR_b group, or a heteroarylalkyl(C₁-C₆) group, R₈ represents a linear or branched (C₁-C₆)alkyl group, a linear or branched (C₂-C₆)alkenyl group, a linear or branched (C₂-C₆)alkynyl group, -Cy₂, a halogen atom, or —C(O)—R₁₁, R₉ and R₉' independently of one another represent a hydrogen atom, a linear or branched (C₁-C₆)alkyl group, or the substituents of the pair (R₉, R₉') form together with the nitrogen atom carrying them a non-aromatic ring composed of from 5 to 7 ring members, which may contain in addition to the nitrogen atom from 1 to 3 heteroatoms selected from oxygen and nitrogen, it being understood that the nitrogen in question may be substituted by a group representing a linear or branched $(C_1-C_6)$alkyl group, $R_{10}$ represents -Cy$_3$ or -Cy$_3$-alkyl(C$_0$-C$_6$)-Cy$_4$, $R_{11}$ represents a linear or branched $(C_1-C_6)$alkyl group, it being possible for the aryl, heteroaryl, cycloalkyl and heterocycloalkyl groups so defined and the alkyl, alkenyl, alkynyl, alkoxy groups, to be substituted by from 1 to 4 groups selected from optionally substituted linear or branched $(C_1-C_6)$alkyl, optionally substituted linear or branched $(C_1-C_6)$alkoxy, hydroxy, hydroxy$(C_1-C_6)$alkyl, oxo (or N-oxide where appropriate), —C(O)—OR', —C(O)—NR'R", —O—C(O)—NR'R", —NR'R", —O—P(O)(OR')$_2$, —O—P(O)(O$^-$M$^+$)$_2$, linear or branched $(C_1-C_6)$ polyhaloalkyl, halogen, or an aldohexose of formula:

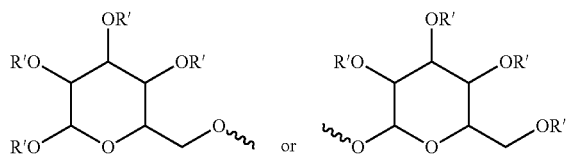

in which each R' is independent;

it being understood that R' and R" independently of one another represent a hydrogen atom or an optionally substituted linear or branched $(C_1-C_6)$alkyl group and M$^+$ represents a pharmaceutically acceptable monovalent cation.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

More especially, compounds of formula (I) to which preference is given are compounds wherein n is an integer equal to 1.

In another embodiment of the invention, an advantageous possibility consists of compounds of formula (I-a):

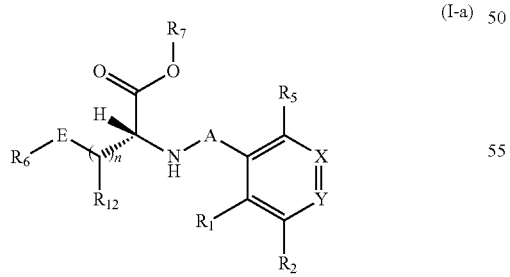

(I-a)

wherein A, E, $R_1$, $R_2$, $R_5$, $R_6$, $R_7$, $R_{12}$, X, Y and n are as defined for formula (I).

Atropisomers are stereoisomers arising because of hindered rotation about a single bond, where energy differences due to steric strain or other contributors create a barrier to rotation that is high enough to allow for isolation of individual conformers. For compounds according to the invention, atropisomers are as follows:

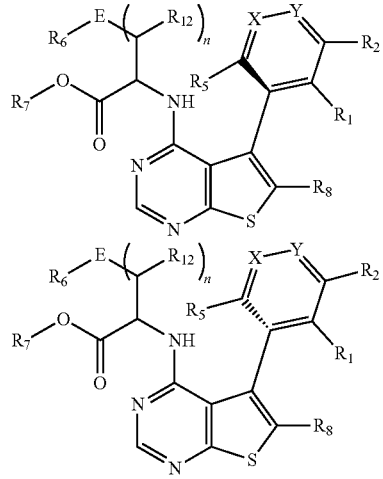

Preferred atropisomer is (5S$_a$) when X represents a C—R$_4$ group and Y represents a C—R$_3$ group.

Advantageously, at least one of the groups selected from R$_2$, R$_3$, R$_4$ and R$_5$ does not represent a hydrogen atom.

Preferably, R$_{12}$ represents a hydrogen atom, a hydroxymethyl group or a hydroxyethyl group. More preferably, R$_{12}$ represents a hydrogen atom.

In the preferred compounds of the invention, R$_1$ represents a linear or branched (C$_1$-C$_6$)alkyl group or a halogen atom. More preferably, R$_1$ represents a methyl group, an ethyl group, a bromine atom or a chlorine atom. Even more preferably, R$_1$ represents a methyl group.

Advantageously, R$_2$ represents a halogen atom, a hydroxy group, a linear or branched (C$_1$-C$_6$)alkoxy group. More preferably, R$_2$ represents a methoxy group, a hydroxy group, a fluorine atom, a bromine atom or a chlorine atom. Even more preferably, R$_2$ represents a chlorine atom.

In some preferred embodiment of the invention, when the substituents of the pair (R$_1$, R$_2$) form together with the carbon atoms carrying them an aromatic ring,

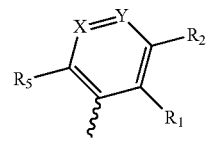

represents

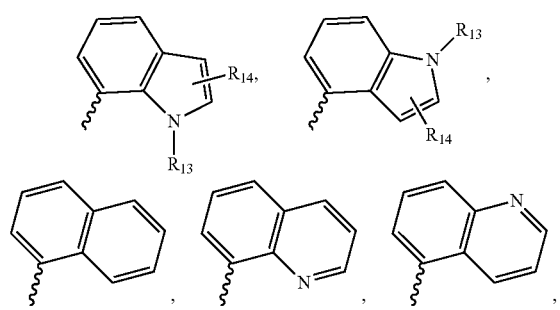

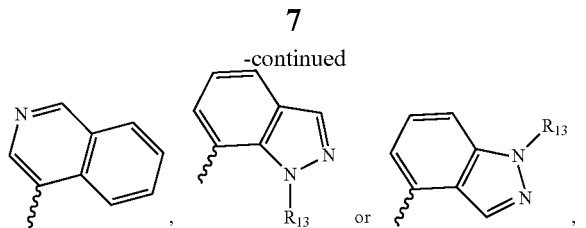

wherein $R_{13}$ represents a hydrogen atom, a linear or branched $(C_1-C_6)$alkyl group or -alkyl$(C_0-C_6)$—$NR_9R_9'$ in which $R_9$ and $R_9'$ are as defined for formula (I), and $R_{14}$ represents a hydrogen atom, a halogen atom or a linear or branched $(C_1-C_6)$alkyl group.

$R_{13}$ represents preferably a hydrogen atom, a methyl group or —$(CH_2)_m$—$NR_9R_9'$ in which m is an integer equal to 2 or 3 and, $R_9$ and $R_9'$ represent a methyl group or the substituents of the pair $(R_9, R_9')$ form together with the nitrogen atom carrying them a pyrrolidinyl, a piperidinyl, a morpholinyl or a 4-methyl-piperazin-1-yl group.

$R_{14}$ represents advantageously a hydrogen atom, a bromine atom, an iodine atom, a chlorine atom or a methyl group. $R_{14}$ is preferably substituted at β position from the nitrogen atom.

Preferably, X represents a C—$R_4$ group. In a preferred embodiment of the invention, Y represents a C—$R_3$ group. $R_3$ advantageously represents a hydrogen atom, a linear or branched $(C_1-C_6)$alkoxy group or —O-alkyl$(C_1-C_6)$—$NR_9R_9'$. $R_4$ preferably represents a hydrogen atom.

In some preferred embodiment of the invention,

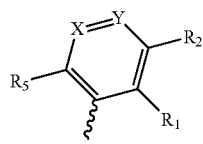

represents

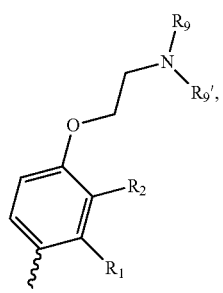

wherein $R_1$, $R_2$, $R_9$ and $R_9'$ are as defined for formula (I).

In the preferred compounds of the invention,

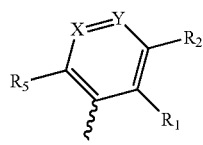

represents

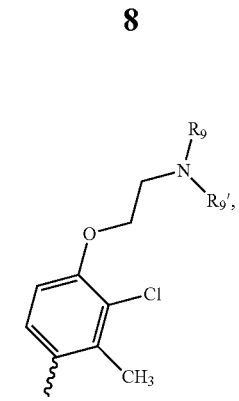

wherein $R_9$ and $R_9'$ are as defined for formula (I).

$R_5$ preferably represents a hydrogen atom.

In an advantageous embodiment, the substituents of the pair $(R_1, R_5)$ are identical and the substituents of the pair $(R_2, R_4)$ are identical. In the preferred compounds of the invention, the substituents of the pair $(R_1, R_5)$ are identical and represent a $(C_1-C_6)$alkyl group, preferably a methyl group, whereas the substituents of the pair $(R_2, R_4)$ are identical and represent a halogen atom, preferably a chlorine atom, or a hydrogen atom.

In another embodiment of the invention, E represents a phenyl group, a pyridin-2-yl, a cyclohexyl group, a pyrazol-1-yl group, a cyclopentyl group, an indol-4-yl group, a cyclopropyl group, a pyridin-3-yl group, an indol-3-yl group, a naphth-1-yl group, an imidazol-4-yl group or a pyridin-4-yl group. Advantageously, E represents a phenyl group.

In the preferred compounds of the invention, $R_6$ represents a hydrogen atom; a fluorine atom; a chlorine atom; a bromine atom; a methyl group; a trifluoromethyl group; a hydroxy group; a methoxy group; a linear $(C_1-C_6)$alkoxy group substituted by halogen atoms, a —C(O)—NR'R" group or a —NR'R" group; a cyano; a nitro group; an aminomethyl group; a benzyl group; —O-alkyl$(C_1-C_6)$—$R_{10}$; —C(O)—$NR_9R_9'$. Preferably, $R_6$ represents a methoxy group, a 2,2,2-trifluoroethoxy group or —O-alkyl$(C_1-C_6)$—$R_{10}$.

In another embodiment of the invention, an advantageous possibility consists of compounds of formula (I-b):

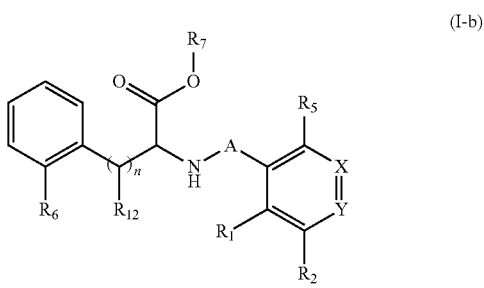

(I-b)

wherein $R_1$, $R_2$, $R_5$, $R_6$, $R_7$, $R_{12}$, X, Y, A and n are as defined for formula (I).

In another embodiment of the invention, an advantageous possibility consists of compounds of formula (I-c):

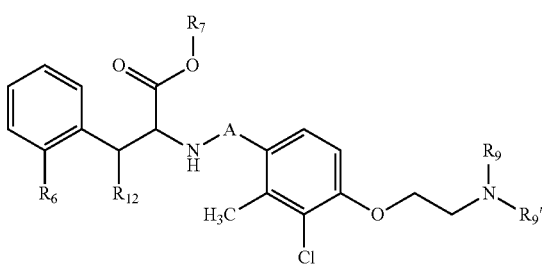

(I-c)

wherein $R_6$, $R_7$, $R_9$, $R_9'$, $R_{12}$ and A are as defined for formula (I).

Preferably, $R_7$ represents a hydrogen atom, a —CHR$_a$R$_b$ group, an optionally substituted linear or branched ($C_1$-$C_8$) alkyl group, or a heteroarylalkyl($C_1$-$C_6$) group. Preferably, $R_7$ represents a —CHR$_a$R$_b$ group in which R$_a$ represents a hydrogen atom or a methyl group and R$_b$ represents a —O—C(O)—O—($C_1$-$C_8$)alkyl group; a —O—C(O)—O—cycloalkyl group; a —O—C(O)—NR$_c$R$_c'$ group, in which R$_c$ and R$_c'$ independently of one another represent a hydrogen atom, a linear or branched ($C_1$-$C_8$)alkyl group, a ($C_1$-$C_6$)alkoxy($C_1$-$C_6$)alkyl group, a ($C_1$-$C_6$)alkoxycarbonyl($C_1$-$C_6$)alkyl group, or the substituents of the pair (R$_c$, R$_c'$) form together with the nitrogen atom carrying them a non-aromatic ring composed of from 5 to 7 ring members, which may contain in addition to the nitrogen atom from 1 to 3 heteroatoms selected from oxygen and nitrogen; or a —O—P(O)(OH)$_2$ group. Preferred $R_7$ groups are as follows: hydrogen; methyl; ethyl; (5-methyl-2-oxo-1,3-dioxol-4-yl) methyl; a —CHR$_a$R$_b$ group in which R$_a$ represents a methyl group and R$_b$ represents a —O—C(O)—O—CH$_2$CH$_3$ group or a —O—C(O)—N(CH$_3$)$_2$ group. Even more preferably, $R_7$ represents hydrogen.

In the preferred compounds of the invention, $R_8$ represents a linear or branched ($C_2$-$C_6$)alkynyl group, an aryl group or a heteroaryl group. More preferably, $R_8$ represents a prop-1-yn-1-yl group, a phenyl group or a furan-2-yl group. In a more preferred embodiment, $R_8$ represents a prop-1-yn-1-yl group, a 4-fluorophenyl group or a 5-fluorofuran-2-yl group. Even more preferentially, $R_8$ represents a 4-fluorophenyl group.

In the preferred compounds of the invention, $R_9$ and $R_9'$ independently of one another represent a linear or branched ($C_1$-$C_6$)alkyl group, or the substituents of the pair ($R_9$, $R_9'$) form together with the nitrogen atom carrying them a non-aromatic ring composed of from 5 to 7 ring members, which may contain in addition to the nitrogen atom from 1 to 3 heteroatoms selected from oxygen and nitrogen, it being understood that the nitrogen in question may be substituted by a linear or branched ($C_1$-$C_6$)alkyl group. More preferably, $R_9$ and $R_9'$ represent a methyl group, or the substituents of the pair ($R_9$, $R_9'$) form together a 4-methyl-piperazinyl group.

Advantageously, $R_{10}$ represents -Cy$_3$ or -Cy$_3$-alkyl(C$_0$-C$_6$)-Cy$_4$. Preferably, $R_{10}$ represents -Cy$_3$ or -Cy$_3$-Cy$_4$.

Cy$_3$ preferably represents a cycloalkyl group, particularly, a cyclopentyl group. In a preferred embodiment, Cy$_3$ represents an aryl group, particularly, a phenyl group.

Advantageously, Cy$_3$ represents a heteroaryl group, particularly, a pyrimidinyl group, a pyrazolyl group or a pyridinyl group. More preferably, Cy$_3$ represents a pyrimidin-4-yl group, a pyrazol-5-yl group or a pyridin-2-yl group. In the preferred compounds of the invention, Cy$_3$ represents a pyrimidin-4-yl group. In another embodiment of the invention, Cy$_3$ represents a heteroaryl group which is substituted by an optionally substituted linear or branched ($C_1$-$C_6$)alkyl group, an optionally substituted linear or branched ($C_1$-$C_6$) alkoxy group or a linear or branched ($C_1$-$C_6$)polyhaloalkyl group. Preferably, Cy$_3$ represents a heteroaryl group which is substituted by a 2,2,2-trifluoroethoxy group, a 2-methoxyethyl group, an ethoxy group; a tert-butyl group, an ethyl group, a n-butyl group, a 2,2,2-trifluoroethyl group or a methyl group.

Cy$_4$ preferably represents a phenyl group, a pyridinyl group, a pyridazinyl group, a pyrazinyl group, a pyrimidinyl group or a morpholinyl group. More preferably, Cy$_4$ represents a phenyl group.

Other compounds of the invention to which preference is given are those wherein,
$R_{10}$ represents

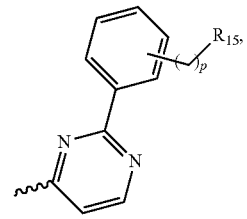

in which p is an integer equal to 0 or 1 and $R_{15}$ represents a hydrogen atom, a hydroxy group, an optionally substituted linear or branched ($C_1$-$C_6$)alkyl group, a linear or branched ($C_1$-$C_6$)alkoxy group, a —O—(CHR$_{16}$—CHR$_{17}$—O)$_q$—R' group, a —O—P(O)(OR')$_2$ group, a —O—P(O)(O$^-$M$^+$)$_2$ group, a —O—C(O)—NR$_{18}$R$_{19}$ group, a di($C_1$-$C_6$)alkylamino($C_1$-$C_6$)alkoxy group, a halogen atom, or an aldohexose of formula:

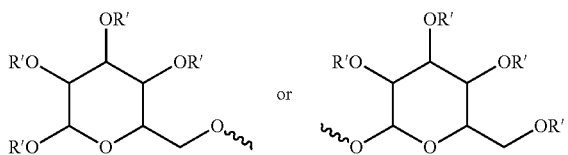

in which each R' is independent;
it being understood that:
   R' represents a hydrogen atom or a linear or branched ($C_1$-$C_6$)alkyl group,
   $R_{16}$ represents a hydrogen atom or a ($C_1$-$C_6$)alkoxy($C_1$-$C_6$)alkyl group,
   $R_{17}$ represents a hydrogen atom or a hydroxy($C_1$-$C_6$)alkyl group,
   $R_{18}$ represents a hydrogen atom or a ($C_1$-$C_6$)alkoxy($C_1$-$C_6$)alkyl group,
   $R_{19}$ represents a ($C_1$-$C_6$)alkoxy($C_1$-$C_6$)alkyl group, a —(CH$_2$)$_r$—NR$_9$R$_9'$ group or a —(CH$_2$)$_r$—O—(CHR$_{16}$—CHR$_{17}$—O)$_q$—R' group,
   q is an integer equal to 1, 2 or 3 and r is an integer equal to 0 or 1,
   M$^+$ represents a pharmaceutically acceptable monovalent cation.

The aldohexose according to the invention is preferably D-mannose. Advantageously, $R_{15}$ represents a methoxy group, a 2-methoxyethoxy group or fluorine. Preferably, the group —(CH$_2$)$_p$—R$_{15}$ is located at ortho position of the phenyl group.

Among the preferred compounds of the invention there may be mentioned:

N-[5-{3-chloro-2-methyl-4-[2-(4-methylpiperazin-1-yl)ethoxy]phenyl}-6-(4-fluoro phenyl)thieno[2,3-d]pyrimidin-4-yl]-2-[(1-methyl-1H-pyrazol-5-yl)methoxy]-D-phenylalanine N-[5-{3-chloro-2-methyl-4-[2-(4-methylpiperazin-1-yl)ethoxy]phenyl}-6-(4-fluoro phenyl)thieno[2,3-d]pyrimidin-4-yl]-2-[(2-ethoxypyrimidin-4-yl)methoxy]-D-phenylalanine N-[5-{3-chloro-2-methyl-4-[2-(4-methylpiperazin-1-yl)ethoxy]phenyl}-6-(4-fluoro phenyl)thieno[2,3-d]pyrimidin-4-yl]-2-{[2-(2-methoxyphenyl)pyrimidin-4-yl]methoxy}-D-phenylalanine N-[5-{3-chloro-2-methyl-4-[2-(4-methylpiperazin-1-yl)ethoxy]phenyl}-6-(furan-2-yl)thieno[2,3-d]pyrimidin-4-yl]-2-methoxy-D-phenylalanine N-[5-{3-chloro-2-methyl-4-[2-(4-methylpiperazin-1-yl)ethoxy]phenyl}-6-(5-fluorofuran-2-yl)thieno[2,3-d]pyrimidin-4-yl]-2-methoxy-D-phenylalanine N-[5-{3-chloro-2-methyl-4-[2-(4-methylpiperazin-1-yl)ethoxy]phenyl}-6-(5-fluoro furan-2-yl)thieno[2,3-d]pyrimidin-4-yl]-2-(2,2,2-trifluoroethoxy)-D-phenylalanine N-[5-{3-chloro-2-methyl-4-[2-(4-methylpiperazin-1-yl)ethoxy]phenyl}-6-(5-fluoro furan-2-yl)thieno[2,3-d]pyrimidin-4-yl]-2-(pyridin-2-ylmethoxy)-D-phenylalanine N-[5-{3-chloro-2-methyl-4-[2-(4-methylpiperazin-1-yl)ethoxy]phenyl}-6-(5-fluoro furan-2-yl)thieno[2,3-d]pyrimidin-4-yl]-2-[(1-methyl-1H-pyrazol-5-yl)methoxy]-D-phenylalanine N-[5-{3-chloro-2-methyl-4-[2-(4-methylpiperazin-1-yl)ethoxy]phenyl}-6-(5-fluoro furan-2-yl)thieno[2,3-d]pyrimidin-4-yl]-2-[(1-ethyl-1H-pyrazol-5-yl)methoxy]-D-phenylalanine N-[5-{3-chloro-2-methyl-4-[2-(4-methylpiperazin-1-yl)ethoxy]phenyl}-6-(5-fluoro furan-2-yl)thieno[2,3-d]pyrimidin-4-yl]-2-[(2-ethoxypyrimidin-4-yl)methoxy]-D-phenylalanine 2-[(1-butyl-1H-pyrazol-5-yl)methoxy]-N-[5-{3-chloro-2-methyl-4-[2-(4-methyl piperazin-1-yl)ethoxy]phenyl}-6-(5-fluorofuran-2-yl)thieno[2,3-d]pyrimidin-4-yl]-D-phenylalanine N-[5-{3-chloro-2-methyl-4-[2-(4-methylpiperazin-1-yl)ethoxy]phenyl}-6-(5-fluoro furan-2-yl)thieno[2,3-d]pyrimidin-4-yl]-2-{[2-(2,2,2-trifluoroethoxy)pyrimidin-4-yl]methoxy}-D-phenylalanine N-[5-{3-chloro-2-methyl-4-[2-(4-methylpiperazin-1-yl)ethoxy]phenyl}-6-(5-fluoro furan-2-yl)thieno[2,3-d]pyrimidin-4-yl]-2-{[2-(2-methoxyphenyl)pyrimidin-4-yl]methoxy}-D-phenylalanine N-[5-{3-chloro-2-methyl-4-[2-(4-methylpiperazin-1-yl)ethoxy]phenyl}-6-(prop-1-yn-1-yl)thieno[2,3-d]pyrimidin-4-yl]-2-methoxy-D-phenylalanine 2-[(1-tert-butyl-1H-pyrazol-5-yl)methoxy]-N-[5-{3-chloro-2-methyl-4-[2-(4-methyl piperazin-1-yl)ethoxy]phenyl}-6-(prop-1-yn-1-yl)thieno[2,3-d]pyrimidin-4-yl]-D-phenylalanine N-[5-{3-chloro-2-methyl-4-[2-(4-methylpiperazin-1-yl)ethoxy]phenyl}-6-(prop-1-yn-1-yl)thieno[2,3-d]pyrimidin-4-yl]-2-{[2-(2-methoxyethyl)pyrimidin-4-yl]methoxy}-D-phenylalanine N-[5-{3-chloro-2-methyl-4-[2-(4-methylpiperazin-1-yl)ethoxy]phenyl}-6-(prop-1-yn-1-yl)thieno[2,3-d]pyrimidin-4-yl]-2-{[1-(2,2,2-trifluoroethyl)-1H-pyrazol-5-yl]methoxy}-D-phenylalanine N-[5-{3-chloro-2-methyl-4-[2-(4-methylpiperazin-1-yl)ethoxy]phenyl}-6-(prop-1-yn-1-yl)thieno[2,3-d]pyrimidin-4-yl]-2-{[2-(morpholin-4-yl)pyrimidin-4-yl]methoxy}-D-phenylalanine N-[5-{3-chloro-2-methyl-4-[2-(4-methylpiperazin-1-yl)ethoxy]phenyl}-6-(prop-1-yn-1-yl)thieno[2,3-d]pyrimidin-4-yl]-2-{[2-(2,2,2-trifluoroethoxy)pyrimidin-4-yl]methoxy}-D-phenylalanine N-[5-{3-chloro-2-methyl-4-[2-(4-methylpiperazin-1-yl)ethoxy]phenyl}-6-(prop-1-yn-1-yl)thieno[2,3-d]pyrimidin-4-yl]-2-{[2-(2-methoxyphenyl)pyrimidin-4-yl]methoxy}-D-phenylalanine N-[5-{3-chloro-4-[2-(dimethylamino)ethoxy]-2-methylphenyl}-6-(prop-1-yn-1-yl) thieno[2,3-d]pyrimidin-4-yl]-2-{[1-(2,2,2-trifluoroethyl)-1H-pyrazol-5-yl]methoxy}-D-phenylalanine N-[5-{3-chloro-4-[2-(dimethylamino)ethoxy]-2-methylphenyl}-6-(prop-1-yn-1-yl) thieno[2,3-d]pyrimidin-4-yl]-2-{[2-(morpholin-4-yl)pyrimidin-4-yl]methoxy}-D-phenylalanine N-[5-{3-chloro-4-[2-(dimethylamino)ethoxy]-2-methylphenyl}-6-(prop-1-yn-1-yl) thieno[2,3-d]pyrimidin-4-yl]-2-{[2-(2,2,2-trifluoroethoxy)pyrimidin-4-yl]methoxy}-D-phenylalanine N-[5-{3-chloro-4-[2-(dimethylamino)ethoxy]-2-methylphenyl}-6-(prop-1-yn-1-yl) thieno[2,3-d]pyrimidin-4-yl]-2-{[2-(2-methoxyphenyl)pyrimidin-4-yl]methoxy}-D-phenylalanine N-[5-{3-chloro-4-[2-(dimethylamino)ethoxy]-2-methylphenyl}-6-(4-fluorophenyl) thieno[2,3-d]pyrimidin-4-yl]-2-({2-[2-(2-methoxyethoxy)phenyl]pyrimidin-4-yl}methoxy)-D-phenylalanine ethyl N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-2-{[2-(2-methoxyphenyl)pyrimidin-4-yl]methoxy}-D-phenylalaninate ethyl N-[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]-2-{[2-(2-methoxyphenyl)pyrimidin-4-yl]methoxy}-D-phenylalaninate ethyl N-[(5S$_a$)-5-{3-chloro-4-[2-(dimethylamino)ethoxy]-2-methylphenyl}-6-(prop-1-yn-1-yl)thieno[2,3-d]pyrimidin-4-yl]-2-{[2-(2-methoxyphenyl)pyrimidin-4-yl]methoxy}-D-phenylalaninate N-[5-{3,5-dichloro-2,6-dimethyl-4-[2-(4-methylpiperazin-1-yl) ethoxy]phenyl}-6-(4-fluorophenyl)thieno[2,3-d]pyrimidin-4-yl]-2-{[2-(2-methoxyphenyl)pyrimidin-4-yl]methoxy}-D-phenylalanine The invention relates also to a process for the preparation of compounds of formula (I), which process is characterised in that there is used as starting material the compound of formula (II-a):

(II-a)

wherein Z represents bromine or iodine and A is as defined for formula (I) in which 1 is linked to the chlorine atom and 2 is linked to the Z group, which compound of formula (II-a) is subjected to coupling with a compound of formula (III):

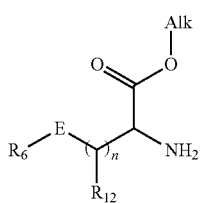

(III)

wherein $R_6$, $R_{12}$, E and n are as defined for formula (I), and Alk represents a linear or branched ($C_1$-$C_6$)alkyl group, to yield the compound of formula (IV):

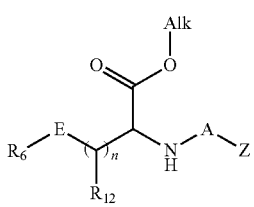

(IV)

wherein $R_6$, $R_{12}$, A, E and n are as defined for formula (I) and, Z and Alk is as defined before,
compound of formula (IV) which is further subjected to coupling with compound of formula (V):

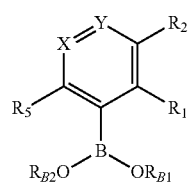

(V)

wherein $R_1$, $R_2$, $R_5$, X and Y are as defined for formula (I), and $R_{B1}$ and $R_{B2}$ represent a hydrogen atom, a linear or branched ($C_1$-$C_6$) alkyl group, or $R_{B1}$ and $R_{B2}$ form with the oxygen carrying them an optionally methylated ring, to yield the compound of formula (VI):

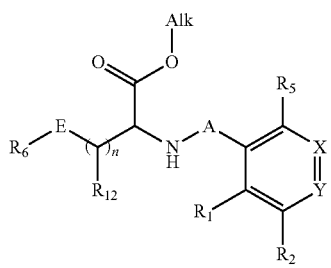

(VI)

wherein $R_1$, $R_2$, $R_5$, $R_6$, $R_{12}$, X, Y, A, E and n are as defined for formula (I) and Alk is as defined before,
the Alk-O—C(O)— ester function of which compound of formula (VI) is hydrolysed to yield the carboxylic acid, which may optionally be reacted with an alcohol of formula $R_7'$—OH or a chlorinated compound of formula $R_7'$—Cl wherein $R_7'$ represents a linear or branched ($C_1$-$C_8$)alkyl group, a —CHR$_a$R$_b$ group, an aryl group, a heteroaryl group, an arylalkyl($C_1$-$C_6$) group, or a heteroarylalkyl($C_1$-$C_6$) group, $R_a$ and $R_b$ are as defined for formula (I),
to yield the compound of formula (I), which may be purified according to a conventional separation technique, which is converted, if desired, into its addition salts with a pharmaceutically acceptable acid or base and which is optionally separated into its isomers according to a conventional separation technique, it being understood that at any moment considered appropriate during the course of the process described above, some groups (hydroxy, amino . . . ) of the starting reagents or of the synthesis intermediates can be protected, subsequently deprotected and functionalized, as required by the synthesis.

In an other embodiment of the invention, compounds of formula (I) may be obtained using an alternative process, which process is characterised in that there is used as starting material the compound of formula (II-b):

(II-b)

wherein A is as defined in formula (I) in which 1 is linked to the chlorine atom and 2 is linked to the iodine atom, which compound of formula (II-b) is subjected to coupling with a compound of formula (V):

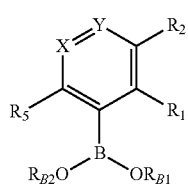

(V)

wherein $R_1$, $R_2$, $R_5$, X and Y are as defined for formula (I), and $R_{B1}$ and $R_{B2}$ represent a hydrogen atom, a linear or branched ($C_1$-$C_6$) alkyl group, or $R_{B1}$ and $R_{B2}$ form with the oxygen carrying them an optionally methylated ring, to yield the compound of formula (VII):

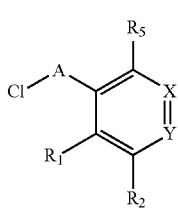

(VII)

wherein $R_1$, $R_2$, $R_5$, A, X and Y are as defined in formula (I), which compound of formula (VII) is further subjected to coupling with a compound of formula (III):

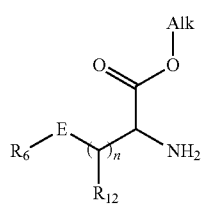

wherein $R_6$, $R_{12}$, E and n are as defined for formula (I), and Alk represents a linear or branched ($C_1$-$C_6$)alkyl group,
to yield the compound of formula (VI):

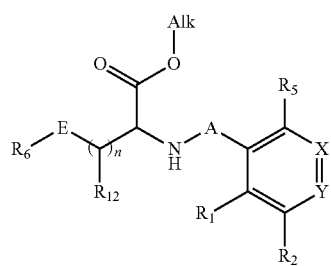

wherein $R_1$, $R_2$, $R_5$, $R_6$, $R_{12}$, X, Y, A, E and n are as defined for formula (I) and Alk is as defined before,
the Alk-O—C(O)— ester function of which compound of formula (VI) is hydrolysed to yield the carboxylic acid, which may optionally be reacted with an alcohol of formula $R_7'$—OH or a chlorinated compound of formula $R_7'$—Cl wherein $R_7'$ represents a linear or branched ($C_1$-$C_8$)alkyl group, a —$CHR_aR_b$ group, an aryl group, a heteroaryl group, an arylalkyl($C_1$-$C_6$) group, or a heteroarylalkyl($C_1$-$C_6$) group, $R_a$ and $R_b$ are as defined for formula (I),
to yield the compound of formula (I), which may be purified according to a conventional separation technique, which is converted, if desired, into its addition salts with a pharmaceutically acceptable acid or base and which is optionally separated into its isomers according to a conventional separation technique,
it being understood that at any moment considered appropriate during the course of the process described above, some groups (hydroxy, amino . . . ) of the starting reagents or of the synthesis intermediates can be protected, subsequently deprotected and functionalized, as required by the synthesis.

The compounds of formulae (II-a), (II-b), (III), (V), $R_7'$—OH and $R_7'$—Cl are either commercially available or can be obtained by the person skilled in the art using conventional chemical reactions described in the literature.

Pharmacological study of the compounds of the invention has shown that they have pro-apoptotic properties. The ability to reactivate the apoptotic process in cancerous cells is of major therapeutic interest in the treatment of cancers and of immune and auto-immune diseases.

More especially, the compounds according to the invention will be useful in the treatment of chemo- or radio-resistant cancers.

Among the cancer treatments envisaged there may be mentioned, without implying any limitation, treatment of cancers of the bladder, brain, breast and uterus, chronic lymphoid leukaemias, cancer of the colon, œsophagus and liver, lymphoblastic leukaemias, acute myeloid leukaemias, lymphomas, melanomas, malignant haemopathies, myelomas, ovarian cancer, non-small-cell lung cancer, prostate cancer, pancreatic cancer and small-cell lung cancer.

The present invention relates also to pharmaceutical compositions comprising at least one compound of formula (I) in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration, especially tablets or dragées, sublingual tablets, sachets, paquets, capsules, glossettes, lozenges, suppositories, creams, ointments, dermal gels, and drinkable or injectable ampoules.

The dosage varies according to the sex, age and weight of the patient, the administration route, the nature of the therapeutic indication, or of any associated treatments, and ranges from 0.01 mg to 1 g per 24 hours in one or more administrations.

Furthermore, the present invention relates also to the combination of a compound of formula (I) with an anticancer agent selected from genotoxic agents, mitotic poisons, anti-metabolites, proteasome inhibitors, kinase inhibitors and antibodies, and also to pharmaceutical compositions comprising that type of combination and their use in the manufacture of medicaments for use in the treatment of cancer.

Advantageously, the present invention relates to the combination of a compound of formula (I) with an EGFR inhibitor, and also to pharmaceutical compositions comprising that type of combination.

In another embodiment, the present invention relates to the combination of a compound of formula (I) with a mTOR/PI3K inhibitor, and also to pharmaceutical compositions comprising that type of combination.

In a preferred embodiment, the present invention relates to the combination of a compound of formula (I) with a MEK inhibitor, and also to pharmaceutical compositions comprising that type of combination.

Preferably, the present invention relates to the combination of a compound of formula (I) with a HER2 inhibitor, and also to pharmaceutical compositions comprising that type of combination.

Advantageously, the present invention relates to the combination of a compound of formula (I) with a RAF inhibitor, and also to pharmaceutical compositions comprising that type of combination.

In another embodiment, the present invention relates to the combination of a compound of formula (I) with a EGFR/HER2 inhibitor, and also to pharmaceutical compositions comprising that type of combination.

In a preferred embodiment, the present invention relates to the combination of a compound of formula (I) with a taxane, and also to pharmaceutical compositions comprising that type of combination.

In another embodiment, the present invention relates to the combination of a compound of formula (I) with a proteasome inhibitor, an immunomodulator or an alkylating agent, and also to pharmaceutical compositions comprising that type of combination.

The combination of a compound of formula (I) with an anticancer agent may be administered simultaneously or sequentially. The administration route is preferably the oral route, and the corresponding pharmaceutical compositions may allow the instantaneous or delayed release of the active ingredients. The compounds of the combination may more-over be administered in the form of two separate pharmaceutical compositions, each containing one of the active ingredients, or in the form of a single pharmaceutical composition, in which the active ingredients are in admixture.

The compounds of the invention may also be used in combination with radiotherapy in the treatment of cancer.

Finally, the compounds of the invention may be linked to monoclonal antibodies or fragments thereof or linked to scaffold proteins that can be related or not to monoclonal antibodies.

Antibody fragments must be understood as fragments of Fv, scFv, Fab, F(ab')2, F(ab'), scFv-Fc type or diabodies, which generally have the same specificity of binding as the antibody from which they are descended. According to the present invention, antibody fragments of the invention can be obtained starting from antibodies by methods such as digestion by enzymes, such as pepsin or papain, and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

Scaffold proteins that can be related or not to monoclonal antibodies are understood to mean a protein that contains or not an immunoglobulin fold and that yields a binding capacity similar to a monoclonal antibody. The man skilled in the art knows how to select the protein scaffold. More particularly, it is known that, to be selected, such a scaffold should display several features as follow (Skerra A., J. Mol. Recogn. 2000, 13, 167-187): phylogenetically good conservation, robust architecture with a well-known three-dimensional molecular organization (such as, for example, crystallography or NMR), small size, no or only a low degree of post-translational modifications, easy to produce, express and purify. Such a protein scaffold can be, but without limitation, a structure selected from the group consisting in fibronectin and preferentially the tenth fibronectin type III domain (FNfn10), lipocalin, anticalin (Skerra A., J. Biotechnol. 2001, 74(4):257-75), the protein Z derivative from the domain B of staphylococcal protein A, thioredoxin A or any protein with a repeated domain such as an "ankyrin repeat" (Kohl et al., PNAS 2003, 100(4), 1700-1705), "armadillo repeat", "leucine-rich repeat" or "tetratricopeptide repeat". There could also be mentioned a scaffold derivative from toxins (such as, for example, scorpion, insect, plant or mollusc toxins) or protein inhibitors of neuronal nitric oxide synthase (PIN).

The following Preparations and Examples illustrate the invention but do not limit it in any way.

GENERAL PROCEDURES

All reagents obtained from commercial sources were used without further purification.

Anhydrous solvents were obtained from commercial sources and used without further drying.

Flash chromatography was performed on ISCO CombiFlash Rf 200i with pre-packed silica-gel cartridges (RediSep® Rf Gold High Performance).

Thin layer chromatography was conducted with 5×10 cm plates coated with Merck Type 60 F254 silica-gel.

Microwave heating was performed in an Anton Parr MonoWave or CEM Discover® instrument.

Preparative HPLC purifications were performed on an Armen Spot Liquid Chromatography system with a Gemini-NX® 10 µM C18, 250 mm×50 mm i.d. column running at a flow rate of 118 mL min$^{-1}$ with UV diode array detection (210-400 nm) using 25 mM aqueous $NH_4HCO_3$ solution and MeCN as eluents unless specified otherwise.

Analytical LC-MS: The compounds of the present invention were characterized by high performance liquid chromatography-mass spectroscopy (HPLC-MS) on Agilent HP1200 with Agilent 6140 quadrupole LC/MS, operating in positive or negative ion electrospray ionisation mode. Molecular weight scan range is 100 to 1350. Parallel UV detection was done at 210 nm and 254 nm. Samples were supplied as a 1 mM solution in ACN, or in THF/$H_2O$ (1:1) with 5 µL loop injection. LCMS analyses were performed on two instruments, one of which was operated with basic, and the other with acidic eluents.

Basic LCMS: Gemini-NX, 3 µm, C18, 50 mm×3.00 mm i.d. column at 23° C., at a flow rate of 1 mL min$^{-1}$ using 5 mM ammonium bicarbonate (Solvent A) and acetonitrile (Solvent B) with a gradient starting from 100% Solvent A and finishing at 100% Solvent B over various/certain duration of time.

Acidic LCMS: ZORBAX Eclipse XDB-C18, 1.8 µm, 50 mm×4.6 mm i.d. column at 40° C., at a flow rate of 1 mL min$^{-1}$ using 0.02% v/v aqueous formic acid (Solvent A) and 0.02% v/v formic acid in acetonitrile (Solvent B) with a gradient starting from 100% Solvent A and finishing at 100% Solvent B over various/certain duration of time.

$^1$H-NMR measurements were performed on Bruker Avance III 500 MHz spectrometer and Bruker Avance III 400 MHz spectrometer, using DMSO-$d_6$ or $CDCl_3$ as solvent. $^1$H NMR data is in the form of delta values, given in part per million (ppm), using the residual peak of the solvent (2.50 ppm for DMSO-$d_6$ and 7.26 ppm for $CDCl_3$) as internal standard.

Splitting patterns are designated as: s (singlet), d (doublet), t (triplet), q (quartet), quint (quintet), m (multiplet), br s (broad singlet), dd (doublet of doublets), td (triplet of doublets), dt (doublet of triplets), ddd (doublet of doublet of doublets).

Combination gas chromatography and low resolution mass spectrometry were performed on Agilent 6850 gas chromatograph and Agilent 5975C mass spectrometer using 15 m×0.25 mm column with 0.25 µm HP-5MS coating and helium as carrier gas. Ion source: EI$^+$, 70 eV, 230° C., quadrupole: 150° C., interface: 300° C.

HRMS were determined on a Shimadzu IT-TOF, ion source temperature 200° C., ESI+/−, ionization voltage: (+−)4.5 kV. Mass resolution min. 10000.

Elementary analyses were performed on a Thermo Flash EA 1112 Elemental Analyzer.

List of Abbreviations

| Abbreviation | Name |
|---|---|
| 2-Me—THF | 2-methyl-tetrahydrofurane |
| Ac | acetyl |
| Ad | adamantyl |
| aq. | aqueous |
| AtaPhos | bis(di-tert-butyl(4-dimethylaminophenyl)phosphine) dichloropalladium(II) |
| BuPAd2 | butyl-di(adamant-1-yl)phosphane |
| cc. | concentrated |
| DAST | diethylaminosulfur trifluoride |

-continued

| Abbreviation | Name |
|---|---|
| dba | dibenzylideneacetone |
| DCM | methylene chloride |
| DIPA | diisopropylamine |
| DMA | dimethylacetamide |
| DME | 1,2-dimethoxyethane |
| DMF | dimethylformamide |
| DMSO | dimethyl sulfoxide |
| dppf | 1,1'-bis(diphenylphosphino)ferrocene |
| eq. | equivalent |
| Et | ethyl |
| HILIC | hydrophilic interaction liquid chromatography |
| HMDS | hexamethyldisilazane |
| $^i$Pr | isopropyl |
| LDA | lithium diisopropylamide |
| Me | methyl |
| MeCN | acetonitrile |
| MTBE | methyl tert-butyl ether |
| MW | microwave |
| NBS | N-bromosuccinimide |
| $^n$Bu | n-butyl |
| NCS | N-chlorosuccinimide |
| Ph | phenyl |
| P$^t$Bu$_3$ × HBF$_4$ | tri-tert-butylphosphonium tetrafluoroborate |
| PCy$_3$ × HBF$_4$ | tricyclohexylphosphonium tetrafluoroborate |
| Q-Phos | 1,2,3,4,5-pentaphenyl-1'-(di-tert-butylphosphino)ferrocene |
| r.t. | room temperature |
| TBAF | tetrabutyl ammonium fluoride |
| $^t$Bu | tert-butyl |
| TEA | triethylamine |
| TFA | trifluoroacetic acid |
| THF | tetrahydrofurane |
| TIPSCl | triisopropylsilyl chloride |
| XantPhos | 4,5-bis(diphenylphosphino)-9,9-dimethylxanthene |

General Procedure Ia 1 eq. of the appropriate 4-chloro-thieno[2,3-d]pyrimidine derivative, 2 eq. of the appropriate amino acid derivative and 2 eq. K$_2$CO$_3$ were mixed in $^t$BuOH:water 4:1 (4 mL/mmol) and stirred at reflux temperature (or in MW reactor at 100° C. if it is needed) until no further conversion was observed. The mixture was then diluted with water, acidified with 1M HCl solution (to pH=1, or to pH=6 in the presence of a basic amino group) and extracted with EtOAc, or the precipitate formed after acidification was isolated by filtration. In the case of extractive purification the combined organic phases were washed with brine, dried over MgSO$_4$, filtered and the filtrate was concentrated under reduced pressure. The crude product was purified via preparative reversed phase chromatography using 25 mM aqueous NH$_4$HCO$_3$ and acetonitrile as eluents unless otherwise stated.

General Procedure Ib 1 eq. of the appropriate 4-chloro-thieno[2,3-d]pyrimidine derivative, 2 eq. of the appropriate amino acid derivative and 3 eq. K$_2$CO$_3$ were mixed in DMSO (10 mL/mmol) and stirred at 50° C. until no further conversion was observed. The mixture was then diluted with water, acidified with 1M HCl solution (to pH=1, or to pH=6 in the presence of a basic amino group) and extracted with EtOAc, or the precipitate formed after acidification was isolated by filtration. In the case of extractive purification the combined organic phases were washed with brine, dried over MgSO$_4$, filtered and the filtrate was concentrated under reduced pressure. The crude product was purified via preparative reversed phase chromatography using 25 mM aqueous NH$_4$HCO$_3$ and acetonitrile as eluents unless otherwise stated.

General Procedure Ic 1 eq. of the appropriate 4-chloro-thieno[2,3-d]pyrimidine derivative, 1.5 eq. of the appropriate amino acid derivative and 1.5 eq. Cs$_2$CO$_3$ were mixed in DMSO (6 mL/mmol) and stirred at 70° C. until no further conversion was observed. The mixture was then diluted with water, acidified with 1M HCl solution (to pH=1, or to pH=6 in the presence of a basic amino group) and extracted with EtOAc, or the precipitate formed after acidification was isolated by filtration. In the case of extractive purification the combined organic phases were washed with brine, dried over MgSO$_4$, filtered and the filtrate was concentrated under reduced pressure. The crude product was purified via preparative reversed phase chromatography using 25 mM aqueous NH$_4$HCO$_3$ solution and acetonitrile as eluents unless otherwise stated.

General Procedure IIa 1 eq. of the appropriate 5- (or 6)-iodo-thieno[2,3-d]pyrimidine derivative and 3 eq. of the appropriate boronic acid derivative were dissolved in DME (15 mL/mmol), then 5 eq. K$_2$CO$_3$, 0.2 eq. Pd$_2$dba$_3$, 0.4 eq. $^n$BuPAd$_2$ and water (5 mL/mmol) were added and the mixture was stirred at 60° C. in MW reactor until no further conversion was observed. The volatiles were then removed in vacuo and the residue was purified via preparative reversed phase chromatography, using 25 mM aqueous NH$_4$HCO$_3$ solution and acetonitrile as eluents unless otherwise stated.

General Procedure IIb 1 eq. of the appropriate 5-iodo-thieno[2,3-d]pyrimidine derivative and 5 eq. of the appropriate boronic acid derivative were dissolved in 2-Me-THF (8 mL/mmol), then 5 eq. K$_2$CO$_3$, 0.1 eq. Q-Phos and 0.05 eq. Pd$_2$dba$_3$ were added and the mixture was stirred at 80° C. until no further conversion was observed. The mixture was filtered through a pad of Celite, the filtrate was concentrated under reduced pressure. The crude product was purified via flash chromatography using heptane and EtOAc as eluents unless otherwise stated.

General Procedure IIc 1 eq. of the appropriate 5-(or 6)-iodo-thieno[2,3-d]pyrimidine derivative and 1.1 eq. of the appropriate boronic acid derivative were dissolved in 2-Me-THF (8 mL/mmol), then 1.1 eq. Ag$_2$CO$_3$ and 0.1 eq. Pd(PPh$_3$)$_4$ were added and the mixture was stirred at 100° C. until no further conversion was observed. The mixture was filtered through a pad of Celite, the filtrate was concentrated under reduced pressure. The crude product was purified via flash chromatography using heptane and EtOAc as eluents unless otherwise stated.

General Procedure IId 1 eq. of the appropriate 5-iodo-thieno[2,3-d]pyrimidine derivative and 3 eq. of the appropriate boronic acid derivative were dissolved in dioxane:water 2:1 mixture (10 mL/mmol), then 2 eq. Cs$_2$CO$_3$, 5 mol % Pd(OAc)$_2$ and 0.2 eq. P$^t$Bu$_3$×HBF$_4$ were added and the mixture was stirred at 120° C. in MW reactor until no further conversion was observed. The mixture was neutralized with 1M HCl solution and extracted with DCM. The combined organic phases were dried over $Na_2SO_4$, filtered and the filtrate was concentrated in vacuo. The crude product was purified via preparative reversed phase chromatography using 0.1% aqueous TFA solution and acetonitrile as eluents unless otherwise stated.

General Procedure IIIa 1 eq. of the appropriate 6-iodo-thieno[2,3-d]pyrimidine derivative and 4 eq. of the appropriate boronic acid derivative were dissolved in dioxane:water 4:1 mixture (10 mL/mmol), then 2.2 eq. $Cs_2CO_3$ and 0.1 eq. $Pd(dppf)Cl_2$ were added and the mixture was stirred at 40° C. until no further conversion was observed. The mixture was then diluted with water and extracted with DCM. The combined organic phases were washed with water, dried over $MgSO_4$, filtered and the filtrate was concentrated under reduced pressure. The crude product was purified using preparative reversed phase chromatography using 25 mM aqueous $NH_4HCO_3$ solution and acetonitrile as eluents unless otherwise stated.

General Procedure IIIb 1 eq. of the appropriate 6-iodo-thieno[2,3-d]pyrimidine derivative and 3 eq. of the appropriate boronic acid derivative were dissolved in THF:water 1:1 mixture (10 mL/mmol), then 3 eq. $Cs_2CO_3$ and 0.1 eq. AtaPhos were added and the mixture was stirred at 100° C. in MW reactor until no further conversion was observed. The volatiles were evaporated under reduced pressure, and the residue was purified via preparative reversed phase chromatography using 25 mM aqueous $NH_4HCO_3$ solution and acetonitrile as eluents unless otherwise stated.

General Procedure IVa 1 eq. Preparation 4i was dissolved in dry THF (5 mL/mmol) and cooled to −78° C. LDA solution (1.2 eq. 2M in THF, heptane, EtPh) was added dropwise under Argon and the mixture was stirred for 1.5 hours. Then 1.2 eq. of the appropriate electrophilic-reagent either in solution (dissolved in 3 mL/mmol dry THF), or neat was added at −78° C. and the mixture was allowed to warm up to r.t. It was stirred until no further conversion was observed. The reaction mixture was quenched by the careful addition of cc. $NH_4Cl$ solution. The mixture was extracted with MTBE, the organic layer was washed with brine, dried over $Na_2SO_4$, filtered and the filtrate was concentrated under reduced pressure. The crude product was purified via flash chromatography using heptane and EtOAc as eluents unless otherwise stated.

General Procedure Va 1 eq. of the appropriate acetal was stirred in 2M HCl solution (3 mL/mmol) at 60° C. until no further conversion was observed. The reaction mixture was cooled to 0° C., then 5.7 eq. NaOH was added portionwise. The pH was adjusted to 8 using 10% $K_2CO_3$ solution, then 2 eq. sodium borohydride was added portionwise keeping the temperature below 5° C. After the addition the mixture was stirred at 0° C. until no further conversion was observed. The mixture was extracted with EtOAc, the combined organic phases were dried over $Na_2SO_4$, filtered and the filtrate was concentrated under reduced pressure. The crude product was purified via flash chromatography using heptane and EtOAc as eluents unless otherwise stated.

General Procedure Vb

Step A

To a solution of 1 eq. of the appropriate N-alkyl pyrazole in dry THF (1.5 mL/mmol), 1.1 eq. ″BuLi was added dropwise at −78° C. The mixture was stirred for 30 minutes and then allowed to warm up to 0° C. where it was stirred for 30 minutes, then cooled back to −78° C. again. 1.1 eq. DMF was added dropwise, then the reaction mixture was allowed to reach r.t. and it was stirred overnight. The mixture was quenched with cc. $NH_4Cl$ solution. The phases were separated and the aqueous layer was extracted with EtOAc. The combined organic layers were dried over $Na_2SO_4$, filtered and the filtrate was concentrated under reduced pressure. The residue was used in the next step without further purification.

Step B

To a solution of 1 eq. of the appropriate crude aldehyde in EtOH (0.5 mL/mmol), 1.3 eq. sodium borohydride was added portionwise at −15° C. and the reaction mixture was stirred at r.t. until no further conversion was observed. The mixture was poured onto crushed ice and stirred for 16 hours. The precipitate was filtered off, and the filtrate was concentrated under reduced pressure. The oily phase was separated, and the aqueous layer was extracted with EtOAc. The combined organic layers were dried over $Na_2SO_4$, filtered and the filtrate was concentrated under reduced pressure. The product was further purified by flash chromatography if necessary.

General Procedure Vc

To the mixture of 1.2 eq. of the appropriate amidine salt and 1 eq. Preparation 8a in dry methanol (0.5 mL/mmol) 1.2 eq. sodium methoxide was added portionwise and the mixture was stirred at 75° C. until no further conversion was observed. The reaction mixture was cooled and concentrated under reduced pressure. Water was added to the residue, and it was extracted with DCM. The combined organic layers were dried over $MgSO_4$, filtered and the filtrate was concentrated under reduced pressure. The crude product was purified via flash chromatography using heptane and EtOAc as eluents unless otherwise stated.

General Procedure Vd

To the mixture of 1.2 eq. of the appropriate hydrazine or hydrazine hydrochloride and 1 eq. Preparation 8a in dry methanol (0.5 mL/mmol) 1.2 eq. sodium methoxide was added portionwise and the mixture was stirred at 75° C. until no further conversion was observed. The reaction mixture was cooled and concentrated under reduced pressure. Water was added to the residue, and it was extracted with DCM. The combined organic phases were dried over $MgSO_4$, filtered and the filtrate was concentrated under reduced pressure. The crude product was purified via flash chromatography using heptane and EtOAc as eluents unless otherwise stated.

General Procedure Ve 1 eq. of the appropriate acetal was stirred with 1M HCl solution (3 mL/mmol) at 50° C. until no further conversion was observed. The reaction mixture was cooled to 0° C., then 2.85 eq. solid NaOH was added portionwise. The pH was adjusted to 8 using 10% $K_2CO_3$ solution, then 2 eq. sodium borohydride was added portionwise keeping the temperature below 5° C. and stirred at 0° C. until no further conversion was observed. The mixture was extracted with EtOAc, the combined organic phases were dried over $Na_2SO_4$, filtered and the filtrate was concentrated under reduced pressure. The crude product was purified via flash chromatography using heptane and EtOAc as eluents unless otherwise stated.

General Procedure VI 1 eq. of the appropriate phenol derivative, 2 eq. of the appropriate alcohol derivative, and 3 eq. $PPh_3$ were dissolved in dry toluene (7 mL/mmol) under $N_2$ atmosphere, then 3 eq. di-tert-butyl azodicarboxylate was added at r.t. Then the mixture was stirred at 50° C. until no further conversion was observed. The volatiles were removed in vacuo and the residue was purified via flash chromatography using heptane and EtOAc (and MeOH if needed) as eluents. If necessary, the product was further purified via preparative reversed phase chromatography using 25 mM aqueous $NH_4HCO_3$ solution and acetonitrile as eluents unless otherwise stated.

General Procedure VII 1 eq. of the appropriate ester derivative was dissolved in THF (15 mL/mmol) then 10 eq. LiOH×$H_2O$ and water (15 mL/mmol) were added. The mixture was stirred at r.t. (or at 60° C. if needed) until no further conversion was observed. The pH was adjusted to 6 with 1M HCl solution, then the mixture was diluted with brine, extracted with DCM or EtOAc. The organic layer was dried over $Na_2SO_4$, filtered and the filtrate was concentrated under reduced pressure. The crude product was purified via preparative reversed phase chromatography using 25 mM aqueous $NH_4HCO_3$ solution and acetonitrile as eluents unless otherwise stated.

General Procedure VIII 1 eq. of the appropriate indole derivative and 2 eq. of the appropriate alcohol derivative were dissolved in dry toluene (8 mL/mmol) under $N_2$ atmosphere, and the mixture was cooled to 0° C., then 2 eq. 2-(tributyl-phosphanylidene) acetonitrile was added. Then the mixture was heated to 100° C. and stirred until no further conversion was observed. The volatiles were removed in vacuo, then water (4 mL/mmol) 2M NaOH solution (1 mL/mmol) were added and the mixture was stirred until no further conversion was observed. The mixture was then acidified with 1M HCl solution to pH=6 and extracted with DCM. The combined organic phases were dried over $Na_2SO_4$, filtered and the filtrate was concentrated under reduced pressure. The crude product was purified via preparative reversed phase chromatography using aqueous 40 mM $NH_4OAc$ (pH=4, adjusted with AcOH) solution and acetonitrile as eluents unless otherwise stated.

General Procedure IXa

Step A 1 eq. Preparation 9b was dissolved in dry toluene (8 mL/mmol), then 1.18 eq. $PPh_3$, 1.1 eq. of the appropriate alcohol derivative and 1.18 eq. diethylazodicarboxylate (40% solution in toluene) were added at r.t. The mixture was stirred at r.t. until no further conversion was observed. The resulting precipitate was filtered off and the filtrate was washed sequentially with 10% $KHSO_4$ solution, water, sat. $NaHCO_3$ solution and water again. The organic phase was dried over $Na_2SO_4$, filtered and the filtrate was concentrated under reduced pressure. The residue was agitated with diethyl-ether (5 mL/mmol), the insoluble material was filtered off and the filtrate was concentrated under reduced pressure to obtain the crude product.

Step B

The product of Step A was treated with 10 eq. HCl solution (4.9M in MeOH) and it was stirred at r.t. until no further conversion was observed. Then the mixture was concentrated under reduced pressure. The residue was partitioned between cold EtOAc and ice-cold water, the phases were separated and the organic phase was extracted with ice-cold 5% $KHSO_4$ solution. The combined aqueous phase was basified with solid $Na_2CO_3$, and the product was extracted with EtOAc. The organic phase was dried over $Na_2SO_4$, filtered and the filtrate was concentrated under reduced pressure to obtain the methyl ester of the title product.

Step C 1 eq. of the methyl ester obtained in Step B was dissolved in MeOH (9 mL/mmol), then 1.05 eq. NaOH and water (1 mL/mmol) were added and the mixture was stirred at r.t. until no further conversion was observed. Methanol was removed under reduced pressure and the mixture was neutralized using 1M HCl solution, then it was extracted with DCM. The organic phase was dried over $Na_2SO_4$, filtered and the filtrate was concentrated under reduced pressure to obtain the O-alkylated amino acid derivative which was used without further purification.

General Procedure IXb

Step A 1 eq. Preparation 9b was dissolved in dry DMF (10 mL/mmol) and 4 eq. $K_2CO_3$ and 2 eq. of the appropriate alkylating agent was added at r.t. The mixture was stirred at 50° C. until no further conversion was observed. The mixture was diluted with water, then extracted with DCM. The organic phase was dried over $Na_2SO_4$, filtered and the filtrate was concentrated under reduced pressure. The crude material was purified via flash chromatography using DCM and methanol as eluents unless otherwise stated.

Step B and Step C are the same as described in General procedure IXa.

Preparation 1a: 5-Bromo-4-chloro-6-iodo-thieno[2,3-d]pyrimidine

Step A: 6-Iodo-3H-thieno[2,3-d]pyrimidin-4-one

A 2 L round bottomed flask equipped with mechanical stirrer, thermometer and reflux condenser was charged with the solution of 433 mL acetic acid, 13 mL sulfuric acid and 87 mL water. 69.3 g 3H-thieno[2,3-d]pyrimidin-4-one (0.46 mol), 51.9 g periodic acid (0.23 mol) and 104 g iodine (0.41 mol) were added to the stirred solution, which was heated to 60° C. for 1 hour. The resulting suspension was cooled to r.t., filtered off, washed with a mixture of acetic acid and water (5:1) and then with diethyl ether. The resulting beige crystalline solid was air dried. $^1$H NMR (500 MHz, DMSO-$d_6$) δ: 12.57 (br s, 1H), 8.09 (s, 1H), 7.65 (s, 1H)

Step B: 4-Chloro-6-iodo-thieno[2,3-d]pyrimidine

A 1 L round bottomed flask equipped with mechanical stirrer, thermometer, reflux condenser and a CaCl$_2$-tube was charged with 113 mL phosphorous oxychloride and 35 mL N,N-dimethylaniline (0.29 mol). 75.54 g 6-iodo-3H-thieno[2,3-d]pyrimidin-4-one (0.27 mol) was added to the mixture in portions during 5 minutes. The reaction mixture was stirred at 105° C. for 1 hour. The resulting suspension was cooled to 10° C., filtered and washed with hexane. The crude product was added to ice water and stirred for 10 minutes, filtered off, washed with cold water, diethyl ether and air dried. Beige crystalline solid was obtained. $^1$H NMR (400 MHz, DMSO-$d_6$) δ: 8.89 (s, 1H), 7.98 (s, 1H)

Step C: Preparation 1a

A 2 L round bottomed flask equipped with mechanical stirrer, thermometer and a bubbler was charged with 600 mL acetonitrile. 84.9 g 4-chloro-6-iodo-thieno[2,3-d]pyrimidine (0.29 mol), 50.9 g NBS (0.29 mol) and 8.5 mL tetrafluoroboric acid diethyl ether complex were added. The reaction mixture was stirred at r.t. for 16 hours. Further 22.9 g (0.12 mol) NBS was added to the mixture in three portions. After cooling the suspension to 0° C. and stirring for further 1 hour the precipitate was filtered off, washed with acetonitrile and air dried. The product was obtained as beige crystalline solid. $^1$H NMR (500 MHz, DMSO-$d_6$) δ: 8.88 (s, 1H)

Preparation 1b: 4-Chloro-5,6-diiodo-thieno[2,3-d]pyrimidine

Step A: 5,6-Diiodo-3H-thieno[2,3-d]pyrimidin-4-one

To a well stirred slurry of 61.3 g 3H-thieno[2,3-d]pyrimidin-4-one (396 mmol), 92.4 g periodic acid (405 mmol), 1 L acetic acid, 200 mL water, 6 mL cc. sulfuric acid, and 203 g iodine (799 mmol) were added. The reaction mixture was heated to 110° C. and stirred for 3 hours. The suspension was cooled to r.t. then 940 mL diethyl ether was added and the mixture was stirred further at 10° C. for 30 minutes. The precipitate was filtered off, washed with a 2:1 mixture of diethyl ether and ethanol (100 mL), finally with diethyl ether (3×250 mL), then it was air dried to give the product as a tan powder. $^1$H NMR (500 MHz, DMSO-$d_6$) δ: 12.60 (br s, 1H), 8.13 (s, 1H)

Step B: Preparation 1b

To a well stirred slurry of 180 g 5,6-diiodo-3H-thieno[2,3-d]pyrimidin-4-one (445 mmol) in 2.5 L phosphorous oxychloride 64 mL N,N-dimethylaniline was added. The reaction mixture was heated to 105° C. and stirred for 1.5 hours. The resulting suspension was cooled to r.t. and 1.5 L hexane was added and it was stirred for an additional 20 minutes. The precipitate was filtered off, washed with hexane (3×500 mL) and water (3×100 mL) then air dried to give the product as a grey crystalline solid. $^1$H NMR (400 MHz, DMSO-$d_6$) δ: 8.88 (s, 1H)

Preparation 1c: 4-Chloro-5-iodo-thieno[2,3-d]pyrimidine 52.8 g Preparation 1b (125 mmol) was dissolved in 400 mL dry THF and cooled to 0° C. 100 mL $^t$BuMgCl (200 mmol, 2M in diethyl ether) was added over 15 minutes. Then 50 mL water was added and the solution was decanted and concentrated under reduced pressure. The crude product was sonicated in a mixture of acetonitrile and water (3:1) and then collected by filtration. $^1$H NMR (400 MHz, DMSO-$d_6$) δ: 8.95 (s, 1H), 8.45 (s, 1H)

Preparation 2a: 4-Chloro-6-ethyl-5-iodo-thieno[2,3-d]pyrimidine

Step A: 6-Ethyl-3H-thieno[2,3-d]pyrimidin-4-one

The mixture of 701 g 2-amino-5-ethyl-thiophene-3-carboxylic acid ethyl ester (3.52 mol) and 2200 mL formamide was heated to 200° C. and the lower boiling point solvents were distilled off. After 2 hours further 250 mL formamide was added and the mixture was stirred at the same temperature for another hour then at r.t. for 16 hours. The resulting mixture was poured into 7.5 L water and the precipitate was filtered off, washed with 1.5 L toluene and 3 L water then air dried to give the product as a brown crystalline solid.
$^1$H NMR (500 MHz, DMSO-$d_6$) δ: 12.40 (br s, 1H), 8.05 (s, 1H), 7.11 (t, 1H), 2.85 (qd, 2H), 1.27 (t, 3H)

Step B: 6-Ethyl-5-iodo-3H-thieno[2,3-d]pyrimidin-4-one

The mixture of 301 g 6-ethyl-3H-thieno[2,3-d]pyrimidin-4-one (1.67 mol), 847 g iodine (3.34 mol), 1040 g silver sulfate (3.34 mol) and 1.7 L ethanol was stirred at r.t. for 3 days. The resulting precipitate was filtered off and washed with ethanol (3×400 mL). The product was eluted from the filter cake with the following procedure: the filter cake was stirred with 800 mL DMF at 50° C. for 1 hour then the suspension was filtered. This sequence was repeated 6 times. The combined organic layer was evaporated to dryness to give the product as a tan crystalline solid.

Step C: Preparation 2a

The mixture of stirred 880 mL phosphorous oxychloride and 102 mL N,N-dimethylaniline was heated to 95° C. and 220 g 6-ethyl-5-iodo-3H-thieno[2,3-d]pyrimidin-4-one (0.719 mol) was added quickly at the same temperature and then stirred for 15 minutes. The reaction mixture was cooled to 80° C. and poured on a stirred mixture of water (1 L), crushed ice (2 kg) and DCM (700 mL). The resulting mixture was stirred for further 30 minutes while the temperature was kept below 20° C. The phases were separated, the inorganic layer was extracted with DCM (100 mL) and the organic layer was washed with water (100 mL). The combined organic layer was dried over MgSO$_4$, filtered and the filtrate was concentrated under reduced pressure to give the product as a tan crystalline solid. $^1$H NMR (400 MHz, DMSO-$d_6$) δ: 8.79 (s, 1H), 3.02 (q, 2H), 1.39 (t, 3H)

Preparation 2b: 5-Bromo-4-chloro-6-(4-fluorophenyl)thieno[2,3-d]pyrimidine 75.08 g Preparation 1a (200 mmol), 53.63 g 2-(4-fluorophenyl)-4,4,5,5-tetramethyl-1,3,2-dioxaborolane (240 mmol), 130 g cesium carbonate (400 mmol), 2.245 g Pd(OAc)$_2$ (10 mmol) and 8.50 g $^t$BuX-Phos (20 mmol) were placed in a 2 L flask. 600 mL THF and 200 mL water were added, and then stirred overnight at 70° C. under argon atmosphere. THF was evaporated, and then the product was collected by filtration. The crude product was sonicated in 250 mL acetonitrile and filtered again. Then Preparation 2b was crystallized from EtOH/THF (2:1). $^1$H NMR (400 MHz, DMSO-d$_6$) δ: 9.02 (s, 1H), 7.80-7.77 (m, 2H), 7.47-7.43 (m, 2H)

Preparation 2c: 4-Chloro-5-iodo-6-(prop-1-ynyl)-thieno[2,3-d]pyrimidine 42.24 g Preparation 1b (100 mmol), 3.509 g Pd(PPh$_3$)$_2$Cl (5 mmol) and 1.904 g CuI (10 mmol) were dissolved in 400 mL DIPA, then propyne was bubbled through the reaction mixture, which was stirred at r.t. until no further conversion was observed. The volatiles were evaporated under reduced pressure and the crude product was purified via flash chromatography using heptane/EtOAc as eluents. $^1$H NMR (400 MHz, DMSO-d$_6$) δ: 8.92 (s, 1H), 2.25 (s, 3H)

Preparation 2d: 4-Chloro-5-iodo-6-isopropyl-thieno[2,3-d]pyrimidine

Step A: 6-Isopropyl-5-iodo-3H-thieno[2,3-d]pyrimidin-4-one

The mixture of 2.858 g (14.7 mmol) 6-isopropyl-3H-thieno[2,3-d]pyrimidin-4-one, 7.468 g (29.4 mmol) iodine, 9.175 g (29.4 mmol) silver sulfate, and 55 mL ethanol was stirred at r.t. for 3 days. The mixture was diluted with Et$_2$O, the resulting precipitate was filtered off and used without further purification.

$^1$H NMR (400 MHz, DMSO-d$_6$) δ: 12.49 (br s, 1H), 8.11 (s, 1H), 3.35 (m, 1H, overlapped by H$_2$O signal), 1.28 (d, 6H)

MS (M−H): 319.0

Step B: Preparation 2d

The mixture of 15 mL (161 mmol) phosphorous oxychloride and 1.9 mL (14.7 mmol) N,N-dimethylaniline was heated to 95° C. and 25.9 g (14.7 mmol) 6-isopropyl-5-iodo-3H-thieno[2,3-d]pyrimidin-4-one (0.719 mol) was added quickly and then stirred for further 15 minutes at this temperature. The reaction mixture was cooled to 80° C. and poured into a stirred mixture of icy water (300 g) and EtOAc (200 mL). The resulting mixture was stirred for further 30 minutes while the temperature was kept below 20° C. The phases were separated, the inorganic layer was extracted with EtOAc (100 mL) and the organic layer was washed with water and NaHCO$_3$ solution. The combined organic layer was dried over MgSO$_4$, filtered and the filtrate was concentrated under reduced pressure and purified via flash chromatography using heptane and EtOAC as eluents to give the title product.

$^1$H NMR (400 MHz, CDCl$_3$) δ: 8.78 (s, 1H), 3.63 (septet, 1H), 1.41 (d, 6H)

MS (M+H): 339.0

Preparation 3a: (2R)-2-[(6-ethyl-5-iodo-thieno[2,3-d]pyrimidin-4-yl)amino]-3-phenyl-propanoic acid Using General Procedure 1a and Preparation 2a as the appropriate 4-chloro-thieno[2,3-d]pyrimidine derivative and D-phenylalanine as the appropriate amino acid derivative, Preparation 3a was obtained.

$^1$H NMR (500 MHz, DMSO-d$_6$) δ: 8.44 (s, 1H), 7.45 (d, 1H), 7.30-7.20 (m, 5H), 5.07 (m, 1H), 3.35 (dd, 1H), 3.16 (dd, 1H), 2.82 (q, 2H), 1.22 (t, 3H)

HRMS calculated for C$_{17}$H$_{16}$IN$_3$O$_2$S: 453.0008; found: 454.0064 (M+H).

Preparation 4a: 4-chloro-5-[3-chloro-2-methyl-4-[2-(4-methylpiperazin-1-yl)ethoxy]phenyl]-6-iodo-thieno[2,3-d]pyrimidine Step A: 4-chloro-5-[3-chloro-2-methyl-4-[2-(4-methylpiperazin-1-yl)ethoxy]phenyl]thieno[2,3-d]pyrimidine Using General Procedure IIa and Preparation 1c as the appropriate 5-iodo-thieno[2,3-d]pyrimidine derivative and Preparation B4 as the appropriate boronic acid derivative, and purifying the product via flash chromatography using DCM and MeOH as eluents gave 4-chloro-5-[3-chloro-2-methyl-4-[2-(4-methylpiperazin-1-yl)ethoxy]phenyl]thieno[2,3-d]pyrimidine. $^1$H NMR (400 MHz, DMSO-d$_6$) δ: 8.98 (s, 1H), 7.97 (s, 1H), 7.22 (d, 1H), 7.09 (s, 1H), 4.25-4.16 (m, 2H), 2.76 (t, 2H), 2.54 (br s, 4H), 2.32 (br s, 4H), 2.14 (s, 3H), 2.06 (s, 3H)

Step B: Preparation 4a 10.935 g 4-chloro-5-[3-chloro-2-methyl-4-[2-(4-methyl-piperazin-1-yl)ethoxy]phenyl]thieno[2,3-d]pyrimidine (25 mmol) was dissolved in 250 mL dry THF and cooled to −78° C. 25 mL LDA solution (50 mmol, 2M in THF, heptane, ethyl benzene) was added dropwise under Argon atmosphere and the mixture was stirred for 15 minutes. Then 12.69 g (50 mmol) iodine was added at −78° C. and the mixture was allowed to warm up to r.t. Then the mixture was diluted with EtOAc and was washed with NH$_4$Cl solution then with Na$_2$S$_2$O$_3$ solution, dried over Na$_2$SO$_4$, filtered and concentrated under reduced pressure. The crude product was purified via flash chromatography using DCM and MeOH as eluents to obtain Preparation 4a. $^1$H NMR (500 MHz, DMSO-d$_6$) δ: 8.93 (s, 1H), 7.15 (d, 1H), 7.13 (d, 1H), 4.22 (t, 2H), 2.77 (t, 2H), 2.56 (br s, 4H), 2.34 (br s, 4H), 2.16 (s, 3H), 2.00 (s, 3H)

Preparation 4b: 4-chloro-5-[3-chloro-2-methyl-4-[2-(4-methylpiperazin-1-yl)ethoxy]phenyl]-6-(2-furyl)thieno[2,3-d]pyrimidine Using General Procedure IIa and Preparation 4a as the appropriate 6-iodo-thieno[2,3-d]pyrimidine derivative and 2-(2-furyl)-4,4,5,5-tetramethyl-1,3,2-dioxaborolane as the appropriate boronic acid derivative, Preparation 4b was obtained. MS: (M+H)=503.0

Preparation 4c: 4-chloro-5-[3-chloro-2-methyl-4-[2-(4-methylpiperazin-1-yl)ethoxy]phenyl]-6-(5-fluoro-2-furyl)thieno[2,3-d]pyrimidine Using General Procedure IIIa and Preparation 4a as the appropriate 6-iodo-thieno[2,3-d]pyrimidine derivative and 2-(5-fluoro-2-furyl)-4,4,5,5-tetramethyl-1,3,2-dioxaborolane as the appropriate boronic acid derivative, Preparation 4c was obtained. $^1$H NMR (500 MHz, DMSO-d$_6$) δ: 8.93 (s, 1H), 7.24 (d, 1H), 7.18 (d, 1H), 5.92 (dd, 1H), 5.68 (t, 1H), 4.23 (t, 2H), 2.79 (t, 2H), 2.58 (br s, 4H), 2.38 (br s, 4H), 2.19 (s, 3H), 2.05 (s, 3H)

HRMS calculated for $C_{24}H_{23}N_4O_2FSCl_2$: 520.0903; found: 521.0972 (M+H).

Preparation 4d: 2-chloro-4-(4-chloro-6-iodo-thieno[2,3-d]pyrimidin-5-yl)-3-methyl-phenol Step A: [2-chloro-4-(4-chlorothieno[2,3-d]pyrimidin-5-yl)-3-methyl-phenoxy]-triisopropyl-silane Using General Procedure IIa and Preparation 1c as the appropriate 5-iodo-thieno[2,3-d]pyrimidine derivative and Preparation B3 as the appropriate boronic acid derivative, [2-chloro-4-(4-chlorothieno[2,3-d]pyrimidin-5-yl)-3-methyl-phenoxy]-triisopropyl-silane was obtained. $^1$H NMR (400 MHz, DMSO-$d_6$) δ: 8.95 (s, 1H), 7.98 (s, 1H), 7.13 (d, 1H), 6.91 (d, 1H), 2.05 (s, 3H), 1.40-1.29 (m, 3H), 1.10 (dd, 18H)

Step B: [2-chloro-4-(4-chloro-6-iodothieno[2,3-d]pyrimidin-5-yl)-3-methyl-phenoxy]-triisopropyl-silane 33.7 g [2-chloro-4-(4-chlorothieno[2,3-d]pyrimidin-5-yl)-3-methyl-phenoxy]-triisopropyl-silane (72 mmol) was dissolved in 300 mL dry THF and cooled to −78° C. 43.2 mL LDA solution (86.4 mmol, 2M in THF, heptane, ethyl benzene) was added dropwise under Argon and the mixture was stirred for 15 minutes. Then 23.8 g iodine (93.7 mmol) was added at −78° C. and the mixture was allowed to warm up to r.t. Then the mixture was diluted with EtOAc and was washed with NH$_4$Cl solution then with Na$_2$S$_2$O$_3$ solution. The organic layer was dried over Na$_2$SO$_4$, filtered and concentrated under reduced pressure. $^1$H NMR (400 MHz, DMSO-$d_6$) δ: 8.91 (s, 1H), 7.05 (d, 1H), 6.97 (d, 1H), 1.99 (s, 3H), 1.39-1.30 (m, 3H), 1.10 (dd, 18H)

Step C: Preparation 4d 10.0 g [2-chloro-4-(4-chloro-6-iodothieno[2,3-d]pyrimidin-5-yl)-3-methyl-phenoxy]-triisopropyl-silane (16.85 mmol) was dissolved in 100 mL dry THF and 18.5 mL TBAF solution (18.5 mmol, 1M in THF) was added and the mixture was stirred at r.t. for 10 minutes. Then the mixture was diluted with EtOAc and washed with 1M HCl solution and brine. The organic layer was dried over Na$_2$SO$_4$, filtered and concentrated under reduced pressure. The crude product was purified via flash chromatography using heptane and EtOAc as eluents to obtain Preparation 4d. HRMS calculated for $C_{13}H_7Cl_2IN_2OS$: 435.8701, found: 436.8780 (M+H).

Preparation 4e: 2-[2-chloro-4-(4-chloro-6-iodo-thieno[2,3-d]pyrimidin-5-yl)-3-methyl-phenoxy]-N,N-dimethyl-ethanamine Using General Procedure VI and Preparation 4d as the appropriate phenol derivative and N,N-dimethylethanolamine as the appropriate alcohol, Preparation 4e was obtained. MS (M+H): 508.0

Preparation 4f: 2-chloro-4-[4-chloro-6-(3-thienyl)thieno[2,3-d]pyrimidin-5-yl]-3-methyl-phenol Using General Procedure IIIa and Preparation 4d as the appropriate 6-iodo-thieno[2,3-d]pyrimidine derivative and thiophene-3-boronic acid pinacol ester as the appropriate boronic acid derivative, Preparation 4f was obtained. MS (M+H): 393.0

Preparation 4g: 4-chloro-5-[3-chloro-2-methyl-4-[2-(4-methylpiperazin-1-yl)ethoxy]phenyl]-6-(3-thienyl)thieno[2,3-d]pyrimidine Using General Procedure VI and Preparation 4f as the the appropriate 6-iodo-thieno[2,3-d]pyrimidine derivative and 2-(4-methylpiperazin-1-yl)ethanol as the appropriate alcohol, Preparation 4g was obtained.
$^1$H NMR (500 MHz, DMSO-$d_6$) δ: 8.94 (s, 1H), 7.60 (dd, 1H), 7.56 (dd, 1H), 7.19 (d, 1H), 7.12 (d, 1H), 6.79 (dd, 1H), 4.21 (t, 1H), 2.77 (t, 1H), 2.56 (br, 4H), 2.33 (br, 4H), 2.15 (s, 3H), 2.04 (s, 3H)
HRMS calculated for $C_{24}H_{24}Cl_2N_4OS_2$: 518.0769; found: 519.0852 (M+H).

Preparation 4h: 4-[2-[2-chloro-4-[4-chloro-6-(3-thienyl)thieno[2,3-d]pyrimidin-5-yl]-3-methyl-phenoxy]ethyl]morpholine Using General Procedure VI and Preparation 4f as the appropriate phenol derivative and 2-morpholinoethanol as the appropriate alcohol, Preparation 4h was obtained.

Preparation 4i: 4-chloro-5-(1-naphthyl)thieno[2,3-d]pyrimidine

Step A: ethyl 2-amino-4-(1-naphthyl)thiophene-3-carboxylate 50.00 g 1-(1-naphthyl)ethanone (293.8 mmol), 43.66 g ethyl cyanoacetate (386.0 mmol), 18.84 g sulfur (587.5 mmol), 8.4 mL AcOH and 38.39 g morpholine were dissolved in 300 mL EtOH and stirred at 60° C. until no further conversion was observed. The volatiles were removed in vacuo, and the residue was purified via flash chromatography using heptane and EtOAc as eluents to obtain ethyl 2-amino-4-(1-naphthyl)thiophene-3-carboxylate. HRMS calculated for $C_{17}H_{15}NO_2S$: 297.0823; found: 298.0891 (M+H).

Step B: 5-(1-naphthyl)-3H-thieno[2,3-d]pyrimidin-4-one 9.40 g ethyl 2-amino-4-(1-naphthyl)thiophene-3-carboxylate (31.6 mmol) was dissolved in 45 mL formamide and stirred at 200° C. until no further conversion was observed. The mixture was cooled to r.t. and poured into water. The precipitated solid was filtered, washed with water, then dried to obtain 5-(1-naphthyl)-3H-thieno[2,3-d]pyrimidin-4-one. HRMS calculated for $C_{16}H_{10}N_2OS$: 278.0514; found: 279.0582 (M+H).

Step C: Preparation 4i 8.50 g 5-(1-naphthyl)-3H-thieno[2,3-d]pyrimidin-4-one (30.5 mmol), 4.07 g N,N-dimethylaniline (33.6 mmol) and 22.8 mL phosphorus oxychloride (244 mmol) were stirred at 100° C. for 1 hour. The mixture was cooled to r.t. and poured into stirred icy water. The precipitated solid was filtered and recrystallized from acetonitrile to obtain Preparation 4i. HRMS calculated for $C_{16}H_9N_2SCl$: 296.0175; found: 297.0255 (M+H).

Preparation 4j: 4-chloro-5-(3-chloro-2-methyl-phenyl)-6-ethyl-thieno[2,3-d]pyrimidine Using General Procedure IIb and Preparation 2a as the appropriate 5-iodo-thieno[2,3-d]pyrimidine derivative and (3-chloro-2-methyl-phenyl)boronic acid as the appropriate boronic acid derivative, Preparation 4j was obtained.

$^1$H NMR (400 MHz, DMSO-d$_6$) δ: 8.89 (s, 1H), 7.55 (dd, 1H), 7.33 (t, 1H), 7.23 (dd, 1H), 2.65 (m, 2H), 2.03 (s, 3H), 1.17 (t, 3H)

HRMS calculated for C$_{15}$H$_{12}$Cl$_2$N$_2$S: 322.0098; found: 323.0164 (M+H).

Preparation 4k: 4-chloro-6-ethyl-5-(1-naphthyl)thieno[2,3-d]pyrimidine

Using General Procedure IIb and Preparation 2a as the appropriate 5-iodo-thieno[2,3-d]pyrimidine derivative and 1-naphthaleneboronic acid neopentyl glycol ester as the appropriate boronic acid derivative, Preparation 4k was obtained.

$^1$H NMR (400 MHz, DMSO-d$_6$) δ: 8.91 (s, 1H), 8.07 (dd, 1H), 8.03 (dm, 1H), 7.63 (dd, 1H), 7.55 (tm, 1H), 7.51 (dd, 1H), 7.44 (tm, 1H), 7.33 (dm, 1H), 2.61 (q, 2H), 1.13 (t, 3H)

HRMS calculated for C$_{18}$H$_{13}$ClN$_2$S: 324.0488; found: 325.0562 (M+H).

Preparation 4l: 4-chloro-6-methyl-5-(1-naphthyl)thieno[2,3-d]pyrimidine

Using General Procedure IVa and methyl-iodide as the appropriate electrophile, Preparation 4l was obtained.

$^1$H NMR (400 MHz, DMSO-d$_6$) δ: 8.90 (s, 1H), 8.04 (dd, 2H), 7.63 (dd, 1H), 7.54 (td, 1H), 7.49 (dd, 1H), 7.43 (td, 1H), 7.32 (d, 1H), 2.28 (s, 3H)

MS (M+H): 311.0

Preparation 4m: [4-chloro-5-(1-naphthyl)thieno[2,3-d]pyrimidin-6-yl]methanol

Step A: 4-chloro-5-(1-naphthyl)thieno[2,3-d]pyrimidine-6-carbaldehyde

Using General Procedure IVa and DMF as the appropriate electrophile, 4-chloro-5-(1-naphthyl)thieno[2,3-d]pyrimidine-6-carbaldehyde was obtained. $^1$H NMR (400 MHz, CDCl$_3$) δ: 9.65 (s, 1H), 9.00 (s, 1H), 8.07 (d, 1H), 7.99 (d, 1H), 7.68-7.52 (m, 3H), 7.47 (t, 1H), 7.33 (d, 1H)

Step B: Preparation 4m 4-chloro-5-(1-naphthyl)thieno[2,3-d]pyrimidine-6-carbaldehyde was dissolved in THF:MeOH 1:1 (4 mL/mmol) and 3 eq. NaBH$_4$ was added at 0° C. The mixture was stirred for 10 minutes, then quenched with 1M citric acid. The mixture was extracted with DCM, washed with NaHCO$_3$ solution and brine, dried over Na$_2$SO$_4$, filtered and the filtrate was concentrated in vacuo. The crude product was purified via flash chromatography using heptane and EtOAc as eluents to obtain Preparation 4m.

$^1$H NMR (400 MHz, DMSO-d$_6$) δ: 8.92 (s, 1H), 8.06 (d, 1H), 8.03 (d, 1H), 7.62 (m, 1H), 7.58-7.49 (m, 2H), 7.44 (m, 1H), 7.35 (d, 1H), 5.99 (t, 1H), 4.54 (dd, 1H), 4.33 (dd, 1H)

MS (M+H): 327.0

Preparation 4n1 and Preparation 4n2: 1-[4-chloro-5-(1-naphthyl)thieno[2,3-d]pyrimidin-6-yl]ethanol Using General Procedure IVa and acetaldehyde as the appropriate electrophilic reagent the crude product was obtained as a mixture of diastereoisomers that were separated by sequential flash chromatography using DCM-acetone and heptane-MTBE as eluents. The order of elution of the diastereomeric-pairs was the same in both eluent systems.

Preparation 4n1 was obtained as the earlier eluting diastereoisomer (racemate).

$^1$H NMR (400 MHz, CDCl$_3$) δ: 8.85 (s, 1H), 7.99 (d, 1H), 7.95 (d, 1H), 7.60-7.49 (m, 2H), 7.46-7.34 (m, 3H), 4.84 (m, 1H), 2.06 (d, 1H) 1.53 (d, 3H)

MS (M+H): 341.0

Preparation 4n2 was obtained as the later eluting diastereoisomer (racemate).

$^1$H NMR (400 MHz, CDCl$_3$) δ: 8.85 (s, 1H), 7.99 (d, 1H), 7.94 (d, 1H), 7.60-7.49 (m, 2H), 7.46 (dd, 1H) 7.43-7.37 (m, 1H), 7.27 (overlap, 1H), 4.98 (m, 1H), 2.14 (d, 1H) 1.35 (d, 3H)

MS (M+H): 341.0

Preparation 4o: 1-[4-chloro-5-(1-naphthyl)thieno[2,3-d]pyrimidin-6-yl]ethanone 157 mg Dess-Martin reagent (0.37 mmol) was dissolved in 2 mL DCM, then a mixture of Preparation 4n1 and Preparation 4n2 (120 mg, 0.35 mmol dissolved in 10 mL DCM) was added and the mixture was stirred until no further conversion was observed. Then the mixture was diluted with DCM, washed with NaOH and NaHCO$_3$ solutions and brine, dried over Na$_2$SO$_4$, filtered and concentrated under reduced pressure. The crude product was purified via flash chromatography using heptane and EtOAc as eluents to obtain Preparation 4o.

$^1$H NMR (500 MHz, DMSO-d$_6$) δ: 9.09 (s, 1H), 8.16 (dd, 1H), 8.08 (d, 1H), 7.72-7.65 (m, 2H), 7.62-7.57 (m, 1H), 7.52-7.43 (m, 2H), 1.71 (s, 3H)

MS (M+H): 339.0

Preparation 4p: 2-[4-chloro-5-(1-naphthyl)thieno[2,3-d]pyrimidin-6-yl]propan-2-ol Using General Procedure IVa and acetone as the appropriate electrophile, Preparation 4p was obtained.

$^1$H NMR (400 MHz, CDCl$_3$) δ: 8.80 (s, 1H), 7.98 (d, 1H), 7.92 (d, 1H), 7.59-7.46 (m, 2H), 7.46-7.34 (m, 2H), 7.30 (d, 1H), 2.53 (br s, 1H), 1.54 (s, 3H), 1.21 (s, 3H)

MS (M+H): 355.0

Preparation 4q: 4-chloro-6-isopropyl-5-(1-naphthyl)thieno[2,3-d]pyrimidine

Step A: 6-isopropyl-5-(1-naphthyl)-3H-thieno[2,3-d]pyrimidin-4-one 250 mg Preparation 4p (0.705 mmol) and 1.75 mL Et$_3$SiH (10.9 mmol) were placed in a flask and treated with 10 mL TFA at −10° C. The mixture was then stirred at 50° C. until no further conversion was observed. The mixture was then diluted with DCM, neutralized with solid K$_2$CO$_3$ and NaHCO$_3$ solution. After separation of the phases the organic phase was washed with brine, dried over Na$_2$SO$_4$, filtered and concentrated in vacuo to obtain 6-isopropyl-5-(1-naphthyl)-3H-thieno[2,3-d]pyrimidin-4-one as a crude intermediate. MS (M+H): 321.0

Step B: Preparation 4q 2 mL phosphorous oxychloride and 0.161 mL N,N-dimethylaniline (1.27 mmol) were placed in a flask under Argon and 1.22 g 6-isopropyl-5-(1-naphthyl)-3H-thieno[2,3-d]pyrimidin-4-one was added to the mixture in portions during 5 minutes. The reaction mixture was stirred at 100° C. until no further conversion was observed. The mixture was cooled to r.t. and poured into stirred icy water. The obtained aqueous media was neutralized by the careful addition of solid NaHCO$_3$. After the evolution of gas have ceased, the product was extracted three times with DCM. The combined organic layer was dried over Na$_2$SO$_4$, filtered and concentrated under reduced pressure. The crude product was purified via flash chromatography using heptane and EtOAc as eluents to obtain Preparation 4q.

$^1$H NMR (500 MHz, CDCl$_3$) δ: 8.80 (s, 1H), 7.97 (d, 1H), 7.94 (d, 1H), 7.57 (dd, 1H), 7.54-7.49 (m, 1H), 7.42-7.37 (m, 2H), 7.34 (d, 1H), 3.02 (septet, 1H), 1.31 (d, 3H), 1.20 (d, 3H)

MS (M+H): 339.0

Preparation 4r: 4-chloro-6-(difluoromethyl)-5-(1-naphthyl)thieno[2,3-d]pyrimidine 0.250 g 4-chloro-5-(1-naphthyl)thieno[2,3-d]pyrimidine-6-carbaldehyde (Step A intermediate in the synthesis of Preparation 4m, 0.77 mmol) was dissolved in 7 mL DCM, then 270 µl DAST (1.16 mmol) was added. The mixture was stirred at r.t. until no further conversion was observed. The mixture was then diluted with DCM and washed with water, then with NaHCO$_3$ solution and brine. The organic phase was dried over Na$_2$SO$_4$, filtered and concentrated under reduced pressure. The crude product was purified via flash chromatography using heptane and EtOAc as eluents to obtain Preparation 4r.

$^1$H NMR (500 MHz, CDCl$_3$) δ: 8.97 (s, 1H), 8.04 (d, 1H), 7.97 (d, 1H), 7.62-7.54 (m, 2H), 7.49-7.43 (m, 2H), 7.28 (d, 1H), 6.47 (t, 1H)

MS (M+H): 347.0

Preparation 4s: 4-chloro-6-iodo-5-(1-naphthyl)thieno[2,3-d]pyrimidine

Using General Procedure IVa and iodine as the appropriate electrophilic reagent, Preparation 4s was obtained.

$^1$H NMR (400 MHz, DMSO-d$_6$) δ: 8.94 (s, 1H), 8.10 (dm, 1H), 8.05 (dm, 1H), 7.66 (dm, 1H), 7.56 (tm, 1H), 7.48 (dd, 1H), 7.44 (tm, 1H), 7.31 (dm, 1H)

HRMS calculated for C$_{16}$H$_8$N$_2$SClI: 421.9141; found: 422.9211 (M+H).

Preparation 4t: 4-chloro-5-(3-chloro-2-methyl-phenyl)-6-iodo-thieno[2,3-d]pyrimidine Step A: 4-chloro-5-(3-chloro-2-methyl-phenyl)thieno[2,3-d]pyrimidine Using General Procedure IIb and Preparation 1c as the appropriate 5-iodo-thieno[2,3-d]pyrimidine derivative and (3-chloro-2-methyl-phenyl)boronic acid as the appropriate boronic acid derivative 4-chloro-5-(3-chloro-2-methyl-phenyl)thieno[2,3-d]pyrimidine was obtained. $^1$H NMR (400 MHz, CDCl$_3$) δ: 8.89 (s, 1H), 7.47 (dd, 1H), 7.43 (s, 1H), 7.20 (t, 1H), 7.14 (dd, 1H), 2.14 (s, 3H)

Step B: Preparation 4t

Using General Procedure IVa and 4-chloro-5-(3-chloro-2-methyl-phenyl)thieno[2,3-d]pyrimidine instead of Preparation 4i and iodine as the appropriate electrophilic reagent, Preparation 4t was obtained. $^1$H NMR (400 MHz, CDCl$_3$) δ: 8.82 (s, 1H), 7.52 (dd, 1H), 7.25 (t, 1H), 7.05 (dd, 1H), 2.09 (s, 3H)

Preparation 4u: 4-chloro-5-(3-chloro-2-methyl-phenyl)-6-isopropyl-thieno[2,3-d]pyrimidine Using General Procedure IIb and Preparation 2d as the appropriate 5-iodo-thieno[2,3-d]pyrimidine derivative and (3-chloro-2-methyl-phenyl)boronic acid as the appropriate boronic acid derivative, Preparation 4u was obtained.

$^1$H NMR (400 MHz, DMSO-d$_6$) δ: 8.90 (s, 1H), 7.56 (dd, 1H), 7.34 (t, 1H), 7.29-7.22 (m, 1H), 2.94 (septet, 1H), 2.04 (s, 3H), 1.26 (d, 3H), 1.22 (d, 3H)

HRMS calculated for C$_{16}$H$_{14}$N$_2$SCl$_2$: 336.0255; found: 337.0335 (M+H).

Preparation 4v: 4-chloro-6-ethyl-5-(1H-indol-4-yl)thieno[2,3-d]pyrimidine

The mixture of 0.664 g Preparation 2a (2.0 mmol), 0.400 g 1H-indol-4-ylboronic acid (1.2 eq, 2.4 mmol), 44.9 mg Pd(OAc)$_2$ (10 mol %, 0.2 mmol), 152 mg PCy$_3$×HBF$_4$ (20 mol %, 0.4 mmol), 1.96 g Cs$_2$CO$_3$ (3.0 eq, 6.0 mmol) in 7.3 mL dimethoxyethane and 7.3 mL water was heated in microwave reactor at 100° C. until no further conversion was observed. The crude reaction mixture was filtered through a pad of Celite, washed with 2×10 mL MTBE and 2×10 mL water. The two layers of the filtrate were separated and the organic layer was washed with brine, then dried over Na$_2$SO$_4$, filtered and concentrated in vacuo. The residue was purified via preparative reversed phase chromatography using water (containing 0.1% TFA) and acetonitrile as eluents to obtain Preparation 4v. $^1$H NMR (400 MHz, DMSO-d$_6$) δ: 11.22 (br s, 1H), 8.87 (s, 1H), 7.49 (dm, 1H), 7.32 (m, 1H), 7.19 (dd, 1H), 6.95 (dm, 1H), 5.96 (m, 1H), 2.67 (m, 2H), 1.14 (t, 3H)

HRMS calculated for C$_{16}$H$_{12}$ClN$_3$S: 313.0440; found 314.0508 (M+H).

Preparation 4w: 4-chloro-5-(1-naphthyl)-6-vinyl-thieno[2,3-d]pyrimidine

Using General Procedure IIc and Preparation 4s as the appropriate 6-iodo-thieno[2,3-d]pyrimidine derivative and vinylboronic acid pinacol ester as the appropriate boronic acid derivative, Preparation 4w was obtained.

$^1$H NMR (500 MHz, DMSO-d$_6$) δ: 8.95 (s, 1H), 8.09 (d, 1H), 8.05 (d, 1H), 7.65 (dd, 1H), 7.56 (t, 1H), 7.52 (dd, 1H), 7.45 (t, 1H), 7.35 (d, 1H), 6.34 (dd, 1H), 5.90 (d, 1H), 5.45 (d, 1H)

HRMS calculated for C$_{18}$H$_{11}$ClN$_2$S: 322.0331; found 323.0415 (M+H).

Preparation 4x: 4-chloro-5-(1-naphthyl)-6-[(E/Z)-prop-1-enyl]thieno[2,3-d]pyrimidine Step A: 5,5-dimethyl-2-[(Z/E)-prop-1-enyl]-1,3,2-dioxaborinane To a solution of 0.172 g (Z)-prop-1-en-1-yl boronic acid (2.0 mmol, 9:1 Z/E isomer mixture) and 0.208 g neopentyl glycol (2.0 mmol) in 6 mL 2-Me-THF 20 mg Amberlyst 15H$^+$ ionic exchange resin was added and it was stirred at r.t. until no further conversion was observed. The conversion was followed by $^1$H-NMR measurement in CDCl$_3$ solution. The mixture was filtered through a pad of celite, washed with 2×3 mL 2-Me-THF and the filtrate was concentrated in vacuo. The resulting crude material was sufficiently pure for the next step as a 87:13 mixture of Z/E isomers according to NMR measurement. $^1$H NMR (400 MHz, CDCl$_3$) δ: 6.57-6.43 (m, 1H), 5.39-5.27 (dd, 1H), 3.67 (s, 4H), 1.95-1.83 (dd, 3H), 0.97 (s, 6H)

Step B: Preparation 4x

Using General Procedure IIc and Preparation 4s as the appropriate 6-iodo-thieno[2,3-d]pyrimidine derivative and 5,5-dimethyl-2-[(Z/E)-prop-1-enyl]-1,3,2-dioxaborinane (Z/E-mixture, Step A) as the appropriate boronic acid derivative, Preparation 4x was obtained as a 63:37 mixture of Z/E isomers.

$^1$H NMR (500 MHz, DMSO-d$_6$) δ: 8.95-8.90 (s, 1H), 8.11-8.06 (m, 1H), 8.06-8.01 (m, 1H), 7.67-7.60 (m, 1H), 7.58-7.52 (m, 1H), 7.52-7.48 (m, 1H), 7.46-7.40 (m, 1H), 7.36-7.29 (m, 1H), 6.45-5.90 (m, 1H), 6.10-6.04 (m, 1H), 2.06-1.72 (dd, 3H)

HRMS calculated for C$_{19}$H$_{13}$ClN$_2$S: 336.0488; found 337.0541 (M+H).

Preparation 4y: 4-chloro-6-isopropenyl-5-(1-naphthyl)thieno[2,3-d]pyrimidine

Using General Procedure IIc and Preparation 4s as the appropriate 6-iodo-thieno[2,3-d]pyrimidine derivative and 2-isopropenyl-4,4,5,5-tetramethyl-1,3,2-dioxaborolane as the appropriate boronic acid derivative, Preparation 4y was obtained.

$^1$H NMR (500 MHz, DMSO-d$_6$) δ: 8.83 (s, 1H), 7.96 (d, 1H), 7.92 (d, 1H), 7.55-7.37 (m, 5H), 5.23 (m, 1H), 5.12 (m, 1H), 1.65 (dd, 3H)

HRMS calculated for C$_{19}$H$_{13}$ClN$_2$S: 336.0488; found 337.0551 (M+H).

Preparation 4z: 4-chloro-5-(1-naphthyl)-6-[(E)-prop-1-enyl]thieno[2,3-d]pyrimidine Step A: 5,5-dimethyl-2-[(E)-prop-1-enyl]-1,3,2-dioxaborinane To a solution of 0.172 g (E)-prop-1-en-1-yl boronic acid (2.0 mmol) and 0.208 g neopentyl glycol (2.0 mmol) in 6 mL 2-Me-THF 20 mg Amberlyst 15H$^+$ ionic exchange resin was added and it was stirred at r.t. until no further conversion was observed. The conversion was followed by $^1$H-NMR measurement in CDCl$_3$ solution. The mixture was filtered through a pad of celite, washed with 2×3 mL 2-Me-THF and the filtrate was concentrated in vacuo. The resulting crude material was sufficiently pure for the next step. It contained only the E-stereoisomer. $^1$H NMR (400 MHz, CDCl$_3$) δ: 6.57 (m, 1H), 5.39 (dd, 1H), 3.63 (s, 4H), 1.83 (dd, 3H), 0.97 (s, 6H)

Step B: Preparation 4z

Using General Procedure IIcIIIb and Preparation 4s as the appropriate 6-iodo-thieno[2,3-d]pyrimidine derivative and 5,5-dimethyl-2-[(E)-prop-1-enyl]-1,3,2-dioxaborinane (Step A) as the appropriate boronic acid derivative, Preparation 4z was obtained.

$^1$H NMR (500 MHz, DMSO-d$_6$) δ: 8.90 (s, 1H), 8.09 (d, 1H), 8.04 (d, 1H), 7.64 (dd, 1H), 7.58-7.53 (m, 1H), 7.50 (dd, 1H), 7.44 (m, 1H), 7.34 (d, 1H), 6.45 (m, 1H), 6.10-6.03 (m, 1H), 1.72 (dd, 3H)

HRMS calculated for C$_{19}$H$_{13}$ClN$_2$S: 336.0488; found 337.0550 (M+H).

Preparation 5a: (2R)-2-[[5-(3-chloro-2-methyl-phenyl)-6-iodo-thieno[2,3-d]pyrimidin-4-yl]amino]-3-phenyl-propanoic acid Using General Procedure Ib and Preparation 4t as the appropriate 4-chloro-thieno[2,3-d]pyrimidine derivative and D-phenylalanine as the appropriate amino acid derivative, Preparation 5a was synthesized. The crude product was purified via preparative reversed phase chromatography using 0.1% TFA solution and acetonitrile as eluents and Preparation 5a was obtained as a 1:1 mixture of diastereoisomers.

$^1$H NMR (500 MHz, DMSO-d$_6$) δ: 13.15 (br s, 1H), 8.42-8.41 (s, 1H), 7.62-7.54 (d, 1H), 7.39-7.17 (t, 1H), 7.21-7.01 (m, d, 1H), 7.21 (m, 4H), 6.82-6.79 (d, 1H), 5.15-5.11 (d, 1H), 4.82-4.76 (q, 1H), 3.23-3.14 (dd, 1H), 2.73-2.67 (dd, 1H), 2.02-1.80 (s, 3H)

HRMS calculated for C$_{22}$H$_{17}$N$_2$O$_2$SClI: 548.9775; found 549.9842 and 549.9864 (M+H).

Preparation 5b: (2R)-2-[[(5S$_a$)-5-[3-chloro-2-methyl-4-[2-(4-methylpiperazin-1-yl) ethoxy]phenyl]-6-iodo-thieno[2,3-d]pyrimidin-4-yl]amino]-3-[2-[(2-methylpyrazol-3-yl)methoxy]phenyl] propanoic acid Using General Procedure Ib and Preparation 4a as the appropriate 4-chloro-thieno[2,3-d]pyrimidine derivative and Preparation A1 as the appropriate amino acid derivative, followed by HILIC purification, Preparation 5b was obtained as the later eluting diastereoisomer. MS: (M+H)=802.0

Preparation 5c: (2R)-2-[[5-[3-chloro-2-methyl-4-[2-(4-methylpiperazin-1-yl)ethoxy]phenyl]-6-iodo-thieno[2,3-d]pyrimidin-4-yl]amino]-3-[2-[(2-ethylpyrazol-3-yl)methoxy]phenyl]propanoic acid Using General Procedure Ib and Preparation 4a as the appropriate 4-chloro-thieno[2,3-d]pyrimidine derivative and Preparation A7 as the appropriate amino acid derivative, followed by HILIC purification, Preparation 5c was obtained as the later eluting diastereomer. MS: (M+H)=816.0

Preparation 6a: (2R)-2-[[5-bromo-6-(4-fluorophenyl)thieno[2,3-d]pyrimidin-4-yl]amino]-3-(2-hydroxyphenyl)propanoic acid Using General Procedure Ib and Preparation 2b as the appropriate 4-chloro-thieno[2,3-d]pyrimidine derivative, and (2R)-2-amino-3-(2-hydroxyphenyl)propanoic acid as the appropriate amino acid derivative, Preparation 6a was obtained, isolated by filtration.

$^1$H NMR (400 MHz, DMSO-d$_6$) δ: 12.90 (br s, 1H), 9.65 (br s, 1H), 8.41 (s, 1H), 7.70 (m, 2H), 7.45-7.34 (m, 3H), 7.18 (dd, 1H), 7.04 (td, 1H), 6.80 (d, 1H), 6.72 (t, 1H), 4.96 (m, 1H), 3.31 (dd, 1H), 3.08 (dd, 1H)

MS (M+H): 488.0

Preparation 6b: (2R)-3-(2-hydroxyphenyl)-2-[(5-iodo-6-prop-1-ynyl-thieno[2,3-d]pyrimidin-4-yl)amino]propanoic acid Using General Procedure Ib and Preparation 2c as the appropriate 4-chloro-thieno[2,3-d]pyrimidine derivative, and (2R)-2-amino-3-(2-hydroxyphenyl)propanoic acid as the appropriate amino acid derivative, Preparation 6b was obtained. The product was isolated by filtration instead of chromatography. MS: (M+H)=480.0

Preparation 6c: methyl (2R)-2-[(6-ethyl-5-iodo-thieno[2,3-d]pyrimidin-4-yl)amino]-3-phenyl-propanoate 3.246 g Preparation 2a (10 mmol), 3.70 g [(1R)-1-benzyl-2-methoxy-2-oxo-ethyl]ammonium chloride (17 mmol) and 13.03 g $Cs_2CO_3$ (40 mmol) were dissolved in 15 mL DMSO and stirred at r.t. under $N_2$ atmosphere until no further conversion was observed. The mixture was then acidified with 2M HCl solution to pH=1 and extracted with 2×300 mL EtOAc. The combined organic phases were washed with $NaHCO_3$ solution, dried over $Na_2SO_4$, filtered and concentrated under reduced pressure. The crude product was purified via flash chromatography using heptane and EtOAc as eluents to obtain Preparation 6c.

$^1$H NMR (500 MHz, DMSO-$d_6$) δ: 8.39 (s, 1H), 7.33 (d, 1H), 7.30 (m, 2H), 7.25-7.22 (m, 3H), 5.11 (m, 1H), 3.69 (s, 3H), 3.33 (dd, 1H), 3.18 (dd, 1H), 2.82 (q, 2H), 1.23 (t, 3H) HRMS calculated for $C_{18}H_{18}IN_3O_2S$: 467.0164; found 468.0242 (M+H).

Preparation 7a: ethyl (2R)-2-[[5-[3-chloro-2-methyl-4-[2-(4-methylpiperazin-1-yl) ethoxy]phenyl]-6-(4-fluorophenyl)thieno[2,3-d]pyrimidin-4-yl]amino]-3-(2-hydroxyphenyl)propanoate Step A: (2R)-2-[[5-[3-chloro-2-methyl-4-[2-(4-methylpiperazin-1-yl)ethoxy]phenyl]-6-(4-fluorophenyl)thieno[2,3-d]pyrimidin-4-yl]amino]-3-(2-hydroxyphenyl)propanoic acid Using General Procedure IId and Preparation 6a as the appropriate 5-iodo-thieno[2,3-d]pyrimidine derivative and Preparation B4 as the appropriate boronic acid derivative, (2R)-2-[[5-[3-chloro-2-methyl-4-[2-(4-methylpiperazin-1-yl)ethoxy]phenyl]-6-(4-fluorophenyl) thieno[2,3-d]pyrimidin-4-yl]amino]-3-(2-hydroxyphenyl)propanoic acid was obtained. HRMS calculated for $C_{35}H_{35}ClFN_5O_4S$: 675.2082; found 676.2097 (M+H).

Step B: Preparation 7a 2.3 g (2R)-2-[[5-[3-chloro-2-methyl-4-[2-(4-methylpiperazin-1-yl)ethoxy]phenyl]-6-(4-fluorophenyl)thieno[2,3-d]pyrimidin-4-yl]amino]-3-(2-hydroxyphenyl)propanoic acid (3.4 mmol) was dissolved in 20 mL 1.25 M HCl in EtOH and stirred at 40° C. overnight. The mixture was then diluted with $NaHCO_3$ solution and extracted with DCM. The combined organic phases were dried over $Na_2SO_4$, filtered and concentrated in vacuo. The crude product was purified via flash chromatography using DCM and MeOH as eluents to obtain Preparation 7a. HRMS calculated for $C_{37}H_{39}ClFN_5O_4S$: 703.2395; found 704.2417 (M+H).

Preparation 7ad2: ethyl (2R)-2-[[(5$S_a$)-5-[3-chloro-2-methyl-4-[2-(4-methylpiperazin-1-yl)ethoxy]phenyl]-6-(4-fluorophenyl)thieno[2,3-d]pyrimidin-4-yl]amino]-3-(2-hydroxyphenyl)propanoate Step A: (2R)-2-[[(5$S_a$)-5-[3-chloro-2-methyl-4-[2-(4-methylpiperazin-1-yl)ethoxy]phenyl]-6-(4-fluorophenyl)thieno[2,3-d]pyrimidin-4-yl]amino]-3-(2-hydroxyphenyl)propanoic acid Using General Procedure IId and Preparation 6a as the appropriate 5-iodo-thieno[2,3-d]pyrimidine derivative and Preparation B4 as the appropriate boronic acid derivative, (2R)-2-[[5-[3-chloro-2-methyl-4-[2-(4-methylpiperazin-1-yl)ethoxy]phenyl]-6-(4-fluorophenyl) thieno[2,3-d]pyrimidin-4-yl]amino]-3-(2-hydroxyphenyl)propanoic acid was obtained as a mixture of diastereomers. The mixture was separated via flash chromatography using HILIC eluents. The earlier eluting diastereoisomer was collected as Preparation 7a1. MS (M+H): 676.2

The later eluting diastereoisomer was collected as Preparation 7a2. MS (M+H): 676.2

Step B: Preparation 7ad2

44.51 g of Preparation 7a2 (6.67 mmol) was dissolved in 85 mL 1.25 M HCl in EtOH and stirred at 40° C. overnight. The mixture was then cautiously diluted with $NaHCO_3$ solution and extracted with DCM. The combined organic phases were dried over $Na_2SO_4$, filtered and concentrated in vacuo. The crude product was purified via flash chromatography using DCM and MeOH as eluents to obtain Preparation 7ad2.

$^1$H NMR (500 MHz, DMSO-$d_6$) δ: 9.49 (s, 1H), 8.40 (s, 1H), 7.34 (d, 1H), 7.27-7.21 (m, 3H), 7.20-7.14 (m, 2H), 7.00 (td, 1H), 6.71 (dd, 1H), 6.60 (td, 1H), 6.39 (dd, 1H), 5.03 (d, 1H), 4.92 (m, 1H), 4.26 (t, 2H), 4.03 (m, 2H), 3.03 (dd, 1H), 2.78 (t, 2H), 2.54 (br, 4H), 2.36 (dd, 1H), 2.30 (br, 4H), 2.12 (s, 3H), 1.83 (s, 3H), 1.10 (t, 3H)

HRMS calculated for $C_{37}H_{39}ClFN_5O_4S$: 703.2395; found 704.2450 (M+H).

Preparation 7b: ethyl (2R)-2-[[(5$S_a$)-5-[3-chloro-2-methyl-4-[2-(4-methylpiperazin-1-yl)ethoxy]phenyl]-6-prop-1-ynyl-thieno[2,3-d]pyrimidin-4-yl]amino]-3-(2-hydroxyphenyl)propanoate Step A: (2R)-2-[[(5$S_a$)-5-[3-chloro-2-methyl-4-[2-(4-methylpiperazin-1-yl)ethoxy]phenyl]-6-prop-1-ynyl-thieno[2,3-d]pyrimidin-4-yl]amino]-3-(2-hydroxy phenyl)propanoic acid Using General Procedure IIb and Preparation 6b as the appropriate 5-iodo-thieno[2,3-d]pyrimidine derivative and Preparation B4 as the appropriate boronic acid derivative, Ataphos as catalyst and THF:water 3:1 as solvent a mixture diastereoisomers was obtained. They were separated via flash chromatography using HILIC eluents. The diastereoisomer eluting later was collected as (2R)-2-[[(5$S_a$)-5-[3-chloro-2-methyl-4-[2-(4-methylpiperazin-1-yl)ethoxy]phenyl]-6-prop-1-ynyl-thieno[2,3-d]pyrimidin-4-yl]amino]-3-(2-hydroxy phenyl)propanoic acid. MS: (M+H): 620.2

Step B: Preparation 7b 2.3 g (2R)-2-[[(5$S_a$)-5-[3-chloro-2-methyl-4-[2-(4-methylpiperazin-1-yl)ethoxy]phenyl]-6-prop-1-ynyl-thieno[2,3-d]pyrimidin-4-yl]amino]-3-(2-hydroxyphenyl)propanoic acid (3.71 mmol) was dissolved in 20 mL 1.25M HCl in EtOH and stirred at 40° C. overnight. The mixture was then diluted with $NaHCO_3$ solution and extracted with DCM. The combined organic phases were dried over $Na_2SO_4$, filtered and concentrated in vacuo. The crude product was purified via flash chromatography using EtOAc or DCM and MeOH as eluents to obtain Preparation 7b.

$^1$H NMR (500 MHz, DMSO-$d_6$) δ: 9.47 (s, 1H), 8.41 (s, 1H), 7.21 (s, 1H), 7.21 (s, 1H), 7.00 (td, 1H), 6.70 (dd, 1H), 6.60 (td, 1H), 6.34 (d, 1H), 5.11 (d, 1H), 4.89 (m, 1H), 4.27

(t, 2H), 4.03 (m, 2H), 3.06 (dd, 1H), 2.79 (t, 2H), 2.55 (br, 4H), 2.40 (dd, 1H), 2.30 (br, 4H), 2.12 (s, 3H), 2.00 (s, 3H), 1.97 (s, 3H), 1.11 (t, 3H)

HRMS calculated for $C_{34}H_{38}ClN_5O_4S$: 647.2333; found 648.2385 (M+H).

Preparation 7c: ethyl (2R)-2-[[5-[3-chloro-4-(2-dimethylaminoethyloxy)-2-methyl-phenyl]-6-prop-1-ynyl-thieno[2,3-d]pyrimidin-4-yl]amino]-3-(2-hydroxyphenyl) propanoate

Step A: (2R)-2-[[(5S$_a$)-5-[3-chloro-4-(2-dimethylaminoethyloxy)-2-methyl-phenyl]-6-prop-1-ynyl-thieno[2,3-d]pyrimidin-4-yl]amino]-3-(2-hydroxyphenyl)propanoic acid Using General Procedure IId and Preparation 6b as the appropriate 5-iodo-thieno[2,3-d]pyrimidine derivative and Preparation B5 as the appropriate boronic acid derivative, a mixture diastereoisomers was obtained. They were separated via flash chromatography using HILIC eluents. The diastereoisomer eluting later was collected as (2R)-2-[[(5S$_a$)-5-[3-chloro-4-(2-dimethylaminoethyloxy)-2-methyl-phenyl]-6-prop-1-ynyl-thieno[2,3-d]pyrimidin-4-yl]amino]-3-(2-hydroxyphenyl)propanoic acid. MS (M+H): 565.2

Step B: Preparation 7c 2.3 g (2R)-2-[[(5S$_a$)-5-[3-chloro-4-(2-dimethylaminoethyloxy)-2-methyl-phenyl]-6-prop-1-ynyl-thieno[2,3-d]pyrimidin-4-yl]amino]-3-(2-hydroxyphenyl)propanoic acid (4.07 mmol) was dissolved in 20 mL 1.25M HCl in EtOH and stirred at 40° C. overnight. The mixture was then diluted with NaHCO$_3$ solution and extracted with DCM. The combined organic phases were dried over Na$_2$SO$_4$, filtered and concentrated in vacuo. The crude product was purified via flash chromatography using DCM and MeOH as eluents to obtain Preparation 7c.

$^1$H NMR (500 MHz, DMSO-d$_6$) δ: 9.45 (s, 1H), 8.41 (s, 1H), 7.21 (s, 1H), 7.21 (s, 1H), 7.00 (td, 1H), 6.70 (dd, 1H), 6.60 (td, 1H), 6.34 (d, 1H), 5.12 (d, 1H), 4.89 (m, 1H), 4.26 (m, 2H), 4.03 (m, 2H), 3.06 (dd, 1H), 2.74 (t, 2H), 2.39 (dd, 1H), 2.27 (s, 6H), 2.01 (s, 3H), 1.97 (s, 3H), 1.11 (t, 3H)

HRMS calculated for $C_{31}H_{33}ClN_4O_4S$: 592.1911; found 593.1954 (M+H).

Preparation 7d: ethyl (2R)-2-[[5-bromo-6-(4-fluorophenyl)thieno[2,3-d]pyrimidin-4-yl]amino]-3-(2-hydroxyphenyl)propanoate 2.5 g of Preparation 6a (5.1 mmol) was dissolved in 20 mL 1.25M HCl in EtOH and stirred at 40° C. overnight. The resulting mixture was diluted with aq. NaHCO$_3$ solution and extracted with DCM. The combined organic phases were dried over Na$_2$SO$_4$, filtered and concentrated in vacuo. The crude product was purified via flash chromatography using heptane and EtOAc as eluents to obtain Preparation 7d. $^1$H NMR (400 MHz, DMSO-d$_6$) δ: 9.67 (s, 1H), 8.42 (s, 1H), 7.70 (m, 2H), 7.43-7.37 (m, 3H), 7.14 (dd, 1H), 7.05 (td, 1H), 6.80 (dd, 1H), 6.72 (td, 1H), 5.01 (m, 1H), 4.12 (q, 2H), 3.26 (dd, 1H), 3.14 (dd, 1H), 1.17 (t, 3H)

Preparation 7e: methyl (2R)-2-[[6-ethyl-5-(4-hydroxy-2-methyl-phenyl)thieno[2,3-d]pyrimidin-4-yl]amino]-3-phenyl-propanoate 934 mg Preparation 6c (2 mmol), 903 mg Preparation B6 (2.4 mmol), 231 mg Pd(PPh$_3$)$_4$ (0.2 mmol), 662 mg Ag$_2$CO$_3$ (2.4 mmol) and 81 µL methanol (2 mmol) were dissolved in 20 mL 2-Me-THF and stirred in MW reactor at 110° C. until no further conversion was observed. The mixture was filtered through Celite, diluted with 100 mL EtOAc then 2.5 mL TBAF (1M solution in THF) was added and the mixture was stirred at r.t. until no further conversion was observed. The mixture was then washed with NH$_4$Cl solution and brine, dried over Na$_2$SO$_4$, filtered and concentrated and purified via flash chromatography using heptane and EtOAc as eluents to obtain Preparation 7e as a mixture of diastereoisomers.

$^1$H NMR (400 MHz, CDCl$_3$) δ: 8.43-8.43 (s, 1H), 7.26-6.80 (m, 7H), 6.76-6.64 (m, 2H), 5.18 (m, 1H), 5.03 (m, 1H), 3.66-3.65 (s, 3H), 3.16-3.13 (dd, 1H), 2.73 (dd, 1H), 2.57 (m, 2H), 2.07-1.80 (s, 3H), 1.18-1.17 (t, 3H)

MS (M+H): 448.2

Preparation 7f: methyl (2R)-2-[[5-(3,5-dichloro-4-hydroxy-2-methyl-phenyl)-6-ethyl-thieno[2,3-d]pyrimidin-4-yl]amino]-3-phenyl-propanoate 402 mg Preparation 7e (0.898 mmol) and 300 mg NCS (2.245 mmol) were dissolved in 5 mL THF and stirred at 60° C. until no further conversion was observed. The volatiles were removed in vacuo, the residue was purified via flash chromatography using heptane and EtOAc as eluents to obtain the title product as a mixture of diastereoisomers.

$^1$H NMR (500 MHz, DMSO-d$_6$) δ: 10.46-10.44 (s, 1H), 8.40-8.38 (s, 1H), 7.29-7.24 (s, 1H), 7.20 (m, 3H), 6.80-6.78 (d, 2H), 5.09-5.01 (d, 1H), 4.95 (m, 1H), 3.59-3.58 (s, 3H), 3.15-3.13 (dd, 1H), 2.78-2.61 (dd, 1H), 2.53 (q, 2H), 2.02-1.84 (s, 3H), 1.11 (t, 3H)

HRMS calculated for $C_{25}H_{23}Cl_2N_3O_3S$: 515.0837; found 516.0908 (M+H).

Preparation 7g: methyl (2R)-2-[[5-(3-chloro-4-hydroxy-2-methyl-phenyl)-6-ethyl-thieno[2,3-d]pyrimidin-4-yl]amino]-3-phenyl-propanoate Using General Procedure IIc and Preparation 6c as the appropriate 5-iodo-thieno[2,3-d]pyrimidine derivative and Preparation B2 as the appropriate boronic acid derivative, Preparation 7g was obtained as a mixture of diastereoisomers. MS (M+H): 482.1

Preparation 7gd1: methyl (2R)-2-[[(5S$_a$)-5-(3-chloro-4-hydroxy-2-methyl-phenyl)-6-ethyl-thieno[2,3-d]pyrimidin-4-yl]amino]-3-phenyl-propanoate The diastereoisomers of Preparation 7g were separated via flash chromatography using heptane and EtOAc as eluents. The diastereoisomer eluting later was collected as Preparation 7gd1.

$^1$H NMR (500 MHz, DMSO-d$_6$) δ: 10.53 (s, 1H), 8.36 (s, 1H), 7.23 (m, 2H), 7.20 (m, 1H), 7.04 (d, 1H), 6.98 (d, 1H), 6.80 (m, 2H), 5.11 (d, 1H), 4.90 (m, 1H), 3.57 (s, 3H), 3.10 (dd, 1H), 2.63 (dd, 1H), 2.51-2.46 (m, 2H), 1.86 (s, 3H), 1.10 (t, 3H)

HRMS calculated for $C_{25}H_{24}ClN_3O_3S$: 481.1227; found 482.1313 (M+H).

Preparation 7h: (2R)-2-[[6-ethyl-5-(1H-indol-4-yl)thieno[2,3-d]pyrimidin-4-yl]amino]-3-phenyl-propanoic acid Using General Procedure Ib and Preparation 4v as the the appropriate 4-chloro-thieno[2,3-d]pyrimidine derivative and (2R)-2-amino-3-(2-hydroxyphenyl)propanoic acid as the appropriate amino acid derivative, Preparation 7h was obtained as a mixture of diastereoisomers.

$^1$H NMR (500 MHz, DMSO-d$_6$) δ: 12.71-12.59 (br s, 1H), 11.48-11.37 (s, 1H), 8.35-8.30 (s, 1H), 7.64-7.53 (d, 1H), 7.45-7.39 (dd, 1H), 7.30-7.08 (t, 1H), 7.17-6.33 (m, 6H), 6.07-6.01 (s, 1H), 5.27 (d, 1H), 4.59/4.50 (m, 1H), 2.98-2.83 (dd, 1H), 2.56 (m, 2H), 2.35-2.15 (dd, 1H), 1.11-1.09 (t, 3H)

HRMS calculated for C$_{25}$H$_{22}$N$_4$O$_2$S: 442.1463; found 443.1529 and 443.1538 (M+H).

Preparation 7i: methyl (2R)-2-[[5-(3-chloro-1H-indol-4-yl)-6-ethyl-thieno[2,3-d]pyrimidin-4-yl]amino]-3-phenyl-propanoate

Step A: methyl (2R)-2-[[6-ethyl-5-(1H-indol-4-yl)thieno[2,3-d]pyrimidin-4-yl]amino]-3-phenyl-propanoate 8.87 g Preparation 7h (20 mmol) was dissolved in 60 mL MeOH and 5.88 mL cc. H$_2$SO$_4$ (60 mmol) was added. The mixture was stirred at r.t. under N$_2$ atmosphere for 2 hours. The mixture was then poured into icy water, the precipitate was filtered to obtain methyl (2R)-2-[[6-ethyl-5-(1H-indol-4-yl)thieno[2,3-d]pyrimidin-4-yl]amino]-3-phenyl-propanoate as a mixture of diastereoisomers.

$^1$H NMR (400 MHz, DMSO-d$_6$) δ: 11.52-11.43 (s, 1H), 8.39-8.34 (s, 1H), 7.65-7.57 (d, 1H), 7.47-7.42 (t, 1H), 7.30-7.11 (dd, 1H), 7.18-6.79 (m, 2H), 7.02 (m, 1H), 6.93 (m, 1H), 6.65 (m, 1H), 6.34 (m, 1H), 6.05 (dt, 1H), 5.28 (m, 1H), 4.71-4.62 (m, 1H), 3.55-3.41 (s, 3H), 2.91-2.77 (dd, 1H), 2.57 (m, 2H), 2.37-2.23 (dd, 1H), 1.11-1.10 (t, 3H)

MS (M+H): 457.2 and 457.2

Step B: Preparation 7i 8.477 g methyl (2R)-2-[[6-ethyl-5-(1H-indol-4-yl)thieno[2,3-d]pyrimidin-4-yl]amino]-3-phenyl-propanoate (18.5 mmol), 2.47 g NCS (18.5 mmol) and 30 mL abs. THF were stirred at r.t. until no further conversion was observed. Then the mixture was poured into icy water and was extracted with EtOAc. The combined organic phases were dried over Na$_2$SO$_4$, filtered and concentrated under reduced pressure. The crude product was purified via flash chromatography using heptane and EtOAc as eluents to obtain Preparation 7i as a mixture of diastereoisomers.

$^1$H NMR (500 MHz, DMSO-d$_6$) δ: 11.73-11.65 (d, 1H), 8.35-8.31 (s, 1H), 7.63-7.56 (d, 1H), 7.62-7.54 (d, 1H), 7.44-7.15 (dd, 1H), 7.20-7.03 (m, 3H), 7.04-6.84 (d, 1H), 6.70-6.44 (dm, 2H), 5.09-4.98 (d, 1H), 4.80-4.72 (m, 1H), 3.51-3.38 (s, 3H), 2.93-2.81 (dd, 1H), 2.52 (m, 2H), 2.46-2.29 (dd, 1H), 1.10-1.09 (t, 3H)

HRMS calculated for C$_{26}$H$_{23}$ClN$_4$O$_2$S: 490.1230; found 491.1282 and 491.1316 (M+H).

Preparation 7j: 4-chloro-5-(3-chloro-1H-indol-4-yl)-6-ethyl-thieno[2,3-d]pyrimidine The mixture of 1.099 g Preparation 4v (3.5 mmol) and 0.572 g NCS (4.2 mmol) in 20 mL CCl$_4$ was stirred at r.t. until no further conversion was observed. The mixture was then poured onto crushed ice, and it was extracted with DCM. The combined organic layers were dried over Na$_2$SO$_4$, filtered and concentrated under reduced pressure. The crude product was purified via flash chromatography using heptane and EtOAc as eluents to obtain 4-chloro-5-(3-chloro-1H-indol-4-yl)-6-ethyl-thieno[2,3-d]pyrimidine Preparation 7j. $^1$H NMR (400 MHz, CDCl$_3$) δ: 8.79 (s, 1H), 8.33 (br s, 1H), 7.47 (dd, 1H), 7.31 (t, 1H), 7.18 (d, 1H), 7.03 (dd, 1H), 2.73 (m, 2H), 1.24 (t, 3H)

Preparation 8a: (E)-4-(Dimethylamino)-1,1-dimethoxy-but-3-en-2-one 502.1 g 1,1-dimethoxypropan-2-one (4.25 mol) and 506.4 g 1,1-dimethoxy-N,N-dimethyl-methanamine (4.25 mol) were mixed in a 2 L flask and stirred at 105° C. for 3 hours. The formed MeOH was removed continuously via distillation. When MeOH formation stopped (at 65° C. head temperature) the reaction mixture was vacuum distilled (decreasing the pressure slowly to 30 mbar) to remove side products and unreacted starting materials. The crude product was distilled at 0.1 mbar. Fractions were collected between 107-118° C. head temperature (bath temperature 160-165° C.) to give a yellow oil. $^1$H NMR (500 MHz, DMSO-d$_6$) δ: 7.59 (d, 1H), 5.17 (d, 1H), 4.42 (s, 1H), 3.25 (s, 6H), 3.09 (s, 3H), 2.78 (s, 3H)

Preparation 8b: 4-(Dimethoxymethyl)-2-methylsulfonyl-pyrimidine

Step A: 4-(Dimethoxymethyl)-2-methylsulfanyl-pyrimidine 198 g sodium methoxide (3.67 mmol) was dissolved in 3 L MeOH and cooled to 0° C. 322 g thiocarbamide (4.23 mol) was added portionwise and the mixture was stirred for 1 hour. Then 488 g Preparation 8a (2.82 mol) was added dropwise at 0° C., then it was heated to 70° C. until no further conversion was observed. It was cooled to r.t., 237 mL methyl iodide (3.81 mol) was added dropwise, keeping the temperature below 28° C., and the resulting mixture was stirred overnight at r.t. It was filtered, the filtrate was concentrated under reduced pressure, diluted with EtOAc, washed with water and brine. The combined aqueous layers were extracted with EtOAc. The combined organic layers were dried over Na$_2$SO$_4$, filtered and concentrated under reduced pressure. The residue was dissolved in 500 mL Et$_2$O, filtered through a pad of silica, using Et$_2$O as eluent. The filtrate was concentrated under reduced pressure to give a light brown oil. $^1$H NMR (400 MHz, DMSO-d$_6$) δ: 8.69 (d, 1H), 7.23 (d, 1H), 5.22 (s, 1H), 3.33 (s, 6H), 2.52 (s, 3H)

Step B: Preparation 8b

To a solution of 180 g 4-(dimethoxymethyl)-2-methylsulfanyl-pyrimidine (940 mmol) in 1.5 L methanol and 1.5 L water 752 g Oxone® (potassium peroxymonosulfate, 1220 mmol) was added portionwise at −5° C., then stirred at 0° C. overnight. The reaction mixture was concentrated under reduced pressure to half volume using a 30° C. bath and then the mixture was filtered, and the precipitate was washed with DCM. The filtrate was extracted with DCM. The combined organic layers were dried over MgSO$_4$, filtered and concentrated under reduced pressure to give a light brown oil. $^1$H NMR (400 MHz, CDCl$_3$) δ: 8.98 (d, 1H), 7.97 (d, 1H), 5.36 (s, 1H), 3.47 (s, 6H), 3.39 (s, 3H)

Preparation 9a: methyl (2R)-2-amino-3-(2-hydroxyphenyl)propanoate hydrochloride 24.6 g (2R)-2-amino-3-(2-hydroxyphenyl)propanoic acid (136 mmol) was stirred at r.t. in 900 mL solution of 3M HCl in methanol for 40 hours. The reaction mixture was concentrated under reduced pressure keeping the bath temperature below 40° C. The residue was triturated with diethyl ether to give the product as a cream colored shining powder. HRMS calculated for $C_{11}H_{15}NO_3$ (free base): 209.1052; found 210.1128 (M+H).

Preparation 9b: methyl (2R)-2-(tert-butoxycarbonylamino)-3-(2-hydroxyphenyl) propanoate 16.7 g Preparation 9a (73.0 mmol) was suspended in 180 mL DCM. 30.5 mL (219 mmol) TEA was added and the solution was cooled using a water-ice bath. A solution of 15.6 g di-tert-butyl bicarbonate (73.0 mmol) in 75 mL DCM was added slowly (2.5 hours). The mixture was stirred overnight at r.t. Then 100 mL water was added and the organic phase was separated, washed with water, 1M HCl solution and finally with water again. The organic phase was dried over $Na_2SO_4$, filtered and the filtrate was concentrated under reduced pressure to obtain the product as an oil.

Preparation A1: (2R)-2-amino-3-[2-[(2-methylpyrazol-3-yl)methoxy]phenyl]propanoic acid Using General procedure IXa and (2-methylpyrazol-3-yl)methanol as the appropriate alcohol derivative, Preparation A1 was obtained. MS (M+H): 276.2

Preparation A2: (2R)-2-amino-3-[2-[(2-ethoxypyrimidin-4-yl)methoxy]phenyl]propanoic acid Using General procedure IXa and Preparation C1 as the appropriate alcohol derivative, Preparation A2 was obtained. MS (M+H): 318.1

Preparation A3: (2R)-2-amino-3-[2-[(2-butylpyrazol-3-yl)methoxy]phenyl]propanoic acid Using General procedure IXa and Preparation C2 as the appropriate alcohol derivative, Preparation A3 was obtained. MS (M+H): 318.2

Preparation A4: (2R)-2-amino-3-[2-[[2-(2-methoxyphenyl)pyrimidin-4-yl]methoxy]phenyl]propanoic acid Using General procedure IXa and Preparation C3 as the appropriate alcohol derivative, Preparation A4 was obtained. MS (M+H): 380.2

Preparation A5: (2R)-2-amino-3-[2-(2-pyridylmethoxy)phenyl]propanoic acid

Using General procedure IXa and 2-pyridylmethanol as the appropriate alcohol derivative, Preparation A5 was obtained. MS (M+H): 273.1

Preparation A6: (2R)-2-amino-3-[2-(2,2,2-trifluoroethoxy)phenyl]propanoic acid

Using General procedure IXb and 2,2,2-trifluoroethyl trifluoromethanesulfonate as the appropriate alkylating reagent, Preparation A6 was obtained. MS (M+H): 264.1

Preparation A7: (2R)-2-amino-3-[2-[(2-ethylpyrazol-3-yl)methoxy]phenyl]propanoic acid Using General procedure IXa and (2-ethylpyrazol-3-yl)methanol as the appropriate alcohol derivative, Preparation A7 was obtained. HRMS calculated for $C_{15}H_{19}N_3O_3$: 289.1426, found: 290.1512 (M+H).

Preparation A8: (2R)-2-amino-3-[2-[[2-(2,2,2-trifluoroethoxy)pyrimidin-4-yl]methoxy]phenyl]propanoic acid Using General procedure IXa and Preparation C8 as the appropriate alcohol derivative, Preparation A8 was obtained. MS (M+H): 372.1

Preparation A9: (2R)-2-amino-3-[2-[2-(dimethylamino)-2-oxo-ethoxy]phenyl]propanoic acid Using General procedure IXb and 2-chloro-N,N-dimethylacetamide as the appropriate alkylating reagent, Preparation A9 was obtained. MS (M+H): 267.1

Preparation A10: (2R)-2-amino-3-[2-(2-cyclopentylethoxy)phenyl]propanoic acid

Using General procedure IXa and 2-cyclopentylethanol as the appropriate alcohol derivative, Preparation A10 was obtained. MS (M+H): 278.2

Preparation A11: (2R)-2-amino-3-(2-phenethyloxyphenyl)propanoic acid hydrochloride Using General procedure IXa and 2-phenylethanol as the appropriate alcohol derivative, Preparation A11 was obtained. MS (M+H): 286.1

Preparation A12: (2R)-2-amino-3-[2-(3-phenylpropoxy)phenyl]propanoic acid

Using General procedure IXa and 3-phenylpropan-1-ol as the appropriate alcohol derivative, Preparation A12 was obtained. MS (M+H): 300.2

Preparation A13: (2R)-2-amino-3-[2-[(3-chlorophenyl)methoxy]phenyl]propanoic acid Using General procedure IXa and (3-chlorophenyl)methanol as the appropriate alcohol derivative, Preparation A13 was obtained. MS (M+H): 306.1

Preparation A14: (2R)-2-amino-3-[2-[2-(4-methylpiperazin-1-yl)ethoxy]phenyl]propanoic acid Using General procedure IXa and 2-(4-methylpiperazin-1-yl)ethanol as the appropriate alcohol derivative, Preparation A14 was obtained. MS (M+H): 308.2

Preparation A15: (2R)-2-amino-3-[2-(2-dimethylaminoethyloxy)phenyl]propanoic acid Using General procedure IXa and 2-(dimethylamino)ethanol as the appropriate alcohol derivative, Preparation A15 was obtained. MS (M+H): 253.2

Preparation A16: (2R)-2-amino-3-[2-[3-(dimethylamino)propoxy]phenyl]propanoic acid Using General procedure IXa and 3-(dimethylamino)propan-1-ol as the appropriate alcohol derivative, Preparation A16 was obtained. MS (M+H): 267.2

Preparation B1: 3-methyl-4-(3,3,4,4-tetramethyl-borolan-1-yl)-1H-indole 1.87 g 4-bromo-3-methyl-1H-indole (8.9 mmol), 5.028 g bis(pinacolato)diboron (19.6 mmol), and 2.65 g potassium acetate (26.7 mmol) were dissolved in 35 mL dry DMF under Argon, then 652 mg [1,1'-bis(diphenylphosphino)ferrocene]dichloropalladium(II) (0.89 mmol) was added. The reaction mixture was heated to 85° C. and stirred until no further conversion was observed. Then it was concentrated under reduced pressure and purified via flash chromatography using heptane and EtOAc as eluents to obtain Preparation B1.

$^1$H NMR (400 MHz, CDCl$_3$) δ: 7.92 (br s, 1H), 7.56 (d, 1H), 7.42 (dd, 1H), 7.16 (t, 1H), 7.01 (d, 1H), 2.47 (d, 3H), 1.40 (s, 12H)

HRMS calculated for C$_{15}$H$_{20}$NO$_2$B: 257.1587; found 258.1665 (M+H).

Preparation B2: 2-Chloro-3-methyl-4-(4,4,5,5-tetramethyl-1,3,2-dioxaborolan-2-yl) phenol

Step A: (4-Bromo-2-chloro-phenoxy)-trimethyl-silane 20.8 g 4-bromo-2-chloro-phenol (100 mmol) was dissolved in 150 mL dry THF then 24.2 g HMDS (150 mmol) was added. The reaction mixture was stirred at 85° C. under argon atmosphere for 1.5 hours then concentrated under reduced pressure. The resulted crude product was used without further purification. $^1$H NMR (200 MHz, CDCl$_3$) δ: 7.49 (d, 1H), 7.23 (dd, 1H), 6.75 (d, 1H), 0.26 (s, 9H)

Step B: 4-Bromo-2-chloro-3-methyl-phenol 48 mL "BuLi solution (120 mmol, 2.5 M in hexanes) was added dropwise to a solution of 12.1 g dry DIPA (120 mmol) in 250 mL dry THF at −78° C. under argon atmosphere. The mixture was stirred for 30 minutes at the same temperature then 28.0 g (4-bromo-2-chloro-phenoxy)-trimethyl-silane (100 mmol) was added dropwise. After 2.5 hours 21.3 g MeI (150 mmol) was added dropwise then the cooling bath was removed and the mixture was stirred overnight. The reaction was quenched with 100 mL NH$_4$OH solution and 200 mL NH$_4$Cl solution then extracted with EtOAc. The organic phase was dried over Na$_2$SO$_4$, filtered and the filtrate was concentrated under reduced pressure. The resulting dark mass was refluxed with pure hexane several times (150-150 mL aliquots) and decanted leaving a black tar behind. The combined organic phases were concentrated under reduced pressure affording 19.0 g crude product, which was used without further purification. $^1$H NMR (200 MHz, CDCl$_3$) δ: 7.32 (d, 1H), 6.76 (d, 1H), 5.62 (s, 1H), 2.49 (s, 3H)

Step C: (4-Bromo-2-chloro-3-methyl-phenoxy)-trimethyl-silane 20.8 g HMDS (129 mmol) was added to the solution of 19.0 g 4-bromo-2-chloro-3-methyl-phenol (86.0 mmol) in 150 mL dry THF. The mixture was stirred at 85° C. under argon balloon for 1.5 hours and then concentrated under reduced pressure. The obtained product was used without further purification. $^1$H NMR (200 MHz, CDCl$_3$) δ: 7.30 (d, 1H), 6.63 (d, 1H), 2.50 (s, 3H), 0.28 (s, 9H)

Step D: Preparation B2

A solution of 25.2 g (4-bromo-2-chloro-3-methyl-phenoxy)-trimethyl-silane (86.0 mmol) in 250 mL dry THF was cooled to −78° C. under argon and then 38 mL "BuLi solution (94.6 mmol, 2.5M in hexanes) was added dropwise. After 5 minutes 19.2 g 2-isopropoxy-4,4,5,5-tetramethyl-1,3,2-dioxaborolane (103 mmol) was added dropwise. The cooling bath was removed and the mixture was slowly allowed to warm up to r.t. Then the mixture was added to 200 mL NH$_4$Cl solution and extracted with EtOAc. The combined organic layers were concentrated under reduced pressure and passed through a pad of silica gel using hexane and EtOAc as eluents. The crude product was recrystallized from a mixture of EtOAc and hexane to obtain Preparation B2. $^1$H NMR (500 MHz, DMSO-d$_6$) δ: 10.40 (s, 1H), 7.42 (d, 1H), 6.80 (d, 1H), 2.49 (s, 3H), 1.27 (s, 12H)

Preparation B3: [2-Chloro-3-methyl-4-(4,4,5,5-tetramethyl-1,3,2-dioxaborolan-2-yl) phenoxy]-triisopropyl-silane

Step A: (4-Bromo-2-chloro-phenoxy)-triisopropyl-silane 200 g 4-bromo-2-chloro-phenol (0.97 mol) and 126 mL TIPSCl (1.18 mol) were dissolved in 1.6 L DCM. 167 g imidazole (2.45 mol) was added and the mixture was stirred at r.t. for 2 hours. Then the volatiles were evaporated under reduced pressure and the residue was dissolved in 1.5 L EtOAc. The mixture was washed with brine, dried over Na$_2$SO$_4$, filtered and the filtrate was concentrated under reduced pressure. The triisopropylsilyl hydroxide impurity was removed by distillation (120° C. at 0.01 mmHg). The residue was filtered through a short pad of silica with hexane and concentrated under reduced pressure. The product (colourless oil) was used in the next step without further purification.

$^1$H NMR (400 MHz, CDCl$_3$) δ: 7.49 (d, 1H), 7.21 (dd, 1H), 6.78 (d, 1H), 1.31 (septet, 3H), 1.14 (d, 18H)

MS (EI, 70 eV) m/z (% relative intensity, [ion]): 63 (30), 79 (24), 93 (41), 170 (17), 235 (19), 251 (16), 265 (24), 293 (23), 319 (77), 321 (100), 323 (28), 362 (1, [M+]).

Step B: (4-Bromo-2-chloro-3-methyl-phenoxy)-triisopropyl-silane 76.0 mL dry DIPA (0.54 mol) was dissolved in 1.2 L dry THF under argon atmosphere and 51.2 mL "BuLi solution (0.512 mol, 10M in hexanes) was added dropwise at −78° C. The mixture was stirred for 45 minutes at the same temperature. Then 178 g (4-bromo-2-chloro-phenoxy)-triisopropyl-silane (0.488 mol) was added dropwise at −78° C. and the white suspension was stirred until no further conversion was observed. Then 36.5 mL MeI (0.586 mmol) was added at this temperature and the reaction mixture was stirred overnight without further cooling. The volatiles were evaporated under reduced pressure. The residue was dissolved in 1.5 L EtOAc, washed with brine. The organic phase was dried over Na$_2$SO$_4$, filtered and the filtrate was concentrated under reduced pressure. The crude product was filtered through a short pad of silica using hexane as eluent and concentrated under reduced pressure to obtain the product as pale yellow oil. $^1$H NMR (400 MHz, CDCl$_3$) δ: 7.30 (d, 1H), 6.68 (d, 1H), 2.53 (s, 3H), 1.32 (septet, 3H), 1.14 (d, 18H)

Step C: Preparation B3

178 g (4-bromo-2-chloro-3-methyl-phenoxy)-triisopropyl-silane (0.472 mol) was dissolved in 1.4 L dry THF under argon atmosphere and 52 mL ⁿBuLi solution (0.52 mol, 10M in hexanes) was added dropwise at −78° C. The mixture was stirred for 5 minutes at this temperature. Then 116 mL 2-isopropoxy-4,4,5,5-tetramethyl-1,3,2-dioxaborolane (0.569 mol) was added and the mixture was allowed to warm up to r.t. The volatiles were evaporated under reduced pressure. The residue was dissolved in 1.5 L EtOAc, washed with brine. The organic phase was dried over $Na_2SO_4$, filtered and the filtrate was concentrated under reduced pressure. The 2-isopropoxy-4,4,5,5-tetramethyl-1,3,2-dioxaborolane impurity was removed by distillation (80° C. at 0.01 mmHg). The crude product was triturated in MeOH affording Preparation B3 as a white solid. $^1$H NMR (400 MHz, CDCl$_3$) δ: 7.53 (d, 1H), 6.74 (d, 1H), 2.60 (s, 3H), 1.34 (s, 12H), 1.32 (m, 3H), 1.12 (d, 18H)

Preparation B4: 1-[2-[2-Chloro-3-methyl-4-(4,4,5,5-tetramethyl-1,3,2-dioxaborolan-2-yl)phenoxy]ethyl]-4-methyl-piperazine 10.0 g Preparation B2 (37.2 mmol), 8.7 g 2-(4-methyl-piperazin-1-yl)ethanol (60.3 mmol) and 15.8 g PPh$_3$ (60.3 mmol) were dissolved in 100 mL dry toluene and then 27 mL diethyl azodicarboxylate (60.3 mmol, 40% solution in toluene) was added dropwise. The mixture was stirred at 50° C. under argon until no further conversion was observed. The volatiles were evaporated under reduced pressure and 100 mL Et$_2$O was added. The precipitated white crystals were filtered off and washed with Et$_2$O. The filtrate was concentrated under reduced pressure and purified via flash chromatography using CHCl$_3$ and MeOH as eluents. The resulting light brown oil was crystallized from hexane to give Preparation B4 as an off-white solid. $^1$H NMR (500 MHz, DMSO-d$_6$) δ: 7.56 (d, 1H), 6.99 (d, 1H), 4.15 (t, 2H), 2.72 (t, 2H), 2.51 (s, 3H), 2.50 (br s, 4H), 2.29 (br s, 4H), 2.13 (s, 3H), 1.29 (s, 12H)

Preparation B5: 1-[2-[2-Chloro-3-methyl-4-(4,4,5,5-tetramethyl-1,3,2-dioxaborolan-2-yl)phenoxy]ethyl]-4-methyl-piperazine 10.0 g Preparation B2 (37.2 mmol), 5.366 g N,N-dimethylethanolamine (60.3 mmol) and 15.8 g PPh$_3$ (60.3 mmol) were dissolved in 100 mL dry toluene and then 27 mL diethyl azodicarboxylate (60.3 mmol, 40% solution in toluene) was added dropwise. The mixture was stirred at 50° C. under argon until no further conversion was observed. The volatiles were evaporated under reduced pressure and 100 mL Et$_2$O was added. The precipitated white crystals were filtered off and washed with Et$_2$O. The filtrate was concentrated under reduced pressure and purified via flash chromatography using CHCl$_3$ and MeOH as eluents. The resulting light brown oil was crystallized from hexane to give Preparation B5. $^1$H NMR (400 MHz, DMSO-d$_6$) δ: 7.56 (d, 1H), 6.99 (d, 1H), 4.13 (t, 2H), 2.66 (t, 2H), 2.51 (s, 3H), 2.23 (s, 6H), 1.29 (s, 12H)

Preparation B6: [4-(5,5-dimethyl-1,3,2-dioxaborinan-2-yl)-3-methyl-phenoxy]-triisopropyl-silane Step A: 4-(5,5-dimethyl-1,3,2-dioxaborinan-2-yl)-3-methyl-phenol 4.675 g (4-hydroxy-2-methyl-phenyl)boronic acid (30.76 mmol), 3.204 neopentyl glycol (32.9 mmol), Amberlyst 15H$^+$ and 150 mL 2-Me-THF were stirred at r.t. under N$_2$ atmosphere until no further conversion was observed. The mixture was then filtered through Celite and the filtrate was concentrated under reduced pressure to obtain 4-(5,5-dimethyl-1,3,2-dioxaborinan-2-yl)-3-methyl-phenol. $^1$H NMR (400 MHz, CDCl$_3$) δ: 7.64 (m, 1H), 6.60 (m, 2H), 5.23 (br s, 1H), 3.75 (s, 4H), 2.47 (s, 3H), 1.01 (s, 6H)

Step B: Preparation B6

30.76 mmol 4-(5,5-dimethyl-1,3,2-dioxaborinan-2-yl)-3-methyl-phenol, 8.56 mL TIPSCl (40 mmol) and 4.19 g imidazole (61.52 mmol) were dissolved in 100 mL DCM and stirred at r.t. under N$_2$ atmosphere until no further conversion was observed. Imidazolium hydrochloride was removed by filtration, the filtrate was concentrated under reduced pressure and purified via flash chromatography using heptane and EtOAc as eluents to obtain Preparation B6. $^1$H NMR (400 MHz, CDCl$_3$) δ: 7.62 (d, 1H), 6.68-6.66 (m, 2H), 3.76 (s, 4H), 2.47 (s, 3H), 1.32-1.21 (m, 3H), 1.11 (d, 18H), 1.03 (s, 6H)

Preparation B7: 2-(3-bromo-2-methyl-phenyl)-4,4,5,5-tetramethyl-1,3,2-dioxaborolane 2.362 g 2,6-dibromo-toluene (9.45 mmol) was dissolved in 10 mL dry THF under N$_2$ atmosphere and the mixture was cooled to −78° C. Then 5.2 mL nBuLi (2.0M in pentane, 10.4 mmol) was added dropwise and the mixture was stirred for 15 minutes. Then 2.31 mL 2-isopropoxy-4,4,5,5-tetramethyl-1,3,2-dioxaborolane (11.3 mmol) was added dropwise and the mixture was allowed to warm up to r.t. It was stirred until no further conversion was observed. Then the mixture was quenched with aqueous NH$_4$Cl solution, then extracted with EtOAc. The combined organic layer was dried over Na$_2$SO$_4$, filtered and the filtrate was concentrated under reduced pressure. The crude product was purified via flash chromatography using heptane and EtOAc as eluents to obtain Preparation B7. $^1$H NMR (400 MHz, CDCl$_3$) δ: 7.67 (d, 1H), 7.62 (d, 1H), 7.10 (t, 1H), 2.53 (s, 3H), 1.29 (s, 12H)

Preparation C1: (2-ethoxypyrimidin-4-yl)methanol

Step A: 4-(dimethoxymethyl)-2-ethoxy-pyrimidine 1500 mg Preparation 8b (6.46 mmol) was dissolved in 60 mL ethanol, then 527 mg sodium ethoxide (7.75 mmol) was added and the mixture was stirred at r.t. for 1 hour. The volatiles were evaporated under reduced pressure and the residue was purified via flash chromatography using heptane and EtOAc as eluents to give 4-(dimethoxymethyl)-2-ethoxy-pyrimidine. MS (M+H): 199.2

Step B: Preparation C1

Using General Procedure Va and 4-(dimethoxymethyl)-2-ethoxy-pyrimidine as the appropriate acetal, Preparation C1 was obtained. MS (M+H): 155.2

Preparation C2: (1-Butyl-1H-pyrazol-5-yl)methanol

Using General Procedure Vb and 1-butylpyrazole as the appropriate alkyl pyrazole, Preparation C2 was obtained.
$^1$H NMR (400 MHz, DMSO-d$_6$) δ: 7.30 (d, 1H), 6.12 (d, 1H), 5.23 (t, 1H), 4.49 (d, 2H), 4.06 (t, 2H), 1.72 (m, 2H), 1.26 (m, 2H), 0.88 (t, 3H)
MS (M+H): 155.2

Preparation C3: [2-(2-methoxyphenyl)pyrimidin-4-yl]methanol

Step A: 4-(dimethoxymethyl)-2-(2-methoxyphenyl)pyrimidine

Using General Procedure Vc and 2-methoxybenzamidine acetic acid salt as the appropriate amidine salt, 4-(dimethoxymethyl)-2-(2-methoxyphenyl)pyrimidine was obtained. 1H NMR (400 MHz, DMSO-$d_6$) δ: 8.93 (d, 1H), 7.55-7.44 (m, 3H), 7.16 (d, 1H), 7.06 (m, 1H), 5.31 (s, 1H), 3.76 (s, 3H), 3.37 (s, 6H)

Step B: Preparation C3

261 mg 4-(dimethoxymethyl)-2-(2-methoxyphenyl)pyrimidine (1.0 mmol) was dissolved in 2 mL HCl in dioxane (4M solution), then 2 mL water was added and this mixture was stirred at 50° C. for 16 hours. The reaction mixture was cooled to 0° C., then 320 mg NaOH (8.0 mmol) was added portionwise. The pH was adjusted to 8 using 10% $K_2CO_3$ solution, then 76 mg sodium borohydride (2.0 mmol) was added and the mixture was stirred for 30 minutes at 0° C. The reaction mixture was diluted with 5 mL water and extracted with EtOAc. The combined organic phases were dried over $Na_2SO_4$, filtered and the filtrate was concentrated under reduced pressure. The crude product was purified via flash chromatography using heptane and EtOAc as eluents to give Preparation C3. $^1$H NMR (400 MHz, DMSO-$d_6$) δ: 8.84 (d, 1H), 7.50-7.42 (m, 3H), 7.14 (d, 1H), 7.03 (m, 1H), 5.66 (t, 1H), 4.58 (d, 2H), 3.75 (s, 3H)

Preparation C4: (1-tert-Butyl-1H-pyrazol-5-yl)methanol

Step A: 1-tert-butyl-5-(dimethoxymethyl)-1H-pyrazole

Using General Procedure Vd and tert-butylhydrazine hydrochloride as the appropriate hydrazine hydrochloride, 1-tert-butyl-5-(dimethoxymethyl)-1H-pyrazole was obtained. 1H NMR (400 MHz, DMSO-$d_6$) δ: 7.34 (d, 1H), 6.34 (d, 1H), 5.74 (s, 1H), 3.24 (s, 6H), 1.57 (s, 9H)
Note: 1-tert-butyl-3-(dimethoxymethyl)-1H-pyrazole was also obtained. $^1$H NMR (400 MHz, DMSO-$d_6$) δ: 7.75 (d, 1H), 6.18 (d, 1H), 5.34 (s, 1H), 3.24 (s, 6H), 1.50 (s, 9H)

Step B: Preparation C4

Using General Procedure Ve and 1-tert-butyl-5-(dimethoxymethyl)-1H-pyrazole as the appropriate acetal, Preparation C4 was obtained. $^1$H NMR (400 MHz, DMSO-$d_6$) δ: 7.27 (d, 1H), 6.19 (d, 1H), 5.31 (t, 1H), 4.61 (d, 2H), 1.56 (s, 9H)

Preparation C5: [2-(2-methoxyethyl)pyrimidin-4-yl]methanol

Step A: 4-(dimethoxymethyl)-2-(2-methoxyethyl)pyrimidine

Using General Procedure Vc and 3-methoxypropanamidine hydrochloride as the appropriate amidine hydrochloride, 4-(dimethoxymethyl)-2-(2-methoxyethyl)pyrimidine was obtained. $^1$H NMR (400 MHz, DMSO-$d_6$) δ: 8.78 (d, 1H), 7.38 (d, 1H), 5.25 (s, 1H), 3.80 (t, 2H), 3.33 (s, 6H), 3.22 (s, 3H), 3.11 (t, 2H)

Note: 2-[4-(dimethoxymethyl)pyrimidin-2-yl]-N,N-dimethyl-ethanamine was also obtained. MS (M+H): 226.2

Step B: Preparation C5

Using General Procedure Va and 4-(dimethoxymethyl)-2-(2-methoxyethyl)pyrimidine as the appropriate acetal, Preparation C5 was obtained. $^1$H NMR (400 MHz, DMSO-$d_6$) δ: 8.70 (d, 1H), 7.39 (d, 1H), 5.60 (t, 1H), 4.52 (d, 2H), 3.78 (t, 2H), 3.22 (s, 3H), 3.06 (t, 2H)

Preparation C6: [1-(2,2,2-Trifluoroethyl)-1H-pyrazol-5-yl]methanol

Step A: 5-(dimethoxymethyl)-1-(2,2,2-trifluoroethyl)-4,5-dihydro-1H-pyrazol-5-ol Using General Procedure Vd in the absence of sodium methoxide and using ethanol instead of methanol and 2,2,2-trifluoroethylhydrazine (70 w/w % in water) as the appropriate hydrazine, 5-(dimethoxymethyl)-1-(2,2,2-trifluoroethyl)-4,5-dihydro-1H-pyrazol-5-ol was obtained. $^1$H NMR (400 MHz, DMSO-$d_6$) δ: 6.83 (t, 1H), 6.03 (s, 1H), 4.30 (s, 1H), 3.95 (m, 1H), 3.47 (m, 1H), 3.40 (d, 6H), 2.88 (m, 1H), 2.50 (m, 1H)

Step B: Preparation C6

Using General Procedure Ve and 5-(dimethoxymethyl)-1-(2,2,2-trifluoroethyl)-4,5-dihydro-1H-pyrazol-5-ol as the appropriate acetal, Preparation C6 was obtained. $^1$H NMR (400 MHz, DMSO-$d_6$) δ: 7.48 (d, 1H), 6.27 (d, 1H), 5.46 (t, 1H), 5.08 (q, 2H), 4.56 (d, 2H)

Preparation C7: (2-(Morpholin-4-yl)pyrimidin-4-yl)methanol

Step A: 4-[4-(dimethoxymethyl)pyrimidin-2-yl]morpholine 25.0 g Preparation 8b (107.6 mmol) was dissolved in 161 mL morpholine and the mixture was stirred at r.t. until no further conversion was observed. Then it was concentrated under reduced pressure and the crude product was purified via flash chromatography using heptane and EtOAc as eluents to obtain 4-[4-(dimethoxymethyl)pyrimidin-2-yl]morpholine.

Step B: Preparation C7

Using General Procedure Va and 4-[4-(dimethoxymethyl)pyrimidin-2-yl]morpholine as the appropriate acetal, Preparation C7 was obtained. $^1$H NMR (400 MHz, DMSO-$d_6$) δ: 8.35 (d, 1H), 6.75 (dm, 1H), 5.431 (t, 1H), 4.36 (dm, 2H), 3.67 (m, 4H), 3.63 (m, 4H)

Preparation C8: [2-(2,2,2-trifluoroethoxy)pyrimidin-4-yl]methanol

Step A: 4-(dimethoxymethyl)-2-(2,2,2-trifluoroethoxy)pyrimidine 5.00 g Preparation 8b (21.5 mmol) was dissolved in 54 mL dry acetonitrile, then 5.95 g $K_2CO_3$ (43.1 mmol) and 3.24 g 2,2,2-trifluoroethanol (32.3 mmol) were added, and the mixture was stirred at 60° C. until no further conversion was observed. The reaction mixture was cooled, filtered, the solid was washed with EtOAc, then the filtrate was concentrated under reduced pressure. The crude product was purified via flash chromatography using heptane and EtOAc as eluents to give 4-(dimethoxymethyl)-2-(2,2,2-trifluoroethoxy)pyrimidine. $^1$H NMR (400 MHz, DMSO-$d_6$) δ: 8.74 (d, 1H), 7.32 (d, 1H), 5.25 (s, 1H), 5.05 (q, 2H), 3.34 (s, 6H)

Step B: Preparation C8

Using General Procedure Va and 4-(dimethoxymethyl)-2-(2,2,2-trifluoroethoxy)pyrimidine as the appropriate acetal, Preparation C8 was obtained. $^1$H NMR (400 MHz, DMSO-$d_6$) δ: 8.65 (d, 1H), 7.32 (d, 1H), 5.69 (t, 1H), 5.02 (q, 2H), 4.51 (d, 2H)

Preparation C9: [2-(2-Fluorophenyl)pyrimidin-4-yl]methanol

Step A: 2-Fluoro-N'-hydroxy-benzamidine

The mixture of 11.48 g hydroxylamine hydrochloride (165 mmol), 13.87 g NaHCO$_3$ (165 mmol) and 120 mL MeOH was stirred at r.t. for 30 minutes. Then 10 g 2-fluorobenzonitrile (82.6 mmol) was added and the mixture was stirred at 75° C. until no further conversion was observed. The solvent was partially evaporated under reduced pressure, the residue was filtered, washed with MeOH. The filtrate was concentrated under reduced pressure, then diluted with water and extracted with EtOAc. The combined organic phases were dried over Na$_2$SO$_4$, filtered and the filtrate was concentrated under reduced pressure to give 2-fluoro-N-hydroxy-benzamidine.

Step B: 2-Fluorobenzamidine 12.67 g 2-fluoro-N-hydroxy-benzamidine (81.55 mmol) was dissolved in 300 mL AcOH at 0° C. and 9.24 mL Ac$_2$O (97.86 mmol) was added. The mixture was stirred at r.t. until no further conversion was observed. Then 630 mg 10% Pd/C was added and the mixture was stirred under H$_2$ atmosphere (4 bars) until no further conversion was observed. The mixture was filtered through celite and the filtrate was concentrated under reduced pressure to obtain 2-fluorobenzamidine acetate. MS (M(free base)+H): 139.4

Step C: 4-(Dimethoxymethyl)-2-(2-fluorophenyl)pyrimidine

Using General Procedure Vc and 2-fluorobenzamidine as the appropriate amidine, 4-(dimethoxymethyl)-2-(2-fluorophenyl)pyrimidine was obtained. MS (M+H): 249.2

Step D: Preparation C9

Using General Procedure Va and 4-(dimethoxymethyl)-2-(2-fluorophenyl)pyrimidine as the appropriate acetal, Preparation C9 was obtained. MS (M+H): 205.2

Preparation C10: [2-[2-(2-methoxyethoxy)phenyl]pyrimidin-4-yl]methanol

Step A: N'-Hydroxy-2-methoxyethoxy-benzamidine 2 eq. hydroxylamine hydrochloride was dissolved in MeOH (1 mL/mmol), then 2 eq. NaHCO$_3$ was added. The mixture was stirred at r.t. for 20 minutes, then 1 eq. 2-methoxyethoxy-benzonitrile was added and the mixture was stirred at reflux until no further conversion was observed. MeOH was partially evaporated, the residue was filtered and the filtrate was concentrated under reduced pressure. The obtained N-hydroxy-2-(2-methoxyethoxy)benzamidine was used without further purification.
$^1$H NMR (400 MHz, CDCl$_3$) δ: 9.48 (s, 1H), 7.45 (m, 1H), 7.34 (m, 1H), 7.08 (d, 1H), 6.94 (td, 1H), 5.65 (br s, 2H), 4.17 (m, 2H), 3.67 (m, 2H), 3.31 (s, 3H)
MS (M+H): 211.2

Step B: 2-methoxyethoxy-benzamidine 8.22 g N'-hydroxy-2-(2-methoxyethoxy)benzamidine (39.1 mmol) was dissolved in 80 mL AcOH at 0° C., then 4.43 mL Ac$_2$O (46.92 mmol) was added dropwise. The mixture was stirred at r.t. until no further conversion was observed. 575 mg 10% Pd/C was added and the mixture was stirred under H$_2$ atmosphere (4 bars) until no further conversion was observed. The mixture was filtered through celite and the filtrate was concentrated under reduced pressure to obtain 2-(2-methoxyethoxy)benzamidine acetate. MS (M+H): 195.2

Step C: 4-(Dimethoxymethyl)-2-[2-methoxyethoxyphenyl]pyrimidine

Using General procedure Vc and 2-(2-methoxyethoxy)benzamidine acetate as the appropriate amidine salt, 4-(dimethoxymethyl)-2-[2-methoxyethoxy-phenyl]pyrimidine was obtained.
$^1$H NMR (400 MHz, CDCl$_3$) δ: 8.92 (d, 1H), 7.55 (m, 1H), 7.47 (m, 1H), 7.45 (m, 1H), 7.17 (d, 1H), 7.08 (m, 1H), 5.29 (s, 1H), 4.12 (m, 2H), 3.57 (m, 2H), 3.36 (s, 6H), 3.20 (s, 3H)
MS (M+H): 305.0

Step D: Preparation C10

Using General Procedure Va and 4-(dimethoxymethyl)-2-[2-methoxyethoxy-phenyl]pyrimidine as the appropriate acetal, Preparation C10 was obtained.
$^1$H NMR (400 MHz, CDCl$_3$) δ: 8.84 (d, 1H), 7.53 (m, 1H), 7.47 (m, 1H), 7.43 (m, 1H), 7.14 (d, 1H), 7.05 (td, 1H), 5.64 (t, 1H), 4.58 (d, 2H), 4.11 (m, 2H), 3.57 (m, 2H), 3.21 (s, 3H)
MS (M+H): 261.0

Example 1: N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-2-methoxy-D-phenylalanine and Example 2: N-[(5R$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-2-methoxy-D-phenylalanine Using General Procedure VI and Preparation 7a as the appropriate phenol derivative and methanol as the appropriate alcohol, then hydrolyzing the formed intermediate according to General Procedure VII, Example 1 was obtained as the earlier eluting diastereoisomer. HRMS calculated for C$_{36}$H$_{37}$ClFN$_5$O$_4$S: 689.2240, found: 345.6182 (M+2H).
Example 2 was obtained as the later eluting diastereoisomer. HRMS calculated for C$_{36}$H$_{37}$ClFN$_5$O$_4$S: 689.2240, found: 345.6185 (M+2H).

Example 3: N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-2-[(1-methyl-1H-pyrazol-5-yl) methoxy]-D-phenylalanine Using General Procedure VI and Preparation 7ad2 as the appropriate phenol derivative and (2-methylpyrazol-3-yl) methanol as the appropriate alcohol, then hydrolyzing the formed intermediate according to General Procedure VII, Example 3 was obtained. HRMS calculated for $C_{40}H_{41}ClFN_7O_4S$: 769.2613, found: 385.6378 (M+2H).

Example 4: N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-2-[(2-ethoxypyrimidin-4-yl) methoxy]-D-phenylalanine and

Example 5: N-[(5R$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-2-[(2-ethoxypyrimidin-4-yl) methoxy]-D-phenylalanine Using General Procedure VI and Preparation 7a as the appropriate phenol derivative and Preparation C1 as the appropriate alcohol, then hydrolyzing the formed intermediate according to General Procedure VII, a mixture of diastereoisomers was obtained. They were separated via preparative reversed phase chromatography using 40 mM aqueous $NH_4OAc$ solution (pH=4, adjusted with AcOH) and acetonitrile as eluents, Example 4 was obtained as the earlier eluting diastereoisomer. HRMS calculated for $C_{42}H_{43}ClFN_7O_5S$: 811.2719, found: 406.6417 (M+2H).

Example 5 was obtained as the later eluting diastereoisomer. HRMS calculated for $C_{42}H_{43}ClFN_7O_5S$: 811.2719, found: 406.6436 (M+2H).

Example 6: 2-[(1-butyl-1H-pyrazol-5-yl)methoxy]-N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-D-phenylalanine Using General Procedure VI and Preparation 7ad2 as the appropriate phenol derivative and Preparation C2 as the appropriate alcohol, then hydrolyzing the formed intermediate according to General Procedure VII, Example 6 was obtained. HRMS calculated for $C_{43}H_{47}ClFN_7O_4S$: 811.3082, found: 406.6616 (M+2H).

Example 7: N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-2-{[2-(2-methoxyphenyl)pyrimidin-4-yl]methoxy}-D-phenylalanine Using General Procedure VI and Preparation 7ad2 as the appropriate phenol derivative and Preparation C3 as the appropriate alcohol, then hydrolyzing the formed intermediate according to General Procedure VII, Example 7 was obtained. HRMS calculated for $C_{47}H_{45}ClFN_7O_5S$: 873.2875, found: 437.6498 (M+2H).

Example 8: N-[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]-2-methoxy-D-phenylalanine and

Example 9: N-[(5R$_a$)-5-{3-chloro-2-methyl-4-[2-(4-methylpiperazin-1-yl)ethoxy]phenyl}-6-(furan-2-yl)thieno[2,3-d]pyrimidin-4-yl]-2-methoxy-D-phenylalanine Using General Procedure Ic and Preparation 4b as the appropriate 4-chloro-thieno[2,3-d]pyrimidine derivative and (2R)-2-amino-3-(2-methoxyphenyl)propanoic acid as the appropriate amino acid derivative, Example 8 was obtained as the earlier eluting diastereoisomer. HRMS calculated for $C_{34}H_{36}ClN_5O_5S$: 661.2126, found: 662.2203 (M+H).

Example 9 was obtained as the later eluting diastereoisomer. HRMS calculated for $C_{34}H_{36}ClN_5O_5S$: 661.2126, found: 662.2203 (M+H).

Example 10: 2-chloro-N-[5-{3-chloro-2-methyl-4-[2-(4-methylpiperazin-1-yl)ethoxy]phenyl}-6-(furan-2-yl)thieno[2,3-d]pyrimidin-4-yl]-D-phenylalanine, diastereoisomer 1

Using General Procedure Ic and Preparation 4b as the appropriate 4-chloro-thieno[2,3-d]pyrimidine derivative and (2R)-2-amino-3-(2-chlorophenyl)propanoic acid as the appropriate amino acid derivative, Example 10 was obtained as the earlier eluting diastereoisomer. HRMS calculated for $C_{33}H_{33}Cl_2N_5O_4S$: 665.1630, found: 666.1670 (M+H).

Example 11: 2-carbamoyl-N-[5-{3-chloro-2-methyl-4-[2-(4-methylpiperazin-1-yl) ethoxy]phenyl}-6-(furan-2-yl)thieno[2,3-d]pyrimidin-4-yl]-D-phenylalanine Step A: 5-[3-chloro-2-methyl-4-[2-(4-methylpiperazin-1-yl)ethoxy]phenyl]-4-fluoro-6-(2-furyl)thieno[2,3-d]pyrimidine A mixture of 150 mg Preparation 4b (0.3 mmol) and 380 mg silver fluoride (3.0 mmol) in 6 mL toluene was heated at reflux temperature for 3 hours. Then it was cooled to r.t., and the inorganic components were filtered off. The filtrate was concentrated under reduced pressure to obtain the crude product which was used in the next step without further purification.

Step B: Example 11

A mixture of 316 mg 5-[3-chloro-2-methyl-4-[2-(4-methylpiperazin-1-yl)ethoxy]phenyl]-4-fluoro-6-(2-furyl)thieno [2,3-d]pyrimidine (0.65 mmol), 271 mg (2R)-2-amino-3-(2-carbamoylphenyl)propanoic acid (1.30 mmol) and 424 mg $Cs_2CO_3$ (1.30 mmol) in 6 mL DMSO was stirred at 40° C. for 30 minutes. The mixture was diluted with water, the pH was adjusted to 5 using 1M HCl solution and extracted with DCM. The organic phase was dried over $Na_2SO_4$, filtered and the filtrate was concentrated under reduced pressure. The crude product was purified via preparative reversed phase chromatography using 0.1% aqueous TFA solution and acetonitrile as eluents. The diastereoisomer eluting earlier was collected as Example 11. HRMS calculated for $C_{34}H_{35}ClN_6O_5S$: 674.2078, found: 675.2146 (M+H).

Example 12: N-[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]-2-(pyridin-2-ylmethoxy)-D-phenylalanine and

Example 13: N-[(5R$_a$)-5-{3-chloro-2-methyl-4-[2-(4-methylpiperazin-1-yl)ethoxy]phenyl}-6-(furan-2-yl)thieno[2,3-d]pyrimidin-4-yl]-2-(pyridin-2-ylmethoxy)-D-phenylalanine Using General Procedure Ic and Preparation 4b as the appropriate 4-chloro-thieno[2,3-d]pyrimidine derivative and Preparation A5 as the appropriate amino acid derivative, Example 12 was obtained as the later eluting diastereoisomer. HRMS calculated for $C_{39}H_{39}ClN_6O_5S$: 738.2391, found: 370.1269 (M+2H).
Example 13 was obtained as the earlier eluting diastereoisomer. HRMS calculated for $C_{39}H_{39}ClN_6O_5S$: 738.2391, found: 370.1263 (M+2H).

Example 14: N-[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]-2-hydroxy-D-phenylalanine

Step A: (2R)-2-[[(5S$_a$)-5-[3-chloro-2-methyl-4-[2-(4-methylpiperazin-1-yl)ethoxy]phenyl]-6-iodo-thieno[2,3-d]pyrimidin-4-yl]amino]-3-(2-hydroxyphenyl)propanoic acid Using General Procedure Ic and Preparation 4a as the appropriate 4-chloro-thieno[2,3-d]pyrimidine derivative and (2R)-2-amino-3-(2-hydroxyphenyl)propanoic acid a mixture of diastereoisomers was obtained. They were separated via HILIC chromatography. (2R)-2-[[(5S$_a$)-5-[3-chloro-2-methyl-4-[2-(4-methylpiperazin-1-yl)ethoxy]phenyl]-6-iodo-thieno[2,3-d]pyrimidin-4-yl]amino]-3-(2-hydroxyphenyl)propanoic acid was obtained as the later eluting diastereoisomer. MS (M+H): 708.0

Step B: Example 14

Using General procedure IIIb and (2R)-2-[[(5S$_a$)-5-[3-chloro-2-methyl-4-[2-(4-methyl piperazin-1-yl)ethoxy]phenyl]-6-iodo-thieno[2,3-d]pyrimidin-4-yl]amino]-3-(2-hydroxy phenyl)propanoic acid as the appropriate 6-iodo-thieno[2,3-d]pyrimidine derivative and 2-(5-fluoro-2-furyl)-4,4,5,5-tetramethyl-1,3,2-dioxaborolane as the appropriate boronic ester derivative, Example 14 was obtained. HRMS calculated for $C_{33}H_{33}ClFN_5O_5S$: 665.1875, found: 333.6012 (M+2H).

Example 15: N-[(5R$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]-2-methoxy-D-phenylalanine and

Example 16: N-[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]-2-methoxy-D-phenylalanine Using General Procedure Ib and Preparation 4c as the appropriate 4-chloro-thieno[2,3-d]pyrimidine derivative and (2R)-2-amino-3-(2-methoxyphenyl)propanoic acid as the appropriate amino acid derivative, Example 15 was obtained as the later eluting diastereoisomer. HRMS calculated for $C_{34}H_{35}ClFN_5O_5S$: 679.2031, found: 680.2100 (M+H).
Example 16 was obtained as the earlier eluting diastereoisomer. HRMS calculated for $C_{34}H_{35}ClFN_5O_5S$: 679.2031, found: 680.2092 (M+H).

Example 17: N-[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]-2-(2,2,2-trifluoroethoxy)-D-phenylalanine

Step A: ethyl (2R)-2-[[(5S$_a$)-5-[3-chloro-2-methyl-4-[2-(4-methylpiperazin-1-yl)ethoxy]phenyl]-6-iodo-thieno[2,3-d]pyrimidin-4-yl]amino]-3-(2-hydroxyphenyl)propanoate 876 mg (2R)-2-[[(5S)-5-[3-chloro-2-methyl-4-[2-(4-methylpiperazin-1-yl)ethoxy]phenyl]-6-iodo-thieno[2,3-d]pyrimidin-4-yl]amino]-3-(2-hydroxyphenyl)propanoic acid (1.24 mmol) was dissolved in 5 mL ethanol then 0.05 mL concentrated sulfuric acid was added and the mixture was stirred at 70° C. for 2 hours. Then the mixture was diluted with water, the pH was set to 5 using 1M $NaHCO_3$ solution and extracted with DCM. The organic phase was dried over $Na_2SO_4$, filtrated and the filtrate was concentrated under reduced pressure. The crude product was purified via flash chromatography using DCM and MeOH as eluents to obtain ethyl (2R)-2-[[(5S$_a$)-5-[3-chloro-2-methyl-4-[2-(4-methylpiperazin-1-yl)ethoxy]phenyl]-6-iodo-thieno[2,3-d]pyrimidin-4-yl]amino]-3-(2-hydroxyphenyl) propanoate. MS (M+H): 736.1

Step B: ethyl (2R)-2-[[(5S$_a$)-5-[3-chloro-2-methyl-4-[2-(4-methylpiperazin-1-yl)ethoxy]phenyl]-6-iodo-thieno[2,3-d]pyrimidin-4-yl]amino]-3-[2-(2,2,2-trifluoroethoxy)phenyl]propanoate 648 mg ethyl (2R)-2-[[(5S$_a$)-5-[3-chloro-2-methyl-4-[2-(4-methylpiperazin-1-yl)ethoxy]phenyl]-6-iodo-thieno[2,3-d]pyrimidin-4-yl]amino]-3-(2-hydroxyphenyl)propanoate (0.88 mmol) was dissolved in 10 mL DMF then 415 mg $K_2CO_3$ (3.00 mmol) and 348 mg 2,2,2-trifluoroethyl trifluoromethanesulfonate (1.50 mmol) were added at r.t. The mixture was stirred at 50° C. for 5 hours. The reaction mixture was diluted with brine, extracted with DCM. The organic phase was dried over $Na_2SO_4$, filtered and the filtrate was concentrated under reduced pressure. The crude material was purified via flash chromatography using DCM and methanol as eluents to obtain ethyl (2R)-2-[[(5S$_a$)-5-[3-chloro-2-methyl-4-[2-(4-methylpiperazin-1-yl)ethoxy]phenyl]-6-iodo-thieno[2,3-d]pyrimidin-4-yl]amino]-3-[2-(2,2,2-trifluoroethoxy)phenyl]propanoate. MS (M+H): 818.1

Step C: Example 17

Ethyl (2R)-2-[[(5S)-5-[3-chloro-2-methyl-4-[2-(4-methylpiperazin-1-yl)ethoxy]phenyl]-6-iodo-thieno[2,3-d]pyrimidin-4-yl]amino]-3-[2-(2,2,2-trifluoroethoxy)phenyl]propanoate was hydrolyzed according to General procedure VII to give (2R)-2-[[(5S$_a$)-5-[3-chloro-2-methyl-4-[2-(4-methylpiperazin-1-yl)ethoxy]phenyl]-6-iodo-thieno[2,3-d]pyrimidin-4-yl]amino]-3-[2-(2,2,2-trifluoroethoxy)phenyl] propanoic acid. This compound was used as the appropriate 6-iodo-thieno[2,3-d]pyrimidine derivative and converted to Example 17 according to General Procedure IIIb, using 2-(5-fluoro-2-furyl)-4,4,5,5-tetramethyl-1,3,2-dioxaborolane as the appropriate boronic acid derivative. HRMS calculated for $C_{35}H_{34}ClF_4N_5O_5S$: 747.1905, found: 374.6006 (M+2H).

Example 18: N-[(5R$_a$)-5-{3-chloro-2-methyl-4-[2-(4-methylpiperazin-1-yl)ethoxy]phenyl}-6-(5-fluoro-furan-2-yl)thieno[2,3-d]pyrimidin-4-yl]-2-(pyridin-2-ylmethoxy)-D-phenylalanine and Example 19: N-[(5S$_a$)-5-{3-chloro-2-methyl-4-[2-(4-methylpiperazin-1-yl)ethoxy]phenyl}-6-(5-fluoro-furan-2-yl)thieno[2,3-d]pyrimidin-4-yl]-2-(pyridin-2-ylmethoxy)-D-phenylalanine Using General Procedure Ic and Preparation 4c as the appropriate 4-chloro-thieno[2,3-d]pyrimidine derivative and Preparation A5 as the appropriate amino acid derivative, Example 18 was obtained as the earlier eluting diastereoisomer. HRMS calculated for $C_{39}H_{38}ClFN_6O_5S$: 756.2296, found: 379.1230 (M+2H).
Example 19 was obtained as the later eluting diastereoisomer. HRMS calculated for $C_{39}H_{38}ClFN_6O_5S$: 756.2296, found: 379.1230 (M+2H).

Example 20: N-[(5S$_a$)-5-{3-chloro-2-methyl-4-[2-(4-methylpiperazin-1-yl)ethoxy]phenyl}-6-(5-fluoro-furan-2-yl)thieno[2,3-d]pyrimidin-4-yl]-2-[(1-methyl-1H-pyrazol-5-yl)methoxy]-D-phenylalanine Using General Procedure IIIb and Preparation 5b as the appropriate 6-iodo-thieno[2,3-d]pyrimidine derivative and 2-(5-fluoro-2-furyl)-4,4,5,5-tetramethyl-1,3,2-dioxaborolane as the appropriate boronic acid derivative, Example 20 was obtained. HRMS calculated for $C_{38}H_{39}ClFN_7O_5S$: 759.2406, found: 380.6271 (M+2H).

Example 21: N-[(5S$_a$)-5-{3-chloro-2-methyl-4-[2-(4-methylpiperazin-1-yl)ethoxy]phenyl}-6-(5-fluoro-furan-2-yl)thieno[2,3-d]pyrimidin-4-yl]-2-[(1-ethyl-1H-pyrazol-5-yl)methoxy]-D-phenylalanine Using General Procedure IIIb and Preparation 5c as the appropriate 6-iodo-thieno[2,3-d]pyrimidine derivative and 2-(5-fluoro-2-furyl)-4,4,5,5-tetramethyl-1,3,2-dioxaborolane as the appropriate boronic acid derivative, Example 21 was obtained. HRMS calculated for $C_{39}H_{41}ClFN_7O_5S$: 773.2562, found: 387.6358 (M+2H).

Example 22: N-[(5S$_a$)-5-{3-chloro-2-methyl-4-[2-(4-methylpiperazin-1-yl)ethoxy]phenyl}-6-(5-fluoro-furan-2-yl)thieno[2,3-d]pyrimidin-4-yl]-2-[(2-ethoxypyrimidin-4-yl)methoxy]-D-phenylalanine Using General Procedure Ic and Preparation 4c as the appropriate 4-chloro-thieno[2,3-d]pyrimidine derivative and Preparation A2 as the appropriate amino acid derivative, Example 22 was obtained as the later eluting diastereoisomer. HRMS calculated for $C_{40}H_{41}ClFN_7O_6S$: 801.2512, found: 401.6326 (M+2H).

Example 23: 2-[(1-butyl-1H-pyrazol-5-yl)methoxy]-N-[(5R$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]-D-phenylalanine and Example 24: 2-[(1-butyl-1H-pyrazol-5-yl)methoxy]-N-[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]-D-phenylalanine Using General Procedure Ic and Preparation 4c as the appropriate 4-chloro-thieno[2,3-d]pyrimidine derivative and Preparation A3 as the appropriate amino acid derivative, Example 23 was obtained as the earlier eluting diastereoisomer. HRMS calculated for $C_{41}H_{45}ClFN_7O_5S$: 801.2875, found: 401.6502 (M+2H).
Example 24 was obtained as the later eluting diastereoisomer. HRMS calculated for $C_{41}H_{45}ClFN_7O_5S$: 801.2875, found: 401.6505 (M+2H).

Example 25: N-[(5R$_a$)-5-{3-chloro-2-methyl-4-[2-(4-methylpiperazin-1-yl)ethoxy]phenyl}-6-(5-fluoro-furan-2-yl)thieno[2,3-d]pyrimidin-4-yl]-2-{[2-(2,2,2-trifluoro ethoxy)pyrimidin-4-yl]methoxy}-D-phenylalanine and Example 26: N-[(5S$_a$)-5-{3-chloro-2-methyl-4-[2-(4-methylpiperazin-1-yl)ethoxy]phenyl}-6-(5-fluoro-furan-2-yl)thieno[2,3-d]pyrimidin-4-yl]-2-{[2-(2,2,2-trifluoro ethoxy)pyrimidin-4-yl]methoxy}-D-phenylalanine Using General Procedure Ic and Preparation 4c as the appropriate 4-chloro-thieno[2,3-d]pyrimidine derivative and Preparation A8 as the appropriate amino acid derivative, Example 25 was obtained as the earlier eluting diastereoisomer. HRMS calculated for $C_{40}H_{38}ClF_4N_7O_6S$: 855.2228, found: 428.6181 (M+2H).
Example 26 was obtained as the later eluting diastereoisomer. HRMS calculated for $C_{40}H_{38}ClF_4N_7O_6S$: 855.2228, found: 428.6193 (M+2H).

Example 27: N-[(5S$_a$)-5-{3-chloro-2-methyl-4-[2-(4-methylpiperazin-1-yl)ethoxy]phenyl}-6-(5-fluoro-furan-2-yl)thieno[2,3-d]pyrimidin-4-yl]-2-{[2-(2-methoxyphenyl)pyrimidin-4-yl]methoxy}-D-phenylalanine Step A: ethyl (2R)-2-[[(5S$_a$)-5-[3-chloro-2-methyl-4-[2-(4-methylpiperazin-1-yl)ethoxy]phenyl]-6-(5-fluoro-2-furyl)thieno[2,3-d]pyrimidin-4-yl]amino]-3-(2-hydroxyphenyl) propanoate 0.97 g Example 14 (1.46 mmol) was dissolved in 15 mL HCl solution (1.25M in EtOH) and stirred at 40° C. overnight. The mixture was cooled to r.t., neutralized with aqueous NaHCO$_3$ solution and the mixture was extracted with DCM. The organic phase was dried over Na$_2$SO$_4$, filtered and the filtrate was concentrated under reduced pressure. The residue was purified via flash chromatography using DCM and MeOH as eluents to obtain ethyl (2R)-2-[[(5S$_a$)-5-[3-chloro-2-methyl-4-[2-(4-methylpiperazin-1-yl) ethoxy]phenyl]-6-(5-fluoro-2-furyl)thieno[2,3-d]pyrimidin-4-yl]amino]-3-(2-hydroxy phenyl)propanoate.
$^1$H NMR (400 MHz, DMSO-d$_6$) δ: 9.48 (br s, 1H), 8.39 (s, 1H), 7.30 (s, 2H), 7.01 (td, 1H), 6.72 (d, 1H), 6.64 (t, 1H), 6.41 (d, 1H), 5.83 (m, 1H), 5.56 (t, 1H), 5.08 (d, 1H), 4.94 (m, 1H), 4.30 (t, 2H), 4.03 (m, 2H), 3.07 (dd, 1H), 2.81 (t, 2H), 2.56 (br, 4H), 2.36 (dd, 1H), 2.32 (br, 4H), 2.14 (s, 3H), 1.91 (s, 3H)
MS (M+H): 694.2

Step B: Example 27

Using General Procedure VI and ethyl (2R)-2-[[(5S$_a$)-5-[3-chloro-2-methyl-4-[2-(4-methyl piperazin-1-yl)ethoxy] phenyl]-6-(5-fluoro-2-furyl)thieno[2,3-d]pyrimidin-4-yl] amino]-3-(2-hydroxyphenyl)propanoate as the appropriate phenol derivative and Preparation C3 as the appropriate alcohol derivative, then hydrolyzing the formed intermediate according to General Procedure VII, Example 27 was obtained. HRMS calculated for $C_{45}H_{43}ClFN_7O_6S$: 863.2668, found: 432.6414 (M+2H).

Example 28: N-[(5$S_a$)-5-{3-chloro-4-[2-(dimethylamino)ethoxy]-2-methylphenyl}-6-(5-fluorofuran-2-yl)thieno[2,3-d]pyrimidin-4-yl]-2-hydroxy-D-phenylalanine

Step A: 2-[2-chloro-4-[4-chloro-6-(5-fluoro-2-furyl)thieno[2,3-d]pyrimidin-5-yl]-3-methyl-phenoxy]-N,N-dimethyl-ethanamine Using General Procedure IIIb and Preparation 4e as the appropriate 6-iodo-thieno[2,3-d]pyrimidine derivative and 2-(5-fluoro-2-furyl)-4,4,5,5-tetramethyl-1,3,2-dioxaborolane as the appropriate boronic acid derivative, 2-[2-chloro-4-[4-chloro-6-(5-fluoro-2-furyl) thieno[2,3-d]pyrimidin-5-yl]-3-methyl-phenoxy]-N,N-dimethyl-ethanamine was obtained.

Step B: Example 28

Using General Procedure Ib and 2-[2-chloro-4-[4-chloro-6-(5-fluoro-2-furyl)thieno[2,3-d]pyrimidin-5-yl]-3-methyl-phenoxy]-N,N-dimethyl-ethanamine as the appropriate 4-chloro-thieno[2,3-d]pyrimidine derivative and 2-hydroxy-D-phenylalanine as the appropriate amino acid derivative, Example 28 was obtained as the later eluting diastereoisomer. HRMS calculated for $C_{30}H_{28}ClFN_4O_5S$: 610.1453, found: 611.1503 (M+H).

Example 29: N-[(5$S_a$)-5-{3-chloro-2-methyl-4-[2-(4-methylpiperazin-1-yl)ethoxy]phenyl}-6-(thiophen-3-yl)thieno[2,3-d]pyrimidin-4-yl]-3-pyridin-2-yl-D-alanine and

Example 30: N-[(5$R_a$)-5-{3-chloro-2-methyl-4-[2-(4-methylpiperazin-1-yl)ethoxy]phenyl}-6-(thiophen-3-yl)thieno[2,3-d]pyrimidin-4-yl]-3-pyridin-2-yl-D-alanine Using General Procedure Ic and Preparation 4g as the appropriate 4-chloro-thieno[2,3-d]pyrimidine derivative and (2R)-2-amino-3-(2-pyridyl)propanoic acid as the appropriate amino acid derivative, a mixture of diastereoisomers was obtained. They were separated via preparative reversed phase chromatography using 40 mM aqueous NH$_4$OAc solution (pH=4, adjusted with AcOH) and acetonitrile as eluents. Example 29 was obtained as the earlier eluting diastereoisomer. HRMS calculated for $C_{32}H_{33}ClN_6O_3S_2$: 648.1744, found: 649.1811 (M+H).
Example 30 was obtained as the later eluting diastereoisomer. HRMS calculated for $C_{32}H_{33}ClN_6O_3S_2$: 648.1744, found: 649.1816 (M+H).

Example 31: N-[(5$R_a$)-5-{3-chloro-2-methyl-4-[2-(4-methylpiperazin-1-yl)ethoxy]phenyl}-6-(thiophen-3-yl)thieno[2,3-d]pyrimidin-4-yl]-3-cyclohexyl-D-alanine and

Example 32: N-[(5$S_a$)-5-{3-chloro-2-methyl-4-[2-(4-methylpiperazin-1-yl)ethoxy]phenyl}-6-(thiophen-3-yl)thieno[2,3-d]pyrimidin-4-yl]-3-cyclohexyl-D-alanine Using General Procedure Ic and Preparation 4g as the appropriate 4-chloro-thieno[2,3-d]pyrimidine derivative and (2R)-2-amino-3-cyclohexyl-propanoic acid as the appropriate amino acid derivative, Example 31 was obtained as the earlier eluting diastereoisomer. HRMS calculated for $C_{33}H_{40}ClN_5O_3S_2$: 653.2261, found: 327.6194 (M+2H).
Example 32 was obtained as the later eluting diastereoisomer. HRMS calculated for $C_{33}H_{40}ClN_5O_3S_2$: 653.2261, found: 327.6195 (M+2H).

Example 33: N-[(5$R_a$)-5-{3-chloro-2-methyl-4-[2-(4-methylpiperazin-1-yl)ethoxy]phenyl}-6-(thiophen-3-yl)thieno[2,3-d]pyrimidin-4-yl]-2-fluoro-D-phenylalanine and

Example 34: N-[(5$S_a$)-5-{3-chloro-2-methyl-4-[2-(4-methylpiperazin-1-yl)ethoxy]phenyl}-6-(thiophen-3-yl)thieno[2,3-d]pyrimidin-4-yl]-2-fluoro-D-phenylalanine Using General Procedure Ic and Preparation 4g as the appropriate 4-chloro-thieno[2,3-d]pyrimidine derivative and (2R)-2-amino-3-(2-fluorophenyl)propanoic acid as the appropriate amino acid derivative, Example 33 was obtained as the later eluting diastereoisomer. HRMS calculated for $C_{33}H_{33}ClFN_5O_3S_2$: 665.1697, found: 666.1776 (M+H).
Example 34 was obtained as the earlier eluting diastereoisomer. HRMS calculated for C33H$_{33}$ClFN$_5$O$_3$S$_2$: 665.1697, found: 666.1776 (M+H).

Example 35: N-[(5$R_a$)-5-{3-chloro-2-methyl-4-[2-(morpholin-4-yl)ethoxy]phenyl}-6-(thiophen-3-yl)thieno[2,3-d]pyrimidin-4-yl]-3-pyridin-2-yl-D-alanine and

Example 36: N-[(5$S_a$)-5-{3-chloro-2-methyl-4-[2-(morpholin-4-yl)ethoxy]phenyl}-6-(thiophen-3-yl)thieno[2,3-d]pyrimidin-4-yl]-3-pyridin-2-yl-D-alanine Using General Procedure Ic and Preparation 4h as the appropriate 4-chloro-thieno[2,3-d]pyrimidine derivative and (2R)-2-amino-3-(2-pyridyl)propanoic acid as the appropriate amino acid derivative, Example 35 was obtained as the earlier eluting diastereoisomer. HRMS calculated for $C_{31}H_{30}ClN_5O_4S_2$: 635.1428, found: 636.1499 (M+H).
Example 36 was obtained as the later eluting diastereoisomer. HRMS calculated for $C_{31}H_{30}ClN_5O_4S_2$: 635.1428, found: 636.1508 (M+H).

Example 37: 2-(aminomethyl)-N-[(5$R_a$)-5-{3-chloro-2-methyl-4-[2-(morpholin-4-yl) ethoxy]phenyl}-6-(thiophen-3-yl)thieno[2,3-d]pyrimidin-4-yl]-D-phenylalanine and

Example 38: 2-(aminomethyl)-N-[(5$S_a$)-5-{3-chloro-2-methyl-4-[2-(morpholin-4-yl) ethoxy]phenyl}-6-(thiophen-3-yl)thieno[2,3-d]pyrimidin-4-yl]-D-phenylalanine Using General Procedure Ic and Preparation 4h as the appropriate 4-chloro-thieno[2,3-d]pyrimidine derivative and (2R)-2-amino-3-[2-(aminomethyl)phenyl]propanoic acid as the appropriate amino acid derivative, Example 37 was obtained as the earlier eluting diastereoisomer. HRMS calculated for $C_{33}H_{34}ClN_5O_4S_2$: 663.1741, found: 664.1808 (M+H).

Example 38 was obtained as the later eluting diastereoisomer. HRMS calculated for $C_{33}H_{34}ClN_5O_4S_2$: 663.1741, found: 664.1825 (M+H).

Example 39: N-[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]-2-methoxy-D-phenylalanine Using General Procedure VI and Preparation 7b as the appropriate phenol derivative and methanol as the appropriate alcohol derivative, then hydrolyzing the formed intermediate according to General Procedure VII, Example 39 was obtained. HRMS calculated for $C_{33}H_{36}ClN_5O_4S$: 633.2176, found: 317.6163 (M+2H).

Example 40: 2-[(1-tert-butyl-1H-pyrazol-5-yl)methoxy]-N-[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]-D-phenylalanine Using General Procedure VI and Preparation 7b as the appropriate phenol derivative and Preparation C4 as the appropriate alcohol derivative, then hydrolyzing the formed intermediate according to General Procedure VII, Example 40 was obtained. HRMS calculated for $C_{40}H_{46}ClN_7O_4$: 755.3021 found: 378.6573 (M+2H).

Example 41: N-[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]-2-{[2-(2-methoxyethyl) pyrimidin-4-yl]methoxy}-D-phenylalanine Using General Procedure VI and Preparation 7b as the appropriate phenol derivative and Preparation C5 as the appropriate alcohol derivative, then hydrolyzing the formed intermediate according to General Procedure VII, Example 41 was obtained. HRMS calculated for $C_{40}H_{44}ClN_7O_5S$: 769.2813, found: 385.6476 (M+2H).

Example 42: N-[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]-2-{[1-(2,2,2-trifluoroethyl)-1H-pyrazol-5-yl]methoxy}-D-phenylalanine Using General Procedure VI and Preparation 7b as the appropriate phenol derivative and Preparation C6 as the appropriate alcohol derivative, then hydrolyzing the formed intermediate according to General Procedure VII, Example 42 was obtained. HRMS calculated for $C_{38}H_{39}ClF_3N_7O_4S$: 781.2425, found: 391.6300 (M+2H).

Example 43: N-[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]-2-{[2-(morpholin-4-yl) pyrimidin-4-yl]methoxy}-D-phenylalanine Using General Procedure VI and Preparation 7b as the appropriate phenol derivative and Preparation C7 as the appropriate alcohol derivative, then hydrolyzing the formed intermediate according to General Procedure VII, Example 43 was obtained. HRMS calculated for $C_{41}H_{45}ClN_8O_5S$: 796.2922, found: 399.1546 (M+2H).

Example 44: N-[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]-2-{[2-(2,2,2-trifluoroethoxy)pyrimidin-4-yl]methoxy}-D-phenylalanine Using General Procedure VI and Preparation 7b as the appropriate phenol derivative and Preparation C8 as the appropriate alcohol derivative, then hydrolyzing the formed intermediate according to General Procedure VII, Example 44 was obtained. HRMS calculated for $C_{39}H_{39}ClF_3N_7O_5S$: 809.2374, found: 405.6262 (M+2H).

Example 45: N-[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]-2-{[2-(2-methoxyphenyl)pyrimidin-4-yl]methoxy}-D-phenylalanine Using General Procedure VI and Preparation 7b as the appropriate phenol derivative and Preparation C3 as the appropriate alcohol derivative, then hydrolyzing the formed intermediate according to General Procedure VII, Example 45 was obtained. HRMS calculated for $C_{44}H_{44}ClN_7O_5S$: 817.2813, found: 409.6494 (M+2H).

Example 46: N-[(5S$_a$)-5-{3-chloro-4-[2-(dimethylamino)ethoxy]-2-methylphenyl}-6-(prop-1-yn-1-yl)thieno[2,3-d]pyrimidin-4-yl]-2-{[1-(2,2,2-trifluoroethyl)-1H-pyrazol-5-yl]methoxy}-D-phenylalanine Using General Procedure VI and Preparation 7c as the appropriate phenol derivative and Preparation C6 as the appropriate alcohol derivative, then hydrolyzing the formed intermediate according to General Procedure VII, Example 46 was obtained. HRMS calculated for $C_{35}H_{34}ClF_3N_6O_4S$: 726.2003, found: 727.2092 (M+H).

Example 47: N-[(5S$_a$)-5-{3-chloro-4-[2-(dimethylamino)ethoxy]-2-methylphenyl}-6-(prop-1-yn-1-yl)thieno[2,3-d]pyrimidin-4-yl]-2-{[2-(morpholin-4-yl) pyrimidin-4-yl]methoxy}-D-phenylalanine Using General Procedure VI and Preparation 7c as the appropriate phenol derivative and Preparation C7 as the appropriate alcohol derivative, then hydrolyzing the formed intermediate according to General Procedure VII, Example 47 was obtained. HRMS calculated for $C_{38}H_{40}ClN_7O_5S$: 741.2500, found: 371.6331 (M+2H).

Example 48: N-[(5S$_a$)-5-{3-chloro-4-[2-(dimethylamino)ethoxy]-2-methylphenyl}-6-(prop-1-yn-1-yl)thieno[2,3-d]pyrimidin-4-yl]-2-{[2-(2,2,2-trifluoroethoxy)pyrimidin-4-yl]methoxy}-D-phenylalanine Using General Procedure VI and Preparation 7c as the appropriate phenol derivative and Preparation C8 as the appropriate alcohol derivative, then hydrolyzing the formed intermediate according to General Procedure VII, Example 48 was obtained. HRMS calculated for $C_{36}H_{34}ClF_3N_6O_5S$: 754.1952, found: 755.1971 (M+H).

Example 49: N-[(5S$_a$)-5-{3-chloro-4-[2-(dimethylamino)ethoxy]-2-methylphenyl}-6-(prop-1-yn-1-yl)thieno[2,3-d]pyrimidin-4-yl]-2-{[2-(2-methoxyphenyl)pyrimidin-4-yl]methoxy}-D-phenylalanine Using General Procedure VI and Preparation 7c as the appropriate phenol derivative and Preparation C3 as the appropriate alcohol derivative, then hydrolyzing the formed intermediate according to General Procedure VII, Example 49 was obtained. HRMS calculated for $C_{41}H_{39}ClN_6O_5S$: 762.2391, found: 371.6323 (M+2H).

Example 50: N-[(5S$_a$)-5-{3-chloro-4-[2-(dimethylamino)ethoxy]-2-methylphenyl}-6-(4-fluorophenyl)thieno[2,3-d]pyrimidin-4-yl]-2-{[2-(2-fluorophenyl)pyrimidin-4-yl]methoxy}-D-phenylalanine Step A: ethyl (2R)-2-[[5-bromo-6-(4-fluorophenyl)thieno[2,3-d]pyrimidin-4-yl]amino]-3-[2-[[2-(2-fluorophenyl)pyrimidin-4-yl]methoxy]phenyl]propanoate Using General Procedure VI and Preparation 7d as the appropriate phenol derivative and Preparation C9 as the appropriate alcohol derivative, ethyl (2R)-2-[[5-bromo-6-(4-fluorophenyl)thieno[2,3-d]pyrimidin-4-yl]amino]-3-[2-[[2-(2-fluorophenyl)pyrimidin-4-yl]methoxy]phenyl]propanoate was obtained. $^1$H NMR (400 MHz, DMSO-d$_6$) δ: 8.84 (d, 1H), 8.39 (s, 1H), 7.95 (td, 1H), 7.58-7.52 (m, 3H), 7.39-7.24 (m, 8H), 7.13 (d, 1H), 6.95 (t, 1H), 5.29-5.15 (m, 3H), 4.16 (q, 2H), 3.63 (dd, 1H), 3.25 (dd, 1H), 1.19 (t, 3H)

Step B: ethyl (2R)-2-[[5-[3-chloro-4-(2-dimethylaminoethyloxy)-2-methyl-phenyl]-6-(4-fluorophenyl)thieno[2,3-d]pyrimidin-4-yl]amino]-3-[2-[[2-(2-fluorophenyl)pyrimidin-4-yl]methoxy]phenyl]propanoate 1 eq. ethyl (2R)-2-[[5-bromo-6-(4-fluorophenyl)thieno[2,3-d]pyrimidin-4-yl]amino]-3-[2-[[2-(2-fluorophenyl)pyrimidin-4-yl]methoxy]phenyl]propanoate and 1.2 eq. Preparation B5 were dissolved in dioxan (5 mL/mmol), then 5 mol % AtaPhos, 3 eq. $Cs_2CO_3$ and water (5 mL/mmol) were added and the mixture was stirred at 70° C. under argon atmosphere until no further conversion was observed. Then the mixture was diluted with EtOAc and was washed with brine. The organic phase was dried over $Na_2SO_4$, filtered and the filtrate was concentrated under reduced pressure. The crude product was purified via flash chromatography using DCM and MeOH as eluents to obtain ethyl (2R)-2-[[5-[3-chloro-4-(2-dimethylaminoethyloxy)-2-methyl-phenyl]-6-(4-fluorophenyl)thieno[2,3-d]pyrimidin-4-yl]amino]-3-[2-[[2-(2-fluorophenyl)pyrimidin-4-yl]methoxy]phenyl]propanoate as a mixture of diastereoisomers. MS (M+H): 834.6

Step C: Example 50

Using General Procedure VII and ethyl (2R)-2-[[5-[3-chloro-4-(2-dimethylaminoethyl oxy)-2-methyl-phenyl]-6-(4-fluorophenyl)thieno[2,3-d]pyrimidin-4-yl]amino]-3-[2-[[2-(2-fluorophenyl)pyrimidin-4-yl]methoxy]phenyl]propanoate as the appropriate ester derivative, Example 50 was obtained as the later eluting diastereoisomer. HRMS calculated for $C_{43}H_{37}ClF_2N_6O_4S$: 806.2254, found: 807.2343 (M+H).

Example 51: N-[(5S$_a$)-5-{3-chloro-4-[2-(dimethylamino)ethoxy]-2-methylphenyl}-6-(4-fluorophenyl)thieno[2,3-d]pyrimidin-4-yl]-2-({2-[2-(2-methoxyethoxy)phenyl]pyrimidin-4-yl}methoxy)-D-phenylalanine Step A: ethyl (2R)-2-[[5-bromo-6-(4-fluorophenyl)thieno[2,3-d]pyrimidin-4-yl]amino]-3-[2-[[2-[2-(2-methoxyethoxy)phenyl]pyrimidin-4-yl]methoxy]phenyl]propanoate Using General Procedure VI and Preparation 7d as the appropriate phenol derivative and Preparation C10 as the appropriate alcohol derivative, ethyl (2R)-2-[[5-bromo-6-(4-fluorophenyl)thieno[2,3-d]pyrimidin-4-yl]amino]-3-[2-[[2-[2-(2-methoxyethoxy)phenyl]pyrimidin-4-yl]methoxy]phenyl]propanoate was obtained. $^1$H NMR (400 MHz, DMSO-d$_6$) δ: 8.80 (d, 1H), 8.41 (s, 1H), 7.57-7.53 (m, 3H), 7.46-7.23 (m, 7H), 7.16 (d, 1H), 7.07 (d, 1H), 7.03 (t, 1H), 6.94 (t, 1H), 5.28-5.23 (m, 1H), 5.19 (dd, 2H), 4.18-4.11 (m, 4H), 3.61-3.57 (m, 3H), 3.27 (dd, 1H), 3.21 (s, 3H), 1.19 (t, 3H)

Step B: ethyl (2R)-2-[[5-[3-chloro-4-(2-dimethylaminoethyloxy)-2-methyl-phenyl]-6-(4-fluorophenyl)thieno[2,3-d]pyrimidin-4-yl]amino]-3-[2-[[2-[2-(2-methoxyethoxy)phenyl]pyrimidin-4-yl]methoxy]phenyl]propanoate 1 eq. ethyl (2R)-2-[[5-bromo-6-(4-fluorophenyl)thieno[2,3-d]pyrimidin-4-yl]amino]-3-[2-[[2-[2-(2-methoxyethoxy)phenyl]pyrimidin-4-yl]methoxy]phenyl]propanoate and 1.2 eq. Preparation B5 were dissolved in dioxan (5 mL/mmol), then 5 mol % AtaPhos, 3 eq. $Cs_2CO_3$ and water (5 mL/mmol) were added and the mixture was stirred at 70° C. under argon atmosphere until no further conversion was observed. Then the mixture was diluted with EtOAc and was washed with brine. The organic phase was dried over $Na_2SO_4$, filtered and the filtrate was concentrated under reduced pressure. The crude product was purified via flash chromatography using DCM and MeOH as eluents to obtain ethyl (2R)-2-[[5-[3-chloro-4-(2-dimethylaminoethyloxy)-2-methyl-phenyl]-6-(4-fluorophenyl) thieno[2,3-d]pyrimidin-4-yl]amino]-3-[2-[[2-[2-(2-methoxyethoxy)phenyl]pyrimidin-4-yl]methoxy]phenyl]propanoate as a mixture of diastereoisomers. MS (M+H): 890.6

Step C: Example 51

Using General Procedure VII and ethyl (2R)-2-[[5-[3-chloro-4-(2-dimethylaminoethyl oxy)-2-methyl-phenyl]-6-(4-fluorophenyl)thieno[2,3-d]pyrimidin-4-yl]amino]-3-[2-[[2-[2-(2-methoxyethoxy)phenyl]pyrimidin-4-yl]methoxy]phenyl]propanoate as the appropriate ester derivative, Example 51 was obtained as the later eluting diastereoisomer. HRMS calculated for $C_{46}H_{44}ClFN_6O_6S$: 862.2716, found: 432.1442 (M+2H).

Example 52: N-[(5R$_a$)-5-(3,5-dichloro-4-hydroxy-2-methylphenyl)-6-ethylthieno[2,3-d]pyrimidin-4-yl]-D-phenylalanine and Example 53: N-[(5S$_a$)-5-(3,5-dichloro-4-hydroxy-2-methylphenyl)-6-ethylthieno[2,3-d]pyrimidin-4-yl]-D-phenylalanine Using General Procedure VII and Preparation 7f as the appropriate ester derivative, a mixture of diastereoisomers was obtained. They were separated via preparative reversed phase chromatography using 0.1% aqueous TFA solution and acetonitrile as eluents.

Example 52 was obtained as the earlier eluting diastereomer. HRMS calculated for $C_{24}H_{21}Cl_2N_3O_3S$: 501.0681, found: 502.0755 (M+H).

Example 53 was obtained as the later eluting diastereomer. HRMS calculated for $C_{24}H_{21}Cl_2N_3O_3S$: 501.0681, found: 502.0772 (M+H).

Example 54: N-((5S$_a$)-5-{3,5-dichloro-2-methyl-4-[2-(4-methylpiperazin-1-yl)ethoxy]phenyl}-6-ethyl-thieno[2,3-d]pyrimidin-4-yl)-D-phenylalanine and Example 55: N-((5R$_a$)-5-{3,5-dichloro-2-methyl-4-[2-(4-methylpiperazin-1-yl)ethoxy]phenyl}-6-ethyl-thieno[2,3-d]pyrimidin-4-yl)-D-phenylalanine Using General Procedure VI and Preparation 7f as the appropriate phenol derivative and 2-(4-methylpiperazin-1-yl)ethanol as the appropriate alcohol derivative, then hydrolyzing the formed intermediate according to General Procedure VII, Example 54 was obtained as the later eluting diastereoisomer. HRMS calculated for $C_{31}H_{35}Cl_2N_5O_3S$: 627.1838, found: 628.1935 (M+H).

Example 55 was obtained as the earlier eluting diastereoisomer. HRMS calculated for $C_{31}H_{35}Cl_2N_5O_3S$: 627.1838, found: 628.1932 (M+H).

Example 56: N-{(5S$_a$)-5-[3-chloro-4-(2-hydroxy-ethoxy)-2-methylphenyl]-6-ethyl thieno[2,3-d]pyrimidin-4-yl}-D-phenylalanine Using General Procedure VI and Preparation 7gd1 as the appropriate phenol derivative and 10 eq. ethylene glycol as the appropriate alcohol derivative, then hydrolyzing the formed intermediate according to General Procedure VII, Example 56 was obtained. HRMS calculated for $C_{26}H_{26}ClN_3O_4S$: 511.1333, found: 512.1390 (M+H).

Example 57: N-{(5S$_a$)-5-[4-(carboxymethoxy)-3-chloro-2-methylphenyl]-6-ethylthieno[2,3-d]pyrimidin-4-yl}-D-phenylalanine Using General Procedure VI and Preparation 7gd1 as the appropriate phenol derivative and 2-hydroxy-N,N-dimethylacetamide as the appropriate alcohol derivative, then hydrolyzing the formed intermediate according to General Procedure VII, Example 57 was obtained. HRMS calculated for $C_{26}H_{24}ClN_3O_5S$: 525.1125, found: 526.1217 (M+H).

Example 58: N-((5R$_a$)-5-{3-chloro-4-[2-(dimethyl-amino)ethoxy]-2-methylphenyl}-6-ethylthieno[2,3-d]pyrimidin-4-yl)-L-phenylalanine and Example 59: N-((5S$_a$)-5-{3-chloro-4-[2-(dimethyl-amino)ethoxy]-2-methylphenyl}-6-ethylthieno[2,3-d]pyrimidin-4-yl)-L-phenylalanine Using General Procedure VI and Preparation 7g as the appropriate phenol derivative and 2-(dimethylamino)ethanol as the appropriate alcohol derivative, then hydrolyzing the formed intermediate according to General Procedure VII, a mixture of diastereoisomers was obtained. They were separated via preparative reversed phase chromatography using 40 mM aqueous $NH_4OAc$ solution (pH=4, adjusted with AcOH) and acetonitrile as eluents. Example 58 was obtained as the earlier eluting diastereoisomer. HRMS calculated for $C_{28}H_{31}ClN_4O_3S$: 538.1805, found: 539.1869 (M+H).

Example 59 was obtained as the later eluting diastereoisomer. HRMS calculated for $C_{28}H_{31}ClN_4O_3S$: 538.1805, found: 539.1866 (M+H).

Example 60: N-((5S$_a$)-5-{3-chloro-4-[3-(dimethyl-amino)propoxy]-2-methylphenyl}-6-ethylthieno[2,3-d]pyrimidin-4-yl)-D-phenylalanine Using General Procedure VI and Preparation 7gd1 as the appropriate phenol derivative and 3-(dimethylamino)propanol as the appropriate alcohol derivative, then hydrolyzing the formed intermediate according to General Procedure VII, Example 60 was obtained. HRMS calculated for $C_{29}H_{33}ClN_4O_3S$: 552.1962, found: 553.2036 (M+H).

Example 61: N-((5S$_a$)-5-{3-chloro-2-methyl-4-[2-(morpholin-4-yl)ethoxy]phenyl}-6-ethylthieno[2,3-d]pyrimidin-4-yl)-D-phenylalanine Using General Procedure VI and Preparation 7gd1 as the appropriate phenol derivative and 2-morpholinoethanol as the appropriate alcohol derivative, then hydrolyzing the formed intermediate according to General Procedure VII, Example 61 was obtained. HRMS calculated for $C_{30}H_{33}ClN_4O_4S$: 580.1911, found: 581.1981 (M+H).

Example 62: N-((5S$_a$)-5-{3-chloro-2-methyl-4-[2-(4-methylpiperazin-1-yl)ethoxy]phenyl}-6-ethylthieno[2,3-d]pyrimidin-4-yl)-D-phenylalanine and Example 63 N-((5R$_a$)-5-{3-chloro-2-methyl-4-[2-(4-methylpiperazin-1-yl)ethoxy]phenyl}-6-ethylthieno[2,3-d]pyrimidin-4-yl)-D-phenylalanine Using General Procedure VI and Preparation 7g as the appropriate phenol derivative and 2-(4-methylpiperazin-1-yl)ethanol as the appropriate alcohol derivative, then hydrolyzing the formed intermediate according to General Procedure VII, Example 62 was obtained as the earlier eluting diastereoisomer. HRMS calculated for $C_{31}H_{36}ClN_5O_3S$: 593.2227, found: 594.2313 (M+H).

Example 63 was obtained as the later eluting diastereoisomer. HRMS calculated for $C_{31}H_{36}ClN_5O_3S$: 593.2227, found: 594.2304 (M+H).

Example 64: N-((5S$_a$)-5-{3-chloro-2-methyl-4-[3-(4-methylpiperazin-1-yl)propoxy]phenyl}-6-ethylthieno[2,3-d]pyrimidin-4-yl)-D-phenylalanine Using General Procedure VI and Preparation 7gd1 as the appropriate phenol derivative and 3-(4-methylpiperazin-1-yl)propan-1-ol as the appropriate alcohol derivative, then hydrolyzing the formed intermediate according to General Procedure VII, Example 64 was obtained. HRMS calculated for $C_{32}H_{38}ClN_5O_3S$: 607.2384, found: 608.2444 (M+H).

Example 65: N-((5S$_a$)-5-{3-chloro-2-methyl-4-[2-(4-methylpiperazin-1-yl)ethoxy]phenyl}-6-[5-(methoxycarbonyl)-4-methylfuran-2-yl]thieno[2,3-d]pyrimidin-4-yl)-2-methoxy-D-phenylalanine and Example 66: N-((5R$_a$)-5-{3-chloro-2-methyl-4-[2-(4-methylpiperazin-1-yl)ethoxy]phenyl}-6-[5-(methoxycarbonyl)-4-methylfuran-2-yl]thieno[2,3-d]pyrimidin-4-yl)-2-methoxy-D-phenylalanine Step A: [4-chloro-5-[3-chloro-2-methyl-4-[2-(4-methylpiperazin-1-yl)ethoxy]phenyl]thieno[2,3-d]pyrimidin-6-yl]-trimethyl-stannane 1.97 g 4-chloro-5-[3-chloro-2-methyl-4-[2-(4-methylpiperazin-1-yl)ethoxy]phenyl]thieno[2,3-d]pyrimidine (4.50 mmol, from Step A of Preparation 4a) was dissolved in 40 mL dry THF under N$_2$ atmosphere, and the mixture was cooled to −78° C. Then 4.5 mL LDA (9 mmol, 2M solution in heptane, THF and ethyl benzene) was added and the mixture was stirred at −78° C. for 1 hour. Then 13.5 mL Me$_3$SnCl solution (13.5 mmol, 1M in hexane) was added and the mixture was allowed to warm up to r.t. The mixture was then diluted with cc. NH$_4$Cl solution and extracted with diethyl ether. The organic phase was dried over Na$_2$SO$_4$, filtered and the filtrate was concentrated under reduced pressure. Then it was dissolved in 60 mL EtOAc, and 40 mL saturated NaF solution was added, and it was stirred at r.t. overnight. Then it was filtered, the phases of the filtrate were separated. The aqueous phase was extracted with EtOAc. The combined organic phases were dried over Na$_2$SO$_4$, filtered and the filtrate was concentrated under reduced pressure. The crude product was purified via flash chromatography using DCM and MeOH as eluents to obtain [4-chloro-5-[3-chloro-2-methyl-4-[2-(4-methylpiperazin-1-yl)ethoxy] phenyl]thieno[2,3-d]pyrimidin-6-yl]-trimethyl-stannane. HRMS calculated for C$_{23}$H$_{30}$N$_4$OSCl$_2$Sn: 600.0539, found: 601.0584 (M+H).

Step B: methyl 5-[4-chloro-5-[3-chloro-2-methyl-4-[2-(4-methylpiperazin-1-yl)ethoxy]phenyl]thieno[2,3-d]pyrimidin-6-yl]-3-methyl-furan-2-carboxylate 900 mg [4-chloro-5-[3-chloro-2-methyl-4-[2-(4-methylpiperazin-1-yl)ethoxy]phenyl]thieno[2,3-d]pyrimidin-6-yl]-trimethyl-stannane (1.50 mmol), 657 mg methyl 5-bromo-3-methyl-furan-2-carboxylate (3 mmol), 29 mg CuI (0.15 mmol), 29 mg Pd(PhCN)$_2$Cl$_2$ (0.075 mmol), 46 mg Ph$_3$As (0.15 mmol) and 2 mL NMP were stirred at 100° C. until no further conversion was observed. Then the mixture was diluted with EtOAc and washed with saturated NaF solution. The aqueous phase was extracted with EtOAc. The combined organic phases were dried over Na$_2$SO$_4$, filtered and the filtrate was concentrated under reduced pressure. The crude product was purified via flash chromatography using DCM and MeOH as eluents to obtain methyl 5-[4-chloro-5-[3-chloro-2-methyl-4-[2-(4-methylpiperazin-1-yl)ethoxy]phenyl]thieno[2,3-d]pyrimidin-6-yl]-3-methyl-furan-2-carboxylate. HRMS calculated for C$_{27}$H$_{28}$Cl$_2$N$_4$O$_4$S: 574.1208, found: 575.1263 (M+H).

Step C: Example 65

Using General Procedure Ib and methyl 5-[4-chloro-5-[3-chloro-2-methyl-4-[2-(4-methyl piperazin-1-yl)ethoxy]phenyl]thieno[2,3-d]pyrimidin-6-yl]-3-methyl-furan-2-carboxylate as the appropriate 4-chloro-thieno[2,3-d]pyrimidine derivative and (2R)-2-amino-3-(2-methoxyphenyl)propanoic acid as the appropriate amino acid derivative Example 65 was obtained as the earlier eluting diastereoisomer. HRMS calculated for C$_{37}$H$_{40}$ClN$_5$O$_7$S: 733.23369, found: 367.6263 (M+2H).
Example 66 was obtained as the later eluting diastereoisomer. HRMS calculated for C$_{37}$H$_{40}$ClN$_5$O$_7$S: 733.23369, found: 367.6223 (M+2H).

Example 67: N-[6-ethyl-5-(3-hydroxy-2-methylphenyl)thieno[2,3-d]pyrimidin-4-yl]-D-phenylalanine Using General Procedure IId and Preparation 3a as the appropriate 5-iodo-thieno[2,3-d]pyrimidine derivative and 2-methyl-3-(4,4,5,5-tetramethyl-1,3,2-dioxaborolan-2-yl)phenol as the appropriate boronic acid derivative, Example 67 was obtained as a mixture of diastereoisomers. HRMS calculated for C$_{24}$H$_{23}$N$_3$O$_3$S: 433.1460, found: 434.1545 and 434.1535 (M+H).

Example 68: N-[6-ethyl-5-(3-fluoro-2-methylphenyl)thieno[2,3-d]pyrimidin-4-yl]-D-phenylalanine Using General Procedure IIa and Preparation 3a as the appropriate 5-iodo-thieno[2,3-d]pyrimidine derivative and (3-fluoro-2-methyl-phenyl)boronic acid as the appropriate boronic acid derivative, Example 68 was obtained as a mixture of diasteromeres. HRMS calculated for C$_{24}$H$_{22}$FN$_3$O$_2$S: 435.1417, found: 436.1489 and 436.1484 (M+H).

Example 69: N-[6-ethyl-(5S$_a$)-5-(3-fluoro-2-methylphenyl)thieno[2,3-d]pyrimidin-4-yl]-D-phenylalanine and Example 70: N-[6-ethyl-(5R$_a$)-5-(3-fluoro-2-methylphenyl)thieno[2,3-d]pyrimidin-4-yl]-D-phenylalanine Diastereoisomers of Example 68 were separated by preparative reversed phase chromatography using 25 mM aqueous NH$_4$HCO$_3$ solution and acetonitrile as eluents.
Example 69 was obtained as the earlier eluting diastereoisomer. HRMS calculated for C$_{24}$H$_{22}$FN$_3$O$_2$S: 435.1417, found: 436.1481 (M+H).
Example 70 was obtained as the later eluting diastereoisomer. HRMS calculated for C$_{24}$H$_{22}$FN$_3$O$_2$S: 435.1417, found: 436.1498 (M+H).

Example 71: N-[6-ethyl-5-(1H-indol-7-yl)thieno[2,3-d]pyrimidin-4-yl]-D-phenylalanine, diastereoisomer 1 and Example 72: N-[6-ethyl-5-(1H-indol-7-yl)thieno[2,3-d]pyrimidin-4-yl]-D-phenylalanine, diastereoisomer 2

Using General Procedure IIa and Preparation 3a as the appropriate 5-iodo-thieno[2,3-d]pyrimidine derivative and 7-(4,4,5,5-tetramethyl-1,3,2-dioxaborolan-2-yl)-1H-indole as the appropriate boronic acid derivative, a mixture of diastereoisomers was obtained. They were separated via preparative reversed phase chromatography using 0.1% aqueous TFA solution and acetonitrile as eluents. Example 71 was obtained as the earlier eluting diastereoisomer. HRMS calculated for C$_{25}$H$_{22}$N$_4$O$_2$S: 442.1463, found: 443.1540 (M+H).

Example 72 was obtained as the later eluting diastereoisomer. HRMS calculated for $C_{25}H_{22}N_4O_2S$: 442.1463, found: 443.1537 (M+H).

Example 73: N-[6-ethyl-(5$S_a$)-5-(1H-indol-4-yl)thieno[2,3-d]pyrimidin-4-yl]-D-phenylalanine and Example 74: N-[6-ethyl-(5$R_a$)-5-(1H-indol-4-yl)thieno[2,3-d]pyrimidin-4-yl]-D-phenylalanine The diastereoisomers of Preparation 7h were separated by preparative reversed phase chromatography using 0.1% aqueous TFA solution and acetonitrile as eluents.
Example 73 was obtained as the earlier eluting diastereoisomer. HRMS calculated for $C_{25}H_{22}N_4O_2S$: 442.1463, found: found: 443.1529 (M+H).
Example 74 was obtained as the later eluting diastereoisomer. HRMS calculated for $C_{25}H_{22}N_4O_2S$: 442.1463, found: 443.1538 (M+H).

Example 75: N-[6-ethyl-(5$S_a$)-5-(3-methoxy-2-methylphenyl)thieno[2,3-d]pyrimidin-4-yl]-D-phenylalanine and Example 76: N-[6-ethyl-(5$R_a$)-5-(3-methoxy-2-methylphenyl)thieno[2,3-d]pyrimidin-4-yl]-D-phenylalanine Using General Procedure IIb and Preparation 3a as the appropriate 5-iodo-thieno[2,3-d]pyrimidine derivative and 2-(3-methoxy-2-methyl-phenyl)-4,4,5,5-tetramethyl-1,3,2-dioxaborolane as the appropriate boronic acid derivative, using DME:water 5:1 instead of 2-Me-THF, and separating the diastereoisomers by preparative reversed phase chromatography using 25 mM aqueous $NH_4HCO_3$ solution and acetonitrile as eluents,
Example 75 was obtained as the earlier eluting diastereoisomer. HRMS calculated for $C_{25}H_{25}N_3O_3S$: 447.1617, found: 448.1701 (M+H).
Example 76 was obtained as the later eluting diastereoisomer. HRMS calculated for $C_{25}H_{25}N_3O_3S$: 447.1617, found: 448.1672 (M+H).

Example 77: N-[(5$R_a$)-5-(2-chloro-3-methylpyridin-4-yl)-6-ethylthieno[2,3-d]pyrimidin-4-yl]-D-phenylalanine and Example 78 N-[(5$S_a$)-5-(2-chloro-3-methylpyridin-4-yl)-6-ethylthieno[2,3-d]pyrimidin-4-yl]-D-phenylalanine Using General Procedure IIb and Preparation 3a as the appropriate 5-iodo-thieno[2,3-d]pyrimidine derivative and 2-chloro-3-methyl-4-(4,4,5,5-tetramethyl-1,3,2-dioxaborolan-2-yl)pyridine as the appropriate boronic acid derivative, using DME:water 5:1 instead of 2-Me-THF, and separating the diastereoisomers by preparative reversed phase chromatography using 0.1% aqueous TFA solution and acetonitrile as eluents,
Example 77 was obtained as the earlier eluting diastereoisomer. HRMS calculated for $C_{23}H_{21}ClN_4O_2S$: 452.1074, found: 453.1158 (M+H).
Example 78 was obtained as the later eluting diastereoisomer. HRMS calculated for $C_{23}H_{21}ClN_4O_2S$: 452.1074, found: 453.1165 (M+H).

Example 79: N-[6-ethyl-5-(naphthalen-1-yl)thieno[2,3-d]pyrimidin-4-yl]-D-phenylalanine Using General Procedure IIb and Preparation 3a as the appropriate 5-iodo-thieno[2,3-d]pyrimidine derivative and 4,4,5,5-tetramethyl-2-(1-naphthyl)-1,3,2-dioxaborolane as the appropriate boronic acid derivative, a mixture of diastereoisomers was obtained. It was purified via preparative reversed phase chromatography using 0.1% aqueous TFA solution and acetonitrile as eluents, Example 79 was obtained as the mixture of diastereoisomers.
HRMS calculated for $C_{27}H_{23}N_3O_2S$: 453.1511, found: 454.1580 and 454.1580 (M+H).

Example 80: N-[6-ethyl-5-(quinolin-5-yl)thieno[2,3-d]pyrimidin-4-yl]-D-phenylalanine Using General Procedure IIa and Preparation 3a as the appropriate 5-iodo-thieno[2,3-d]pyrimidine derivative and 5-(4,4,5,5-tetramethyl-1,3,2-dioxaborolan-2-yl)quinolone as the appropriate boronic acid derivative, a mixture of diastereoisomers was obtained. It was purified via preparative reversed phase chromatography using 40 mM aqueous $NH_4OAc$ solution (pH=4, adjusted with AcOH) and acetonitrile as eluents. Example 80 was obtained as a mixture of diastereoisomers. HRMS calculated for $C_{26}H_{22}N_4O_2S$: 454.1463, found: 455.1554 and 455.1518 (M+H).

Example 81: N-[6-ethyl-(5$S_a$)-5-(isoquinolin-4-yl)thieno[2,3-d]pyrimidin-4-yl]-D-phenylalanine and Example 82: N-[6-ethyl-(5$R_a$)-5-(isoquinolin-4-yl)thieno[2,3-d]pyrimidin-4-yl]-D-phenylalanine Step A: 4-chloro-6-ethyl-5-(4-isoquinolyl)thieno[2,3-d]pyrimidine Using General Procedure IIc and Preparation 2a as the appropriate 5-iodo-thieno[2,3-d]pyrimidin and 4-(4,4,5,5-tetramethyl-1,3,2-dioxaborolan-2-yl)isoquinoline as the appropriate boronic acid derivative, 4-chloro-6-ethyl-5-(4-isoquinolyl)thieno[2,3-d]pyrimidine was obtained.
$^1$H NMR (500 MHz, DMSO-$d_6$) δ: 9.46 (s, 1H), 8.93 (s, 1H), 8.50 (s, 1H), 8.26 (m, 1H), 7.74 (m, 2H), 7.42 (m, 1H), 2.65 (q, 2H), 1.14 (t, 3H)
HRMS calculated for $C_{17}H_{12}ClN_3S$: 325.0440; found 326.0502 (M+H).

Step B: N-[6-ethyl-5-(isoquinolin-4-yl)thieno[2,3-d]pyrimidin-4-yl]-D-phenylalanine Using General Procedure 1a, the product of Step A as the appropriate 4-chloro-thieno[2,3-d]pyrimidine derivative and D-phenylalanine as the appropriate amino acid derivative N-[6-ethyl-5-(isoquinolin-4-yl)thieno[2,3-d]pyrimidin-4-yl]-D-phenylalanine was obtained as a mixture of diastereoisomers. They were separated via preparative reversed phase chromatography using water and acetonitrile as eluents. Example 81 was obtained as the earlier eluting diastereoisomer. HRMS calculated for $C_{26}H_{22}N_4O_2S$: 454.1463, found: 455.1526 (M+H).
Example 82 was obtained as the later eluting diastereoisomer. HRMS calculated for $C_{26}H_{22}N_4O_2S$: 454.1463, found: 455.1538 (M+H).

Example 83: N-[6-ethyl-(5S$_a$)-5-(1-methyl-1H-indol-7-yl)thieno[2,3-d]pyrimidin-4-yl]-D-phenylalanine and Example 84: N-[6-ethyl-(5R$_a$)-5-(1-methyl-1H-indol-7-yl)thieno[2,3-d]pyrimidin-4-yl]-D-phenylalanine Using General Procedure IIb and Preparation 3a as the appropriate 5-iodo-thieno[2,3-d]pyrimidine derivative and 1-methyl-7-(4,4,5,5-tetramethyl-1,3,2-dioxaborolan-2-yl) indole as the appropriate boronic acid derivative, a mixture of diastereoisomers was obtained. They were separated via preparative reversed phase chromatography using 40 mM aqueous NH$_4$OAc solution (pH=4, adjusted with AcOH) and acetonitrile as eluents. Example 83 was obtained as the earlier eluting diastereoisomer. HRMS calculated for C$_{26}$H$_{24}$N$_4$O$_2$S: 456.1620, found: 457.1671 (M+H). Example 84 was obtained as the later eluting diastereoisomer. HRMS calculated for C$_{26}$H$_{22}$N$_4$O$_2$S: 456.1620, found: 457.1701 (M+H).

Example 85: N-[6-ethyl-(5S$_a$)-5-(3-methyl-1H-indol-4-yl)thieno[2,3-d]pyrimidin-4-yl]-D-phenylalanine and Example 86: N-[6-ethyl-(5R$_a$)-5-(3-methyl-1H-indol-4-yl)thieno[2,3-d]pyrimidin-4-yl]-D-phenylalanine Using General Procedure IIc and Preparation 3a as the appropriate 5-iodo-thieno[2,3-d]pyrimidine derivative and 3-methyl-4-(4,4,5,5-tetramethyl-1,3,2-dioxaborolan-2-yl)-1H-indole as the appropriate boronic acid derivative, a mixture of diastereoisomers was obtained. They were separated via preparative reversed phase chromatography using 40 mM aqueous NH$_4$OAc solution (pH=4, adjusted with AcOH) and acetonitrile as eluents. HRMS calculated for C$_{26}$H$_{24}$N$_4$O$_2$S: 456.1620, found: 457.1691 (M+H). Example 86 was obtained as the later eluting diastereoisomer. HRMS calculated for C$_{26}$H$_{24}$N$_4$O$_2$S: 456.1620, found: 457.1688 (M+H).

Example 87: N-[6-ethyl-5-(1-methyl-1H-indazol-4-yl)thieno[2,3-d]pyrimidin-4-yl]-D-phenylalanine Using General Procedure IIa and Preparation 3a as the appropriate 5-iodo-thieno[2,3-d]pyrimidine derivative and 1-methyl-4-(4,4,5,5-tetramethyl-1,3,2-dioxaborolan-2-yl) indazole as the appropriate boronic acid derivative, Example 87 was obtained as a mixture of diastereoisomers. HRMS calculated for C$_{25}$H$_{23}$N$_5$O$_2$S: 457.1572, found: 458.1646 and 458.1648 (M+H).

Example 88: N-[6-ethyl-(5S$_a$)-5-(1-methyl-1H-indazol-7-yl)thieno[2,3-d]pyrimidin-4-yl]-D-phenylalanine and Example 89: N-[6-ethyl-(5R$_a$)-5-(1-methyl-1H-indazol-7-yl)thieno[2,3-d]pyrimidin-4-yl]-D-phenylalanine Using General Procedure IIa and Preparation 3a as the appropriate 5-iodo-thieno[2,3-d]pyrimidine derivative and (1-methylindazol-7-yl)boronic acid as the appropriate boronic acid derivative, Example 88 was obtained as the earlier eluting diastereoisomer. HRMS calculated for C$_{25}$H$_{23}$N$_2$O$_2$S: 457.1572, found: 458.1641 (M+H). Example 89 was obtained as the later eluting diastereoisomer. HRMS calculated for C$_{25}$H$_{23}$N$_2$O$_2$S: 457.1572, found: 458.1634 (M+H).

Example 90: N-[(5S$_a$)-5-(3-chloro-4-hydroxy-2-methylphenyl)-6-ethylthieno[2,3-d]pyrimidin-4-yl]-D-phenylalanine and Example 91: N-[(5R$_a$)-5-(3-chloro-4-hydroxy-2-methylphenyl)-6-ethylthieno[2,3-d]pyrimidin-4-yl]-D-phenylalanine 500 mg Preparation 7e (1.12 mmol) and 157 mg NCS (1.173 mmol) were dissolved in 30 mL THF and the mixture was stirred at 60° C. overnight. The solvent was evaporated under reduced pressure and the residue was purified via flash chromatography using heptane and EtOAc as eluents to obtain methyl 2-[[5-(3-chloro-4-hydroxy-2-methyl-phenyl)-6-ethyl-thieno[2,3-d] pyrimidin-4-yl]amino]-3-phenyl-propanoate as a mixture of diastereoisomers (along with other regioisomers). The crude mixture was hydrolysed according to General Procedure VII. The diastereoisomers were purified and separated via preparative reversed phase chromatography using 25 mM aqueous NH$_4$HCO$_3$ solution and acetonitrile as eluents. Example 90 was obtained as the later eluting diastereoisomer. HRMS calculated for C$_{24}$H$_{22}$ClN$_3$O$_3$S: 467.1070, found: 468.1153 (M+H). Example 91 was obtained as the earlier eluting diastereoisomer. HRMS calculated for C$_{24}$H$_{22}$ClN$_3$O$_3$S: 467.1070, found: 468.1143 (M+H).

Example 92: N-[(5R$_a$)-5-(2,3-dichlorophenyl)-6-ethylthieno[2,3-d]pyrimidin-4-yl]-D-phenylalanine and Example 93: N-[(5S$_a$)-5-(2,3-dichlorophenyl)-6-ethylthieno[2,3-d]pyrimidin-4-yl]-D-phenylalanine Using General Procedure IIa and Preparation 3a as the appropriate 5-iodo-thieno[2,3-d]pyrimidine derivative and (2,3-dichlorophenyl)boronic acid as the appropriate boronic acid derivative, using Xantphos instead of "BuPAd$_2$, a mixture of diastereoisomers was obtained. They were separated via preparative reversed phase chromatography using 0.1% aqueous TFA solution and acetonitrile as eluents, Example 92 was obtained as the earlier eluting diastereoisomer. HRMS calculated for C$_{23}$H$_{19}$Cl$_2$N$_3$O$_2$S: 471.0575, found: 472.0667 (M+H). Example 93 was obtained as the later eluting diastereoisomer. HRMS calculated for C$_{23}$H$_{19}$Cl$_2$N$_3$O$_2$S: 471.0575, found: 472.0654 (M+H).

Example 94: N-[(5R$_a$)-5-(3,4-dichloro-2-methylphenyl)-6-ethylthieno[2,3-d]pyrimidin-4-yl]-D-phenylalanine and Example 95: N-[(5S$_a$)-5-(3,4-dichloro-2-methylphenyl)-6-ethylthieno[2,3-d]pyrimidin-4-yl]-D-phenylalanine Using General Procedure IIb and Preparation 3a as the appropriate 5-iodo-thieno[2,3-d]pyrimidine derivative and (3,4-dichloro-2-methyl-phenyl)boronic acid as the appropriate boronic acid derivative, using Xantphos as ligand instead of Q-Phos and DME:water 4:1 instead of 2-Me-THF, a mixture of diastereoisomers was obtained. They were separated via preparative reversed phase chromatography using 0.1% aqueous TFA solution and acetonitrile as eluents, Example 94 was obtained as the earlier eluting diastereoisomer. HRMS calculated for $C_{24}H_{21}Cl_2N_3O_2S$: 485.0731, found: 486.0816 (M+H).
Example 95 was obtained as the later eluting diastereoisomer. HRMS calculated for $C_{24}H_{21}Cl_2N_3O_2S$: 485.0731, found: 486.0797 (M+H).

Example 96: N-[(5$R_a$)-5-(3-bromo-2-methylphenyl)-6-ethylthieno[2,3-d]pyrimidin-4-yl]-D-phenylalanine and

Example 97: N-[(5$S_a$)-5-(3-bromo-2-methylphenyl)-6-ethylthieno[2,3-d]pyrimidin-4-yl]-D-phenylalanine Using General Procedure IIa and Preparation 3a as the appropriate 5-iodo-thieno[2,3-d]pyrimidine derivative and Preparation B7 as the appropriate boronic acid derivative, a mixture of diastereoisomers was obtained. They were separated via preparative reversed phase chromatography using 40 mM aqueous $NH_4OAc$ solution (pH=4, adjusted with AcOH) and acetonitrile as eluents. Example 96 was obtained as the earlier eluting diastereoisomer. HRMS calculated for $C_{24}H_{22}BrN_3O_2S$: 495.0616, found: 496.0673 (M+H).
Example 97 was obtained as the later eluting diastereoisomer. HRMS calculated for $C_{24}H_{22}BrN_3O_2S$: 495.0616, found: 496.0687 (M+H).

Example 98: N-[6-ethyl-5-(1H-indazol-4-yl)thieno[2,3-d]pyrimidin-4-yl]-D-phenylalanine Using General Procedure IIa and Preparation 3a as the appropriate 5-iodo-thieno[2,3-d]pyrimidine derivative and 1H-indazol-4-ylboronic acid as the appropriate boronic acid derivative, then purifying the crude product via preparative reversed phase chromatography using 0.1% aqueous TFA solution and acetonitrile as eluents, gave Example 98 as a mixture of diastereoisomers. HRMS calculated for $C_{24}H_{21}N_5O_2S$: 443.1416, found: 444.1485 and 444.1481 (M+H).

Example 99: N-[6-ethyl-5-(quinolin-8-yl)thieno[2,3-d]pyrimidin-4-yl]-D-phenylalanine Using General Procedure IId and Preparation 3a as the appropriate 5-iodo-thieno[2,3-d]pyrimidine derivative and 8-quinolylboronic acid as the appropriate boronic acid derivative, Example 99 was obtained as a mixture of diastereoisomers. HRMS calculated for $C_{26}H_{23}N_4O_2S$: 454.1463, found: 455.1558 (M+H).

Example 100: N-[6-ethyl-(5$R_a$)-5-(naphthalen-1-yl)thieno[2,3-d]pyrimidin-4-yl]-D-phenylalanine and

Example 101: N-[6-ethyl-(5$S_a$)-5-(naphthalen-1-yl)thieno[2,3-d]pyrimidin-4-yl]-D-phenylalanine Separating the diastereoisomers of Example 79, using preparative reversed phase chromatography using 0.1% aqueous TFA solution and acetonitrile as eluents, Example 100 was obtained as the earlier eluting diastereoisomer. HRMS calculated for HRMS calculated for $C_{27}H_{23}N_3O_2S$: 453.1511, found: 454.1596 (M+H).
Example 101 was obtained as the later eluting diastereoisomer. HRMS calculated for HRMS calculated for $C_{27}H_{23}N_3O_2S$: 453.1511, found: 454.1577 (M+H).

Example 102: N-[6-ethenyl-(5$S_a$)-5-(naphthalen-1-yl)thieno[2,3-d]pyrimidin-4-yl]-D-phenylalanine and

Example 103: N-[6-ethenyl-(5$R_a$)-5-(naphthalen-1-yl)thieno[2,3-d]pyrimidin-4-yl]-D-phenylalanine Using General Procedure Ia and Preparation 4w as the appropriate 4-chloro-thieno[2,3-d]pyrimidine derivative and D-phenylalanine as the appropriate amino acid derivative, Example 102 was obtained as the earlier eluting diastereoisomer. HRMS calculated for $C_{27}H_{21}N_3O_2S$: 451.1354, found: 452.1411 (M+H).
Example 103 was obtained as the later eluting diastereoisomer. HRMS calculated for $C_{27}H_{21}N_3O_2S$: 451.1354, found: 452.1412 (M+H).

Example 104: N-[(5$S_a$)-5-(naphthalen-1-yl)-6-((1Z)-prop-1-en-1-yl)thieno[2,3-d]pyrimidin-4-yl]-D-phenylalanine and

Example 105: N-[(5$R_a$)-5-(naphthalen-1-yl)-6-((1Z)-prop-1-en-1-yl)thieno[2,3-d]pyrimidin-4-yl]-D-phenylalanine Using General Procedure Ib and Preparation 4x as the appropriate 4-chloro-thieno[2,3-d]pyrimidine derivative and D-phenylalanine as the appropriate amino acid derivative, a mixture of diastereoisomers was obtained. They were separated via preparative reversed phase chromatography using 40 mM aqueous $NH_4OAc$ solution (pH=4, adjusted with AcOH) and acetonitrile as eluents. Example 104 was obtained as the earlier eluting diastereoisomer. HRMS calculated for $C_{28}H_{23}N_3O_2S$: 465.1511, found: 466.1577 (M+H).
Example 104 μlso contains 55% of Example 108.
Example 105 was obtained as the later eluting diastereoisomer. HRMS calculated for $C_{28}H_{23}N_3O_2S$: 465.1511, found: 466.1578 (M+H).
Example 105 μlso contains 55% Example 109.

Example 106: N-[(5$S_a$)-5-(naphthalen-1-yl)-6-(prop-1-en-2-yl)thieno[2,3-d]pyrimidin-4-yl]-D-phenylalanine and

Example 107: N-[(5$R_a$)-5-(naphthalen-1-yl)-6-(prop-1-en-2-yl)thieno[2,3-d]pyrimidin-4-yl]-D-phenylalanine Using General Procedure Ia and Preparation 4y as the appropriate 4-chloro-thieno[2,3-d]pyrimidine derivative and D-phenylalanine as the appropriate amino acid derivative, a mixture of diastereoisomers was obtained. They were separated via preparative reversed phase chromatography using 40 mM aqueous $NH_4OAc$ solution (pH=4, adjusted with AcOH) and acetonitrile as eluents. Example 106 was obtained as the earlier eluting diastereoisomer. HRMS calculated for $C_{28}H_{23}N_3O_2S$: 465.1511, found: 466.1581 (M+H).
Example 107 was obtained as the later eluting diastereoisomer. HRMS calculated for $C_{28}H_{23}N_3O_2S$: 465.1511, found: 466.1597 (M+H).

Example 108: N-{(5S$_a$)-5-(naphthalen-1-yl)-6-[(1E)-prop-1-en-1-yl]thieno[2,3-d]pyrimidin-4-yl}-D-phenylalanine and

Example 109: N-{(5R$_a$)-5-(naphthalen-1-yl)-6-[(1E)-prop-1-en-1-yl]thieno[2,3-d]pyrimidin-4-yl}-D-phenylalanine Using General Procedure Ia and Preparation 4z as the appropriate 4-chloro-thieno[2,3-d]pyrimidine derivative and D-phenylalanine as the appropriate amino acid derivative, a mixture of diastereoisomers was obtained. They were separated via preparative reversed phase chromatography using 40 mM aqueous NH$_4$OAc solution (pH=4, adjusted with AcOH) and acetonitrile as eluents. Example 108 was obtained as the earlier eluting diastereoisomer. HRMS calculated for $C_{28}H_{23}N_3O_2S$: 465.1511, found: 466.1593 (M+H).
Example 109 was obtained as the later eluting diastereoisomer. HRMS calculated for $C_{28}H_{23}N_3O_2S$: 465.1511, found: 466.1581 (M+H).

Example 110: N-[5-(3-chloro-2-methylphenyl)-6-ethylthieno[2,3-d]pyrimidin-4-yl]-3-(1H-pyrazol-1-yl)alanine Using General Procedure Ic and Preparation 4j as the appropriate 4-chloro-thieno[2,3-d]pyrimidine derivative and methyl 2-amino-3-pyrazol-1-yl-propanoate hydrochloride as the appropriate amino acid derivative, then hydrolyzing the formed intermediate according to General Procedure VII, a mixture of diastereoisomers was obtained. It was purified via preparative reversed phase chromatography using 0.1% aqueous TFA solution and acetonitrile as eluents, and Example 110 was obtained as the mixture of diastereoisomers. HRMS calculated for $C_{21}H_{20}ClN_5O_2S$: 441.1026, found: 442.1120 and 442.1123 (M+H).

Example 111: N-[(5R$_a$)-5-(3-chloro-2-methylphenyl)-6-ethylthieno[2,3-d]pyrimidin-4-yl]-3-cyclopentyl-D-alanine and

Example 112: N-[(5S$_a$)-5-(3-chloro-2-methylphenyl)-6-ethylthieno[2,3-d]pyrimidin-4-yl]-3-cyclopentyl-D-alanine Using General Procedure Ib and Preparation 4j as the appropriate 4-chloro-thieno[2,3-d]pyrimidine derivative and (2R)-2-amino-3-cyclopentyl-propanoic acid as the appropriate amino acid derivative, a mixture of diastereoisomers was obtained. They were separated via preparative reversed phase chromatography using 0.1% aqueous TFA solution and acetonitrile as eluents. Example 111 was obtained as the earlier eluting diastereoisomer. HRMS calculated for $C_{23}H_{26}ClN_3O_2S$: 443.1434, found: 444.1519 (M+H).
Example 112 was obtained as the later eluting diastereoisomer. HRMS calculated for $C_{23}H_{26}ClN_3O_2S$: 443.1434, found: 444.1518 (M+H).

Example 113: N-[(5S$_a$)-5-(3-chloro-2-methylphenyl)-6-ethylthieno[2,3-d]pyrimidin-4-yl]-D-phenylalanine and

Example 114: N-[(5R$_a$)-5-(3-chloro-2-methylphenyl)-6-ethylthieno[2,3-d]pyrimidin-4-yl]-D-phenylalanine Using General Procedure IIa and Preparation 3a as the appropriate 5-iodo-thieno[2,3-d]pyrimidine derivative and (3-chloro-2-methyl-phenyl)boronic acid as the appropriate boronic acid derivative, a mixture of diastereoisomers was obtained. They were separated via preparative reversed phase chromatography using 40 mM aqueous NH$_4$OAc solution (pH=4, adjusted with AcOH) and acetonitrile as eluents. Example 113 was obtained as the earlier eluting diastereoisomer. HRMS calculated for $C_{24}H_{22}ClN_3O_2S$: 451.1121, found: 452.1192 (M+H).
Example 114 was obtained as the later eluting diastereoisomer. HRMS calculated for $C_{24}H_{22}ClN_3O_2S$: 451.1121, found: 452.1174 (M+H).

Example 115: N-[(5S$_a$)-5-(3-chloro-2-methylphenyl)-6-ethylthieno[2,3-d]pyrimidin-4-yl]-L-phenylalanine and

Example 116: N-[(5R$_a$)-5-(3-chloro-2-methylphenyl)-6-ethylthieno[2,3-d]pyrimidin-4-yl]-L-phenylalanine Using General Procedure Ib and Preparation 4j as the appropriate 4-chloro-thieno[2,3-d]pyrimidine derivative and L-phenylalanine as the appropriate amino acid derivative, a mixture of diastereoisomers was obtained. They were separated via preparative reversed phase chromatography using 0.1% aqueous TFA solution and acetonitrile as eluents.
Example 115 was obtained as the earlier eluting diastereoisomer. HRMS calculated for $C_{24}H_{22}ClN_3O_2S$: 451.1121, found: 452.1207 (M+H).
Example 116 was obtained as the later eluting diastereoisomer. HRMS calculated for $C_{24}H_{22}ClN_3O_2S$: 451.1121, found: 452.1183 (M+H).

Example 117: N-[(5R$_a$)-5-(3-chloro-2-methylphenyl)-6-ethylthieno[2,3-d]pyrimidin-4-yl]-3-cyclohexyl-D-alanine and

Example 118: N-[(5S$_a$)-5-(3-chloro-2-methylphenyl)-6-ethylthieno[2,3-d]pyrimidin-4-yl]-3-cyclohexyl-D-alanine Using General Procedure Ib and Preparation 4j as the appropriate 4-chloro-thieno[2,3-d]pyrimidine derivative and (2R)-2-amino-3-cyclohexyl-propanoic acid as the appropriate amino acid derivative, a mixture of diastereoisomers was obtained. They were separated via preparative reversed phase chromatography using 0.1% aqueous TFA solution and acetonitrile as eluents. Example 117 was obtained as the earlier eluting diastereoisomer. HRMS calculated for $C_{24}H_{28}ClN_3O_2S$: 457.1591, found: 458.1672 (M+H).
Example 118 was obtained as the later eluting diastereoisomer. HRMS calculated for $C_{24}H_{28}ClN_3O_2S$: 457.1591, found: 458.1663 (M+H).

Example 119: N-[5-(3-chloro-2-methylphenyl)-6-ethylthieno[2,3-d]pyrimidin-4-yl]-alpha-methyl-D-phenylalanine Using General Procedure Ib and Preparation 4j as the appropriate 4-chloro-thieno[2,3-d]pyrimidine derivative and (2R)-2-amino-2-methyl-3-phenyl-propanoic acid as the appropriate amino acid derivative, a mixture of diastereoisomers was obtained. It was purified via preparative reversed phase chromatography using 0.1% aqueous TFA solution and acetonitrile as eluents. Example 119 was obtained as a mixture of diastereoisomers. HRMS calculated for $C_{25}H_{24}ClN_3O_2S$: 465.1278, found: 466.1372 and 466.1356 (M+H).

Example 120: N-[(5R$_a$)-5-(3-chloro-2-methylphenyl)-6-ethylthieno[2,3-d]pyrimidin-4-yl]-2-hydroxy-D-phenylalanine and

Example 121: N-[(5S$_a$)-5-(3-chloro-2-methylphenyl)-6-ethylthieno[2,3-d]pyrimidin-4-yl]-2-hydroxy-D-phenylalanine Using General Procedure Ib, Preparation 4j as the appropriate 4-chloro-thieno[2,3-d]pyrimidine derivative, and (2R)-2-amino-3-(2-hydroxyphenyl)propanoic acid as the appropriate amino acid derivative, a mixture of diastereoisomers was obtained. They were separated via preparative reversed phase chromatography using 0.1% aqueous TFA solution and acetonitrile as eluents. Example 120 was obtained as the earlier eluting diastereoisomer. HRMS calculated for $C_{24}H_{22}ClN_3O_3S$: 467.1070, found: 468.1135 (M+H).
Example 121 was obtained as the later eluting diastereoisomer. HRMS calculated for $C_{24}H_{22}ClN_3O_3S$: 467.1070, found: 468.1162 (M+H).

Example 122: (βS)—N-[(5R$_a$)-5-(3-chloro-2-methylphenyl)-6-ethylthieno[2,3-d]pyrimidin-4-yl]-beta-hydroxy-D-phenylalanine and

Example 123: (βS)—N-[(5S$_a$)-5-(3-chloro-2-methylphenyl)-6-ethylthieno[2,3-d]pyrimidin-4-yl]-beta-hydroxy-D-phenylalanine Using General Procedure Ib and Preparation 4j as the appropriate 4-chloro-thieno[2,3-d]pyrimidine derivative and (2R,3S)-3-phenylserine as the appropriate amino acid derivative, a mixture of diastereoisomers was obtained. They were separated via preparative reversed phase chromatography using 0.1% aqueous TFA solution and acetonitrile as eluents.
Example 122 was obtained as the earlier eluting diastereoisomer. HRMS calculated for $C_{24}H_{22}ClN_3O_3S$: 467.1070, found: 468.1151 (M+H).
Example 123 was obtained as the later eluting diastereoisomer. HRMS calculated for $C_{24}H_{22}ClN_3O_3S$: 467.1070, found: 468.1133 (M+H).

Example 124: (βR)—N-[(5R$_a$)-5-(3-chloro-2-methylphenyl)-6-ethylthieno[2,3-d]pyrimidin-4-yl]-beta-hydroxy-L-phenylalanine and

Example 125: (βR)—N-[(5S$_a$)-5-(3-chloro-2-methylphenyl)-6-ethylthieno[2,3-d]pyrimidin-4-yl]-beta-hydroxy-L-phenylalanine Using General Procedure Ib and Preparation 4j as the appropriate 4-chloro-thieno[2,3-d]pyrimidine derivative and (2S,3R)-2-amino-3-hydroxy-3-phenylpropionic acid as the appropriate amino acid derivative, a mixture of diastereoisomers was obtained. They were separated via preparative reversed phase chromatography using 0.1% aqueous TFA solution and acetonitrile as eluents. Example 124 was obtained as the earlier eluting diastereoisomer. HRMS calculated for $C_{24}H_{22}ClN_3O_3S$: 467.1070, found: 468.1144 (M+H).
Example 125 was obtained as the later eluting diastereoisomer. HRMS calculated for $C_{24}H_{22}ClN_3O_3S$: 467.1070, found: 468.1153 (M+H).

Example 126: N-[(5R$_a$)-5-(3-chloro-2-methylphenyl)-6-ethylthieno[2,3-d]pyrimidin-4-yl]-2-cyano-D-phenylalanine and

Example 127 N-[(5S$_a$)-5-(3-chloro-2-methylphenyl)-6-ethylthieno[2,3-d]pyrimidin-4-yl]-2-cyano-D-phenylalanine Using General Procedure Ib and Preparation 4j as the appropriate 4-chloro-thieno[2,3-d]pyrimidine derivative and (2R)-2-amino-3-(2-cyanophenyl)propanoic acid as the appropriate amino acid derivative, a mixture of diastereoisomers was obtained. They were separated via preparative reversed phase chromatography using 0.1% aqueous TFA solution and acetonitrile as eluents. Example 126 was obtained as the earlier eluting diastereoisomer. HRMS calculated for $C_{25}H_{21}ClN_4O_2S$: 476.1074, found: 477.1129 (M+H).
Example 127 was obtained as the later eluting diastereoisomer. HRMS calculated for $C_{25}H_{21}ClN_4O_2S$: 476.1074, found: 477.1134 (M+H).

Example 128: N-[(5R$_a$)-5-(3-chloro-2-methylphenyl)-6-ethylthieno[2,3-d]pyrimidin-4-yl]-2-methoxy-D-phenylalanine and

Example 129: N-[(5S$_a$)-5-(3-chloro-2-methylphenyl)-6-ethylthieno[2,3-d]pyrimidin-4-yl]-2-methoxy-D-phenylalanine Using General procedure Ic and Preparation 4j as the appropriate 4-chloro-thieno[2,3-d]pyrimidine derivative and (2R)-2-amino-3-(2-methoxyphenyl)propanoic acid as the appropriate amino acid derivative, a mixture of diastereoisomers was obtained. They were separated via preparative reversed phase chromatography using 0.1% aqueous TFA solution and acetonitrile as eluents. Example 128 was obtained as the earlier eluting diastereoisomer. HRMS calculated for $C_{25}H_{24}ClN_3O_3S$: 481.1227, found: 482.1320 (M+H).
Example 129 was obtained as the later eluting diastereoisomer. HRMS calculated for $C_{25}H_{24}ClN_3O_3S$: 481.1227, found: 482.1319 (M+H).

Example 130: N-[(5R$_a$)-5-(3-chloro-2-methylphenyl)-6-ethylthieno[2,3-d]pyrimidin-4-yl]-2,6-difluoro-D-phenylalanine and

Example 131: N-[(5S$_a$)-5-(3-chloro-2-methylphenyl)-6-ethylthieno[2,3-d]pyrimidin-4-yl]-2,6-difluoro-D-phenylalanine Using General Procedure Ib and Preparation 4j as the appropriate 4-chloro-thieno[2,3-d]pyrimidine derivative and (2R)-2-amino-3-(2,6-difluorophenyl)propanoic acid as the appropriate amino acid derivative, a mixture of diastereoisomers was obtained. They were separated via preparative reversed phase chromatography using 0.1% aqueous TFA solution and acetonitrile as eluents. Example 130 was obtained as the earlier eluting diastereoisomer. HRMS calculated for $C_{24}H_{20}ClF_2N_3O_2S$: 487.0933, found: 488.1009 (M+H).

Example 131 was obtained as the later eluting diastereoisomer. HRMS calculated for $C_{24}H_{20}ClF_2N_3O_2S$: 487.0933, found: 488.1020 (M+H).

Example 132: (2R)-2-{[(5R$_a$)-5-(3-chloro-2-methylphenyl)-6-ethylthieno[2,3-d]pyrimidin-4-yl]amino}-3-(1H-indol-4-yl)propanoic acid and Example 133: (2R)-2-{[(5S$_a$)-5-(3-chloro-2-methylphenyl)-6-ethylthieno[2,3-d]pyrimidin-4-yl]amino}-3-(1H-indol-4-yl)propanoic acid Using General Procedure Ib and Preparation 4j as the appropriate 4-chloro-thieno[2,3-d]pyrimidine derivative and (2R)-2-amino-3-(1H-indol-4-yl)propanoic acid hydrochloride as the appropriate amino acid derivative, a mixture of diastereoisomers was obtained. They were separated via preparative reversed phase chromatography using 0.1% aqueous TFA solution and acetonitrile as eluents. Example 132 was obtained as the earlier eluting diastereoisomer. HRMS calculated for $C_{26}H_{23}ClN_4O_2S$: 490.1230, found: 491.1289 (M+H).
Example 133 was obtained as the later eluting diastereoisomer. HRMS calculated for $C_{26}H_{23}ClN_4O_2S$: 490.1230, found: 491.1309 (M+H).

Example 134: 2-carbamoyl-N-[(5S$_a$)-5-(3-chloro-2-methylphenyl)-6-ethylthieno[2,3-d]pyrimidin-4-yl]-D-phenylalanine Using General Procedure Ib and Preparation 4j as the appropriate 4-chloro-thieno[2,3-d]pyrimidine derivative and (2R)-2-amino-3-(2-carbamoylphenyl)propanoic acid as the appropriate amino acid derivative, a mixture of diastereoisomers was obtained. They were separated via preparative reversed phase chromatography using 0.1% aqueous TFA solution and acetonitrile as eluents. Example 134 was obtained as the later eluting diastereoisomer. HRMS calculated for $C_{25}H_{23}ClN_4O_3S$: 494.1179, found: 495.1255 (M+H).

Example 135: N-[(5R$_a$)-5-(3-chloro-2-methylphenyl)-6-ethylthieno[2,3-d]pyrimidin-4-yl]-2-nitro-D-phenylalanine and Example 136: N-[(5S$_a$)-5-(3-chloro-2-methylphenyl)-6-ethylthieno[2,3-d]pyrimidin-4-yl]-2-nitro-D-phenylalanine Using General Procedure 1b and Preparation 4j as the appropriate 4-chloro-thieno[2,3-d]pyrimidine derivative and (2R)-2-amino-3-(2-nitrophenyl)propanoic acid as the appropriate amino acid derivative, a mixture of diastereoisomers was obtained. They were separated via preparative reversed phase chromatography using 0.1% aqueous TFA solution and acetonitrile as eluents. Example 135 was obtained as the earlier eluting diastereoisomer. HRMS calculated for $C_{24}H_{21}ClN_4O_4S$: 496.0972, found: 497.1026 (M+H).
Example 136 was obtained as the later eluting diastereoisomer. HRMS calculated for $C_{24}H_{21}ClN_4O_4S$: 496.0972, found: 497.1045 (M+H).

Example 137: N-[(5R$_a$)-5-(3-chloro-2-methylphenyl)-6-ethylthieno[2,3-d]pyrimidin-4-yl]-2-(trifluoromethyl)-D-phenylalanine and Example 138: N-[(5S$_a$)-5-(3-chloro-2-methylphenyl)-6-ethylthieno[2,3-d]pyrimidin-4-yl]-2-(trifluoromethyl)-D-phenylalanine Using General Procedure Ib and Preparation 4j as the appropriate 4-chloro-thieno[2,3-d]pyrimidine derivative and (2R)-2-amino-3-[2-(trifluoromethyl)phenyl]propanoic acid as the appropriate amino acid derivative, a mixture of diastereoisomers was obtained. They were separated via preparative reversed phase chromatography using 0.1% aqueous TFA solution and acetonitrile as eluents. Example 137 was obtained as the earlier eluting diastereoisomer. HRMS calculated for $C_{25}H_{21}ClF_3N_3O_2S$: 519.0995, found: 520.1068 (M+H).
Example 138 was obtained as the later eluting diastereoisomer. HRMS calculated for $C_{25}H_{21}ClF_3N_3O_2S$: 519.0995, found: 520.1047 (M+H).

Example 139: 2-bromo-N-[(5R$_a$)-5-(3-chloro-2-methylphenyl)-6-ethylthieno[2,3-d]pyrimidin-4-yl]-D-phenylalanine and Example 140: 2-bromo-N-[(5S$_a$)-5-(3-chloro-2-methylphenyl)-6-ethylthieno[2,3-d]pyrimidin-4-yl]-D-phenylalanine Using General Procedure Ib and Preparation 4j as the appropriate 4-chloro-thieno[2,3-d]pyrimidine derivative and (2R)-2-amino-3-[2-bromophenyl]propanoic acid as the appropriate amino acid derivative, a mixture of diastereoisomers was obtained. They were separated via preparative reversed phase chromatography using 0.1% aqueous TFA solution and acetonitrile as eluents. Example 139 was obtained as the earlier eluting diastereoisomer. HRMS calculated for $C_{24}H_{21}ClBrN_3O_2S$: 529.0226, found: 530.0312 (M+H).
Example 140 was obtained as the later eluting diastereoisomer. HRMS calculated for $C_{24}H_{21}ClBrN_3O_2S$: 529.0226, found: 530.0294 (M+H).

Example 141: N-[(5R$_a$)-5-(3-chloro-2-methylphenyl)-6-ethylthieno[2,3-d]pyrimidin-4-yl]-2-[2-(dimethylamino)-2-oxoethoxy]-D-phenylalanine and Example 142: N-[(5S$_a$)-5-(3-chloro-2-methylphenyl)-6-ethylthieno[2,3-d]pyrimidin-4-yl]-2-[2-(dimethylamino)-2-oxoethoxy]-D-phenylalanine Using General Procedure Ib and Preparation 4j as the appropriate 4-chloro-thieno[2,3-d]pyrimidine derivative and Preparation A9 as the appropriate amino acid derivative, a mixture of diastereoisomers was obtained. They were separated via preparative reversed phase chromatography using 0.1% aqueous TFA solution and acetonitrile as eluents.
Example 141 was obtained as the earlier eluting diastereoisomer. HRMS calculated for $C_{28}H_{29}ClN_4O_4S$: 552.1598, found: 553.1694 (M+H).
Example 142 was obtained as the later eluting diastereoisomer. HRMS calculated for $C_{28}H_{29}ClN_4O_4S$: 552.1598, found: 553.1673 (M+H).

Example 143: N-[(5R$_a$)-5-(3-chloro-2-methylphenyl)-6-ethylthieno[2,3-d]pyrimidin-4-yl]-2-(2-cyclopentylethoxy)-D-phenylalanine and Example 144: N-[(5S$_a$)-5-(3-chloro-2-methylphenyl)-6-ethylthieno[2,3-d]pyrimidin-4-yl]-2-(2-cyclopentylethoxy)-D-phenylalanine Using General Procedure Ib and Preparation 4j as the appropriate 4-chloro-thieno[2,3-d]pyrimidine derivative and Preparation A10 as the appropriate amino acid derivative, a mixture of diastereoisomers was obtained. They were separated via preparative reversed phase chromatography using 0.1% aqueous TFA solution and acetonitrile as eluents.
Example 143 was obtained as the earlier eluting diastereoisomer. HRMS calculated for $C_{31}H_{34}ClN_3O_3S$: 563.2009, found: 564.2106 (M+H).
Example 144 was obtained as the later eluting diastereoisomer. HRMS calculated for $C_{31}H_{34}ClN_3O_3S$: 563.2009, found: 564.2101 (M+H).

Example 145: N-[(5$R_a$)-5-(3-chloro-2-methylphenyl)-6-ethylthieno[2,3-d]pyrimidin-4-yl]-2-(2-phenylethoxy)-D-phenylalanine and Example 146: N-[(5$S_a$)-5-(3-chloro-2-methylphenyl)-6-ethylthieno[2,3-d]pyrimidin-4-yl]-2-(2-phenylethoxy)-D-phenylalanine Using General Procedure 1b and Preparation 4j as the appropriate 4-chloro-thieno[2,3-d]pyrimidine derivative and Preparation A11 as the appropriate amino acid derivative, a mixture of diastereoisomers was obtained. They were separated via preparative reversed phase chromatography using 0.1% aqueous TFA solution and acetonitrile as eluents.
Example 145 was obtained as the earlier eluting diastereoisomer. HRMS calculated for $C_{32}H_{30}ClN_3O_3S$: 571.1696, found: 572.1769 (M+H).
Example 146 was obtained as the later eluting diastereoisomer. HRMS calculated for $C_{32}H_{30}ClN_3O_3S$: 571.1696, found: 572.1763 (M+H).

Example 147: N-[(5$R_a$)-5-(3-chloro-2-methylphenyl)-6-ethylthieno[2,3-d]pyrimidin-4-yl]-2-(3-phenylpropoxy)-D-phenylalanine and Example 148: N-[(5$S_a$)-5-(3-chloro-2-methylphenyl)-6-ethylthieno[2,3-d]pyrimidin-4-yl]-2-(3-phenylpropoxy)-D-phenylalanine Using General Procedure 1b and Preparation 4j as the appropriate 4-chloro-thieno[2,3-d]pyrimidine derivative and Preparation A12 as the appropriate amino acid derivative, a mixture of diastereoisomers was obtained. They were separated via preparative reversed phase chromatography using 0.1% aqueous TFA solution and acetonitrile as eluents.
Example 147 was obtained as the earlier eluting diastereoisomer. HRMS calculated for $C_{33}H_{32}ClN_3O_3S$: 585.1853, found: 586.1917 (M+H).
Example 148 was obtained as the later eluting diastereoisomer. HRMS calculated for $C33H_{32}ClN_3O_3S$: 585.1853, found: 586.1906 (M+H).

Example 149: 2-[(3-chlorobenzyl)oxy]-N-[(5$R_a$)-5-(3-chloro-2-methylphenyl)-6-ethyl thieno[2,3-d]pyrimidin-4-yl]-D-phenylalanine and Example 150: 2-[(3-chlorobenzyl)oxy]-N-[(5$S_a$)-5-(3-chloro-2-methylphenyl)-6-ethyl thieno[2,3-d]pyrimidin-4-yl]-D-phenylalanine Using General Procedure Ib and Preparation 4j as the appropriate 4-chloro-thieno[2,3-d]pyrimidine derivative and Preparation A13 as the appropriate amino acid derivative, a mixture of diastereoisomers was obtained. They were separated via preparative reversed phase chromatography using 0.1% aqueous TFA solution and acetonitrile as eluents.
Example 149 was obtained as the earlier eluting diastereoisomer. HRMS calculated for $C_{31}H_{27}Cl_2N_3O_3S$: 591.1150, found: 592.1211 (M+H).
Example 150 was obtained as the later eluting diastereoisomer. HRMS calculated for $C_{31}H_{27}Cl_2N_3O_3S$: 591.1150, found: 592.1234 (M+H).

Example 151: N-[(5$R_a$)-5-(3-chloro-2-methylphenyl)-6-ethylthieno[2,3-d]pyrimidin-4-yl]-3-pyridin-2-yl-D-alanine and Example 152: N-[(5$S_a$)-5-(3-chloro-2-methylphenyl)-6-ethylthieno[2,3-d]pyrimidin-4-yl]-3-pyridin-2-yl-D-alanine Using General Procedure Ib and Preparation 4j as the appropriate 4-chloro-thieno[2,3-d]pyrimidine derivative and (2R)-2-amino-3-(2-pyridyl)propanoic acid as the appropriate amino acid derivative, a mixture of diastereoisomers was obtained. They were separated via preparative reversed phase chromatography using 0.1% aqueous TFA solution and acetonitrile as eluents. Example 151 was obtained as the earlier eluting diastereoisomer. HRMS calculated for $C_{23}H_{21}ClN_4O_2S$: 452.1074, found: 453.1146 (M+H).
Example 152 was obtained as the later eluting diastereoisomer. HRMS calculated for $C_{23}H_{21}ClN_4O_2S$: 452.1074, found: 453.1135 (M+H).

Example 153: N-[(5$R_a$)-5-(3-chloro-2-methylphenyl)-6-ethylthieno[2,3-d]pyrimidin-4-yl]-2-[2-(4-methylpiperazin-1-yl)ethoxy]-D-phenylalanine and Example 154: N-[(5$S_a$)-5-(3-chloro-2-methylphenyl)-6-ethylthieno[2,3-d]pyrimidin-4-yl]-2-[2-(4-methylpiperazin-1-yl)ethoxy]-D-phenylalanine Using General Procedure Ib and Preparation 4j as the appropriate 4-chloro-thieno[2,3-d]pyrimidine derivative and Preparation A14 as the appropriate amino acid derivative, a mixture of diastereoisomers was obtained. They were separated via preparative reversed phase chromatography using 0.1% aqueous TFA solution and acetonitrile as eluents.
Example 153 was obtained as the earlier eluting diastereoisomer. HRMS calculated for $C_{31}H_{36}ClN_5O_3S$: 593.2227, found: 594.2297 (M+H).
Example 154 was obtained as the later eluting diastereoisomer. HRMS calculated for $C_{31}H_{36}ClN_5O_3S$: 593.2227, found: 594.2289 (M+H).

Example 155: N-[(5$R_a$)-5-(3-chloro-2-methylphenyl)-6-ethylthieno[2,3-d]pyrimidin-4-yl]-2-[2-(dimethylamino)ethoxy]-D-phenylalanine and Example 156: N-[(5$S_a$)-5-(3-chloro-2-methylphenyl)-6-ethylthieno[2,3-d]pyrimidin-4-yl]-2-[2-(dimethylamino)ethoxy]-D-phenylalanine Using General Procedure Ib and Preparation 4j as the appropriate 4-chloro-thieno[2,3-d]pyrimidine derivative and Preparation A15 as the appropriate amino acid derivative, a mixture of diastereoisomers was obtained. They were separated via preparative reversed phase chromatography using 0.1% aqueous TFA solution and acetonitrile as eluents.
Example 155 was obtained as the earlier eluting diastereoisomer. HRMS calculated for $C_{28}H_{31}ClN_4O_3S$: 538.1805, found: 539.1890 (M+H).

Example 156 was obtained as the later eluting diastereoisomer. HRMS calculated for $C_{28}H_{31}ClN_4O_3S$: 538.1805, found: 539.1887 (M+H).

Example 157: N-[(5$R_a$)-5-(3-chloro-2-methylphenyl)-6-ethylthieno[2,3-d]pyrimidin-4-yl]-2-[3-(dimethylamino)propoxy]-D-phenylalanine and Example 158: N-[(5$S_a$)-5-(3-chloro-2-methylphenyl)-6-ethylthieno[2,3-d]pyrimidin-4-yl]-2-[3-(dimethylamino)propoxy]-D-phenylalanine Using General Procedure Ib and Preparation 4j as the appropriate 4-chloro-thieno[2,3-d]pyrimidine derivative and Preparation A16 as the appropriate amino acid derivative, a mixture of diastereoisomers was obtained. They were separated via preparative reversed phase chromatography using 0.1% aqueous TFA solution and acetonitrile as eluents. Example 157 was obtained as the earlier eluting diastereoisomer. HRMS calculated for $C_{29}H_{33}ClN_4O_3S$: 552.1962, found: 553.2043 (M+H).
Example 158 was obtained as the later eluting diastereoisomer. HRMS calculated for $C_{29}H_{33}ClN_4O_3S$: 552.1962, found: 553.2053 (M+H).

Example 159: 3-cyclopropyl-N-[6-ethyl-5-(naphthalen-1-yl)thieno[2,3-d]pyrimidin-4-yl]-D-alanine Using General Procedure Ib and Preparation 4k as the appropriate 4-chloro-thieno[2,3-d]pyrimidine derivative and (2R)-2-amino-3-cyclopropyl-propanoic acid as the appropriate amino acid derivative, a mixture of diastereoisomers was obtained. They were separated via preparative reversed phase chromatography using 0.1% aqueous TFA solution and acetonitrile as eluents. Example 159 was obtained as the mixture of diastereoisomers. HRMS calculated for $C_{24}H_{23}N_3O_2S$: 417.1511, found: 418.1570 (M+H).

Example 160: (2R)-{[6-ethyl-5-(naphthalen-1-yl)thieno[2,3-d]pyrimidin-4-yl]amino}(phenyl)ethanoic acid, diastereoisomer 1 and Example 161: (2R)-{[6-ethyl-5-(naphthalen-1-yl)thieno[2,3-d]pyrimidin-4-yl]amino}(phenyl)ethanoic acid, diastereoisomer 2

Using General Procedure Ib and Preparation 4k as the appropriate 4-chloro-thieno[2,3-d]pyrimidine derivative and (2R)-2-amino-2-phenyl-acetic acid as the appropriate amino acid derivative, using DMA as solvent instead of DMSO, a mixture of diastereoisomers was obtained. They were separated via preparative reversed phase chromatography using 0.1% aqueous TFA solution and acetonitrile as eluents. Example 160 was obtained as the earlier eluting diastereoisomer. HRMS calculated for $C_{26}H_{21}N_3O_2S$: 439.1354, found: 440.1428 (M+H).
Example 161 was obtained as the later eluting diastereoisomer. HRMS calculated for $C_{26}H_{21}N_3O_2S$: 439.1354, found: 440.1412 (M+H).

Example 162: N-[6-ethyl-(5$S_a$)-5-(naphthalen-1-yl)thieno[2,3-d]pyrimidin-4-yl]-3-pyridin-3-yl-D-alanine and Example 163: N-[6-ethyl-(5$R_a$)-5-(naphthalen-1-yl)thieno[2,3-d]pyrimidin-4-yl]-3-pyridin-3-yl-D-alanine Using General Procedure Ib and Preparation 4k as the appropriate 4-chloro-thieno[2,3-d]pyrimidine derivative and (2R)-2-amino-3-(3-pyridyl)propanoic acid as the appropriate amino acid derivative, a mixture of diastereoisomers was obtained. They were separated via preparative reversed phase chromatography using 40 mM aqueous $NH_4OAc$ solution (pH=4, adjusted with AcOH) and acetonitrile as eluents. Example 162 was obtained as the earlier eluting diastereoisomer. HRMS calculated for $C_{26}H_{22}N_4O_2S$: 454.1463, found: 455.1520 (M+H).
Example 163 was obtained as the later eluting diastereoisomer. HRMS calculated for $C_{26}H_{22}N_4O_2S$: 454.1463, found: 455.1536 (M+H).

Example 164: 3-cyclohexyl-N-[6-ethyl-5-(naphthalen-1-yl)thieno[2,3-d]pyrimidin-4-yl]-D-alanine Using General Procedure Ia and Preparation 4k as the appropriate 4-chloro-thieno[2,3-d]pyrimidine derivative and (2R)-2-amino-3-cyclohexyl-propanoic acid as the appropriate amino acid derivative, a mixture of diastereoisomers was obtained. It was purified via preparative reversed phase chromatography using 0.02% aqueous HCOOH solution and acetonitrile as eluents. Example 164 was obtained as the mixture of diastereoisomers. HRMS calculated for $C_{27}H_{29}N_3O_2S$: 459.1980, found: 460.2042 (M+H).

Example 165: 3-cyclohexyl-N-[6-ethyl-(5$R_a$)-5-(naphthalen-1-yl)thieno[2,3-d]pyrimidin-4-yl]-D-alanine and Example 166: 3-cyclohexyl-N-[6-ethyl-(5$S_a$)-5-(naphthalen-1-yl)thieno[2,3-d]pyrimidin-4-yl]-D-alanine Diastereoisomers of Example 164 were separated via preparative reversed phase chromatography using 40 mM aqueous $NH_4OAc$ solution (pH=4, adjusted with AcOH) and acetonitrile as eluents. Example 165 was obtained as the earlier eluting diastereoisomer. HRMS calculated for $C_{27}H_{29}N_3O_2S$: 459.1980, found: 460.2043 (M+H).
Example 166 was obtained as the later eluting diastereoisomer. HRMS calculated for $C_{27}H_{29}N_3O_2S$: 459.1980, found: 460.2058 (M+H).

Example 167: N-[6-ethyl-5-(naphthalen-1-yl)thieno[2,3-d]pyrimidin-4-yl]-2-methyl-D-phenylalanine, diastereoisomer 1 and Example 168: N-[6-ethyl-5-(naphthalen-1-yl)thieno[2,3-d]pyrimidin-4-yl]-2-methyl-D-phenylalanine, diastereoisomer 2

Using General Procedure Ib and Preparation 4k as the appropriate 4-chloro-thieno[2,3-d]pyrimidine derivative and D-2'-methylphenylalanine as the appropriate amino acid derivative, a mixture of diastereoisomers was obtained. They were separated via preparative reversed phase chromatography using 40 mM aqueous $NH_4OAc$ solution (pH=4, adjusted with AcOH) and acetonitrile as eluents. Example 167 was obtained as the earlier eluting diastereoisomer. HRMS calculated for $C_{28}H_{25}N_3O_2S$: 467.1667, found: 468.1747 (M+H).
Example 168 was obtained as the later eluting diastereoisomer. HRMS calculated for $C_{28}H_{25}N_3O_2S$: 467.1667, found: 468.1748 (M+H).

Example 169: (2R)-2-{[6-ethyl-5-(naphthalen-1-yl)thieno[2,3-d]pyrimidin-4-yl]amino}-4-phenylbutanoic acid Using General Procedure 1a and Preparation 4k as the appropriate 4-chloro-thieno[2,3-d]pyrimidine derivative and (2R)-2-amino-4-phenyl-butanoic acid as the appropriate amino acid derivative, a mixture of diastereoisomers was obtained. It was purified via preparative reversed phase chromatography using 0.02% aqueous HCOOH solution and acetonitrile as eluents. Example 169 was obtained as mixture of diastereoisomers. HRMS calculated for $C_{28}H_{25}N_3O_2S$: 467.1667, found: 468.1731 (M+H).

Example 170: (2R)-2-{[6-ethyl-(5S$_a$)-5-(naphthalen-1-yl)thieno[2,3-d]pyrimidin-4-yl]amino}-4-phenylbutanoic acid and

Example 171: (2R)-2-{[6-ethyl-(5R$_a$)-5-(naphthalen-1-yl)thieno[2,3-d]pyrimidin-4-yl]amino}-4-phenylbutanoic acid Diastereoisomers of Example 169 were separated via preparative reversed phase chromatography using 40 mM aqueous NH$_4$OAc solution (pH=4, adjusted with AcOH) and acetonitrile as eluents. Example 170 was obtained as the earlier eluting diastereoisomer. HRMS calculated for $C_{28}H_{25}N_3O_2S$: 467.1667, found: 468.1733 (M+H).
Example 171 was obtained as the later eluting diastereoisomer. HRMS calculated for $C_{28}H_{25}N_3O_2S$: 467.1667, found: 468.1726 (M+H).

Example 172: N-[6-ethyl-(5R$_a$)-5-(naphthalen-1-yl)thieno[2,3-d]pyrimidin-4-yl]-D-tyrosine and

Example 173: N-[6-ethyl-(5S$_a$)-5-(naphthalen-1-yl)thieno[2,3-d]pyrimidin-4-yl]-D-tyrosine Using General Procedure Ib and Preparation 4k as the appropriate 4-chloro-thieno[2,3-d]pyrimidine derivative and (2R)-2-amino-3-(4-hydroxyphenyl)propanoic acid as the appropriate amino acid derivative, using DMA as solvent instead of DMSO, a mixture of diastereoisomers was obtained. They were separated via preparative reversed phase chromatography using 0.1% aqueous TFA solution and acetonitrile as eluents.
Example 172 was obtained as the earlier eluting diastereoisomer. HRMS calculated for $C_{27}H_{23}N_3O_3S$: 469.1460, found: 470.1539 (M+H).
Example 173 was obtained as the later eluting diastereoisomer. HRMS calculated for $C_{27}H_{23}N_3O_3S$: 469.1460, found: 470.1534 (M+H).

Example 174: N-[6-ethyl-(5S$_a$)-5-(naphthalen-1-yl)thieno[2,3-d]pyrimidin-4-yl]-2-hydroxy-D-phenylalanine and

Example 175: N-[6-ethyl-(5R$_a$)-5-(naphthalen-1-yl)thieno[2,3-d]pyrimidin-4-yl]-2-hydroxy-D-phenylalanine Using General Procedure Ib and Preparation 4k as the appropriate 4-chloro-thieno[2,3-d]pyrimidine derivative and (2R)-2-amino-3-(2-hydroxyphenyl)propanoic acid as the appropriate amino acid derivative, a mixture of diastereoisomers was obtained. They were separated via preparative reversed phase chromatography using 40 mM aqueous NH$_4$OAc solution (pH=4, adjusted with AcOH) and acetonitrile as eluents. Example 174 was obtained as the earlier eluting diastereoisomer. HRMS calculated for $C_{27}H_{23}N_3O_3S$: 469.1460, found: 470.1546 (M+H).
Example 175 was obtained as the later eluting diastereoisomer. HRMS calculated for $C_{27}H_{23}N_3O_3S$: 469.1460, found: 470.1520 (M+H).

Example 176: N-[6-ethyl-(5R$_a$)-5-(naphthalen-1-yl)thieno[2,3-d]pyrimidin-4-yl]-4-fluoro-D-phenylalanine and

Example 177: N-[6-ethyl-(5S$_a$)-5-(naphthalen-1-yl)thieno[2,3-d]pyrimidin-4-yl]-4-fluoro-D-phenylalanine Using General Procedure Ib and Preparation 4k as the appropriate 4-chloro-thieno[2,3-d]pyrimidine derivative and (2R)-2-amino-3-(4-fluorophenyl)propanoic acid as the appropriate amino acid derivative, using DMA as solvent instead of DMSO, a mixture of diastereoisomers was obtained. They were separated via preparative reversed phase chromatography using 0.1% aqueous TFA solution and acetonitrile as eluents.
Example 176 was obtained as the earlier eluting diastereoisomer. HRMS calculated for $C_{27}H_{22}FN_3O_2S$: 471.1417, found: 472.1493 (M+H).
Example 177 was obtained as the later eluting diastereoisomer. HRMS calculated for $C_{27}H_{22}FN_3O_2S$: 471.1417, found: 472.1494 (M+H).

Example 178: N-[6-ethyl-(5R$_a$)-5-(naphthalen-1-yl)thieno[2,3-d]pyrimidin-4-yl]-3-fluoro-D-phenylalanine and

Example 179: N-[6-ethyl-(5S$_a$)-5-(naphthalen-1-yl)thieno[2,3-d]pyrimidin-4-yl]-3-fluoro-D-phenylalanine Using General Procedure Ib and Preparation 4k as the appropriate 4-chloro-thieno[2,3-d]pyrimidine derivative and (2R)-2-amino-3-(3-fluorophenyl)propanoic acid as the appropriate amino acid derivative, a mixture of diastereoisomers was obtained. They were separated via preparative reversed phase chromatography using 0.1% aqueous TFA solution and acetonitrile as eluents. Example 178 was obtained as the earlier eluting diastereoisomer. HRMS calculated for $C_{27}H_{22}FN_3O_2S$: 471.1417, found: 472.1486 (M+H).
Example 179 was obtained as the later eluting diastereoisomer. HRMS calculated for $C_{27}H_{22}FN_3O_2S$: 471.1417, found: 472.1482 (M+H).

Example 180: N-[6-ethyl-(5R$_a$)-5-(naphthalen-1-yl)thieno[2,3-d]pyrimidin-4-yl]-2-fluoro-D-phenylalanine and

Example 181: N-[6-ethyl-(5S$_a$)-5-(naphthalen-1-yl)thieno[2,3-d]pyrimidin-4-yl]-2-fluoro-D-phenylalanine Using General Procedure Ib and Preparation 4k as the appropriate 4-chloro-thieno[2,3-d]pyrimidine derivative and (2R)-2-amino-3-(2-fluorophenyl)propanoic acid as the appropriate amino acid derivative, using DMA as solvent instead of DMSO, a mixture of diastereoisomers was obtained. They were separated via preparative reversed phase chromatography using 0.1% aqueous TFA solution and acetonitrile as eluents.

Example 180 was obtained as the earlier eluting diastereoisomer. HRMS calculated for $C_{27}H_{22}FN_3O_2S$: 471.1417, found: 472.1501 (M+H).

Example 181 was obtained as the later eluting diastereoisomer. HRMS calculated for $C_{27}H_{22}FN_3O_2S$: 471.1417, found: 472.1492 (M+H).

Example 182: N-[6-ethyl-5-(naphthalen-1-yl)thieno[2,3-d]pyrimidin-4-yl]-2-methoxy-D-phenylalanine Using General Procedure Ib and Preparation 4k as the appropriate 4-chloro-thieno[2,3-d]pyrimidine derivative and (2R)-2-amino-3-(2-methoxyphenyl)propanoic acid as the appropriate amino acid derivative, a mixture of diastereoisomers was obtained. It was purified via preparative reversed phase chromatography using 40 mM aqueous $NH_4OAc$ solution (pH=4, adjusted with AcOH) and acetonitrile as eluents. Example 182 was obtained as a mixture of diastereoisomers. HRMS calculated for $C_{28}H_{25}N_3O_3S$: 483.1617, found: 484.1682 and 484.1695 (M+H).

Example 183: 2-chloro-N-[6-ethyl-5-(naphthalen-1-yl)thieno[2,3-d]pyrimidin-4-yl]-D-phenylalanine Using General Procedure Ib and Preparation 4k as the appropriate 4-chloro-thieno[2,3-d]pyrimidine derivative and (2R)-2-amino-3-(2-chlorophenyl)propanoic acid as the appropriate amino acid derivative, a mixture of diastereoisomers was obtained. It was purified via preparative reversed phase chromatography using 0.1% aqueous TFA solution and acetonitrile as eluents. Example 183 was obtained as the mixture of diastereoisomers. HRMS calculated for $C_{27}H_{22}ClN_3O_2S$: 487.1121, found: 488.1198 and 488.1199 (M+H).

Example 184: N-[6-ethyl-(5R$_a$)-5-(naphthalen-1-yl)thieno[2,3-d]pyrimidin-4-yl]-D-tryptophan and Example 185: N-[6-ethyl-(5S$_a$)-5-(naphthalen-1-yl)thieno[2,3-d]pyrimidin-4-yl]-D-tryptophan Using General Procedure Ib and Preparation 4k as the appropriate 4-chloro-thieno[2,3-d]pyrimidine derivative and (2R)-2-amino-3-(1H-indol-3-yl)propanoic acid as the appropriate amino acid derivative, using DMA as solvent instead of DMSO, a mixture of diastereoisomers was obtained. They were separated via preparative reversed phase chromatography using 0.1% aqueous TFA solution and acetonitrile as eluents.

Example 184 was obtained as the earlier eluting diastereoisomer. HRMS calculated for $C_{29}H_{24}N_4O_2S$: 492.1620, found 493.1693 (M+H).

Example 185 was obtained as the later eluting diastereoisomer. HRMS calculated for $C_{29}H_{24}N_4O_2S$: 492.1620, found 493.1690 (M+H).

Example 186: N-[6-ethyl-5-(naphthalen-1-yl)thieno[2,3-d]pyrimidin-4-yl]-3-naphthalen-1-yl-D-alanine, diastereoisomer 1 and Example 187: N-[6-ethyl-5-(naphthalen-1-yl)thieno[2,3-d]pyrimidin-4-yl]-3-naphthalen-1-yl-D-alanine, diastereoisomer 2

Using General Procedure Ib and Preparation 4k as the appropriate 4-chloro-thieno[2,3-d]pyrimidine derivative and (2R)-2-amino-3-(1-naphthyl)propanoic acid as the appropriate amino acid derivative, using DMA as solvent instead of DMSO, a mixture of diastereoisomers was obtained. They were separated via preparative reversed phase chromatography using 0.1% aqueous TFA solution and acetonitrile as eluents.

Example 186 was obtained as the earlier eluting diastereoisomer. HRMS calculated for $C_{31}H_{25}N_3O_2S$: 503.1667, found: 504.1754 (M+H).

Example 187 was obtained as the later eluting diastereoisomer. HRMS calculated for $C_{31}H_{25}N_3O_2S$: 503.1667, found: 504.1758 (M+H).

Example 188: (2R)-biphenyl-2-yl{[6-ethyl-5-(naphthalen-1-yl)thieno[2,3-d]pyrimidin-4-yl]amino}ethanoic acid, diastereoisomer 2

Using General Procedure Ib and Preparation 4k as the appropriate 4-chloro-thieno[2,3-d]pyrimidine derivative and (R)-amino-biphenyl-2-yl-acetic acid as the appropriate amino acid derivative, a mixture of diastereoisomers was obtained. They were separated via preparative reversed phase chromatography using 40 mM aqueous $NH_4OAc$ solution (pH=4, adjusted with AcOH) and acetonitrile as eluents. Example 188 was obtained as the later eluting diastereoisomer. HRMS calculated for $C_{32}H_{25}N_3O_2S$: 515.1667, found: 516.1747 (M+H).

Example 189: (2R)-biphenyl-3-yl{[6-ethyl-5-(naphthalen-1-yl)thieno[2,3-d]pyrimidin-4-yl]amino}ethanoic acid, diastereoisomer 1

Using General Procedure Ib and Preparation 4k as the appropriate 4-chloro-thieno[2,3-d]pyrimidine derivative and (R)-amino-biphenyl-3-yl-acetic acid as the appropriate amino acid derivative, a mixture of diastereoisomers was obtained. They were separated via preparative reversed phase chromatography using 40 mM aqueous $NH_4OAc$ solution (pH=4, adjusted with AcOH) and acetonitrile as eluents. Example 189 was obtained as the earlier eluting diastereoisomer. HRMS calculated for $C_{32}H_{25}N_3O_2S$: 515.1667, found: 516.1743 (M+H).

Example 190: N-[6-ethyl-5-(naphthalen-1-yl)thieno[2,3-d]pyrimidin-4-yl]-D-histidine Using General Procedure Ia and Preparation 4k as the appropriate 4-chloro-thieno[2,3-d]pyrimidine derivative and (2R)-2-amino-3-(1H-imidazol-4-yl)propanoic acid as the appropriate amino acid derivative, a mixture of diastereoisomers was obtained. It was purified via preparative reversed phase chromatography using 0.1% aqueous TFA solution and acetonitrile as eluents. Example 190 was obtained as a mixture of diastereoisomers. HRMS calculated for $C_{24}H_{21}N_5O_2S$: 443.1416, found: 444.1462 and 444.1471 for the two diastereoisomers (M+H).

Example 191: N-[6-ethyl-5-(naphthalen-1-yl)thieno[2,3-d]pyrimidin-4-yl]-3-pyridin-2-yl-D-alanine Using General Procedure Ib and Preparation 4k as the appropriate 4-chloro-thieno[2,3-d]pyrimidine derivative and (2R)-2-amino-3-(2-pyridyl)propanoic acid as the appropriate amino acid derivative, a mixture of diastereoisomers was obtained. It was purified via preparative reversed phase chromatography using 0.1% aqueous TFA solution and acetonitrile as eluents. Example 191 was obtained as a mixture of diastereoisomers. HRMS calculated for $C_{26}H_{22}N_4O_2S$: 454.1463, found: 455.1537 and 455.1558 for the two diastereoisomers (M+H).

Example 192: N-[6-ethyl-5-(naphthalen-1-yl)thieno[2,3-d]pyrimidin-4-yl]-3-pyridin-3-yl-D-alanine Using General Procedure Ib and Preparation 4k as the appropriate 4-chloro-thieno[2,3-d]pyrimidine derivative and 3-(3-pyridyl)-D-alanine as the appropriate amino acid derivative, a mixture of diastereoisomers was obtained. It was purified via preparative reversed phase chromatography using 0.1% aqueous TFA solution and acetonitrile as eluents. Example 192 was obtained as a mixture of diastereoisomers. HRMS calculated for $C_{26}H_{22}N_4O_2S$: 454.1445, found: 455.1545 and 455.1553 for the two diastereoisomers (M+H).

Example 193: N-[6-ethyl-5-(naphthalen-1-yl)thieno[2,3-d]pyrimidin-4-yl]-3-pyridin-4-yl-D-alanine Using General Procedure Ib and Preparation 4k as the appropriate 4-chloro-thieno[2,3-d]pyrimidine derivative and (2R)-2-amino-3-(4-pyridyl)propanoic acid as the appropriate amino acid derivative, a mixture of diastereoisomers was obtained. It was purified via preparative reversed phase chromatography using 0.1% aqueous TFA solution and acetonitrile as eluents. Example 193 was obtained as a mixture of diastereoisomers. HRMS calculated for $C_{26}H_{22}N_4O_2S$: 454.1440, found: 455.1540 and 455.1545 for the two diastereoisomers (M+H).

Example 194: N-[6-ethyl-5-(naphthalen-1-yl)thieno[2,3-d]pyrimidin-4-yl]-1-methyl-D-histidine Using General Procedure Ib and Preparation 4k as the appropriate 4-chloro-thieno[2,3-d]pyrimidine derivative and (2R)-2-amino-3-(1-methylimidazol-4-yl)propanoic acid as the appropriate amino acid derivative, a mixture of diastereoisomers was obtained. It was purified via preparative reversed phase chromatography using 0.1% aqueous TFA solution and acetonitrile as eluents. Example 194 was obtained as a mixture of diastereoisomers. HRMS calculated for $C_{25}H_{23}N_5O_2S$: 457.1572, found: 458.1641 and 458.1654 for the two diastereoisomers (M+H).

Example 195: 1-benzyl-N-[6-ethyl-5-(naphthalen-1-yl)thieno[2,3-d]pyrimidin-4-yl]-D-histidine Using General Procedure Ib and Preparation 4k as the appropriate 4-chloro-thieno[2,3-d]pyrimidine derivative and (2R)-2-amino-3-(1-benzylimidazol-4-yl)propanoic acid as the appropriate amino acid derivative, a mixture of diastereoisomers was obtained. It was purified via preparative reversed phase chromatography using 0.1% aqueous TFA solution and acetonitrile as eluents. Example 195 was obtained as a mixture of diastereoisomers. HRMS calculated for $C_{31}H_{27}N_5O_2S$: 533.1885, found: 534.1934 and 534.1934 for the two diastereoisomers (M+H).

Example 196: N-[6-methyl-5-(naphthalen-1-yl)thieno[2,3-d]pyrimidin-4-yl]-D-phenylalanine Using General Procedure 1a and Preparation 4l as the appropriate 4-chloro-thieno[2,3-d]pyrimidine derivative and D-phenylalanine as the appropriate amino acid derivative, a mixture of diastereoisomers was obtained. It was purified via preparative reversed phase chromatography using 0.1% aqueous TFA solution and acetonitrile as eluents. Example 196 was obtained as a mixture of diastereoisomers. HRMS calculated for $C_{26}H_{21}N_3O_2S$: 439.1354, found: 440.1421 and 440.1429 (M+H).

Example 197: N-[6-(hydroxymethyl)-(5R$_a$)-5-(naphthalen-1-yl)thieno[2,3-d]pyrimidin-4-yl]-D-phenylalanine and

Example 198: N-[6-(hydroxymethyl)-(5S$_a$)-5-(naphthalen-1-yl)thieno[2,3-d]pyrimidin-4-yl]-D-phenylalanine Using General Procedure 1a and Preparation 4m as the appropriate 4-chloro-thieno[2,3-d]pyrimidine derivative and D-phenylalanine as the appropriate amino acid derivative, a mixture of diastereoisomers was obtained. They were separated via preparative reversed phase chromatography using 0.1% aqueous TFA solution and acetonitrile as eluents. Example 197 was obtained as the earlier eluting diastereoisomer. HRMS calculated for $C_{26}H_{21}N_3O_3S$: 455.1304, found: 456.1356 (M+H).
Example 198 was obtained as the later eluting diastereoisomer. HRMS calculated for $C_{26}H_{21}N_3O_3S$: 455.1304, found: 456.1390 (M+H).

Example 199: N-[6-acetyl-(5S$_a$)-5-(naphthalen-1-yl)thieno[2,3-d]pyrimidin-4-yl]-D-phenylalanine and

Example 200: N-[6-acetyl-(5R$_a$)-5-(naphthalen-1-yl)thieno[2,3-d]pyrimidin-4-yl]-D-phenylalanine Using General Procedure 1a and Preparation 4o as the appropriate 4-chloro-thieno[2,3-d]pyrimidine derivative and D-phenylalanine as the appropriate amino acid derivative, a mixture of diastereoisomers was obtained. They were separated via preparative reversed phase chromatography using 40 mM aqueous NH$_4$OAc solution (pH=4, adjusted with AcOH) and acetonitrile as eluents. Example 199 was obtained as the earlier eluting diastereoisomer. HRMS calculated for $C_{27}H_{21}N_3O_3S$: 467.1304, found: 468.1379 (M+H).
Example 200 was obtained as the later eluting diastereoisomer. HRMS calculated for $C_{27}H_{21}N_3O_3S$: 467.1304, found: 468.1377 (M+H).

Example 201: N-[5-(naphthalen-1-yl)-6-(propan-2-yl)thieno[2,3-d]pyrimidin-4-yl]-D-phenylalanine, diastereoisomer 1 and

Example 202: N-[5-(naphthalen-1-yl)-6-(propan-2-yl)thieno[2,3-d]pyrimidin-4-yl]-D-phenylalanine, diastereoisomer 2

Using General Procedure Ib and Preparation 4q as the appropriate 4-chloro-thieno[2,3-d]pyrimidine derivative and D-phenylalanine as the appropriate amino acid derivative, a mixture of diastereoisomers was obtained. They were separated via preparative reversed phase chromatography using 40 mM aqueous NH$_4$OAc solution (pH=4, adjusted with AcOH) and acetonitrile as eluents. Example 201 was obtained as the earlier eluting diastereoisomer. HRMS calculated for $C_{28}H_{25}N_3O_2S$: 467.1667, found: 468.1731 (M+H).

Example 202 was obtained as the later eluting diastereoisomer. HRMS calculated for $C_{28}H_{25}N_3O_2S$: 467.1667, found: 468.1720 (M+H).

Example 203: N-[6-(1-hydroxyethyl)-5-(naphthalen-1-yl)thieno[2,3-d]pyrimidin-4-yl]-D-phenylalanine, diastereoisomer 1 and Example 204: N-[6-(1-hydroxyethyl)-5-(naphthalen-1-yl)thieno[2,3-d]pyrimidin-4-yl]-D-phenylalanine, diastereoisomer 2

Using General Procedure 1a and Preparation 4n1 as the appropriate 4-chloro-thieno[2,3-d]pyrimidine derivative and D-phenylalanine as the appropriate amino acid derivative, a mixture of diastereoisomers was obtained. They were separated via preparative reversed phase chromatography using 0.1% aqueous TFA solution and acetonitrile as eluents. Example 203 was obtained as the earlier eluting diastereoisomer. HRMS calculated for $C_{27}H_{23}N_3O_3S$: 469.1460, found: 470.1511 (M+H).
Example 204 was obtained as the later eluting diastereoisomer. HRMS calculated for $C_{27}H_{23}N_3O_3S$: 469.1460, found: 470.1536 (M+H).

Example 205: N-[6-(1-hydroxyethyl)-5-(naphthalen-1-yl)thieno[2,3-d]pyrimidin-4-yl]-D-phenylalanine, diastereoisomer 3 and Example 206: N-[6-(1-hydroxyethyl)-5-(naphthalen-1-yl)thieno[2,3-d]pyrimidin-4-yl]-D-phenylalanine, diastereoisomer 4

Using General Procedure 1a and Preparation 4n2 as the appropriate 4-chloro-thieno[2,3-d]pyrimidine derivative and D-phenylalanine as the appropriate amino acid derivative, a mixture of diastereoisomers was obtained. They were separated via preparative reversed phase chromatography using 0.1% aqueous TFA solution and acetonitrile as eluents. Example 205 was obtained as the earlier eluting diastereoisomer. HRMS calculated for $C_{27}H_{23}N_3O_3S$: 469.1460, found: 470.1539 (M+H).
Example 206 was obtained as the later eluting diastereoisomer. HRMS calculated for $C_{27}H_{33}N_3O_3S$: 469.1460, found: 470.1534 (M+H).

Example 207: N-[6-(difluoromethyl)-5-(naphthalen-1-yl)thieno[2,3-d]pyrimidin-4-yl]-D-phenylalanine, diastereoisomer 1 and Example 208: N-[6-(difluoromethyl)-5-(naphthalen-1-yl)thieno[2,3-d]pyrimidin-4-yl]-D-phenylalanine, diastereoisomer 2

Using General Procedure 1a and Preparation 4r as the appropriate 4-chloro-thieno[2,3-d]pyrimidine derivative and D-phenylalanine as the appropriate amino acid derivative, a mixture of diastereoisomers was obtained. They were separated via preparative reversed phase chromatography using 40 mM aqueous $NH_4OAc$ solution (pH=4, adjusted with AcOH) and acetonitrile as eluents. Example 207 was obtained as the earlier eluting diastereoisomer. HRMS calculated for $C_{26}H_{19}F_2N_3O_2S$: 475.1166, found: 476.1242 (M+H).
Example 208 was obtained as the later eluting diastereoisomer. HRMS calculated for $C_{26}H_{19}F_2N_3O_2S$: 475.1166, found: 476.1244 (M+H).

Example 209: N-[6-(2-hydroxypropan-2-yl)-(5$R_a$)-5-(naphthalen-1-yl)thieno[2,3-d]pyrimidin-4-yl]-D-phenylalanine and Example 210: N-[6-(2-hydroxypropan-2-yl)-(5$S_a$)-5-(naphthalen-1-yl)thieno[2,3-d]pyrimidin-4-yl]-D-phenylalanine Using General Procedure 1a and Preparation 4p as the appropriate 4-chloro-thieno[2,3-d]pyrimidine derivative and D-phenylalanine as the appropriate amino acid derivative, a mixture of diastereoisomers was obtained. They were separated via preparative reversed phase chromatography using 0.1% aqueous TFA solution and acetonitrile as eluents. Example 209 was obtained as the earlier eluting diastereoisomer. HRMS calculated for $C_{28}H_{25}N_3O_3S$: 483.1617, found: 484.1689 (M+H).
Example 210 was obtained as the later eluting diastereoisomer. HRMS calculated for $C_{28}H_{25}N_3O_3S$: 483.1617, found: 484.1704 (M+H).

Example 211: N-[6-iodo-5-(naphthalen-1-yl)thieno[2,3-d]pyrimidin-4-yl]-D-phenylalanine Using General Procedure 1a and Preparation 4s as the appropriate 4-chloro-thieno[2,3-d]pyrimidine derivative and D-phenylalanine as the appropriate amino acid derivative, using DMA as solvent instead of DMSO, a mixture of diastereoisomers was obtained. It was purified via preparative reversed phase chromatography using 40 mM aqueous $NH_4OAc$ solution (pH=4, adjusted with AcOH) and acetonitrile as eluents. Example 211 was obtained as a mixture of diastereoisomers. HRMS calculated for $C_{25}H_{18}IN_3O_2S$: 551.0164, found: 552.0258 (M+H).

Example 212: N-[(5$R_a$)-5-(3-chloro-2-methylphenyl)-6-ethenyl-thieno[2,3-d]pyrimidin-4-yl]-D-phenylalanine and Example 213: N-[(5$S_a$)-5-(3-chloro-2-methylphenyl)-6-ethenyl-thieno[2,3-d]pyrimidin-4-yl]-D-phenylalanine Using General Procedure IIc and Preparation 5a as the the appropriate 6-iodo-thieno[2,3-d]pyrimidine and vinylboronic acid pinacol ester as the appropriate boronic acid derivative, a mixture of diastereoisomers was obtained. They were separated via preparative reversed phase chromatography using 0.1% aqueous TFA solution and acetonitrile as eluents. Example 212 was obtained as the earlier eluting diastereoisomer. HRMS calculated for $C_{24}H_{20}ClN_3O_2S$: 449.0965, found: 450.1038 (M+H).
Example 213 was obtained as the later eluting diastereoisomer. HRMS calculated for $C_{24}H_{20}ClN_3O_2S$: 449.0965, found: 450.1050 (M+H).

Example 214: N-[(5$R_a$)-5-(3-chloro-2-methylphenyl)-6-(prop-1-en-2-yl)thieno[2,3-d]pyrimidin-4-yl]-D-phenylalanine and Example 215: N-[(5$S_a$)-5-(3-chloro-2-methylphenyl)-6-(prop-1-en-2-yl)thieno[2,3-d]pyrimidin-4-yl]-D-phenylalanine Using General Procedure IIc and Preparation 5a as the the appropriate 6-iodo-thieno[2,3-d]pyrimidine and 2-isopropenyl-4,4,5,5-tetramethyl-1,3,2-dioxaborolane as the appropriate boronic acid derivative, a mixture of diastereoisomers was obtained. They were separated via preparative reversed phase chromatography using 0.1% aqueous TFA solution and acetonitrile as eluents. Example 214 was obtained as the earlier eluting diastereoisomer. HRMS calculated for $C_{25}H_{22}ClN_3O_2S$: 463.1121, found: 464.1178 (M+H).
Example 215 was obtained as the later eluting diastereoisomer. HRMS calculated for $C_{25}H_{22}ClN_3O_2S$: 463.1121, found: 464.1179 (M+H).

Example 216: N-[(5R$_a$)-5-(3-chloro-2-methylphenyl)-6-cyclopropyl-thieno[2,3-d]pyrimidin-4-yl]-D-phenylalanine and Example 217: N-[(5S$_a$)-5-(3-chloro-2-methylphenyl)-6-cyclopropyl-thieno[2,3-d]pyrimidin-4-yl]-D-phenylalanine Using General Procedure IIa and Preparation 5a as the the appropriate 6-iodo-thieno[2,3-d]pyrimidine and cyclopylboronic acid as the appropriate boronic acid derivative, and Bu$_4$NOH instead of K$_2$CO$_3$, a mixture of diastereoisomers was obtained. They were separated via preparative reversed phase chromatography using 0.1% aqueous TFA solution and acetonitrile as eluents. Example 216 was obtained as the earlier eluting diastereoisomer. HRMS calculated for $C_{25}H_{22}ClN_3O_2S$: 463.1121, found: 464.1177 (M+H).
Example 217 was obtained as the later eluting diastereoisomer. HRMS calculated for $C_{25}H_{22}ClN_3O_2S$: 463.1121, found: 464.1182 (M+H).

Example 218: N-[(5S$_a$)-5-(3-chloro-2-methylphenyl)-6-(propan-2-yl)thieno[2,3-d]pyrimidin-4-yl]-L-phenylalanine and Example 219: N-[(5R$_a$)-5-(3-chloro-2-methylphenyl)-6-(propan-2-yl)thieno[2,3-d]pyrimidin-4-yl]-L-phenylalanine Using General Procedure Ib and Preparation 4u as the the appropriate 4-chloro-thieno[2,3-d]pyrimidine derivative and L-phenylalanine as the appropriate amino acid derivative, a mixture of diastereoisomers was obtained. They were separated via preparative reversed phase chromatography using 0.1% aqueous TFA solution and acetonitrile as eluents. Example 218 was obtained as the earlier eluting diastereoisomer. HRMS calculated for $C_{25}H_{24}ClN_3O_2S$: 465.1278, found: 466.1371 (M+H).
Example 219 was obtained as the later eluting diastereoisomer. HRMS calculated for $C_{25}H_{24}ClN_3O_2S$: 465.1278, found: 466.1361 (M+H).

Example 220: N-[(5R$_a$)-5-(3-chloro-2-methylphenyl)-6-(propan-2-yl)thieno[2,3-d]pyrimidin-4-yl]-D-phenylalanine and Example 221: N-[(5S$_a$)-5-(3-chloro-2-methylphenyl)-6-(propan-2-yl)thieno[2,3-d]pyrimidin-4-yl]-D-phenylalanine Using General Procedure Ib and Preparation 4u as the the appropriate 4-chloro-thieno[2,3-d]pyrimidine derivative and D-phenylalanine as the appropriate amino acid derivative, a mixture of diastereoisomers was obtained. They were separated via preparative reversed phase chromatography using 0.1% aqueous TFA solution and acetonitrile as eluents. Example 220 was obtained as the earlier eluting diastereoisomer. HRMS calculated for $C_{25}H_{24}ClN_3O_2S$: 465.1278, found: 466.1348 (M+H).
Example 221 was obtained as the later eluting diastereoisomer. HRMS calculated for $C_{25}H_{24}ClN_3O_2S$: 465.1278, found: 466.1350 (M+H).

Example 222: N-[(5R$_a$)-5-(3-chloro-2-methylphenyl)-6-(propan-2-yl)thieno[2,3-d]pyrimidin-4-yl]-2-methoxy-D-phenylalanine and Example 223: N-[(5S$_a$)-5-(3-chloro-2-methylphenyl)-6-(propan-2-yl)thieno[2,3-d]pyrimidin-4-yl]-2-methoxy-D-phenylalanine Using General Procedure Ib and Preparation 4u as the the appropriate 4-chloro-thieno[2,3-d]pyrimidine derivative and (2R)-2-amino-3-(2-methoxyphenyl)propanoic acid as the appropriate amino acid derivative, a mixture of diastereoisomers was obtained. They were separated via preparative reversed phase chromatography using 0.1% aqueous TFA solution and acetonitrile as eluents. Example 222 was obtained as the earlier eluting diastereoisomer. HRMS calculated for $C_{26}H_{26}ClN_3O_3S$: 495.1383, found: 496.1460 (M+H).
Example 223 was obtained as the later eluting diastereoisomer. HRMS calculated for $C_{26}H_{26}ClN_3O_3S$: 495.1383, found: 496.1454 (M+H).

Example 224: N-[(5R$_a$)-5-(3-chloro-1H-indol-4-yl)-6-ethyl-thieno[2,3-d]pyrimidin-4-yl]-D-phenylalanine and Example 225: N-[(5S$_a$)-5-(3-chloro-1H-indol-4-yl)-6-ethyl-thieno[2,3-d]pyrimidin-4-yl]-D-phenylalanine 522 mg Preparation 7h (1 mmol), 164 mg NCS (1.2 mmol), 15 mL CCl$_4$ and 10 mL THF were stirred at r.t. under N$_2$ atmosphere for 2 hours. Then the mixture was poured into icy water and extracted with DCM. The combined organic phases were dried over Na$_2$SO$_4$, filtered and the filtrate was concentrated under reduced pressure. The formed diastereoisomers were separated via preparative reversed phase chromatography using 40 mM aqueous NH$_4$OAc solution (pH=4, adjusted with AcOH) and acetonitrile as eluents.
Example 224 was obtained as the later eluting diastereoisomer. HRMS calculated for $C_{25}H_{21}ClN_4O_2S$: 476.1074, found: 477.1133 (M+H).
Example 225 was obtained as the earlier eluting diastereoisomer. HRMS calculated for $C_{25}H_{21}ClN_4O_2S$: 476.1074, found: 477.1137 (M+H).

Example 226: N-[(5S$_a$)-5-(3-bromo-1H-indol-4-yl)-6-ethylthieno[2,3-d]pyrimidin-4-yl]-D-phenylalanine and Example 227: N-[(5R$_a$)-5-(3-bromo-1H-indol-4-yl)-6-ethylthieno[2,3-d]pyrimidin-4-yl]-D-phenylalanine 522 mg Preparation 7h (1 mmol), 216 mg NBS (1.2 mmol), 15 mL CCl$_4$ and 5 mL THF were stirred at r.t. under N$_2$ atmosphere for 2 hours. Then the mixture was poured into icy water and extracted with DCM. The combined organic phases were dried over Na$_2$SO$_4$, filtered and the filtrate was concentrated under reduced pressure. The formed diastereoisomers were separated via preparative reversed phase chromatography using 40 mM aqueous NH$_4$OAc solution (pH=4, adjusted with AcOH) and acetonitrile as eluents. Example 226 was obtained as the earlier eluting diastereoisomer. HRMS calculated for C$_{25}$H$_{21}$BrN$_4$O$_2$S: 520.0569, found: 521.0653 (M+H).
Example 227 was obtained as the later eluting diastereoisomer. HRMS calculated for C$_{25}$H$_{21}$BrN$_4$O$_2$S: 520.0569, found: 521.0629 (M+H).

Example 228: N-[6-ethyl-(5S$_a$)-5-(3-iodo-1H-indol-4-yl)thieno[2,3-d]pyrimidin-4-yl]-D-phenylalanine and Example 229: N-[6-ethyl-(5R$_a$)-5-(3-iodo-1H-indol-4-yl)thieno[2,3-d]pyrimidin-4-yl]-D-phenylalanine 522 mg Preparation 7h (1 mmol), 196 mg KOH (3.5 mmol), 15 mL DMF and 267 mg iodine (1.05 mmol) were stirred at r.t. under N$_2$ atmosphere for 18 hours. Then the mixture was poured into icy water and saturated Na$_2$S$_2$O$_3$ solution was added. The mixture was extracted with DCM, the combined organic phases were dried over Na$_2$SO$_4$, filtered and the filtrate was concentrated under reduced pressure. The formed diastereoisomers were separated via preparative reversed phase chromatography using 40 mM aqueous NH$_4$OAc solution (pH=4, adjusted with AcOH) and acetonitrile as eluents. Example 228 was obtained as the earlier eluting diastereoisomer. HRMS calculated for C$_{25}$H$_{21}$IN$_4$O$_2$S: 568.043, found: 569.0498 (M+H).
Example 229 was obtained as the later eluting diastereoisomer. HRMS calculated for C$_{25}$H$_{21}$IN$_4$O$_2$S: 568.043, found: 569.0502 (M+H).

Example 230: N-((5S$_a$)-5-{3-chloro-1l-[2-(dimethylamino)ethyl]-1H-indol-4-yl}-6-ethyl-thieno[2,3-d]pyrimidin-4-yl)-D-phenylalanine and Example 231: N-((5R$_a$)-5-{3-chloro-1-[2-(dimethylamino)ethyl]-1H-indol-4-yl}-6-ethyl-thieno[2,3-d]pyrimidin-4-yl)-D-phenylalanine Using General Procedure VIII and Preparation 7i as the appropriate indole derivative and 2-(N,N-dimethylamino)ethanol as the appropriate alcohol, Example 230 was obtained as the earlier eluting diastereoisomer. HRMS calculated for C$_{29}$H$_{30}$ClN$_5$O$_2$S: 547.1809, found: 548.1902 (M+H).
Example 231 was obtained as the later eluting diastereoisomer. HRMS calculated for C$_{29}$H$_{30}$ClN$_5$O$_2$S: 547.1809, found: 548.1889 (M+H).

Example 232: N-((5R$_a$)-5-{3-chloro-1-[2-(pyrrolidin-1-yl)ethyl]-1H-indol-4-yl}-6-ethyl-thieno[2,3-d]pyrimidin-4-yl)-D-phenylalanine and Example 233: N-((5S$_a$)-5-{3-chloro-1-[2-(pyrrolidin-1-yl)ethyl]-1H-indol-4-yl}-6-ethyl-thieno[2,3-d]pyrimidin-4-yl)-D-phenylalanine Using General Procedure VIII and Preparation 7i as the appropriate indole derivative and 2-pyrrolidin-1-ylethanol as the appropriate alcohol, Example 232 was obtained as the later eluting diastereoisomer. HRMS calculated for C$_{31}$H$_{32}$ClN$_5$O$_2$S: 573.1965, found: 574.2059 (M+H).
Example 233 was obtained as the earlier eluting diastereoisomer. HRMS calculated for C$_{31}$H$_{32}$ClN$_5$O$_2$S: 573.1965, found: 574.2060 (M+H).

Example 234: N-((5R$_a$)-5-{3-chloro-1-[2-(piperidin-1-yl)ethyl]-1H-indol-4-yl}-6-ethyl-thieno[2,3-d]pyrimidin-4-yl)-D-phenylalanine and Example 235: N-((5S$_a$)-5-{3-chloro-1-[2-(piperidin-1-yl)ethyl]-1H-indol-4-yl}-6-ethyl-thieno[2,3-d]pyrimidin-4-yl)-D-phenylalanine Using General Procedure VIII and Preparation 7i as the appropriate indole derivative and 2-(1-piperidyl)ethanol as the appropriate alcohol, a mixture of diastereoisomers was obtained. They were separated via preparative reversed phase chromatography using 0.1% aqueous TFA solution and acetonitrile as eluents. Example 234 was obtained as the earlier eluting diastereoisomer. HRMS calculated for C$_{32}$H$_{34}$ClN$_5$O$_2$S: 587.2122, found: 588.2201 (M+H).
Example 235 was obtained as the later eluting diastereoisomer. HRMS calculated for C$_{32}$H$_{34}$ClN$_5$O$_2$S: 587.2122, found: 588.2199 (M+H).

Example 236: N-((5R$_a$)-5-{3-chloro-1-[2-(morpholin-4-yl)ethyl]-1H-indol-4-yl}-6-ethyl-thieno[2,3-d]pyrimidin-4-yl)-D-phenylalanine and Example 237: N-((5S$_a$)-5-{3-chloro-1-[2-(morpholin-4-yl)ethyl]-1H-indol-4-yl}-6-ethyl-thieno[2,3-d]pyrimidin-4-yl)-D-phenylalanine Using General Procedure VIII and Preparation 7i as the appropriate indole derivative and 2-morpholinoethanol as the appropriate alcohol, Example 236 was obtained as the later eluting diastereoisomer. HRMS calculated for C$_{31}$H$_{32}$ClN$_5$O$_3$S: 589.1914, found: 590.1998 (M+H).
Example 237 was obtained as the earlier eluting diastereoisomer. HRMS calculated for C$_{31}$H$_{32}$ClN$_5$O$_3$S: 589.1914, found: 590.1994 (M+H).

Example 238: N-((5S$_a$)-5-{3-chloro-1-[2-(4-methylpiperazin-1-yl)ethyl]-1H-indol-4-yl}-6-ethyl-thieno[2,3-d]pyrimidin-4-yl)-D-phenylalanine and Example 239: N-((5R$_a$)-5-{3-chloro-1-[2-(4-methylpiperazin-1-yl)ethyl]-1H-indol-4-yl}-6-ethyl-thieno[2,3-d]pyrimidin-4-yl)-D-phenylalanine Using General Procedure VIII and Preparation 7i as the appropriate indole derivative and 2-(4-methylpiperazin-1-yl)ethanol as the appropriate alcohol, Example 238 was obtained as the earlier eluting diastereoisomer. HRMS calculated for C$_{32}$H$_{35}$ClN$_6$O$_2$S: 602.2231, found: 603.2312 (M+H).
Example 239 was obtained as the later eluting diastereoisomer. HRMS calculated for C32H$_{35}$ClN$_6$O$_2$S: 602.2231, found: 603.2311 (M+H).

Example 240: N-((5S$_a$)-5-{3-chloro-1-[3-(4-methylpiperazin-1-yl)propyl]-1H-indol-4-yl}-6-ethyl-thieno[2,3-d]pyrimidin-4-yl)-D-phenylalanine and Example 241: N-((5R$_a$)-5-{3-chloro-1-[3-(4-methylpiperazin-1-yl)propyl]-1H-indol-4-yl}-6-ethyl-thieno[2,3-d]pyrimidin-4-yl)-D-phenylalanine Using General Procedure VIII and Preparation 7i as the appropriate indole derivative and 3-(4-methylpiperazin-1- yl)propan-1-ol as the appropriate alcohol, Example 240 was obtained as the earlier eluting diastereoisomer. HRMS calculated for $C_{33}H_{37}ClN_6O_2S$: 616.2387, found: 617.2466 (M+H).
Example 241 was obtained as the later eluting diastereoisomer. HRMS calculated for $C_{33}H_{37}ClN_6O_2S$: 616.2387, found: 617.2473 (M+H).

Example 242: 3-cyclohexyl-N-[6-ethyl-5-(1H-indol-4-yl)thieno[2,3-d]pyrimidin-4-yl]-D-alanine, diastereoisomer 1 and Example 243: 3-cyclohexyl-N-[6-ethyl-5-(1H-indol-4-yl)thieno[2,3-d]pyrimidin-4-yl]-D-alanine, diastereoisomer 2

Using General Procedure Ia and Preparation 4v as the appropriate 4-chloro-thieno[2,3-d]pyrimidine derivative and (2R)-2-amino-3-cyclohexyl-propanoic acid as the appropriate amino acid derivative, a mixture of diastereoisomers was obtained. They were separated via preparative reversed phase chromatography using 0.1% aqueous TFA solution and acetonitrile as eluents. Example 242 was obtained as the earlier eluting diastereoisomer. HRMS calculated for $C_{25}H_{28}N_4O_2S$: 448.1933, found: 449.1994 (M+H).
Example 243 was obtained as the later eluting diastereoisomer. HRMS calculated for $C_{25}H_{28}N_4O_2S$: 448.1933, found: 449.2006 (M+H).

Example 244: N-[(5S$_a$)-5-(3-chloro-1H-indol-4-yl)-6-ethyl-thieno[2,3-d]pyrimidin-4-yl]-3-pyridin-2-yl-D-alanine and Example 245: N-[(5R$_a$)-5-(3-chloro-1H-indol-4-yl)-6-ethyl-thieno[2,3-d]pyrimidin-4-yl]-3-pyridin-2-yl-D-alanine Using General Procedure Ia and Preparation 7j as the appropriate 4-chloro-thieno[2,3-d]pyrimidine derivative and (2R)-2-amino-3-(2-pyridyl)propanoic acid as the appropriate amino acid derivative, a mixture of diastereoisomers was obtained. They were separated via preparative reversed phase chromatography using 40 mM aqueous NH$_4$OAc solution (pH=4, adjusted with AcOH) and acetonitrile as eluents. Example 244 was obtained as the earlier eluting diastereoisomer. HRMS calculated for $C_{24}H_{20}ClN_5O_2S$: 477.1026, found: 478.1087 (M+H).
Example 245 was obtained as the later eluting diastereoisomer. HRMS calculated for $C_{24}H_{20}ClN_5O_2S$: 477.1026, found: 478.1089 (M+H).

Example 246: N-((5S$_a$)-5-{3-chloro-1-[2-(morpholin-4-yl)ethyl]-1H-indol-4-yl}-6-ethyl-thieno[2,3-d]pyrimidin-4-yl)-3-pyridin-2-yl-D-alanine Step A: methyl (2R)-2-[[(5S$_a$)-5-(3-chloro-1H-indol-4-yl)-6-ethyl-thieno[2,3-d]pyrimidin-4-yl]amino]-3-(2-pyridyl)propanoate 0.13 g Example 244 (0.27 mmol) was dissolved in 13 mL MeOH, then 0.3 mL cc. H$_2$SO$_4$ was added and the mixture was stirred at r.t. until no further conversion was observed. Then it was concentrated under reduced pressure and saturated aqueous NaHCO$_3$ solution was added and the mixture was agitated. The formed precipitate was collected by filtration to obtain methyl (2R)-2-[[(5S$_a$)-5-(3-chloro-1H-indol-4-yl)-6-ethyl-thieno[2,3-d]pyrimidin-4-yl]amino]-3-(2-pyridyl)propanoate.

Step B: Example 246

Using General procedure VIII and methyl (2R)-2-[[(5S$_a$)-5-(3-chloro-1H-indol-4-yl)-6-ethyl-thieno[2,3-d]pyrimidin-4-yl]amino]-3-(2-pyridyl)propanoate as the appropriate indole derivative and 2-morpholinoethanol as the appropriate alcohol, Example 246 was obtained. HRMS calculated for $C_{30}H_{31}ClN_6O_3S$: 590.1867, found: 591.1938 (M+H).

Example 247: N-((5R$_a$)-5-{3-chloro-1-[2-(morpholin-4-yl)ethyl]-1H-indol-4-yl}-6-ethyl-thieno[2,3-d]pyrimidin-4-yl)-3-pyridin-2-yl-D-alanine Step A: methyl (2R)-2-[[(5R$_a$)-5-(3-chloro-1H-indol-4-yl)-6-ethyl-thieno[2,3-d]pyrimidin-4-yl]amino]-3-(2-pyridyl)propanoate 0.157 g Example 245 (0.33 mmol) was dissolved in 15 mL MeOH, then 0.3 mL cc. H$_2$SO$_4$ was added and the mixture was stirred at r.t. until no further conversion was observed. Then it was concentrated under reduced pressure and saturated aqueous NaHCO$_3$ solution was added and the mixture was agitated. The formed precipitate was collected by filtration to obtain methyl (2R)-2-[[(5R$_a$)-5-(3-chloro-1H-indol-4-yl)-6-ethyl-thieno[2,3-d]pyrimidin-4-yl]amino]-3-(2-pyridyl)propanoate.

Step B: Example 247

Using General procedure VIII and methyl (2R)-2-[[(5R$_a$)-5-(3-chloro-1H-indol-4-yl)-6-ethyl-thieno[2,3-d]pyrimidin-4-yl]amino]-3-(2-pyridyl)propanoate as the appropriate amine and 2-morpholinoethanol as the appropriate alcohol Example 247 was obtained. HRMS calculated for $C_{30}H_{31}ClN_6O_3S$: 590.1867, found: 591.1918 (M+H).

Example 248: N-((5S$_a$)-5-{3-chloro-1-[2-(4-methyl-piperazin-1-yl)ethyl]-1H-indol-4-yl}-6-ethyl-thieno[2,3-d]pyrimidin-4-yl)-3-pyridin-2-yl-D-alanine Step A: methyl (2R)-2-[[(5S$_a$)-5-(3-chloro-1H-indol-4-yl)-6-ethyl-thieno[2,3-d]pyrimidin-4-yl]amino]-3-(2-pyridyl)propanoate 0.13 g Example 244 (0.27 mmol) was dissolved in 13 mL MeOH, then 0.3 mL cc. H$_2$SO$_4$ was added and the mixture was stirred at r.t. until no further conversion was observed. Then it was concentrated under reduced pressure and saturated aqueous NaHCO$_3$ solution was added and the mixture was agitated. The formed precipitate was collected by filtration to obtain methyl (2R)-2-[[(5S$_a$)-5-(3-chloro-1H-indol-4-yl)-6-ethyl-thieno[2,3-d]pyrimidin-4-yl]amino]-3-(2-pyridyl)propanoate.

Step B: Example 248

Using General procedure VIII and methyl (2R)-2-[[(5S$_a$)-5-(3-chloro-1H-indol-4-yl)-6-ethyl-thieno[2,3-d]pyrimidin-4-yl]amino]-3-(2-pyridyl)propanoate as the appropriate indole derivative and 2-(4-methylpiperazin-1-yl)ethanol as the appropriate alcohol Example 248 was obtained. HRMS calculated for $C_{31}H_{34}ClN_7O_2S$: 603.2183, found: 302.6172 (M+2H).

Example 249: N-((5R$_a$)-5-{3-chloro-1-[2-(4-methyl-piperazin-1-yl)ethyl]-1H-indol-4-yl}-6-ethyl-thieno[2,3-d]pyrimidin-4-yl)-3-pyridin-2-yl-D-alanine Step A: methyl (2R)-2-[[(5R$_a$)-5-(3-chloro-1H-indol-4-yl)-6-ethyl-thieno[2,3-d]pyrimidin-4-yl]amino]-3-(2-pyridyl)propanoate 0.157 g Example 245 (0.33 mmol) was dissolved in 15 mL MeOH, then 0.3 mL cc. H$_2$SO$_4$ was added and the mixture was stirred at r.t. until no further conversion was observed. Then it was concentrated under reduced pressure and saturated aqueous NaHCO$_3$ solution was added and the mixture was agitated. The formed precipitate was collected by filtration to obtain methyl (2R)-2-[[(5R$_a$)-5-(3-chloro-1H-indol-4-yl)-6-ethyl-thieno[2,3-d]pyrimidin-4-yl]amino]-3-(2-pyridyl)propanoate.

Step B: Example 249

Using General procedure VIII and methyl (2R)-2-[[(5R$_a$)-5-(3-chloro-1H-indol-4-yl)-6-ethylthieno[2,3-d]pyrimidin-4-yl]amino]-3-(2-pyridyl)propanoate as the appropriate indole derivative and 2-(4-methylpiperazin-1-yl)ethanol as the appropriate alcohol Example 249 was obtained. HRMS calculated for C$_{31}$H$_{34}$ClN$_7$O$_2$S: 603.2183, found: 302.6164 (M+2H).

Example 250: N-[6-(difluoromethyl)-(5S$_a$)-5-(naphthalen-1-yl)thieno[2,3-d]pyrimidin-4-yl]-3-pyridin-2-yl-D-alanine and

Example 251: N-[6-(difluoromethyl)-(5R$_a$)-5-(naphthalen-1-yl)thieno[2,3-d]pyrimidin-4-yl]-3-pyridin-2-yl-D-alanine Using General Procedure Ia and Preparation 4r as the appropriate 4-chloro-thieno[2,3-d]pyrimidine derivative and (2R)-2-amino-3-(2-pyridyl)propanoic acid as the appropriate amino acid derivative, a mixture of diastereoisomers was obtained. They were separated via preparative reversed phase chromatography using 40 mM aqueous NH$_4$OAc solution (pH=4, adjusted with AcOH) and acetonitrile as eluents. Example 250 was obtained as the earlier eluting diastereoisomer. HRMS calculated for C$_{25}$H$_{18}$F$_2$N$_4$O$_2$S: 476.1119, found: 477.1195 (M+H).
Example 251 was obtained as the later eluting diastereoisomer. HRMS calculated for C$_{25}$H$_{18}$F$_2$N$_4$O$_2$S: 476.1119, found: 477.1182 (M+H).

Example 252: N-[(5S$_a$)-5-(naphthalen-1-yl)-6-propylthieno[2,3-d]pyrimidin-4-yl]-D-phenylalanine 266 mg Example 108 (0.57 mmol) was dissolved in 10 mL MeOH and 2 mL AcOH, then 61 mg 10% Pd/C was added. The mixture was stirred under H$_2$ atmosphere at 40° C. for 2 hours. It was filtered through Celite and the filtrate was concentrated under reduced pressure. The crude product was purified via preparative reversed phase chromatography using 40 mM aqueous NH$_4$OAc solution (pH=4, adjusted with AcOH) and acetonitrile as eluents to obtain Example 252. HRMS calculated for C$_{28}$H$_{25}$N$_3$O$_2$S: 467.1667, found: 468.1746 (M+H).

Example 253: N-[(5R$_a$)-5-(naphthalen-1-yl)-6-propylthieno[2,3-d]pyrimidin-4-yl]-D-phenylalanine 266 mg Example 109 (0.57 mmol) was dissolved in 10 mL MeOH and 2 mL AcOH, then 61 mg 10% Pd/C was added. The mixture was stirred under H$_2$ atmosphere at 40° C. for 2 hours. It was filtered through Celite and the filtrate was concentrated under reduced pressure. The crude product was purified via preparative reversed phase chromatography using 40 mM aqueous NH$_4$OAc solution (pH=4, adjusted with AcOH) and acetonitrile as eluents to obtain Example 253. HRMS calculated for C$_{28}$H$_{25}$N$_3$O$_2$S: 467.1667, found: 468.1736 (M+H).

Example 254: methyl N-[6-ethyl-(5S$_a$)-5-(naphthalen-1-yl)thieno[2,3-d]pyrimidin-4-yl]-D-phenylalaninate 102 mg Example 101 (0.225 mmol) was dissolved in 2 mL MeOH and the mixture was cooled to 0° C. under N$_2$ atmosphere. Then 135 µL diazomethyl(trimethyl)silane solution (2M in Et$_2$O) was added and the mixture was allowed to warm up to r.t. Then the mixture was concentrated in vacuo and purified via flash chromatography using heptane and EtOAc as eluents to obtain Example 254. HRMS calculated for C$_{28}$H$_{25}$N$_3$O$_2$S: 467.1667, found: 468.1746 (M+H).

Example 255: methyl N-[6-ethyl-(5R$_a$)-5-(naphthalen-1-yl)thieno[2,3-d]pyrimidin-4-yl]-D-phenylalaninate 102 mg Example 100 (0.225 mmol) was dissolved in 2 mL MeOH and the mixture was cooled to 0° C. under N$_2$ atmosphere. Then 135 µL diazomethyl(trimethyl)silane solution (2M in Et$_2$O) was added and the mixture was allowed to warm up to r.t. The mixture was concentrated in vacuo and purified via flash chromatography using heptane and EtOAc as eluents to obtain Example 255. HRMS calculated for C$_{28}$H$_{25}$N$_3$O$_2$S: 467.1667, found: 468.1737 (M+H).

Example 256: ethyl N-[(5S$_a$)-5-{3-chloro-2-methyl-4-[2-(4-methylpiperazin-1-yl) ethoxy]phenyl}-6-(4-fluorophenyl)thieno[2,3-d]pyrimidin-4-yl]-2-{[2-(2-methoxy phenyl)pyrimidin-4-yl]methoxy}-D-phenylalaninate Example 7 was dissolved in HCl solution (20 mL/mmol, 1.25M in EtOH) and the mixture was stirred at r.t. overnight. Then the mixture was neutralized with NaHCO$_3$ solution and it was extracted with DCM. The organic phase was dried over Na$_2$SO$_4$, filtered and the filtrate was concentrated under reduced pressure. The crude product was purified via preparative reversed phase chromatography using 25 mM aqueous NH$_4$HCO$_3$ solution and acetonitrile as eluents to give Example 256. HRMS calculated for C$_{49}$H$_{49}$ClFN$_7$O$_5$S: 901.3188, found: 902.3225 (M+H).

Example 257: ethyl 2-[(1-tert-butyl-1H-pyrazol-5-yl)methoxy]-N-[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]-D-phenylalaninate Example 40 was dissolved in HCl solution (20 mL/mmol, 1.25M in EtOH) and the mixture was stirred at r.t. overnight. Then the mixture was neutralized with NaHCO$_3$ solution and it was extracted with DCM. The organic phase was dried over Na$_2$SO$_4$, filtered and the filtrate was concentrated under reduced pressure. The crude product was purified via preparative reversed phase chromatography using 25 mM aqueous NH$_4$HCO$_3$ solution and acetonitrile as eluents to give Example 257. HRMS calculated for $C_{42}H_{50}ClN_7O_4S$: 783.3334, found: 392.6744 (M+2H).

Example 258: ethyl N-[(5S$_a$)-5-{3-chloro-2-methyl-4-[2-(4-methylpiperazin-1-yl) ethoxy]phenyl}-6-(prop-1-yn-1-yl)thieno[2,3-d]pyrimidin-4-yl]-2-{[2-(2-methoxy phenyl)pyrimidin-4-yl]methoxy}-D-phenylalaninate Example 45 was dissolved in HCl solution (20 mL/mmol, 1.25M in EtOH) and the mixture was stirred at r.t. overnight. Then the mixture was neutralized with NaHCO$_3$ solution and it was extracted with DCM. The organic phase was dried over Na$_2$SO$_4$, filtered and the filtrate was concentrated under reduced pressure. The crude product was purified via preparative reversed phase chromatography using 25 mM aqueous NH$_4$HCO$_3$ solution and acetonitrile as eluents to give Example 258. HRMS calculated for $C_{46}H_{48}ClN_7O_5S$: 845.3126, found: 423.6650 (M+H).

Example 259: ethyl N-[(5S$_a$)-5-{3-chloro-4-[2-(dimethylamino)ethoxy]-2-methyl phenyl}-6-(prop-1-yn-1-yl)thieno[2,3-d]pyrimidin-4-yl]-2-{[2-(2-methoxyphenyl)pyrimidin-4-yl]methoxy}-D-phenylalaninate Example 49 was dissolved in HCl solution (20 mL/mmol, 1.25M in EtOH) and the mixture was stirred at r.t. overnight. Then the mixture was neutralized with NaHCO$_3$ solution and it was extracted with DCM. The organic phase was dried over Na$_2$SO$_4$, filtered and the filtrate was concentrated under reduced pressure. The crude product was purified via preparative reversed phase chromatography using 25 mM aqueous NH$_4$HCO$_3$ solution and acetonitrile as eluents to give Example 259. HRMS calculated for $C_{43}H_{43}ClN_6O_5S$: 790.2704, found: 396.1425 (M+2H).

Example 260: ethyl N-[(5S$_a$)-5-{3-chloro-4-[2-(dimethylamino)ethoxy]-2-methyl phenyl}-6-(4-fluorophenyl)thieno[2,3-d]pyrimidin-4-yl]-2-({2-[2-(2-methoxyethoxy) phenyl]pyrimidin-4-yl}methoxy)-D-phenylalaninate Example 51 was dissolved in HCl solution (20 mL/mmol, 1.25M in EtOH) and the mixture was stirred at 60° C. until no further conversion was observed. Then the mixture was neutralized with NaHCO$_3$ solution and it was extracted with DCM. The organic phase was dried over Na$_2$SO$_4$, filtered and the filtrate was concentrated under reduced pressure. The crude product was purified via preparative reversed phase chromatography using 25 mM aqueous NH$_4$HCO$_3$ solution and acetonitrile as eluents to obtain Example 260. HRMS calculated for $C_{48}H_{48}ClFN_6O_6S$: 890.3029, found: 891.3105 (M+H).

Example 261: (5-methyl-2-oxo-1,3-dioxol-4-yl) methyl N-[(5S$_a$)-5-{3-chloro-4-[2-(dimethylamino)ethoxy]-2-methylphenyl}-6-(4-fluorophenyl)thieno[2,3-d]pyrimidin-4-yl]-2-({2-[2-(2-methoxyethoxy) phenyl]pyrimidin-4-yl}methoxy)-D-phenylalaninate 1 eq. Example 51 and 1.1 eq. 4-(chloromethyl)-5-methyl-1,3-dioxol-2-one were dissolved in DMF (10 mL/mmol), then 2 eq. NaI and 2 eq. Cs$_2$CO$_3$ were added and the mixture was stirred until no further conversion was observed. Then the mixture was directly injected and purified via preparative reversed phase chromatography using 25 mM aqueous NH$_4$HCO$_3$ solution and acetonitrile as eluents to obtain Example 261. HRMS calculated for $C_{51}H_{48}ClFN_6O_9S$: 974.2876, found: 975.2949 (M+H).

Example 262: 1-[(ethoxycarbonyl)oxy]ethyl N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-2-{[2-(2-methoxyphenyl)pyrimidin-4-yl]methoxy}-D-phenylalaninate Example 263: 1-[(dimethylcarbamoyl)oxy]ethyl N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-2-{[2-(2-methoxyphenyl)pyrimidin-4-yl]methoxy}-D-phenylalaninate Example 264: N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-2-({2-[3-(hydroxymethyl) phenyl]pyrimidin-4-yl}methoxy)-D-phenylalanine Example 265: N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-2-({2-[2-(hydroxymethyl) pyridin-4-yl]pyrimidin-4-yl}methoxy)-D-phenylalanine Example 266: N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-2-({2-[6-(hydroxymethyl) pyridazin-4-yl]pyrimidin-4-yl}methoxy)-D-phenylalanine Example 267: N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-2-({2-[6-(hydroxymethyl) pyrazin-2-yl]pyrimidin-4-yl}methoxy)-D-phenylalanine Example 268: N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-2-{[2'-(hydroxymethyl)-2,5'-bipyrimidin-4-yl]methoxy}-D-phenylalanine Example 269: N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-2-({2-[4-(phosphonooxy)phenyl]pyrimidin-4-yl}methoxy)-D-phenylalanine Example 270: N-[5-{3,5-dichloro-2,6-dimethyl-4-[2-(4-methylpiperazin-1-yl) ethoxy]phenyl}-6-(4-fluorophenyl)thieno[2,3-d]pyrimidin-4-yl]-2-{[2-(2-methoxy phenyl)pyrimidin-4-yl]methoxy}-D-phenylalanine Step A: 4-bromo-2,6-dichloro-3,5-dimethyl-phenol 30.16 g 4-bromo-3,5-dimethyl-phenol (150 mmol) was dissolved in a mixture of 75 mL 1,2-dichloroethane and 75 mL acetonitrile, then 40.06 g NCS (300 mmol) was added portionwise and the mixture was stirred at r.t. until no further conversion was observed. Reaction mixture was concentrated under reduced pressure, the residue was dissolved in DCM, washed with water and brine. The organic layer was dried over Na$_2$SO$_4$ and concentrated under reduced pressure and used in the next step without further purification. $^1$H NMR (400 MHz, DMSO-d$_6$): 10.10 (s, 1H), 2.46 (s, 6H)

Step B: 1-bromo-3,5-dichloro-4-methoxy-2,6-dimethyl-benzene

To a solution of 26.0 g 4-bromo-2,6-dichloro-3,5-dimethyl-phenol (96.3 mmol) and 26.6 g K$_2$CO$_3$ (192.6 mmol) in 300 mL MeCN 6.6 mL MeI (105.9 mmol) was added and the mixture was stirred at r.t. until no further conversion was observed. The solids were filtered off and the filtrate was concentrated under reduced pressure. The crude product was dissolved in DCM, washed with water and brine. The organic layer was dried over Na$_2$SO$_4$ and concentrated under reduced pressure and used in the next step without further purification. $^1$H NMR (400 MHz, DMSO-d$_6$): 3.78 (s, 3H), 2.49 (s, 6H)

Step C: 2-(3,5-dichloro-4-methoxy-2,6-dimethyl-phenyl)-4,4,5,5-tetramethyl-1,3,2-dioxaborolane 10.0 g 1-bromo-3,5-dichloro-4-methoxy-2,6-dimethyl-benzene (35.2 mmol) was dissolved in 360 mL dry THF under nitrogen and was cooled to −78° C. with dry ice-acetone. 23.2 mL nBuLi (1.6 M in hexanes) (37.0 mmol) was added and the mixture was stirred for 15 minutes, then 8.6 mL 2-isopropoxy-4,4,5,5-tetramethyl-1,3,2-dioxaborolane (42.24 mmol) was added and the mixture was allowed to warm up to r.t. It was quenched with brine, extracted with DCM, dried over Na$_2$SO$_4$, filtered and concentrated under reduced pressure. The crude product was purified via flash chromatography using heptane and EtOAc as eluents to obtain 2-(3,5-dichloro-4-methoxy-2,6-dimethyl-phenyl)-4,4,5,5-tetramethyl-1,3,2-dioxaborolane. $^1$H NMR (400 MHz, DMSO-d$_6$): 3.81 (s, 3H), 2.33 (s, 6H), 1.34 (s, 12H)

Step D: ethyl 4-(3,5-dichloro-4-methoxy-2,6-dimethyl-phenyl)thiophene-3-carboxylate 3.92 g ethyl 4-bromothiophene-3-carboxylate (16.68 mmol) and 9.9 g 2-(3,5-dichloro-4-methoxy-2,6-dimethyl-phenyl)-4,4,5,5-tetramethyl-1,3,2-dioxaborolane (30.0 mmol) were dissolved in 140 mL dioxane, then 10.87 g Cs$_2$CO$_3$ (33.36 mmol) dissolved in 40 mL water was added. Then 590 mg AtaPhos (0.83 mmol) was added, and the mixture was stirred under nitrogen at reflux temperature until no further conversion was observed. Then it was diluted with DCM and brine. After phase separation the aqueous phase was extracted with DCM. The organic layers were combined and dried over Na$_2$SO$_4$, filtered and concentrated under reduced pressure. The crude product was purified via flash chromatography using heptane and EtOAc as eluents to obtain ethyl 4-(3,5-dichloro-4-methoxy-2,6-dimethyl-phenyl)thiophene-3-carboxylate.
$^1$H NMR (400 MHz, DMSO-d$_6$): 8.53 (d, 1H), 7.47 (d, 1H), 4.02 (q, 2H), 3.83 (s, 3H), 1.95 (s, 6H), 1.00 (t, 3H) HRMS (M+NH$_4$)$^+$=376.0538

Step E: ethyl 4-(3,5-dichloro-4-methoxy-2,6-dimethyl-phenyl)-2,5-diiodo-thiophene-3-carboxylate 2.65 g 4-(3,5-dichloro-4-methoxy-2,6-dimethyl-phenyl)thiophene-3-carboxylate (7.38 mmol) was dissolved in 75 mL acetonitrile, then 2.2 mL fluoroboric acid diethyl ether complex (16.22 mmol) and 3.65 g N-iodosuccinimide (16.23 mmol) was added and the mixture was stirred at r.t. until no further conversion was observed. Reaction mixture was concentrated under reduced pressure, and the crude product was purified via flash chromatography using heptane and EtOAc as eluents to obtain ethyl 4-(3,5-dichloro-4-methoxy-2,6-dimethyl-phenyl)-2,5-diiodo-thiophene-3-carboxylate. $^1$H NMR (400 MHz, DMSO-d$_6$): 3.98 (q, 2H), 3.84 (s, 3H), 1.92 (s, 6H), 0.84 (t, 3H)

Step F: ethyl 4-(3,5-dichloro-4-methoxy-2,6-dimethyl-phenyl)-5-iodo-thiophene-3-carboxylate 5.29 g 4-(3,5-dichloro-4-methoxy-2,6-dimethyl-phenyl)-2,5-diiodo-thiophene-3-carboxylate (8.66 mmol) was dissolved in 90 mL dry THF, then cooled to −78° C. under argon atmosphere. 6.7 mL isopropyl magnesium chloride, lithium chloride complex (1.3 M in THF) (8.66 mmol) was added and the mixture was stirred at −78° C. for 30 minutes. Then saturated aq. NH$_4$Cl was added and the mixture was extracted with ethyl acetate. The organic layer was dried over Na$_2$SO$_4$ and concentrated under reduced pressure. The crude product was purified via flash chromatography using heptane and EtOAc as eluents to obtain ethyl 4-(3,5-dichloro-4-methoxy-2,6-dimethyl-phenyl)-5-iodo-thiophene-3-carboxylate. $^1$H NMR (400 MHz, DMSO-d$_6$): 8.71 (s, 1H), 4.01 (q, 2H), 3.86 (s, 3H), 1.89 (s, 6H), 0.99 (t, 3H)

Step G: ethyl 4-(3,5-dichloro-4-methoxy-2,6-dimethyl-phenyl)-5-(4-fluorophenyl)thiophene-3-carboxylate 4.20 g ethyl 4-(3,5-dichloro-4-methoxy-2,6-dimethyl-phenyl)-5-iodo-thiophene-3-carboxylate (8.66 mmol) and 1.82 g 4-fluorophenylboronic acid (13.0 mmol) were dissolved in 80 mL dioxane, then 5.64 g Cs$_2$CO$_3$ (17.32 mmol) dissolved in 20 mL water was added. Then 500 mg Pd(PPh$_3$)$_4$ (0.43 mmol) was added, and the mixture was stirred under nitrogen at 80° C. until no further conversion was observed. Then it was diluted with DCM and brine. After phase separation the aqueous phase was extracted with DCM. The organic layers were combined and dried over Na$_2$SO$_4$, filtered and concentrated under reduced pressure. The crude product was purified via flash chromatography using heptane and EtOAc as eluents to obtain ethyl 4-(3,5-dichloro-4-methoxy-2,6-dimethyl-phenyl)-5-(4-fluorophenyl)thiophene-3-carboxylate.
$^1$H NMR (400 MHz, DMSO-d$_6$): 8.58 (s, 1H), 7.22-7.10 (m, 4H), 4.03 (q, 2H), 3.82 (s, 3H), 1.92 (s, 6H), 1.00 (t, 3H) HRMS (M+H)$^+$=453.0498

Step H: ethyl 4-(3,5-dichloro-4-methoxy-2,6-dimethyl-phenyl)-5-(4-fluorophenyl)-2-nitro-thiophene-3-carboxylate 1.97 g ethyl 4-(3,5-dichloro-4-methoxy-2,6-dimethyl-phenyl)-5-(4-fluorophenyl)thiophene-3-carboxylate (4.34 mmol) was dissolved in 40 mL dry acetonitrile, then 576 mg nitronium tetrafluoroborate (4.34 mmol) was added and the mixture was stirred at r.t. until no further conversion was observed. Then it was diluted with DCM and brine. After phase separation the aqueous phase was extracted with DCM. The organic layers were combined and dried over Na$_2$SO$_4$, filtered and concentrated under reduced pressure. The crude product was purified via flash chromatography using heptane and EtOAc as eluents to obtain ethyl 4-(3,5-dichloro-4-methoxy-2,6-dimethyl-phenyl)-5-(4-fluorophenyl)-2-nitro-thiophene-3-carboxylate. $^1$H NMR (400 MHz, DMSO-d$_6$): 7.37-7.33 (m, 2H), 7.32-7.26 (m, 2H), 4.14 (q, 2H), 3.82 (s, 3H), 2.06 (s, 6H), 0.88 (t, 3H)

Step I: ethyl 2-amino-4-(3,5-dichloro-4-methoxy-2, 6-dimethyl-phenyl)-5-(4-fluorophenyl)thiophene-3-carboxylate 1.85 g ethyl 4-(3,5-dichloro-4-methoxy-2,6-dimethyl-phenyl)-5-(4-fluorophenyl)-2-nitro-thiophene-3-carboxylate (3.71 mmol) was dissolved in a mixture of 90 mL acetic acid and 18 mL water, then 2.43 g zinc dust (37.1 mmol) was added portionwise and the mixture was stirred at r.t. until no further conversion was observed. Reaction mixture was concentrated under reduced pressure, and the crude product was purified via flash chromatography using heptane and EtOAc as eluents to obtain ethyl 2-amino-4-(3,5-dichloro-4-methoxy-2,6-dimethyl-phenyl)-5-(4-fluorophenyl)thiophene-3-carboxylate.

$^1$H NMR (400 MHz, DMSO-d$_6$): 7.73 (s, 2H), 7.12-7.06 (m, 2H), 7.02-6.97 (m, 2H), 3.86-3.80 (m, 2H), 3.80 (s, 3H), 2.01 (s, 6H), 0.72 (t, 3H)
HRMS (M+H)$^+$=456.0598

Step J: 5-(3,5-dichloro-4-methoxy-2,6-dimethyl-phenyl)-6-(4-fluorophenyl)-3H-thieno[2,3-d]pyrimidin-4-one 1.1 g ethyl 2-amino-4-(3,5-dichloro-4-methoxy-2,6-dimethyl-phenyl)-5-(4-fluorophenyl)thiophene-3-carboxylate (2.35 mmol) was dissolved in 20 mL formamide and it was stirred at 150° C. until no further conversion was observed. Then it was poured onto water and the precipitated product was collected by filtration to give 5-(3,5-dichloro-4-methoxy-2,6-dimethyl-phenyl)-6-(4-fluorophenyl)-3H-thieno[2,3-d]pyrimidin-4-one.

$^1$H NMR (400 MHz, DMSO-d$_6$): 12.53 (br s, 1H), 8.18 (s, 1H), 7.23-7.16 (m, 4H), 3.84 (s, 3H), 1.96 (s, 6H) HRMS (M+H)$^+$=449.0289

Step K: 4-chloro-5-(3,5-dichloro-4-methoxy-2,6-dimethyl-phenyl)-6-(4-fluorophenyl) thieno[2,3-d] pyrimidine 700 mg 5-(3,5-dichloro-4-methoxy-2,6-dimethyl-phenyl)-6-(4-fluorophenyl)-3H-thieno[2,3-d]pyrimidin-4-one (1.56 mmol) was dissolved in 6 mL phosphorous oxychloride and it was stirred at 90° C. until no further conversion was observed. Reaction mixture was concentrated under reduced pressure, then to the crude product icy water was added and it was sonicated for 10 minutes. The precipitated product was collected by filtration to give 4-chloro-5-(3,5-dichloro-4-methoxy-2,6-dimethyl-phenyl)-6-(4-fluorophenyl)thieno[2,3-d]pyrimidine.

$^1$H NMR (400 MHz, DMSO-d$_6$): 9.02 (s, 1H), 7.38-7.26 (m, 4H), 3.86 (s, 3H), 1.99 (s, 6H) HRMS (M+H)$^+$=466.9954

Step L: 2,6-dichloro-4-[4-chloro-6-(4-fluorophenyl) thieno[2,3-d]pyrimidin-5-yl]-3,5-dimethyl-phenol and 4-[4-bromo-6-(4-fluorophenyl)thieno[2,3-d] pyrimidin-5-yl]-2,6-dichloro-3,5-dimethyl-phenol To a stirred solution of 700 mg 4-chloro-5-(3,5-dichloro-4-methoxy-2,6-dimethyl-phenyl)-6-(4-fluorophenyl)thieno [2,3-d]pyrimidine (1.50 mmol) in 15 mL DCM 3.0 mL boron tribromide (1 M in DCM) (3.0 mmol) was added at 0° C. and the mixture was allowed to warm up to r.t. and it was stirred until no further conversion was observed. The mixture was quenched with saturated aq. NH$_4$Cl and extracted with DCM. The combined organic phases were dried over Na$_2$SO$_4$ and concentrated under reduced pressure. The residue was purified via flash chromatography using heptane and EtOAc as eluents to obtain 2,6-dichloro-4-[4-chloro-6-(4-fluorophenyl)thieno[2,3-d]pyrimidin-5-yl]-3,5-dimethyl-phenol and 4-[4-bromo-6-(4-fluorophenyl)thieno[2,3-d]pyrimidin-5-yl]-2,6-dichloro-3,5-dimethyl-phenol as a 37:63 mixture of products.

$^1$H NMR (400 MHz, DMSO-d$_6$): 10.14 (br s, 1H), 9.01 (s, 1H), 7.40-7.23 (m, 4H), 1.95 (s, 6H) and 10.14 (br s, 1H), 8.93 (s, 1H), 7.40-7.23 (m, 4H), 1.93 (s, 6H)

HRMS (M+H)$^+$=452.9800 and 496.9287

Step M: 4-chloro-5-[3,5-dichloro-2,6-dimethyl-4-[2-(4-methylpiperazin-1-yl)ethoxy]phenyl]-6-(4-fluorophenyl)thieno[2,3-d]pyrimidine and 4-bromo-5-[3,5-dichloro-2,6-dimethyl-4-[2-(4-methylpiperazin-1-yl) ethoxy]phenyl]-6-(4-fluorophenyl)thieno[2,3-d] pyrimidine 300 mg mixture of 2,6-dichloro-4-[4-chloro-6-(4-fluorophenyl)thieno[2,3-d]pyrimidin-5-yl]-3,5-dimethyl-phenol and 4-[4-bromo-6-(4-fluorophenyl)thieno[2,3-d]pyrimidin-5-yl]-2,6-dichloro-3,5-dimethyl-phenol (0.62 mmol), 286 mg 2-(4-methylpiperazin-1-yl)ethanol (1.98 mmol) and 520 mg triphenyl phosphine (1.98 mmol) were dissolved in 10 mL dry toluene, then 460 mg ditertbutyl azodicarboxylate (1.98 mmol) was added. The mixture was stirred at 50° C. under nitrogen until no further conversion was observed. The volatiles were evaporated under reduced pressure and the crude intermediate was purified via flash chromatography using EtOAc and methanol as eluents to obtain 4-chloro-5-[3,5-dichloro-2,6-dimethyl-4-[2-(4-methylpiperazin-1-yl)ethoxy]phenyl]-6-(4-fluorophenyl)thieno[2,3-d] pyrimidine and 4-bromo-5-[3,5-dichloro-2,6-dimethyl-4-[2-(4-methylpiperazin-1-yl)ethoxy]phenyl]-6-(4-fluorophenyl) thieno[2,3-d]pyrimidine as a 35:65 mixture of products.

$^1$H NMR (400 MHz, DMSO-d$_6$): 9.02 (S, 1H), 7.40-7.22 (m, 4H), 4.11 (t, 2H), 2.78 (t, 2H), 2.63-2.20 (m, 8H), 2.17 (br s, 3H), 1.98 (s, 6H) and 8.94 (S, 1H), 7.40-7.22 (m, 4H), 4.11 (t, 2H), 2.78 (t, 2H), 2.63-2.20 (m, 8H), 2.15 (br s, 3H), 1.98 (s, 6H)

HRMS (M+H)$^+$=579.0968 and 623.0455

Step N: Example 270

250 mg mixture of 4-chloro-5-[3,5-dichloro-2,6-dimethyl-4-[2-(4-methylpiperazin-1-yl)ethoxy]phenyl]-6-(4-fluorophenyl)thieno[2,3-d]pyrimidine and 4-bromo-5-[3,5-dichloro-2,6-dimethyl-4-[2-(4-methylpiperazin-1-yl) ethoxy]phenyl]-6-(4-fluorophenyl) thieno[2,3-d]pyrimidine (0.41 mmol), 327 mg (2R)-2-amino-3-[2-[[2-(2-methoxy phenyl)pyrimidin-4-yl]methoxy]phenyl]propanoic acid (Preparation A4, 0.86 mmol) and 280 mg Cs$_2$CO$_3$ (0.86 mmol) was dissolved in 5 mL tert-butanol and the mixture was stirred at 70° C. until no further conversion was observed. The solids were filtered off and the filtrate was concentrated under reduced pressure. The crude product was purified via preparative reversed phase chromatography using 25 mM aqueous NH$_4$HCO$_3$ solution and MeCN, Example 270 was obtained. HRMS calculated for C$_{48}$H$_{46}$N$_7$O$_5$FSCl$_2$: 921.2642, found: 461.6398 (M+2H).

Example 271: N-[5-{2,6-dimethyl-4-[2-(4-methyl-piperazin-1-yl)ethoxy]phenyl}-6-(4-fluorophenyl) thieno[2,3-d]pyrimidin-4-yl]-2-{[2-(2-methoxyphenyl)pyrimidin-4-yl]methoxy}-D-phenylalanine Example 272: N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-3-(hydroxymethyl)-2-{[2-(2-methoxyphenyl)pyrimidin-4-yl]methoxy}phenylalanine Example 273: N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-β-hydroxy-2-{[2-(2-methoxy phenyl)pyrimidin-4-yl]methoxy}phenylalanine Example 274: N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-β-(2-hydroxyethyl)-2-{[2-(2-methoxyphenyl)pyrimidin-4-yl]methoxy}phenylalanine Pharmacological Study Example A: Inhibition of Mcl-1 by the Fluorescence Polarisation Technique The relative binding potency of each compound was determined via Fluorescence Polarisation (FP). The method utilised a Fluorescein labelled ligand (Fluorescein-βAla-Ahx-A-REIGAQLRRMADDLNAQY-OH; mw 2,765) which binds to the Mcl-1 protein (such that Mcl-1 corresponds to the UniProtKB® primary accession number: Q07820) leading to an increased anisotropy measured in milli-polarisation (mP) units using a reader. The addition of a compound which binds competitively to the same site as the ligand will result in a greater proportion of unbound ligand in the system indicated by a decrease in mP units.

Method 1:

An 11 point serial dilution of each compound was prepared in DMSO and 2 μl transferred into flat bottomed, low binding, 384-well plate (final DMSO concentration 5%). 38 μl of buffer (10 mM 4-(2-hydroxyethyl)-1-piperazineethanesulfonic acid [HEPES], 150 mM NaCl, 0.05% Tween 20, pH 7.4), containing the Fluorescein labelled ligand (final concentration 1 nM) and Mcl-1 protein (final concentration 5 nM) was then added.

Assay plates were incubated ~2 hours at r.t. before FP was measured on a Biomek Synergy2 reader (Ex. 528 nm, Em. 640 nm, Cut off 510 nm) and mP units calculated. The binding of increasing doses of test compound was expressed as a percentage reduction in mP compared to a window established between '5% DMSO only' and '100% inhibition' controls. 11-point dose response curves were plotted with XL-Fit software using a 4-Parameter Logistic Model (Sigmoidal Dose-Response Model) and the inhibitory concentrations that gave a 50% reduction in mP (IC$_{50}$) were determined. Results obtained using Method 1 are presented in Table 1 below; IC$_{50}$ of Mcl-1 inhibition obtained using Method 1 are not underlined.

Method 2:

An 11 point serial dilution of each compound was prepared in DMSO and 2 μl transferred into flat bottomed, low binding, 384-well plate (final DMSO concentration 5%). 38 μl of buffer (20 mM Na$_2$HPO$_4$, 1 mM EDTA, 50 mM NaCl, pH 7.4), containing the Fluorescein labelled ligand (final concentration 10 nM) and Mcl-1 protein (final concentration 10 nM) was then added.

Assay plates were incubated ~2 hours at r.t. before FP was measured on a Biomek Synergy2 reader (Ex. 528 nm, Em. 640 nm, Cut off 510 nm) and mP units calculated. The binding of increasing doses of test compound was expressed as a percentage reduction in mP compared to a window established between '5% DMSO only' and '100% inhibition' controls (50 μM unlabelled ligand). 11-point dose response curves were plotted with XL-Fit software using a 4-Parameter Logistic Model (Sigmoidal Dose-Response Model) and the inhibitory concentrations that gave a 50% reduction in mP (IC$_{50}$) were determined. Results obtained using Method 2 are presented in Table 1 below; IC$_{50}$ of Mcl-1 inhibition obtained using Method 2 are underlined.

The results show that the compounds of the invention inhibit interaction between the Mcl-1 protein and the fluorescent peptide described hereinbefore.

Example B: In Vitro Cytotoxicity

The cytotoxicity studies were carried out on the H929 multiple myeloma tumour line.

The cells are distributed onto microplates and exposed to the test compounds for 48 hours. The cell viability is then quantified by a colorimetric assay, the Microculture Tetrazolium Assay (Cancer Res., 1987, 47, 939-942).

The results are expressed in IC$_{50}$ (the concentration of compound that inhibits cell viability by 50%) and are presented in Table 1 below.

The results show that the compounds of the invention are cytotoxic.

TABLE 1

IC$_{50}$ of Mcl-1 inhibition (fluorescence polarisation test) and of cytotoxicity for H929 cells

| | IC$_{50}$ (μM) Mcl-1 FP | IC$_{50}$ (M) MTT H929 |
|---|---|---|
| Example 1 | 0.127 | >6.0E−07 |
| Example 2 | 56.9% @ 10 μM | >6.0E−07 |
| Example 3 | 0.114 | 3.18E−07 |
| Example 4 | 0.005 | 2.15E−07 |
| Example 5 | ND | ND |
| Example 6 | 0.013 | >6.0E−07 |
| Example 7 | 0.008 | 1.38E−08 |
| Example 8 | 0.054 | 2.58E−07 |
| Example 9 | 2.697 | >3.75E−06 |
| Example 10 | 72.75% @ 3.3 μM | >3.75E−06 |
| Example 11 | 35.55% @ 10 μM | >3.75E−06 |
| Example 12 | 0.014 | 6.47E−07 |
| Example 13 | 58% @ 10 μM | >3.75E−06 |
| Example 14 | 0.038 | 7.21E−07 |
| Example 15 | 40.05% @ 10 μM | >3.75E−06 |
| Example 16 | 0.006 | 9.93E−08 |
| Example 17 | 0.057 | 2.94E−07 |
| Example 18 | 1.821 | ≥1.14E−07 |
| Example 19 | 0.020 | 1.75E−07 |
| Example 20 | 0.026 | 7.86E−08 |
| Example 21 | 0.006 | 3.97E−08 |
| Example 22 | 0.002 | 8.59E−09 |
| Example 23 | 41.27% @ 1 μM | >6.0E−07 |
| Example 24 | 0.008 | 4.73E−08 |
| Example 25 | 55.5% @ 10 μM | >6.0E−07 |
| Example 26 | 0.012 | 6.36E−09 |
| Example 27 | 0.011 | 2.09E−09 |
| Example 28 | 0.116 | >1.88E−06 |
| Example 29 | 0.063 | 2.52E−06 |
| Example 30 | 68.2% @ 10 μM | >3.75E−06 |

TABLE 1-continued

IC$_{50}$ of Mcl-1 inhibition (fluorescence polarisation test) and of cytotoxicity for H929 cells

| | IC$_{50}$ (μM) Mcl-1 FP | IC$_{50}$ (M) MTT H929 |
|---|---|---|
| Example 31 | 16.7% @ 10 μM | >3.75E−06 |
| Example 32 | 0.007 | >3.75E−06 |
| Example 33 | 54.9% @ 10 μM | ND |
| Example 34 | 0.726 | 4.27E−06 |
| Example 35 | 24.78% @ 10 μM | >3.0E−05 |
| Example 36 | 0.086 | >7.50E−06 |
| Example 37 | 18.7% @ 10 μM | >3.75E−06 |
| Example 38 | 1.871 | >3.75E−06 |
| Example 39 | 0.025 | 4.01E−07 |
| Example 40 | 0.006 | 3.28E−08 |
| Example 41 | 0.006 | 7.38E−09 |
| Example 42 | 0.010 | 6.1E−08 |
| Example 43 | 0.006 | 1.25E−08 |
| Example 44 | 0.007 | 3.44E−09 |
| Example 45 | 0.005 | 8.96E−10 |
| Example 46 | 0.024 | 1.66E−07 |
| Example 47 | 0.008 | 8.39E−08 |
| Example 48 | 0.007 | 1.61E−08 |
| Example 49 | 0.003 | 4.12E−09 |
| Example 50 | 0.007 | >1.50E−07 |
| Example 51 | 0.005 | 2.33E−08 |
| Example 52 | 0.301 | ND |
| Example 53 | 0.020 | ND |
| Example 54 | 0.541 | ND |
| Example 55 | 8.839 | ND |
| Example 56 | 0.019 | ND |
| Example 57 | 0.106 | ND |
| Example 58 | 52.8% @ 10 μM | ND |
| Example 59 | 0.127 | ND |
| Example 60 | 0.092 | ND |
| Example 61 | 0.036 | ND |
| Example 62 | 0.060 | ND |
| Example 63 | 12.18% @ 10 μM | ND |
| Example 64 | 0.025 | ND |
| Example 65 | 0.345 | ≥2.78E−06 |
| Example 66 | 36.9% @ 10 μM | >3.75E−06 |
| Example 67 | 2.079 | ND |
| Example 68 | 0.142 | ND |
| Example 69 | 0.109 | ND |
| Example 70 | 0.974 | ND |
| Example 71 | 39.015 | ND |
| Example 72 | 12.007 | ND |
| Example 73 | 0.276 | ND |
| Example 74 | 0.621 | ND |
| Example 75 | 0.280 | ND |
| Example 76 | 3.177 | ND |
| Example 77 | 75.45% @ 200 μM | ND |
| Example 78 | 0.135 | ND |
| Example 79 | 0.429 | ND |
| Example 80 | 0.487 | ND |
| Example 81 | 20.241 | ND |
| Example 82 | 1.109 | ND |
| Example 83 | 0.258 | ND |
| Example 84 | 4.022 | ND |
| Example 85 | 0.228 | ND |
| Example 86 | 9.976 | ND |
| Example 87 | 62.6% @ 7.4 μM | ND |
| Example 88 | 1.225 | ND |
| Example 89 | 72.13% @ 200 μM | ND |
| Example 90 | 0.023 | ND |
| Example 91 | 6.372 | ND |
| Example 92 | 12.887 | ND |
| Example 93 | 0.080 | ND |
| Example 94 | 6.901 | ND |
| Example 95 | 0.077 | ND |
| Example 96 | 1.628 | ND |
| Example 97 | 0.073 | ND |
| Example 98 | 2.873 | ND |
| Example 99 | 28.3% @ 200 μM | ND |
| Example 100 | 4.747 | ND |
| Example 101 | 0.462 | ND |
| Example 102 | 0.073 | ND |
| Example 103 | 0.715 | ND |
| Example 104 | 0.046 | ND |
| Example 105 | 0.704 | ND |
| Example 106 | 0.065 | ND |
| Example 107 | 0.544 | ND |
| Example 108 | 0.079 | ND |
| Example 109 | 1.858 | ND |
| Example 110 | 0.839 | ND |
| Example 111 | 4.452 | ND |
| Example 112 | 0.104 | ND |
| Example 113 | 0.045 | ND |
| Example 114 | 0.981 | ND |
| Example 115 | 1.753 | ND |
| Example 116 | 1.059 | ND |
| Example 117 | 2.603 | ND |
| Example 118 | 0.056 | ND |
| Example 119 | 1.456 | ND |
| Example 120 | 9.445 | ND |
| Example 121 | 0.167 | ND |
| Example 122 | 10.215 | ND |
| Example 123 | 0.152 | ND |
| Example 124 | 75.7% @ 50 μM | ND |
| Example 125 | 13.710 | ND |
| Example 126 | 41.2% @ 50 μM | ND |
| Example 127 | 0.913 | ND |
| Example 128 | 10.722 | ND |
| Example 129 | 0.053 | ND |
| Example 130 | 67.4% @ 50 μM | ND |
| Example 131 | 0.495 | ND |
| Example 132 | 9.844 | ND |
| Example 133 | 0.079 | ND |
| Example 134 | 0.176 | ND |
| Example 135 | 75.25% @ 50 μM | ND |
| Example 136 | 0.146 | ND |
| Example 137 | 71.05% @ 50 μM | ND |
| Example 138 | 0.664 | ND |
| Example 139 | 32.75% @ 10 μM | ND |
| Example 140 | 0.208 | ND |
| Example 141 | 26.78% @ 10 μM | ND |
| Example 142 | 0.335 | ND |
| Example 143 | 68.85% @ 50 μM | ND |
| Example 144 | 0.154 | ND |
| Example 145 | 3.888 | ND |
| Example 146 | 0.071 | ND |
| Example 147 | 14.236 | ND |
| Example 148 | 0.416 | ND |
| Example 149 | 14.001 | ND |
| Example 150 | 0.528 | ND |
| Example 151 | 71.3% @ 66.7 μM | ND |
| Example 152 | 0.047 | ND |
| Example 153 | 75.7% @ 50 μM | ND |
| Example 154 | 2.316 | 2.03E−05 |
| Example 155 | 63.15% @ 50 μM | ND |
| Example 156 | 0.309 | ND |
| Example 157 | 62.05% @ 50 μM | ND |
| Example 158 | 0.104 | ND |
| Example 159 | 1.770 | ND |
| Example 160 | 11.725 | ND |
| Example 161 | 12.579 | ND |
| Example 162 | 0.597 | ND |
| Example 163 | 8.375 | ND |
| Example 164 | 0.227 | ND |
| Example 165 | 0.315 | ND |
| Example 166 | 0.064 | ND |
| Example 167 | 1.146 | ND |
| Example 168 | 4.775 | ND |
| Example 169 | 2.105 | ND |
| Example 170 | 0.955 | ND |
| Example 171 | 2.775 | ND |
| Example 172 | 28.849 | ND |
| Example 173 | 6.794 | ND |
| Example 174 | 0.466 | ND |
| Example 175 | 3.856 | ND |
| Example 176 | 8.409 | ND |
| Example 177 | 0.957 | ND |
| Example 178 | 3.232 | ND |
| Example 179 | 0.881 | ND |
| Example 180 | 2.104 | ND |

TABLE 1-continued

IC$_{50}$ of Mcl-1 inhibition (fluorescence polarisation test) and of cytotoxicity for H929 cells

| | IC$_{50}$ (μM) Mcl-1 FP | IC$_{50}$ (M) MTT H929 |
|---|---|---|
| Example 181 | 0.299 | ND |
| Example 182 | 0.407 | ND |
| Example 183 | 2.044 | ND |
| Example 184 | 76.8% @ 200 μM | ND |
| Example 185 | 2.533 | ND |
| Example 186 | 7.880 | ND |
| Example 187 | 1.385 | ND |
| Example 188 | 21.302 | ND |
| Example 189 | 8.327 | ND |
| Example 190 | 34.602 | ND |
| Example 191 | 0.171 | ND |
| Example 192 | 2.082 | ND |
| Example 193 | 36.522 | ND |
| Example 194 | 1.752 | ND |
| Example 195 | 14.228 | ND |
| Example 196 | 2.908 | ND |
| Example 197 | 54.1% @ 200 μM | ND |
| Example 198 | 9.862 | ND |
| Example 199 | 0.298 | ND |
| Example 200 | 5.440 | ND |
| Example 201 | 0.136 | ND |
| Example 202 | 0.751 | ND |
| Example 203 | 71.85% @ 100 μM | ND |
| Example 204 | 44.8% @ 100 μM | ND |
| Example 205 | 26.2% @ 100 μM | ND |
| Example 206 | 8.844 | ND |
| Example 207 | 0.136 | ND |
| Example 208 | 0.632 | ND |
| Example 209 | 56.85% @ 200 μM | ND |
| Example 210 | 8.363 | ND |
| Example 211 | 0.668 | ND |
| Example 212 | 12.674 | ND |
| Example 213 | 0.111 | ND |
| Example 214 | 1.911 | ND |
| Example 215 | 0.015 | ND |
| Example 216 | 58.95% @ 10 μM | ND |
| Example 217 | 0.065 | ND |
| Example 218 | 71.5% @ 50 μM | ND |
| Example 219 | 10.940 | ND |
| Example 220 | 31.7% @ 10 μM | ND |
| Example 221 | 0.097 | ND |
| Example 222 | 70% @ 50 μM | ND |
| Example 223 | 0.086 | ND |
| Example 224 | 8.607 | ND |
| Example 225 | 0.053 | ND |
| Example 226 | 0.069 | ND |
| Example 227 | 3.312 | ND |
| Example 228 | 0.025 | ND |
| Example 229 | 6.325 | ND |
| Example 230 | 3.236 | ND |
| Example 231 | 56.75% @ 50 μM | ND |
| Example 232 | 62.2% @ 50 μM | ND |
| Example 233 | 3.408 | ND |
| Example 234 | 68.7% @ 50 μM | ND |
| Example 235 | 1.393 | ND |
| Example 236 | 13.498 | ND |
| Example 237 | 0.569 | ND |
| Example 238 | 2.785 | ND |
| Example 239 | 20.328 | ND |
| Example 240 | 0.958 | ND |
| Example 241 | 14.334 | ND |
| Example 242 | 0.091 | ND |
| Example 243 | 0.073 | ND |
| Example 244 | 0.120 | ND |
| Example 245 | 11.367 | ND |
| Example 246 | 0.293 | >1.50E−05 |
| Example 247 | 11.826 | ND |
| Example 248 | 2.176 | ND |
| Example 249 | 36.761 | ND |
| Example 250 | 0.617 | ND |
| Example 251 | 12.053 | ND |
| Example 252 | 0.223 | ND |
| Example 253 | 1.363 | ND |
| Example 254 | 22.08% @ 200 μM | ND |
| Example 255 | 41.08% @ 200 μM | ND |
| Example 256 | 1.606 | >6.0E−07 |
| Example 257 | 57.15% @ 10 μM | ND |
| Example 258 | 1.070 | 4.28E−07 |
| Example 259 | 1.347 | >6.0E−07 |
| Example 260 | 1.982 | ND |
| Example 261 | ND | ND |
| Example 262 | ND | ND |
| Example 263 | ND | ND |
| Example 264 | ND | ND |
| Example 265 | ND | ND |
| Example 266 | ND | ND |
| Example 267 | ND | ND |
| Example 268 | ND | ND |
| Example 269 | ND | ND |
| Example 270 | 0.055 | 5.22E−07 |
| Example 271 | ND | ND |
| Example 272 | ND | ND |
| Example 273 | ND | ND |
| Example 274 | ND | ND |

Note:
IC$_{50}$ of Mcl-1 inhibition obtained using Method 2 are underlined.
ND: not determined
For partial inhibitors, the percentage fluorescence polarisation inhibition for a given concentration of the test compound is indicated. Accordingly, 45.1% @10 μM means that 45.1% fluorescence polarisation inhibition is observed for a concentration of test compound equal to 10 μM.

Example C: Quantification of the Cleaved Form of PARP In Vivo

The ability of the compounds of the invention to induce apoptosis, by measuring cleaved PARP levels, is evaluated in a xenograft model of AMO-1 multiple myeloma cells. $1 \cdot 10^7$ AMO-1 cells are grafted sub-cutaneously into immunosuppressed mice (SCID strain). 12 to 14 days after the graft, the animals are treated by intraveinous or oral routes with the various compounds. After treatment, the tumour masses are recovered and lysed, and the cleaved form of PARP is quantified in the tumour lysates.

The quantification is carried out using the "Meso Scale Discovery (MSD) ELISA platform" test, which specifically assays the cleaved form of PARP. It is expressed in the form of an activation factor corresponding to the ratio between the quantity of cleaved PARP in the treated mice divided by the quantity of cleaved PARP in the control mice.

The results (presented in Table 2 below) show that the compounds of the invention are capable of inducing apoptosis in AMO-1 tumour cells in vivo.

TABLE 2

Quantification of the cleaved form of PARP in vivo

| | PARP fold |
|---|---|
| Example 7 | 81.4 |
| Example 22 | 222.2 |
| Example 24 | 164.5 |
| Example 40 | 114.3 |
| Example 43 | 114.6 |
| Example 44 | 85.8 |
| Example 45 | 103.7 |
| Example 49 | 138.8 |
| Example 51 | 52.2 |
| Example 256 | 99.5 |
| Example 258 | 132.3 |
| Example 259 | 134.4 |

Example D: Anti-Tumour Activity In Vivo

The anti-tumour activity of the compounds of the invention is evaluated in a xenograft model of AMO-1 multiple myeloma cells.

$1 \times 10^7$ AMO-1 cells are grafted sub-cutaneously into immunosuppressed mice (SCID strain).

6 to 8 days after the graft, when the tumour mass has reached about 150 mm³, the mice are treated with the various compounds in a daily schedule (5-day treatment). The tumour mass is measured twice weekly from the start of treatment.

The compounds of the invention have anti-tumour activities (tumour regression) in the AMO-1 multiple myeloma model with ΔT/C (qualification parameter of the activity of a product, which is measured by subtracting the median tumor volume on the day of last treatment from the median tumor volume on the day of first treatment/tumour volume of the untreated control group on the day of last treatment) ranging from −1.5 to −24.5%. The results obtained show that the compounds of the invention induce significant tumour regression during the treatment period.

Example E: Pharmaceutical Composition: Tablets

| | |
|---|---|
| 1000 tablets containing a dose of 5 mg of a compound selected from Examples 1 to 274 | 5 g |
| Wheat starch | 20 g |
| Maize starch | 20 g |
| Lactose | 30 g |
| Magnesium stearate | 2 g |
| Silica | 1 g |
| Hydroxypropylcellulose | 2 g |

The invention claimed is:
1. A compound of formula (I):

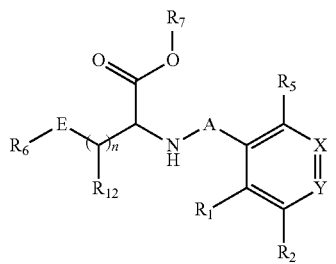

wherein:
A represents the group

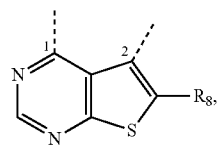

wherein 1 is linked to the —NH— group and 2 is linked to the aromatic ring,
E represents a cycloalkyl group, a heterocycloalkyl group, an aryl group or a heteroaryl group;
X represents a nitrogen atom or a C—$R_4$ group,
Y represents a nitrogen atom or a C—$R_3$ group,
$R_1$ represents a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl group, a hydroxy group, a hydroxy($C_1$-$C_6$)alkyl group, a linear or branched ($C_1$-$C_6$)alkoxy group, —S—($C_1$-$C_6$)alkyl, a cyano group, a nitro group, -alkyl($C_0$-$C_6$)—$NR_9R_9$', —O-alkyl($C_1$-$C_6$)—$NR_9R_9$', —O-alkyl($C_1$-$C_6$)—$R_{10}$, —C(O)—$OR_9$, —O—C(O)—$R_9$, —C(O)—$NR_9R_9$', —$NR_9$—C(O)—$R_9$', —$NR_9$—C(O)—$OR_9$', -alkyl($C_1$-$C_6$)—$NR_9$—C(O)—$R_9$', —$SO_2$—$NR_9R_9$', or —$SO_2$-alkyl ($C_1$-$C_6$),
$R_2$, $R_3$, $R_4$ and $R_5$, independently of one another, represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl group, a hydroxy group, a hydroxy($C_1$-$C_6$)alkyl group, a linear or branched ($C_1$-$C_6$)alkoxy group, —S—($C_1$-$C_6$)alkyl, a cyano group, a nitro group, -alkyl($C_0$-$C_6$)—$NR_9R_9$', —O-alkyl($C_1$-$C_6$)—$NR_9R_9$', —O-alkyl($C_1$-$C_6$)—$R_{10}$, —C(O)—$OR_9$, —O—C(O)—$R_9$, —C(O)—$NR_9R_9$', —$NR_9$—C(O)—$R_9$', —$NR_9$—C(O)—$OR_9$', -alkyl($C_1$-$C_6$)—$NR_9$—C(O)—$R_9$', —$SO_2$—$NR_9R_9$', or —$SO_2$-alkyl ($C_1$-$C_6$),
or the substituents of the pair ($R_1$, $R_2$), together with the carbon atoms carrying them, form an aromatic or non-aromatic ring having from 5 to 7 ring members, which may contain from 1 to 3 heteroatoms selected from oxygen, sulphur and nitrogen, wherein the resulting ring may be substituted by from 1 to 2 groups selected from the group consisting of halogen, linear or branched ($C_1$-$C_6$)alkyl, -alkyl($C_0$-$C_6$)—$NR_9R_9$', —$NR_{11}R_{11}$', -alkyl($C_0$-$C_6$)-$Cy_1$, and oxo,
$R_6$ represents a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl group, a hydroxy group, a linear or branched ($C_1$-$C_6$)alkoxy group, —S—($C_1$-$C_6$)alkyl, a cyano group, a nitro group, -alkyl($C_0$-$C_6$)—$NR_9R_9$', —O-$Cy_1$, -alkyl($C_0$-$C_6$)-$Cy_1$, -alkenyl($C_2$-$C_6$)-$Cy_1$, -alkynyl($C_2$-$C_6$)-$Cy_1$, —O-alkyl($C_1$-$C_6$)—$R_{10}$, —C(O)—$OR_9$, —O—C(O)—$R_9$, —C(O)—$NR_9R_9$', —$NR_9$—C(O)—$R_9$', —$NR_9$—C(O)—$OR_9$', -alkyl($C_1$-$C_6$)—$NR_9$—C(O)—$R_9$', —$SO_2$—$NR_9R_9$', or $SO_2$-alkyl ($C_1$-$C_6$),
$R_7$ represents a hydrogen atom, a linear or branched ($C_1$-$C_8$)alkyl group, a —$CHR_aR_b$ group, an aryl group, a heteroaryl group, an arylalkyl($C_1$-$C_6$) group, or a heteroarylalkyl($C_1$-$C_6$) group,
$R_8$ represents a linear or branched ($C_1$-$C_6$)alkyl group, a linear or branched ($C_2$-$C_6$)alkenyl group, a linear or branched ($C_2$-$C_6$)alkynyl group, -$Cy_2$, a halogen atom, a cyano group, —C(O)—$R_{11}$, or —C(O)—$NR_{11}R_{11}$',
$R_9$ and $R_9$', independently of one another, represent a hydrogen atom, a linear or branched ($C_1$-$C_6$)alkyl group,
or the substituents of the pair, ($R_9$, $R_9$'), together with the nitrogen atom carrying them, form an aromatic or non-aromatic ring having from 5 to 7 ring members, which may contain, in addition to the nitrogen atom, from 1 to 3 heteroatoms selected from oxygen, sulphur and nitrogen, wherein the nitrogen may be substituted by a hydrogen atom or a linear or branched ($C_1$-$C_6$)alkyl group, $R_{10}$ represents -$Cy_3$, -$Cy_3$-alkyl($C_0$-$C_6$)-$Cy_4$, —C(O)—$NR_9NR_9'$, —$NR_9R_9'$, —$OR_9$, —$NR_9$—C(O)—$R_9'$, —O-alkyl($C_1$-$C_6$)—$OR_9$, —$SO_2$—$R_9$, —C(O)—$OR_9$, or —NH—C(O)—NH—$R_9$, $R_{11}$ and $R_{11}'$, independently of another, represent a hydrogen atom or an optionally substituted linear or branched ($C_1$-$C_6$)alkyl group, $R_{12}$ represents a hydrogen atom, a hydroxy group, or a hydroxy($C_1$-$C_6$)alkyl group, $R_a$ represents a hydrogen atom or a linear or branched ($C_1$-$C_6$)alkyl group, $R_b$ represents a —O—C(O)—O—$R_c$ group, a —O—C(O)—$NR_cR_c'$ group, or a —O—P(O)($OR_c$)$_2$ group, $R_c$ and $R_c'$, independently of one another, represent a hydrogen atom, a linear or branched ($C_1$-$C_8$)alkyl group, a cycloalkyl group, a ($C_1$-$C_6$)alkoxy($C_1$-$C_6$)alkyl group, a ($C_1$-$C_6$)alkoxycarbonyl($C_1$-$C_6$)alkyl group, or the substituents of the pair ($R_c$, $R_c'$), together with the nitrogen atom carrying them, form a non-aromatic ring having from 5 to 7 ring members, which may contain, in addition to the nitrogen atom, from 1 to 3 heteroatoms selected from oxygen and nitrogen, wherein the nitrogen may be substituted by a linear or branched ($C_1$-$C_6$)alkyl group, $Cy_1$, $Cy_2$, $Cy_3$ and $Cy_4$, independently of one another, represent a cycloalkyl group, a heterocycloalkyl group, an aryl group or a heteroaryl group, n is an integer equal to 0, 1 or 2, wherein:
"aryl" means a phenyl, naphthyl, biphenyl group,
"heteroaryl" means any mono- or bi-cyclic group composed of from 5 to 10 ring members, having at least one aromatic moiety and containing from 1 to 3 heteroatoms selected from oxygen, sulphur and nitrogen,
"cycloalkyl" means any mono- or bi-cyclic non-aromatic carbocyclic group containing from 3 to 10 ring members,
"heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, and wherein the aryl, heteroaryl, cycloalkyl and heterocycloalkyl groups so defined and the alkyl, alkenyl, alkynyl, alkoxy groups may be substituted by from 1 to 4 groups selected from the group consisting of optionally substituted linear or branched ($C_1$-$C_6$)alkyl, optionally substituted linear or branched ($C_2$-$C_6$)alkenyl, optionally substituted linear or branched ($C_2$-$C_6$) alkynyl, optionally substituted linear or branched ($C_1$-$C_6$)alkoxy, optionally substituted ($C_1$-$C_6$)alkyl-S—, hydroxy, hydroxy($C_1$-$C_6$)alkyl, oxo (or N-oxide where appropriate), nitro, cyano, —C(O)—OR', —O—C(O)—R', —C(O)—NR'R", —O—C(O)—NR'R", —NR'R", —(C=NR')—OR", —O—P(O)(OR')$_2$, —O—P(O)(O$^-$M$^+$)$_2$, linear or branched ($C_1$-$C_6$)polyhaloalkyl, trifluotomethoxy, halogen, and an aldohexose of formula:

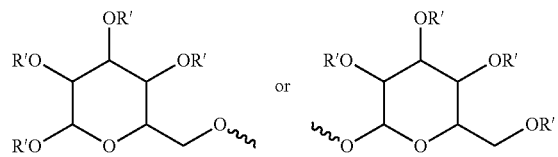

in which each R' is independent;

wherein R' and R", independently of one another, represent a hydrogen atom or an optionally substituted linear or branched ($C_1$-$C_6$)alkyl group and M$^+$ represents a pharmaceutically acceptable monovalent cation, its enantiomers, diastereoisomers and atropisomers, and addition salts thereof with a pharmaceutically acceptable acid or base.

2. The compound according to claim 1, wherein:

$R_1$ and $R_2$, independently of one another, represent a halogen atom, a linear or branched ($C_1$-$C_6$)alkyl group, a hydroxy group, a hydroxy($C_1$-$C_6$)alkyl group, a linear or branched ($C_1$-$C_6$)alkoxy group, or the substituents of the pair ($R_1$, $R_2$), together with the carbon atoms carrying them, form an aromatic ring having from 5 to 7 ring members, which may contain from 1 to 3 nitrogen atoms, wherein the resulting ring may be substituted by from 1 to 2 groups selected from the group consisting of halogen, linear or branched ($C_1$-$C_6$)alkyl, and -alkyl($C_0$-$C_6$)—$NR_9R_9'$, $R_3$ represents a hydrogen atom, a halogen atom, a linear or branched ($C_1$-$C_6$)alkyl group, a hydroxy group, a linear or branched ($C_1$-$C_6$)alkoxy group, or —O-alkyl($C_1$-$C_6$)—$NR_9R_9'$, $R_4$ and $R_5$, independently of one another, represent a hydrogen atom, a halogen atom, a linear or branched ($C_1$-$C_6$)alkyl group, a hydroxy group, or a linear or branched ($C_1$-$C_6$)alkoxy group, $R_6$ represents a hydrogen atom, a halogen atom, a linear or branched ($C_1$-$C_6$)alkyl group, a linear or branched ($C_1$-$C_6$)polyhaloalkyl group, a hydroxy group, a linear or branched ($C_1$-$C_6$)alkoxy group, a cyano group, a nitro group, -alkyl($C_0$-$C_6$)—$NR_9R_9'$, -alkyl($C_0$-$C_6$)-$Cy_1$, —O-alkyl($C_1$-$C_6$)—$R_{10}$, or —C(O)—$NR_9R_9'$, $R_7$ represents a hydrogen atom, a linear or branched ($C_1$-$C_8$)alkyl group, a —$CHR_aR_b$ group, or a heteroarylalkyl($C_1$-$C_6$) group, $R_8$ represents a linear or branched ($C_1$-$C_6$)alkyl group, a linear or branched ($C_2$-$C_6$)alkenyl group, a linear or branched ($C_2$-$C_6$)alkynyl group, -$Cy_2$, a halogen atom, or —C(O)—$R_{11}$, $R_9$ and $R_9'$, independently of one another, represent a hydrogen atom, or a linear or branched ($C_1$-$C_6$)alkyl group, or the substituents of the pair ($R_9$, $R_9'$), together with the nitrogen atom carrying them, form a non-aromatic ring, having from 5 to 7 ring members, which may contain in addition to the nitrogen atom from 1 to 3 heteroatoms selected from oxygen and nitrogen, wherein the nitrogen may be substituted by a linear or branched ($C_1$-$C_6$)alkyl group, $R_{10}$ represents -$Cy_3$ or -$Cy_3$-alkyl($C_0$-$C_6$)-$Cy_4$, $R_{11}$ represents a linear or branched ($C_1$-$C_6$)alkyl group, wherein the aryl, heteroaryl, cycloalkyl and heterocycloalkyl groups so defined and the alkyl, alkenyl, alkynyl, alkoxy groups may be substituted by from 1 to 4 groups selected from the group consisting of optionally substituted linear of branched ($C_1$-$C_6$)alkyl, optionally substituted linear or branched ($C_1$-$C_6$) alkoxy, hydroxy, oxo (or N-oxide where appropriate), —C(O)—OR', —C(O)—NR'R", —O—C(O)—NR'R", —NR'R", —O—P(O)(OR')$_2$, —O—P(O)(O$^-$M$^+$)$_2$, linear or branched ($C_1$-$C_6$)polyhaloalkyl, halogen, and an aldohexose of formula:

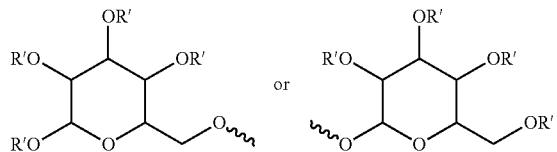

in which each R' is independent; wherein R' and R", independently of one another, represent a hydrogen atom or an optionally substituted linear or branched ($C_1$-$C_6$)alkyl group and M$^+$ represents a pharmaceutically acceptable monovalent cation.

3. The compound according to claim 1, wherein n is an integer equal to 1.

4. The compound according to claim 1, wherein at least one the groups selected from $R_2$, $R_3$, $R_4$ and $R_5$ does not represent a hydrogen atom.

5. The compound according to claim 1, wherein $R_{12}$ represents a hydrogen atom.

6. The compound according to claim 1, wherein $R_1$ represents a linear or branched ($C_1$-$C_6$)alkyl group or a halogen atom.

7. The compound according to claim 1, wherein $R_2$ represents a linear or branched ($C_1$-$C_6$)alkoxy group, a hydroxy group, or a halogen atom.

8. The compound according to claim 1, wherein X represents a C—$R_4$ group.

9. The compound according to claim 1, wherein Y represents a C—$R_3$ group.

10. The compound according to claim 1, wherein $R_4$ and $R_5$ represent a hydrogen atom.

11. The Compound according to claim 1, wherein the substituents of the pair ($R_1$, $R_5$) are identical and the substituents of the pair ($R_2$, $R_4$) are identical.

12. The compound according to claim 1, wherein:

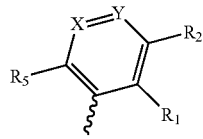

represents

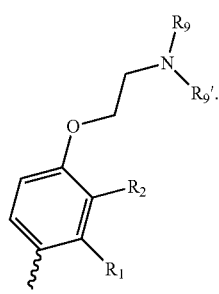

13. The compound according to claim 1, wherein:

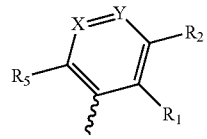

represents

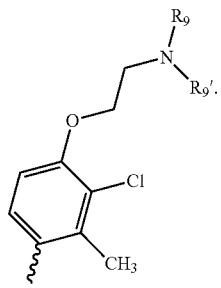

14. The compound according to claim 1, wherein E represents a phenyl group, a pyridin-2-yl, a cyclohexyl group, a pyrazol-1-yl group, a cyclopentyl group, an indol-4-yl group, a cyclopropyl group, a pyridin-3-yl group, an indol-3-yl group, a naphth-1-yl group, an imidazol-4-yl group or a pyridin-4-yl group.

15. The compound according to claim 1, which is a compound of formula (I-b):

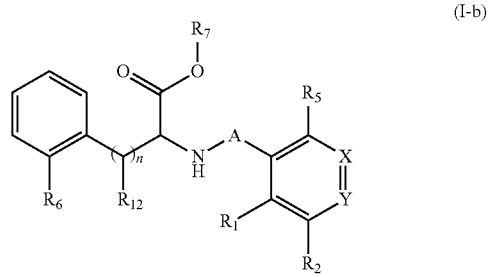

wherein
A represents the group

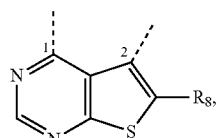

wherein 1 is linked to the —NH— group and 2 is linked to the aromatic ring,
X represents a nitrogen atom or a C—$R_4$ group,
Y represents a nitrogen atom or a C—$R_3$ group,
$R_1$ represents a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl group, a hydroxy group, a hydroxy($C_1$-$C_6$)alkyl group, a linear or branched ($C_1$-$C_6$)alkoxy group, —S—($C_1$-$C_6$)alkyl, a cyano group, a nitro group; -alkyl($C_0$-$C_6$)—$NR_9R_9$', —O-alkyl($C_1$-$C_6$)—$NR_9R_9$', —$NR_9$—C(O)—$OR_9$', —C(O)—$OR_9$, —O—C(O)—$R_9$, —C(O)—$NR_9R_9$', —$NR_9$—C(O)—$R_9$', —$NR_9$—C(O)—$OR_9$', -alkyl($C_1$-$C_6$)—$NR_9$—C(O)—$R_9$', —$SO_2$—$NR_9R_9$', or —$SO_2$-alkyl($C_1$-$C_6$), $R_2$, $R_3$, $R_4$ and $R_5$, independently of one another, represent a hydrogen atom, a halogen atom, a linear Or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl group, a hydroxy group, a hydroxy($C_1$-$C_6$)alkyl group, a linear or branched ($C_1$-$C_6$)alkoxy group, —S—($C_1$-$C_6$)alkyl, a cyano group, a nitro group, -alkyl($C_0$-$C_6$)—$NR_9R_9$', —O-alkyl($C_1$-$C_6$)—$NR_9R_9$', —O-alkyl($C_1$-$C_6$)—$R_{10}$, —C(O)—$OR_9$, —O—C(O)—$R_9$, —C(O)—$NR_9R_9$', —$NR_9$—C(O)—$R_9$', —$NR_9$C(O)—$OR_9$', -alkyl($C_1$-$C_6$)—$NR_9$—C(O)—$R_9$', —$SO_2$—$NR_9R_9$', or —$SO_2$-alkyl($C_1$-$C_6$), or the substituents of the pair ($R_1$, $R_2$), together with the carbon atoms carrying them, form an aromatic or non-aromatic ring having froth 5 to 7 ring members, which may contain from 1 to 0.3 heteroatoms selected from oxygen, sulphur and nitrogen, wherein the resulting ring may be substituted by from 1 to 2 groups selected from the group consisting of halogen, linear or branched ($C_1$-$C_6$)alkyl, -alkyl($C_0$-$C_6$)—$NR_9R_9$', —$NR_{11}R_{11}$', -alkyl($C_0$-$C_6$)-$Cy_1$, and oxo, $R_6$ represents a hydrogen atom, a halogen atom, a linear or branched ($C_1$-$C_6$)alkyl group, a linear or branched ($C_2$-$C_6$)alkenyl group, a linear or branched ($C_2$-$C_6$) alkynyl group, a linear or branched ($C_1$-$C_6$)polyhaloalkyl group, a hydroxy group, a linear or branched ($C_1$-$C_6$)alkoxy group, —S—($C_1$-$C_6$)alkyl, a cyano group, a nitro group, -alkyl($C_0$-$C_6$)—$NR_9R_9$', —O-$Cy_1$, -alkyl($C_0$-$C_6$)-$Cy_1$, -alkenyl($C_2$-$C_6$)-$Cy_1$, -alkynyl($C_2$-$C_6$)-$Cy_1$, —O-alkyl($C_1$-$C_6$)—$R_{10}$, —C(O)—$OR_9$, —O—C(O)—$R_9$, —$SO_2$—$NR_9R_9$', —$NR_9$—C(O)—$R_9$', —$NR_9$—C(O)—$OR_9$', -alkyl($C_1$-$C_6$)—$NR_9$C(O)—$R_9$', —$SO_2$—$NR_9R_9$', or —$SO_2$-alkyl($C_1$-$C_6$), $R_7$ represents a hydrogen atom, a linear or branched ($C_1$-$C_8$)alkyl group, a —$CHR_aR_b$ group, an aryl group, a heteroaryl group, an arylalkyl($C_1$-$C_6$) group, or a heteroarylalkyl($C_1$-$C_6$) group, $R_8$ represents a linear or branched ($C_1$-$C_6$)alkyl group, a linear or branched ($C_2$-$C_6$)alkenyl group, a linear or branched ($C_2$-$C_6$)alkynyl group, -$Cy_2$, a halogen atom, a cyano group, —C(O)—$R_{11}$, or —C(O)—$NR_{11}R_{11}$', $R_9$ and $R_9$', independently of one another, represent a hydrogen atom, a linear or branched ($C_1$-$C_6$)alkyl group, or the substituents of the pair ($R_9$, $R_9$'), together with the nitrogen atom carrying them, form an aromatic or non-aromatic ring having from 5 to 7 ring members, which may contain, in addition to the nitrogen atom, front 1 to 3 heteroatoms selected from oxygen, sulphur and nitrogen, wherein the nitrogen may be substituted by a hydrogen atom or a linear or branched ($C_1$-$C_6$) alkyl group, $R_{10}$ represents -$Cy_3$, -$Cy_3$-alkyl($C_0$-$C_6$)-$Cy_4$, —C(O)—$NR_9R_9$', —$NR_9R_9$', —$OR_9$, —$NR_9$—C(O)—$R_9$', —O-alkyl($C_1$-$C_6$)—$OR_9$, —$SO_2$—$R_9$, —C(O)—$OR_9$, or —NH—C(O)—NH—$R_9$, —$R_{11}$ and $R_{11}$', independently of one another, represent a hydrogen atom or an optionally substituted linear or branched ($C_1$-$C_6$)alkyl group, $R_{12}$ represents a hydrogen atom, a hydroxy group, or hydroxy($C_1$-$C_6$)alkyl group, $R_a$ represents a hydrogen atom or a linear of branched ($C_1$-$C_6$)alkyl group, $R_b$ represents a —O—C(O)—O—$R_c$ group, a —O—C(O)—$NR_cR_c$' group, or a —O—P(O)($OR_c$)$_2$ group, $R_c$ and $R_c$', independently of one another, represent a hydrogen atom, a linear or branched ($C_1$-$C_8$)alkyl group, a cycloalkyl group, a ($C_1$-$C_6$)alkoxy($C_1$-$C_6$) alkyl group, a ($C_1$-$C_6$)alkoxycarbonyl($C_1$-$C_6$)alkyl group, or the substituents of the pair ($R_c$, $R_c$'), together with the nitrogen atom carrying them, form a non-aromatic ring having from 5 to 7 ring members, which may contain, in addition to the nitrogen atom, from 1 to 3 heteroatoms selected from oxygen and nitrogen, wherein the nitrogen may be substituted by a linear or branched ($C_1$-$C_6$)alkyl group, $Cy_1$, $Cy_2$, $Cy_3$ and $Cy_4$, independently of one another, represent a cycloalkyl group, a heterocycloalkyl group, an aryl group or a heteroaryl group, n is an integer equal to 0, 1 or 2, wherein:

"aryl" means a phenyl, naphthyl, biphenyl group,

"heteroaryl" means any mono- or bi-cyclic group composed of from 5 to 10 ring members, having at least one aromatic moiety and containing from 1 to 3 heteroatoms selected from oxygen, sulphur and nitrogen, "cycloalkyl" means any mono- or bi-cyclic iron-aromatic carbocyclic group containing from 3 to 10 ring members, "heterocycloalkyl" means any mono- or bi-cyclic non-aromatic carbocyclic group containing from 3 to 10 ring members and containing from 1 to 3 heteroatoms selected from oxygen, sulphur and nitrogen, which may include fused, bridged or spiro ring systems, and wherein the aryl, heteroaryl, cycloalkyl and heterocycloalkyl groups so defined and the alkyl, alkenyl, alkynyl, alkoxy groups may be substituted by from 1 to 4 groups selected from the group consisting of optionally substituted linear or branched ($C_1$-$C_6$)alkyl, optionally substituted linear or branched ($C_2$-$C_6$)alkenyl, optionally substituted linear or branched ($C_2$-$C_6$) alkynyl, optionally substituted linear or branched ($C_1$-$C_6$)alkoxy, optionally substituted ($C_1$-$C_6$)alkyl-S—, hydroxy, hydroxy($C_1$-$C_6$)alkyl, oxo (or N-oxide where appropriate), nitro, cyano, —C(O)—OR', —O—C(O)—R', —C(O)—NR'R", —O—C(O)—NR'R", —NR'R", —(C=NR')—OR", —O—P(O)(OR')$_2$, —O—P(O)(O$^-$M$^+$)$_2$, linear or branched ($C_1$-$C_6$)polyhaloalkyl, trifluoromethoxy, halogen, and an aldohexose of formula:

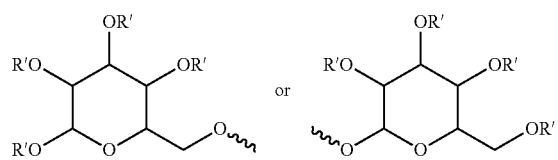

in which each R' is independent;

wherein R' and R", independently of one another, represent a hydrogen atom or an optionally substituted linear or branched ($C_1$-$C_6$)alkyl group and M$^+$ represents a pharmaceutically acceptable monovalent cation, its enantiomers, diastereoisomers and atropisomers, and addition salts thereof with a pharmaceutically acceptable acid or base.

16. The compound according to claim 1, wherein $R_6$ represents a hydrogen atom; a fluorine atom; a chlorine atom; a bromine atom; a methyl group; a trifluoromethyl group; a hydroxy group; a methoxy group; a linear $(C_1-C_6)$ alkoxy group substituted by halogen atoms, a —C(O)—NR'R" group or a —NR'R" group; a cyano; a nitro group; an aminomethyl group; a benzyl group; —O-alkyl$(C_1-C_6)$—$R_{10}$; or —C(O)—$NR_9R_9'$.

17. The compound according to claim 1, wherein $R_7$ represents a hydrogen atom, an optionally substituted linear or branched $(C_1-C_6)$alkyl group, a —$CHR_aR_b$ group, or a heteroarylalkyl$(C_1-C_6)$ group.

18. The compound according to claim 1, wherein $R_8$ represents a linear or branched $(C_2-C_6)$alkynyl group, an aryl group or a heteroaryl group.

19. The compound according to claim 1, wherein $R_9$ and $R_9'$ independently of one another represent a linear or branched $(C_1-C_6)$alkyl group, or the substituents of the pair $(R_9, R_9')$ form together with the nitrogen atom carrying them a non-aromatic ring composed of from 5 to 7 ring members, which may contain in addition to the nitrogen atom from 1 to 3 heteroatoms selected from oxygen and nitrogen, it being understood that the nitrogen in question may be substituted by a linear or branched $(C_1-C_6)$alkyl group.

20. The compound according to claim 1, wherein $R_{10}$ represents -$Cy_3$ or -$Cy_3$-alkyl$(C_0-C_6)$-$Cy_4$.

21. The compound according to claim 20, wherein $Cy_3$ represents a cycloalkyl group, an aryl group or a heteroaryl group.

22. The compound according to claim 20, wherein $Cy_4$ represents phenyl group or a morpholinyl group.

23. The compound according to claim 20, wherein $R_{10}$ represents

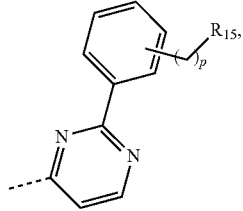

wherein p is an integer equal to 0 or 1 and $R_{15}$ represents a hydrogen atom, a hydroxy group, an optionally substituted linear or branched $(C_1-C_6)$alkyl group, a linear or branched $(C_1-C_6)$alkoxy group, a —O—$(CHR_{16}—CHR_{17}—O)_q$—R' group, a —O—P(O)(OR')$_2$ group, a —O—P(O)(O$^-$M$^+$)$_2$ group, a —O—C(O)—$NR_{18}R_{19}$ group, a di$(C_1-C_6)$alkylamino$(C_1-C_6)$ alkoxy group, a halogen atom, or an aldohexose of formula:

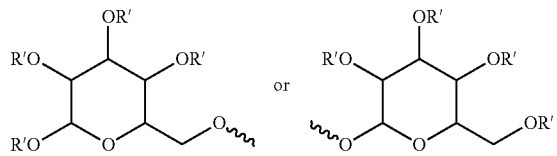

in which each R' is independent;

wherein:
R' represents a hydrogen atom or a linear or branched $(C_1-C_6)$alkyl group;
$R_{16}$ represents a hydrogen atom or a $(C_1-C_6)$alkoxy$(C_1-C_6)$alkyl group,
$R_{17}$ represents a hydrogen atom or a hydroxy$(C_1-C_6)$ alkyl group,
$R_{18}$ represents a hydrogen atom or a $(C_1-C_6)$alkoxy$(C_1-C_6)$alkyl group,
$R_{19}$ represents a $(C_1-C_6)$alkoxy$(C_1-C_6)$alkyl group, a —$(CH_2)_r$—$NR_9R_9'$ group or a —$(CH_2)_r$—O—$(CHR_{16}$—$CHR_{17}$—O)$_q$—R' group,
q is an integer equal to 1, 2 or 3 and r is an integer equal to 0 or 1,
M$^+$ represents a pharmaceutically acceptable monovalent cation.

24. The compound according to claim 23, wherein the aldexose is D-mannose.

25. The compound according to claim 1, which is selected from the group consisting of:
N-[5-{3-chloro-2-methyl-4-[2-(4-methylpiperazin-1-yl) ethoxy]phenyl}-6-(4-fluorophenyl)thieno[2,3-d]pyrimidin-4-yl]-2-[(1-methyl-1H-pyrazol-5-yl) methoxy]-D-phenylalanine,
N-[5-{3-chloro-2-methyl-4-[2-(4-methylpiperazin-1-yl) ethoxy]phenyl}-6-(4-fluorophenyl)thieno[2,3-d]pyrimidin-4-yl]-2-[(2-ethoxypyrimidin-4-yl)methoxy]-D-phenylalanine,
N-[5-{3-chloro-2-methyl-4-[2-(4-methylpiperazin-1-yl) ethoxy]phenyl}-6-(4-fluorophenyl)thieno[2,3-d]pyrimidin-4-yl]-2-{[2-(2-methoxyphenyl)pyrimidin-4-yl] methoxy}-D-phenylalanine,
N-[5-{3-chloro-2-methyl-4-[2-(4-methylpiperazin-1-yl) ethoxy]phenyl}-6-(furan-2-yl)thieno[2,3-d]pyrimidin-4-yl]-2-methoxy-D-phenylalanine,
N-[5-{3-chloro-2-methyl-4-[2-(4-methylpiperazin-1-yl) ethoxy]phenyl}-6-(5-fluorofuran-2-yl)thieno[2,3-d]pyrimidin-4-yl]-2methoxy-D-phenylalanine,
N-[5-{3-chloro-2-methyl-4-[2-(4-methylpiperazin-1-yl) ethoxy]phenyl}-6-(5-fluorofuran-2-yl)thieno[2,3-d]pyrimidin-4-yl]-2-(2,2,2-trifluoroethoxy)-D-phenylalanine,
N-[5-{3-chloro-2-methyl-4-[2-(4-methylpiperazin-1-yl) ethoxy]phenyl}-6-(5-fluorofuran-2-yl)thieno[2,3-d]pyrimidin-4-yl]-2-(pyridin-2-ylmethoxy)-D-phenylalanine,
N-[5-{3-chloro-2-methyl-4-[2-(4-methylpiperazin-1-yl) ethoxy]phenyl}-6-(5-fluorofuran-2-yl)thieno[2,3-d]pyrimidin-4-yl]-2-[(1-methyl-1H-pyrazol-5-yl) methoxy]-D-phenylalanine,
N-[5-{3-chloro-2-methyl-4-[2-(4-methylpiperazin-1-yl) ethoxy]phenyl}-6-(5-fluorofuran-2-yl)thieno[2,3-d]pyrimidin-4-yl]-2-[(1-ethyl-1H-pyrazol-5-yl) methoxy]-D-phenylalanine,
N-[5-{3-chloro-2-methyl-4-[2-(4-methylpiperazin-1-yl) ethoxy]phenyl}-6-(5-fluorofuran-2-yl)thieno[2,3-d]pyrimidin-4-yl]-2-[(2-ethoxypyrimidin-4-yl) methoxy]-D-phenylalanine,
2-[(1-butyl-1H-pyrazol-5yl)methoxy]-N-[5-{3-chloro-2-methyl-4-[2-(4-methyl piperazin-1-yl)ethoxy]phenyl}-6-(5-fluorofuran-2-yl)thieno[2,3-d]pyrimidin-4-yl]-D-phenylalanine,
N-[5-{3-chloro-2-methyl-4-[2-(4-methylpiperazin-1-yl) ethoxy]phenyl}-6-(5-fluorofuran-2-yl)thieno[2,3-d]pyrimidin-4-yl]-2-{[2-(2,2,2-trifluoroethoxy)pyrimidin-4-yl]methoxy}-D-phenylalanine, N-[5-{3-chloro-2-methyl-4-[2-(4-methylpiperazin-1-yl)ethoxy]phenyl}-6-(5-fluorofuran-2-yl)thieno[2,3-d]pyrimidin-4-yl]-2-{[2-(2-methoxyphenyl)pyrimidin-4-yl]methoxy}-D-phenylalanine, N-[5-{3-chloro-2-methyl-4-[2-(4-methylpiperazin-1-yl)ethoxy]phenyl}-6-(prop-1-yn-1-yl)thieno[2,3-d]pyrimidin-4-yl]-2-methoxy-D-phenylalanine, 2-[(1-tert-butyl-1H-pyrazol-5-yl)methoxy]-N-[5-{3-chloro-2-methyl-4-[2-(4-methylpiperazin-1-yl)ethoxy]phenyl}-6-(prop-1-yn-1-yl)thieno[2,3-d]pyrimidin-4-yl]-D-phenylalanine, N-[5-{3-chloro-2-methyl-4-[2-(4methylpiperazin-1-yl)ethoxy]phenyl}-6-(prop-1-yn-1-yl)thieno[2,3-d]pyrimidin-4-yl]-2-{[2-(2-methoxyethyl)pyrimidin-4-yl]methoxy}-D-phenylalanine, N-[5-{3-chloro-2-methyl-4-[2-(4-methylpiperazin-1-yl)ethoxy]phenyl}-6-(prop-1-yn-1-yl)thieno[2,3-d]pyrimidin-4-yl]-2-{[1-(2,2,2-trifluoroethyl)-1H-pyrazol-5-yl]methoxy}-D-phenylalanine, N-[5-{3-chloro-2-methyl-4-[2-(4-methylpiperazin-1-yl)ethoxy]phenyl}-6-(prop-1-yn-1-yl)thieno[2,3-d]pyrimidin-4-yl]-2-{[2-(morpholin-4-yl)pyrimidin-4-yl]methoxy}-D-phenylalanine, N-[5-{3-chloro-2-methyl-4-[2-(4-methylpiperazin-1-yl)ethoxy]phenyl}-6-(prop-1-yn-1-yl)thieno[2,3-d]pyrimidin-4-yl]-2-{[2-(2,2,2-trifluoroethoxy)pyrimidin-4-yl]methoxy}-D-phenylalanine, N-[5-{3-chloro-2-methyl-4-[2-(4-methylpiperazin-1-yl)ethoxy]phenyl}-6-(prop-1-yn-1-yl)thieno[2,3-d]pyrimidin-4-yl]-2-{[2-(2-methoxyphenyl)pyrimidin-4-yl]methoxy}-D-phenylalanine, N-[5-{3-chloro-4-[2-(dimethylamino)ethoxy]-2-methylphenyl}-6-(prop-1-yn-1-yl) thieno[2,3-d]pyrimidin-4-yl]-2-{[1-(2,2,2-trifluoroethyl)-1H-pyrazol-5-yl]methoxy}-D-phenylalanine, N-[5-{3-chloro-4-[2-(dimethylamino)ethoxy]-2-methylphenyl}-6-(prop-1-yn-1-yl) thieno[2,3-d]pyrimidin-4-yl]-2-{[2-(morpholin-4-yl)pyrimidin-4-yl]methoxy}-D-phenylalanine, N-[5-{3-chloro-4-[2-(dimethylamino)ethoxy]-2-methylphenyl}-6-(prop-1-yn-1-yl) thieno[2,3-d]pyrimidin-4-yl]2-{[2-(2,2,2-trifluoroethoxy)pyrimidin-4-yl]methoxy}-D-phenylalanine, N-[5-{3-chloro-4-[2-(dimethylamino)ethoxy]-2-methylphenyl}-6-(prop-1-yn-1-yl) thieno[2,3-d]pyrimidin-4-yl]-2-{[2-(2-methoxyphenyl)pyrimidin-4-yl]methoxy}-D-phenylalanine, N-[5-{3-chloro-4-[2-(dimethylamino)ethoxy]-2-methylphenyl}-6-(4-fluoro phenyl)thieno[2,3-d]pyrimidin-4-yl]-2-({2-[2-(2-methoxyethoxy)phenyl]pyrimidin-4-yl}methoxy)-D-phenylalanine;

ethyl N-[(5S)-5-{3-chloro-2-methyl-4-[2-(4-methylpiperazin-1-yl)ethoxy]phenyl}-6-(4-fluorophenyl)thieno[2,3-d]pyrimidin-4-yl]-2-{[2-(2-methoxyphenyl)pyrimidin-4-yl]methoxy}-D-phenylalaninate;

ethyl N-[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]-2-{[2-(2-methoxyphenyl)pyrimidin-4-yl]methoxy}-D-phenylalaninate;

ethyl N-[(5S$_a$)-5-{3-chloro-4-[2-(dimethylamino)ethoxy]-2-methylphenyl}-6-(prop-1-yn-1-yl)thieno[2,3-d]pyrimidin-4-yl]-2-{[2-(2-methoxyphenyl)pyrimidin-4-yl]methoxy}-D-phenylalaninate; and N-[5-{3,5-dichloro-2,6-dimethyl-4-[2-(4-methylpiperazin-1-yl) ethoxy]phenyl}-6-(4-fluorophenyl)thieno[2,3-d]pyrimidin-4-yl]-2-{[2-(2-methoxyphenyl)pyrimidin-4-yl]methoxy}-D-phenylalanine.

26. A pharmaceutical composition comprising the compound according to claim 1, or an addition salt thereof with a pharmaceutically acceptable acid or base, in combination with one or more pharmaceutically acceptable excipients.

27. A method of treating a condition requiring a pro-apoptotic agent in a subject in need thereof, comprising administration of an effective amount of the compound according to claim 1, alone or in combination with one or more pharmaceutically acceptable excipients.

28. The method according to claim 27, wherein the condition is selected from cancer, auto-immune diseases, and immune system diseases.

29. The method according to claim 27, wherein the condition is selected from cancers of the bladder, brain, breast and uterus, chronic lymphoid leukaemias, cancer of the colon, œsophagus and liver, lymphoblastic leukaemias, acute myeloid leukaemias, lymphomas, melanomas, malignant haemopathies, myelomas, ovarian cancer, non-small-cell lung cancer, prostate cancer, pancreatic cancer, and small-cell lung cancer.

30. A combination of the compound of formula (I) according to claim 1 with an anti-cancer agent selected from genotoxic agents, mitotic poisons, anti-metabolites, proteasome inhibitors, kinase inhibitors and antibodies.

31. A pharmaceutical composition comprising the combination according to claim 30, in combination with one or more pharmaceutically acceptable excipients.

32. A method of treating cancer in a subject in need thereof, comprising administration of an effective amount of the combination according to claim 30, alone or in combination with one or more pharmaceutically acceptable excipients.

33. A method of treating cancer requiring radiotherapy in a subject in need thereof, comprising administration of the compound of formula (I) according to claim 1, alone or in combination with one or more pharmaceutically acceptable excipients.

\* \* \* \* \*

UNITED STATES PATENT AND TRADEMARK OFFICE
CERTIFICATE OF CORRECTION

PATENT NO. : 10,457,687 B2
APPLICATION NO. : 15/737783
DATED : October 29, 2019
INVENTOR(S) : Zoltán Szlávik et al.

Page 1 of 1

It is certified that error appears in the above-identified patent and that said Letters Patent is hereby corrected as shown below:

In the Specification

Column 119, Line 3: "-$NR_9$-C(O)-$OR_{9'}$." should read -- -O-alkyl($C_1$-$C_6$)-$R_{10}$, --.
    Line 23: "froth" should read -- from --.
    Line 24: "0.3" should read -- 3 --.
    Line 39: "-$SO_2$-$NR_9R_{9'}$," should read -- -C(O)-$NR_9R_{9'}$, --.

In the Claims

Column 123, Line 52, Claim 25: "(5S)" should read -- ($5S_a$) --.

Signed and Sealed this
Twenty-fourth Day of December, 2019

Andrei Iancu
*Director of the United States Patent and Trademark Office*